(12) United States Patent  
Hughes et al.

(10) Patent No.: US 9,686,990 B2
(45) Date of Patent: *Jun. 27, 2017

(54) SPIROINDOLINEPIPERIDINE DERIVATIVES

(71) Applicant: SYNGENTA PARTICIPATIONS AG, Basel (CH)

(72) Inventors: David John Hughes, Bracknell (GB); Paul Anthony Worthington, Bracknell (GB); Charles Adam Russell, Bracknell (GB); Eric Daniel Clarke, Bracknell (GB); James Edward Peace, Bracknell (GB); Mark Richard Ashton, Abington (GB); Thomas Stephen Coulter, Abington (GB); Richard Spurring Roberts, Barcelona (ES); Louis-Pierre Molleyres, Basel (CH); Fredrik Cederbaum, Stein (CH); Jerome Cassayre, Stein (CH); Peter Maienfisch, Stein (CH)

(73) Assignee: Syngenta Participations AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 14/859,410

(22) Filed: Sep. 21, 2015

(65) Prior Publication Data
US 2016/0007608 A1   Jan. 14, 2016

Related U.S. Application Data

(62) Division of application No. 13/234,793, filed on Sep. 16, 2011, now Pat. No. 9,174,987, which is a division of application No. 10/517,957, filed as application No. PCT/GB03/02424 on Jun. 4, 2003, now abandoned.

(30) Foreign Application Priority Data

Jun. 14, 2002 (GB) .................................. 0213715.6

(51) Int. Cl.
*A01N 43/90* (2006.01)
*A01N 47/38* (2006.01)
*C07D 471/10* (2006.01)
*A01N 47/34* (2006.01)
*C07D 211/70* (2006.01)
*C07D 211/76* (2006.01)
*C07D 491/10* (2006.01)

(52) U.S. Cl.
CPC ............ *A01N 43/90* (2013.01); *A01N 47/34* (2013.01); *A01N 47/38* (2013.01); *C07D 211/70* (2013.01); *C07D 211/76* (2013.01); *C07D 471/10* (2013.01); *C07D 491/10* (2013.01); *C07B 2200/11* (2013.01)

(58) Field of Classification Search
None
See application file for complete search history.

(56) References Cited

U.S. PATENT DOCUMENTS

| 4,233,307 A | 11/1980 | Ono et al. |
| 4,307,235 A | 12/1981 | Ong et al. |
| 8,309,567 B2 * | 11/2012 | Cassayre |

FOREIGN PATENT DOCUMENTS

| JP | 7-20647 | 1/1995 |
| WO | WO95/01358 A | 1/1995 |
| WO | WO98/25605 A | 6/1998 |
| WO | WO02/47679 A | 6/2002 |
| WO | WO02/083134 A | 10/2002 |

OTHER PUBLICATIONS

Side Reactions in Organic Synthesis (Dorwald, F.A., 2005, Wiley: VCH, Weinheim, p. IX).
'Potent and Selective Ligands for the Dopamine Transporter (DAT): Structure-Activity Relationship Studies of Novel 4-[2-(Diphenylmethoxy)ethyl]-1-(3-phenylpr opyl)piperidine Analogs' Journal of Medicinal Chemistry (1998), 41 (5), 699-705, Dutta et al.

* cited by examiner

*Primary Examiner* — Savitha Rao
*Assistant Examiner* — Gregg Polansky
(74) *Attorney, Agent, or Firm* — Brian D. McAlhaney

(57) ABSTRACT

Insecticidal, acaricidal, nematicidal or molluscicidal compounds of formula (I)

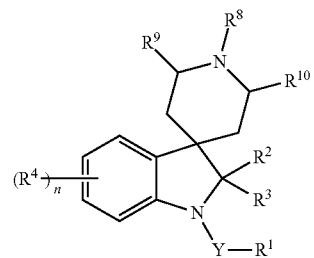

wherein Y is a single bond, C=O, C=S or S(O)$_q$ where q is 0, 1 or 2; and $R^1$, $R^2$, $R^3$, $R^4$, $R^8$, $R^9$ are $R^{10}$ are as defined in the claims or salts or N-oxides thereof, processes for preparing them and compositions containing them.

6 Claims, No Drawings

SPIROINDOLINEPIPERIDINE DERIVATIVES

This application is a divisional application of U.S. Ser. No. 13/234,793 filed Sep. 16, 2011, which is a divisional application of U.S. Ser. No. 10/517,957 filed Aug. 11, 2005, which is a 371 of International Application No. PCT/GB2003/002424 filed Jun. 4, 2003, which claims priority to GB 0213715.6 filed Jun. 14, 2002, the contents of which are incorporated herein by reference.

The present invention relates to spiroindoline derivatives, to processes for preparing them, to insecticidal, acaricidal, molluscicidal and nematicidal compositions comprising them and to methods of using them to combat and control insect, acarine, mollusc and nematode pests.

Spiroindoline derivatives with pharmaceutical properties are disclosed in for example WO9825605, WO9429309, WO9828297 and WO9964002. Synthetic routes to selected compounds with pharmaceutical properties are described in Proc. Natl. Acad. Sci. USA (1995), 92, 7001, Tetrahedron (1997), 53, 10983 and Tetrahedron Letters (1997), 38, 1497. It has now surprisingly been found that certain spiroindolines have insecticidal properties.

The present invention therefore provides a method of combating and controlling insects, acarines, nematodes or molluscs which comprises applying to a pest, to a locus of a pest, or to a plant susceptible to attack by a pest an insecticidally, acaricidally, nematicidally or molluscicidally effective amount of a compound of formula (I):

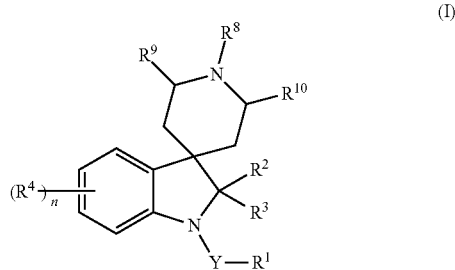

wherein Y is a single bond, C=O, C=S or $S(O)_q$ where q is 0, 1 or 2; $R^1$ is hydrogen, optionally substituted alkyl, optionally substituted alkoxycarbonyl, optionally substituted alkylcarbonyl, aminocarbonyl, optionally substituted alkylaminocarbonyl, optionally substituted dialkylaminocarbonyl, optionally substituted aryl, optionally substituted heteroaryl, optionally substituted alkoxy, optionally substituted aryloxy, optionally substituted heteroaryloxy, optionally substituted heterocyclyloxy, cyano, optionally substituted alkenyl, optionally substituted alkynyl, optionally substituted cycloalkyl, optionally substituted cycloalkenyl, formyl, optionally substituted heterocyclyl, optionally substituted alkylthio, NO or $NR^{13}R^{14}$ where $R^{13}$ and $R^{14}$ are independently hydrogen, $COR^{40}$, optionally substituted alkyl, optionally substituted aryl, optionally substituted heteroaryl, optionally substituted heterocyclyl or $R^{13}$ and $R^{14}$ together with the N atom to which they are attached form a group $N=C(R^{41})-NR^{42}R^{43}$; $R^2$ and $R^3$ are independently hydrogen, halogen, cyano, optionally substituted alkyl, optionally substituted alkoxy, optionally substituted aryl or $C(O)NR^{15}R^{16}$ where $R^{15}$ and $R^{16}$ are independently hydrogen, optionally substituted alkyl, optionally substituted aryl, optionally substituted heteroaryl or optionally substituted heterocyclyl, or $R^2$ and $R^3$ together are =O, or $R^2$ and $R^3$ together with the atoms to which they are attached form a 4, 5, 6, or 7 membered carbocyclic or heterocyclic ring; each $R^4$ is independently halogen, nitro, cyano, optionally substituted $C_{1-8}$ alkyl, optionally substituted $C_{2-6}$ alkenyl, optionally substituted $C_{2-6}$ alkynyl, optionally substituted alkoxycarbonyl, optionally substituted alkylcarbonyl, optionally substituted alkylaminocarbonyl, optionally substituted dialkylaminocarbonyl, optionally substituted $C_{3-7}$ cycloalkyl, optionally substituted aryl, optionally substituted heteroaryl, optionally substituted heterocyclyl, optionally substituted alkoxy, optionally substituted aryloxy, optionally substituted heteroaryloxy, optionally substituted alkylthio or $R^{19}R^{20}N$ where $R^{19}$ and $R^{20}$ are, independently, hydrogen, $C_{1-8}$ alkyl, $C_{3-7}$ cycloalkyl, $C_{3-6}$ alkenyl, $C_{3-6}$ alkynyl, $C_{3-7}$ cycloalkyl($C_{1-4}$)alkyl, $C_{2-6}$ haloalkyl, $C_{1-6}$ alkoxy($C_{1-8}$)alkyl, $C_{1-8}$ alkoxycarbonyl or $R^{19}$ and $R^{20}$ together with the N atom to which they are attached form a five, six or seven-membered heterocyclic ring which may contain one or two further heteroatoms selected from O, N or S and which may be optionally substituted by one or two $C_{1-8}$ alkyl groups, or 2 adjacent groups $R^4$ together with the carbon atoms to which they are attached form a 4, 5, 6, or 7 membered carbocyclic or heterocyclic ring which may be optionally substituted by halogen; n is 0, 1, 2, 3 or 4; $R^8$ is optionally substituted alkyl, optionally substituted alkenyl, optionally substituted alkynyl, optionally substituted cycloalkyl, optionally substituted aryl, optionally substituted alkoxy, optionally substituted aryloxy, optionally substituted alkoxycarbonyl, optionally substituted alkylcarbonyl or optionally substituted alkenylcarbonyl; $R^9$ and $R^{10}$ are independently hydrogen, halogen, optionally substituted alkyl, optionally substituted aryl or $R^9$ and $R^{10}$ together form a group —$CH_2$—, CH=CH— or —$CH_2CH_2$—; $R^{40}$ is H, optionally substituted alkyl, optionally substituted alkoxy, optionally substituted aryl, optionally substituted aryloxy optionally substituted heteroaryl, optionally substituted heteroaryloxy or $NR^{44}R^{45}$; $R^{41}$, $R^{42}$ and $R^{43}$ are each independently H or lower alkyl; $R^{44}$ and $R^{45}$ are independently optionally substituted alkyl, optionally substituted aryl or optionally substituted heteroaryl or salts or N-oxides thereof.

The compounds of formula (I) may exist in different geometric or optical isomers or tautomeric forms. This invention covers all such isomers and tautomers and mixtures thereof in all proportions as well as isotopic forms such as deuterated compounds.

Each alkyl moiety either alone or as part of a larger group (such as alkoxy, alkoxycarbonyl, alkylcarbonyl, alkylaminocarbonyl, dialkylaminocarbonyl) is a straight or branched chain and is, for example, methyl, ethyl, n-propyl, n-butyl, n-pentyl, n-hexyl, iso-propyl, n-butyl, sec-butyl, iso-butyl, tert-butyl or neo-pentyl.

When present, the optional substituents on an alkyl moiety (alone or as part of a larger group such as alkoxy, alkoxycarbonyl, alkylcarbonyl, alkylaminocarbonyl, dialkylaminocarbonyl) include one or more of halogen, nitro, cyano, NCS—, $C_{3-7}$ cycloalkyl (itself optionally substituted with $C_{1-6}$ alkyl or halogen), $C_{5-7}$ cycloalkenyl (itself optionally substituted with $C_{1-6}$ alkyl or halogen), hydroxy, $C_{1-10}$ alkoxy, $C_{1-10}$ alkoxy($C_{1-10}$)alkoxy, tri($C_{1-4}$)alkylsilyl($C_{1-6}$) alkoxy, $C_{1-6}$ alkoxycarbonyl($C_{1-10}$)alkoxy, haloalkoxy, aryl($C_{1-4}$)-alkoxy (where the aryl group is optionally substituted), $C_{3-7}$ cycloalkyloxy (where the cycloalkyl group is optionally substituted with $C_{1-6}$ alkyl or halogen), $C_{2-10}$ alkenyloxy, $C_{2-10}$ alkynyloxy, SH, $C_{1-10}$ alkylthio, $C_{1-10}$ haloalkylthio, aryl($C_{1-4}$)alkylthio (where the aryl group is optionally substituted), $C_{3-7}$ cycloalkylthio (where the cycloalkyl group is optionally substituted with $C_{1-6}$ alkyl or halogen), tri($C_{1-4}$)alkylsilyl($C_{1-6}$)alkylthio, arylthio (where the aryl group is optionally substituted), $C_{1-6}$ alkylsulfonyl, $C_{1-6}$ haloalkylsulfonyl, $C_{1-6}$ alkylsulfinyl, $C_{1-6}$ haloalkylsulfinyl, arylsulfonyl (where the aryl group may be optionally substituted), tri($C_{1-4}$)alkylsilyl, aryldi($C_{1-4}$)alkylsilyl, ($C_{1-4}$)alkyldiarylsilyl, triarylsilyl, $C_{1-10}$ alkylcarbonyl, $HO_2C$, $C_{1-10}$ alkoxycarbonyl, aminocarbonyl, $C_{1-6}$ alkylaminocarbonyl, di($C_{1-6}$ alkyl)aminocarbonyl, N—($C_{1-3}$ alkyl)-N—($C_{1-3}$ alkoxy)aminocarbonyl, $C_{1-6}$ alkylcarbonyloxy, arylcarbonyloxy (where the aryl group is optionally substituted), di($C_{1-6}$)alkylaminocarbonyloxy, oximes such as =NOalkyl, =NOhaloalkyl and =NOaryl (itself optionally substituted), aryl (itself optionally substituted), heteroaryl (itself optionally substituted), heterocyclyl (itself optionally substituted with $C_{1-6}$ alkyl or halogen), aryloxy (where the aryl group is optionally substituted), heteroaryloxy, (where the heteroaryl group is optionally substituted), heterocyclyloxy (where the heterocyclyl group is optionally substituted with $C_{1-6}$ alkyl or halogen), amino, $C_{1-6}$ alkylamino, di($C_{1-6}$)alkylamino, $C_{1-6}$ alkylcarbonylamino, N—($C_{1-6}$)alkylcarbonyl-N—($C_{1-6}$)alkylamino, $C_{2-6}$ alkenylcarbonyl, $C_{2-6}$ alkynylcarbonyl, $C_{3-6}$ alkenyloxycarbonyl, $C_{3-6}$ alkynyloxycarbonyl, aryloxycarbonyl (where the aryl group is optionally substituted) and arylcarbonyl (where the aryl group is optionally substituted).

Alkenyl and alkynyl moieties can be in the form of straight or branched chains, and the alkenyl moieties, where appropriate, can be of either the (E)- or (Z)-configuration. Examples are vinyl, allyl and propargyl.

When present, the optional substituents on alkenyl or alkynyl include those optional substituents given above for an alkyl moiety.

In the context of this specification acyl is optionally substituted $C_{1-6}$ alkylcarbonyl (for example acetyl), optionally substituted $C_{2-6}$ alkenylcarbonyl, optionally substituted $C_{2-6}$ alkynylcarbonyl, optionally substituted arylcarbonyl (for example benzoyl) or optionally substituted heteroarylcarbonyl.

Halogen is fluorine, chlorine, bromine or iodine.

Haloalkyl groups are alkyl groups which are substituted with one or more of the same or different halogen atoms and are, for example, $CF_3$, $CF_2Cl$, $CF_3CH_2$ or $CHF_2CH_2$.

In the context of the present specification the terms "aryl" and "aromatic ring system" refer to ring systems which may be mono-, bi- or tricyclic. Examples of such rings include phenyl, naphthalenyl, anthracenyl, indenyl or phenanthrenyl. A preferred aryl group is phenyl. In addition, the terms "heteroaryl", "heteroaromatic ring" or "heteroaromatic ring system" refer to an aromatic ring system containing at least one heteroatom and consisting either of a single ring or of two or more fused rings. Preferably, single rings will contain up to three and bicyclic systems up to four heteroatoms which will preferably be chosen from nitrogen, oxygen and sulphur. Examples of such groups include furyl, thienyl, pyrrolyl, pyrazolyl, imidazolyl, 1,2,3-triazolyl, 1,2,4-triazolyl, oxazolyl, isoxazolyl, thiazolyl, isothiazolyl, 1,2,3-oxadiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, pyridyl, pyrimidinyl, pyridazinyl, pyrazinyl, 1,2,3-triazinyl, 1,2,4-triazinyl, 1,3,5-triazinyl, benzofuryl, benzisofuryl, benzothienyl, benzisothienyl, indolyl, isoindolyl, indazolyl, benzothiazolyl, benzisothiazolyl, benzoxazolyl, benzisoxazolyl, benzimidazolyl, quinolinyl, isoquinolinyl, cinnolinyl, phthalazinyl, quinazolinyl, quinoxalinyl, naphthyridinyl, benzotriazinyl, purinyl, pteridinyl and indolizinyl. Preferred examples of heteroaromatic radicals include pyridyl, pyrimidyl, triazinyl, thienyl, furyl, oxazolyl, isoxazolyl, and thiazolyl.

The terms heterocycle and heterocyclyl refer to a non-aromatic ring containing up to 10 atoms including one or more (preferably one or two) heteroatoms selected from 0, S and N. Examples of such rings include 1,3-dioxolane, tetrahydrofuran and morpholine.

When present, the optional substituents on heterocyclyl include $C_{1-6}$ alkyl and $C_{1-6}$ haloalkyl as well as those optional substituents given above for an alkyl moiety.

Cycloalkyl includes cyclopropyl, cyclopentyl and cyclohexyl.

Cycloalkenyl includes cyclopentenyl and cyclohexenyl.

When present, the optional substituents on cycloalkyl or cycloalkenyl include $C_{1-3}$ alkyl as well as those optional substituents given above for an alkyl moiety.

Carbocyclic rings include aryl, cycloalkyl and cycloalkenyl groups.

When present, the optional substituents on aryl or heteroaryl are selected independently, from halogen, nitro, cyano, NCS—, $C_{1-6}$ alkyl, $C_{1-6}$ haloalkyl, $C_{1-6}$ alkoxy-($C_{1-6}$)alkyl, $C_{2-6}$ alkenyl, $C_{2-6}$ haloalkenyl, $C_{2-6}$ alkynyl, $C_{3-7}$ cycloalkyl (itself optionally substituted with $C_{1-6}$ alkyl or halogen), $C_{5-7}$ cycloalkenyl (itself optionally substituted with $C_{1-6}$ alkyl or halogen), hydroxy, $C_{1-10}$ alkoxy, $C_{1-10}$ alkoxy($C_{1-10}$)alkoxy, tri($C_{1-4}$)alkyl-silyl($C_{1-6}$)alkoxy, $C_{1-6}$ alkoxycarbonyl($C_{1-10}$)alkoxy, $C_{1-10}$ haloalkoxy, aryl($C_{1-4}$) alkoxy (where the aryl group is optionally substituted with halogen or $C_{1-6}$ alkyl), $C_{3-7}$ cycloalkyloxy (where the cycloalkyl group is optionally substituted with $C_{1-6}$ alkyl or halogen), $C_{2-10}$ alkenyloxy, $C_{2-10}$ alkynyloxy, SH, $C_{1-10}$ alkylthio, $C_{1-10}$ haloalkylthio, aryl($C_{1-4}$)alkylthio $C_{3-7}$ cycloalkylthio (where the cycloalkyl group is optionally substituted with $C_{1-6}$ alkyl or halogen), tri($C_{1-4}$)-alkylsilyl ($C_{1-6}$)alkylthio, arylthio, $C_{1-6}$ alkylsulfonyl, $C_{1-6}$ haloalkylsulfonyl, $C_{1-6}$ alkylsulfinyl, $C_{1-6}$ haloalkylsulfinyl, arylsulfonyl, tri($C_{1-4}$)alkylsilyl, aryldi($C_{1-4}$)-alkylsilyl, ($C_{1-4}$) alkyldiarylsilyl, triarylsilyl, $C_{1-10}$ alkylcarbonyl, $HO_2C$, $C_{1-10}$ alkoxycarbonyl, aminocarbonyl, $C_{1-6}$ alkylaminocarbonyl, di($C_{1-6}$ alkyl)-aminocarbonyl, N—($C_{1-3}$ alkyl)-N—($C_{1-3}$ alkoxy)aminocarbonyl, $C_{1-6}$ alkylcarbonyloxy, arylcarbonyloxy, di($C_{1-6}$)alkylaminocarbonyloxy, aryl (itself optionally substituted with $C_{1-6}$ alkyl or halogen), heteroaryl (itself optionally substituted with $C_{1-6}$ alkyl or halogen), heterocyclyl (itself optionally substituted with $C_{1-6}$ alkyl or halogen), aryloxy (where the aryl group is optionally substituted with $C_{1-6}$ alkyl or halogen), heteroaryloxy (where the heteroaryl group is optionally substituted with $C_{1-6}$ alkyl or halogen), heterocyclyloxy (where the heterocyclyl group is optionally substituted with $C_{1-6}$ alkyl or halogen), amino, $C_{1-6}$ alkylamino, di($C_{1-6}$)alkylamino, $C_{1-6}$ alkylcarbonylamino, N—($C_{1-6}$)alkylcarbonyl-N—($C_{1-6}$)alkylamino, arylcarbonyl, (where the aryl group is itself optionally substituted with halogen or $C_{1-6}$ alkyl) or two adjacent positions on an aryl or heteroaryl system may be cyclised to form a 5, 6 or 7 membered carbocyclic or heterocyclic ring, itself optionally substituted with halogen or $C_{1-6}$ alkyl. Further substituents for aryl or heteroaryl include aryl carbonyl amino (where the aryl group is substituted by $C_{1-6}$ alkyl or halogen), ($C_{1-6}$)alkyloxycarbonylamino ($C_{1-6}$)alkyloxycarbonyl-N—($C_{1-6}$)alkylamino, aryloxycarbonylamino (where the aryl group is substituted by $C_{1-6}$ alkyl or halogen), aryloxycarbonyl-N—($C_{1-6}$)alkylamino, (where the aryl group is substituted by $C_{1-6}$ alkyl or halogen), arylsulphonylamino (where the aryl group is substituted by $C_{1-6}$ alkyl or halogen), arylsulphonyl-N—($C_{1-6}$)alkylamino (where the aryl group is substituted by $C_{1-6}$ alkyl or halogen), aryl-N—($C_{1-6}$)alkylamino (where the aryl group is substituted by $C_{1-6}$ alkyl or halogen), arylamino (where the aryl group is substituted by $C_{1-6}$ alkyl or halogen), heteroaryl amino (where the heteroaryl group is substituted by $C_{1-6}$ alkyl or halogen), heterocyclylamino (where the heterocyclyl group is substituted by $C_{1-6}$ alkyl or halogen), aminocarbonylamino, $C_{1-6}$ alkylaminocarbonyl amino, di($C_{1-6}$)alkylaminocarbonyl amino, arylaminocarbonyl amino where the aryl group is substituted by $C_{1-6}$ alkyl or halogen), aryl-N—($C_{1-6}$)alkylaminocarbonylamino where the aryl group is substituted by $C_{1-6}$ alkyl or halogen), $C_{1-6}$ alkylaminocarbonyl-N—($C_{1-6}$)alkyl amino, di($C_{1-6}$)alkylaminocarbonyl-N—($C_{1-6}$)alkyl amino, arylaminocarbonyl-N—($C_{1-6}$)alkyl amino (where the aryl group is substituted by $C_{1-6}$ alkyl or halogen) and aryl-N—($C_{1-6}$)alkylaminocarbonyl-N—($C_{1-6}$)alkyl amino (where the aryl group is substituted by $C_{1-6}$ alkyl or halogen).

For substituted phenyl moieties, heterocyclyl and heteroaryl groups it is preferred that one or more substituents are independently selected from halogen, $C_{1-6}$ alkyl, $C_{1-6}$ haloalkyl, $C_{1-6}$ alkoxy($C_{1-6}$)alkyl, $C_{1-6}$ alkoxy, $C_{1-6}$ haloalkoxy, $C_{1-6}$ alkylthio, $C_{1-6}$ haloalkylthio, $C_{1-6}$ alkylsulfinyl, $C_{1-6}$ haloalkylsulfinyl, $C_{1-6}$ alkylsulfonyl, $C_{1-6}$ haloalkylsulfonyl, $C_{2-6}$ alkenyl, $C_{2-6}$ haloalkenyl, $C_{2-6}$ alkynyl, $C_{3-7}$ cycloalkyl, nitro, cyano, $CO_2H$, $C_{1-6}$ alkylcarbonyl, $C_{1-6}$ alkoxycarbonyl, $R^{31}R^{32}N$ or $R^{33}R^{34}NC(O)$; wherein $R^{31}$, $R^{32}$, $R^{33}$ and $R^{34}$ are, independently, hydrogen or $C_{1-6}$ alkyl. Further preferred substituents are amino, dialkylamino, aryl and heteroaryl groups.

Haloalkenyl groups are alkenyl groups which are substituted with one or more of the same or different halogen atoms It is to be understood that dialkylamino substituents include those where the dialkyl groups together with the N atom to which they are attached form a five, six or seven-membered heterocyclic ring which may contain one or two further heteroatoms selected from O, N or S and which is optionally substituted by one or two independently selected ($C_{1-6}$)alkyl groups. When heterocyclic rings are formed by joining two groups on an N atom, the resulting rings are suitably pyrrolidine, piperidine, thiomorpholine and morpholine each of which may be substituted by one or two independently selected ($C_{1-6}$) alkyl groups.

Preferably the optional substituents on an alkyl moiety include one or more of halogen, nitro, cyano, $HO_2C$, $C_{1-10}$ alkoxy (itself optionally substituted by $C_{1-10}$ alkoxy), aryl ($C_{1-4}$)alkoxy, $C_{1-10}$ alkylthio, $C_{1-10}$ alkylcarbonyl, $C_{1-10}$ alkoxycarbonyl, $C_{1-6}$ alkylaminocarbonyl, di($C_{1-6}$ alkyl)aminocarbonyl, ($C_{1-6}$)alkylcarbonyloxy, optionally substituted phenyl, heteroaryl, aryloxy, arylcarbonyloxy, heteroaryloxy, heterocyclyl, heterocyclyloxy, $C_{3-7}$ cycloalkyl (itself optionally substituted with ($C_{1-6}$)alkyl or halogen), $C_{3-7}$ cycloalkyloxy, $C_{5-7}$ cycloalkenyl, $C_{1-6}$ alkylsulfonyl, $C_{1-6}$ alkylsulfinyl, tri($C_{1-4}$)alkylsilyl, tri($C_{1-4}$)alkylsilyl($C_{1-6}$)alkoxy, aryldi($C_{1-4}$)alkylsilyl, ($C_{1-4}$)alkyldiarylsilyl and triarylsilyl.

Preferably the optional substituents on alkenyl or alkynyl include one or more of halogen, $C_{3-7}$ cycloalkyl and aryl; the aryl group may be optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino.

A preferred optional substituent for heterocyclyl is $C_{1-6}$ alkyl.

Preferably the optional substituents for cycloalkenyl include $C_{1-3}$ alkyl, halogen and cyano.

One group of preferred compounds are those of formula (IA) which are compounds of formula (I) wherein Y is a single bond, C=O, C=S or $S(O)_q$ where q is 0, 1 or 2; $R^1$ is hydrogen, optionally substituted alkyl, optionally substituted alkoxycarbonyl, optionally substituted alkylcarbonyl, aminocarbonyl, optionally substituted alkylaminocarbonyl, optionally substituted dialkylaminocarbonyl, optionally substituted aryl, optionally substituted heteroaryl, optionally substituted alkoxy, optionally substituted aryloxy, optionally substituted heteroaryloxy, optionally substituted heterocyclyloxy, cyano, optionally substituted alkenyl, optionally substituted alkynyl, optionally substituted cycloalkyl, optionally substituted cycloalkenyl, formyl, optionally substituted heterocyclyl, optionally substituted alkylthio or $NR^{13}R^{14}$ where $R^{13}$ and $R^{14}$ are independently hydrogen, optionally substituted alkyl, optionally substituted aryl, optionally substituted heteroaryl or optionally substituted heterocyclyl; $R^2$ and $R^3$ are independently hydrogen, halogen, cyano, optionally substituted alkyl, optionally substituted alkoxy, optionally substituted aryl or $C(O)NR^{15}R^{16}$ where $R^{15}$ and $R^{16}$ are independently hydrogen, optionally substituted alkyl, optionally substituted aryl, optionally substituted heteroaryl or optionally substituted heterocyclyl, or $R^2$ and $R^3$ together are =O, or $R^2$ and $R^3$ together with the atoms to which they are attached form a 4, 5, 6, or 7 membered carbocylic or heterocyclic ring; each $R^4$ is independently halogen, nitro, cyano, optionally substituted $C_{1-8}$ alkyl, optionally substituted $C_{2-6}$ alkenyl, optionally substituted $C_{2-6}$ alkynyl, optionally substituted alkoxycarbonyl, optionally substituted alkylcarbonyl, optionally substituted alkylaminocarbonyl, optionally substituted dialkylaminocarbonyl, optionally substituted $C_{3-7}$ cycloalkyl, optionally substituted aryl, optionally substituted heteroaryl, optionally substituted heterocyclyl, optionally substituted alkoxy, optionally substituted aryloxy, optionally substituted heteroaryloxy, optionally substituted alkylthio or $R^{19}R^{20}N$ where $R^{19}$ and $R^{20}$ are, independently, hydrogen, $C_{1-8}$ alkyl, $C_{3-7}$ cycloalkyl, $C_{3-6}$ alkenyl, $C_{3-6}$ alkynyl, $C_{3-7}$ cycloalkyl($C_{1-4}$)alkyl, $C_{2-6}$ haloalkyl, $C_{1-8}$ alkoxy($C_{1-8}$)alkyl, $C_{1-8}$ alkoxycarbonyl or $R^{19}$ and $R^{20}$ together with the N atom to which they are attached form a five, six or seven-membered heterocyclic ring which may contain one or two further heteroatoms selected from O, N or S and which may be optionally substituted by one or two $C_{1-8}$ alkyl groups, or 2 adjacent groups $R^4$ together with the carbon atoms to which they are attached form a 4, 5, 6, or 7 membered carbocylic or heterocyclic ring which may be optionally substituted by halogen; n is 0, 1, 2, 3 or 4; $R^8$ is optionally substituted alkyl, optionally substituted alkenyl, optionally substituted alkynyl, optionally substituted cycloalkyl, optionally substituted aryl, optionally substituted alkoxy, optionally substituted aryloxy, optionally substituted alkoxycarbonyl, optionally substituted alkylcarbonyl or optionally substituted alkenylcarbonyl; $R^9$ and $R^{10}$ are independently hydrogen, halogen, optionally substituted alkyl, optionally substituted aryl or $R^9$ and $R^{10}$ together form a group —$CH_2$—, —CH=CH— or —$CH_2CH_2$—; or salts or N-oxides thereof.

Another group of preferred compounds are those of formula (IB) which are compounds of formula (I) wherein Y is a single bond, C=O or $S(O)_q$ where q is 0, 1 or 2; $R^1$ is hydrogen, $C_{1-8}$ alkyl, $C_{1-6}$ haloalkyl, $C_{1-6}$ cyanoalkyl, $C_{3-7}$ cycloalkyl($C_{1-6}$)alkyl, $C_{5-6}$ cycloalkenyl($C_{1-6}$)alkyl, $C_{1-6}$ alkoxy($C_{1-6}$)alkyl, $C_{3-6}$ alkenyloxy($C_{1-6}$)alkyl, $C_{3-6}$ alkynyloxy($C_{1-6}$)alkyl, aryloxy($C_{1-6}$)alkyl, $C_{1-6}$ carboxyalkyl, $C_{1-6}$ alkylcarbonyl($C_{1-6}$)alkyl, $C_{2-6}$ alkenylcarbonyl-($C_{1-6}$)alkyl, $C_{2-6}$ alkynylcarbonyl($C_{1-6}$)alkyl, $C_{1-6}$ alkoxycarbonyl($C_{1-6}$) alkyl, $C_{3-6}$ alkenyloxycarbonyl($C_{1-6}$)alkyl, $C_{3-6}$ alkynyloxycarbonyl($C_{1-6}$)alkyl, aryloxycarbonyl($C_{1-6}$)-alkyl, $C_{1-6}$ alkylthio($C_{1-6}$)alkyl, $C_{1-6}$ alkylsulfinyl($C_{1-6}$)alkyl, $C_{1-6}$ alkylsulfonyl($C_{1-6}$)alkyl, aminocarbonyl($C_{1-6}$)alkyl, $C_{1-6}$ alkylaminocarbonyl($C_{1-6}$)alkyl, di($C_{1-6}$)-alkylaminocarbonyl($C_{1-6}$)alkyl, phenyl($C_{1-4}$)alkyl (wherein the phenyl group may be optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), heteroaryl($C_{1-4}$)alkyl (wherein the heteroaryl group may be substituted by halogen, nitro, cyano, $C_{1-6}$ alkyl, $C_{1-6}$ haloalkyl, $C_{1-6}$ alkoxy or $C_{1-6}$ haloalkoxy), heterocyclyl($C_{1-4}$)alkyl (wherein the heterocyclyl group may be substituted by halogen, cyano, $C_{1-6}$ alkyl, $C_{1-6}$ haloalkyl, $C_{1-6}$ alkoxy or $C_{1-6}$ haloalkoxy), $C_{1-6}$ alkoxycarbonyl, $C_{1-6}$ alkylcarbonyl, aminocarbonyl, $C_{1-6}$ alkylaminocarbonyl, di($C_{1-6}$)alkyl-aminocarbonyl, phenyl (optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), heteroaryl (optionally substituted by halogen, nitro, cyano, $C_{1-6}$ alkyl, $C_{1-6}$ haloalkyl, $C_{1-6}$ alkoxy or $C_{1-6}$ haloalkoxy), $C_{1-6}$ alkoxy, $C_{1-6}$ haloalkoxy, aryloxy (wherein the aryl group may be optionally substituted with halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), heteroaryloxy (wherein the heteroaryl group may be optionally substituted with halogen, nitro, cyano, $C_{1-6}$ alkyl, $C_{1-6}$ haloalkyl, $C_{1-6}$ alkoxy or $C_{1-6}$ haloalkoxy), cyano, $C_{2-6}$ alkenyl, $C_{2-6}$ haloalkenyl, $C_{2-6}$ cyanoalkenyl, aminocarbonyl-($C_{2-6}$)alkenyl, $C_{1-6}$ alkylaminocarbonyl($C_{2-6}$)alkenyl, di($C_{1-6}$)alkylaminocarbonyl($C_{2-6}$)alkenyl, phenyl($C_{2-4}$)alkenyl, (wherein the pentyl group may be optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), $C_{2-6}$ alkynyl, aminocarbonyl($C_{2-6}$)-alkynyl, $C_{1-6}$ alkylaminocarbonyl($C_{2-6}$)-alkynyl, di($C_{1-6}$) alkylaminocarbonyl($C_{2-6}$)alkynyl, $C_{3-7}$ cycloalkyl, $C_{3-7}$ halocycloalkyl, $C_{3-7}$ cyanocycloalkyl, $C_{1-3}$ alkyl($C_{3-7}$)cycloalkyl, $C_{1-3}$ alkyl-($C_{3-7}$)halocycloalkyl, $C_{5-6}$ cycloalkenyl, formyl, heterocyclyl (optionally substituted by halogen, nitro, cyano, $C_{1-6}$ alkyl, $C_{1-6}$ haloalkyl, $C_{1-6}$ alkoxy or $C_{1-6}$ haloalkoxy), $C_{1-8}$ alkylthio, or $R^{13}R^{14}N$ where $R^{13}$ and $R^{14}$ are independently hydrogen, $COR^{43}$, $C_{1-6}$ alkyl, aryl (optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), heteroaryl (optionally substituted by halogen or $C_{1-3}$ alkyl) or $R^{13}$ and $R^{14}$ together with the N atom to which they are attached form a group $N=C(R^{41})$—$NR^{42}R^{43}$ where $R^{41}$, $R^{42}$ and $R^{43}$ are independently H or $C_{1-4}$ lower alkyl; $R^2$ and $R^3$ are independently hydrogen, $C_{1-6}$ alkyl, $C_{1-6}$ haloalkyl, $C_{1-6}$ alkoxy or cyano; each $R^4$ is independently halogen, nitro, cyano, $C_{1-8}$ alkyl, $C_{1-6}$ haloalkyl, $C_{1-6}$ cyanoalkyl, $C_{3-7}$ cycloalkyl($C_{1-6}$)alkyl, $C_{1-6}$ alkoxy($C_{1-6}$)alkyl, $C_{1-6}$ alkoxycarbonyl($C_{1-6}$)alkyl, $C_{1-6}$ alkylcarbonyl($C_{1-6}$)alkyl, $C_{1-6}$ alkylaminocarbonyl($C_{1-6}$)alkyl, di($C_{1-6}$)alkylaminocarbonyl($C_{1-6}$)alkyl, phenyl($C_{1-6}$)alkyl (wherein the phenyl group may be optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), heteroaryl($C_{1-6}$)alkyl (wherein the heteroaryl group is optionally substituted by halogen, nitro, cyano, $C_{1-6}$ alkyl, $C_{1-6}$ haloalkyl, $C_{1-6}$ alkoxy or $C_{1-6}$ haloalkoxy), $C_{2-6}$ alkenyl, $C_{2-6}$ haloalkenyl, $C_{2-6}$ alkynyl, $C_{1-6}$ alkoxycarbonyl, $C_{1-6}$ alkylcarbonyl, $C_{1-6}$ alkylaminocarbonyl, di($C_{1-6}$)alkylaminocarbonyl, $C_{3-7}$ cycloalkyl, phenyl (optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), heteroaryl (optionally substituted by halogen, nitro, cyano, $C_{1-6}$ alkyl, $C_{1-6}$ haloalkyl, $C_{1-6}$ alkoxy or $C_{1-6}$ haloalkoxy), $C_{1-8}$ alkoxy, $C_{1-8}$ haloalkoxy, aryloxy (where the aryl group is optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino) or heteroaryloxy (where the heteroaryl group is optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino); n is 0, 1, 2, 3 or 4; $R^8$ is $C_{1-10}$ alkyl optionally substituted by $C_{1-6}$ alkoxy, halogen, phenyl (itself optionally substituted by optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), heteroaryl (itself optionally substituted by halogen, $C_{1-4}$ alkyl or $C_{1-4}$ alkoxy), $C_{2-6}$ alkenyl optionally substituted by $C_{1-6}$ alkoxy, halogen or phenyl (itself optionally substituted by halogen, $C_{1-4}$ alkyl, $C_{1-4}$ alkoxy, $C_{1-4}$ haloalkyl, CN, $NO_2$, artyl, heteroaryl, amino or dialkylamino), $C_{2-6}$ alkynyl optionally substituted by $C_{1-6}$ alkoxy, halogen or phenyl (itself optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino) or $C(R^{51})(R^{52})$—$[CR^{53}=CR^{54}]$—$R^{55}$ where z is 1 or 2, $R^{51}$ and $R^{52}$ are each independently H, halo or $C_{1-2}$ alkyl, $R^{53}$ and $R^{54}$ are each independently H, halogen, $C_{1-4}$ alkyl or $C_{1-4}$ haloalkyl and $R^{55}$ is aryl (optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino) or heteroaryl (optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamine); $R^9$ and $R^{10}$ are independently hydrogen, $C_{1-2}$ alkyl or halogen; $R^{40}$ is H, $C_{1-6}$ alkyl, $C_{1-6}$ haloalkyl, $C_{1-6}$ alkoxy, $C_{1-6}$ haloalkoxy, phenoxy (wherein the phenyl group may be optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), phenyl (optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), heteroaryl (optionally substituted by halogen, $C_{1-4}$ alkyl or $C_{1-4}$ alkoxy), heteroaryloxy (wherein the heteroaryl group may be optionally substituted by halogen, $C_{1-4}$ alkyl or $C_{1-4}$ alkoxy) or $NR^{44}R^{45}$ where $R^{44}$ and $R^{45}$ are independently $C_{1-6}$ alkyl (optionally substituted with halogen, nitro, cyano, $C_{1-6}$ haloalkyl, $C_{1-6}$ alkoxy or $C_{1-6}$ haloalkoxy), phenyl (optionally substituted with halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino) or heteroaryl (optionally substituted with halogen, nitro, cyano, $C_{1-6}$ alkyl, $C_{1-6}$ haloalkyl, $C_{1-6}$ alkoxy or $C_{1-6}$ haloalkoxy) and salts or N-oxides thereof.

A further group of preferred compounds are those of formula (IC) which are compounds of formula (I) wherein Y is a single bond, C=O or $S(O)_q$ where q is 0, 1 or 2; $R^1$ is hydrogen, $C_{1-8}$ alkyl, $C_{1-6}$ haloalkyl, $C_{1-6}$ cyanoalkyl, $C_{3-7}$ cycloalkyl($C_{1-6}$)alkyl, $C_{5-6}$ cycloalkenyl($C_{1-6}$)alkyl, $C_{1-6}$ alkoxy($C_{1-6}$)alkyl, $C_{3-6}$ alkenyloxy($C_{1-6}$)alkyl, $C_{3-6}$ alkynyloxy($C_{1-6}$)alkyl, aryloxy($C_{1-6}$)alkyl, $C_{1-6}$ carboxyalkyl, $C_{1-6}$ alkylcarbonyl($C_{1-6}$)alkyl, $C_{2-6}$ alkenylcarbonyl-($C_{1-6}$)alkyl, $C_{2-6}$ alkynylcarbonyl($C_{1-6}$)alkyl, $C_{1-6}$ alkoxycarbonyl($C_{1-6}$)alkyl, $C_{3-6}$ alkenyloxycarbonyl($C_{1-6}$)alkyl, $C_{3-6}$ alkynyloxycarbonyl($C_{1-6}$)alkyl, aryloxycarbonyl($C_{1-6}$)-alkyl, $C_{1-6}$ alkylthio($C_{1-6}$)alkyl, $C_{1-6}$ alkylsulfinyl($C_{1-6}$)alkyl, $C_{1-6}$ alkylsulfonyl($C_{1-6}$)alkyl, aminocarbonyl($C_{1-6}$)alkyl, $C_{1-6}$ alkylaminocarbonyl($C_{1-6}$)alkyl, di($C_{1-6}$)-alkylaminocarbonyl($C_{1-6}$)alkyl, phenyl($C_{1-4}$)alkyl (wherein the phenyl group is optionally substituted by halogen, nitro, cyano, $C_{1-6}$ alkyl, $C_{1-6}$ haloalkyl, $C_{1-6}$ alkoxy or $C_{1-6}$ haloalkoxy), heteroaryl($C_{1-4}$)alkyl (wherein the heteroaryl group may be substituted by halogen, nitro, cyano, $C_{1-6}$ alkyl, $C_{1-6}$ haloalkyl, $C_{1-6}$ alkoxy or $C_{1-6}$ haloalkoxy), heterocyclyl($C_{1-4}$)alkyl (wherein the heterocyclyl group may be substituted by halogen, cyano, $C_{1-6}$ alkyl, $C_{1-6}$ haloalkyl, $C_{1-6}$ alkoxy or $C_{1-6}$ haloalkoxy), $C_{1-6}$ alkoxycarbonyl, $C_{1-6}$ alkylcarbonyl, aminocarbonyl, $C_{1-6}$ alkylaminocarbonyl, di($C_{1-6}$)alkylaminocarbonyl, phenyl (optionally substituted by halogen, nitro, cyano, $C_{1-6}$ alkyl, $C_{1-6}$ haloalkyl, $C_{1-6}$ alkoxy or $C_{1-6}$ haloalkoxy), heteroaryl (optionally substituted by halogen, nitro, cyano, $C_{1-6}$ alkyl, $C_{1-6}$ haloalkyl, $C_{1-6}$ alkoxy or $C_{1-6}$ haloalkoxy), $C_{1-6}$ alkoxy, $C_{1-6}$ haloalkoxy, aryloxy (wherein the aryl group may be optionally substituted with halogen, nitro, cyano, $C_{1-6}$ alkyl, $C_{1-6}$ haloalkyl, $C_{1-6}$ alkoxy or $C_{1-6}$ haloalkoxy), heteroaryloxy (wherein the heteroaryl group may be optionally substituted with halogen, nitro, cyano, $C_{1-6}$ alkyl, $C_{1-6}$ haloalkyl, $C_{1-6}$ alkoxy or $C_{1-6}$ haloalkoxy), cyano, $C_{2-6}$ alkenyl, $C_{2-6}$ haloalkenyl, $C_{2-6}$ cyanoalkenyl, aminocarbonyl-($C_{2-6}$)alkenyl, $C_{1-6}$ alkylaminocarbonyl ($C_{2-6}$)alkenyl, di($C_{1-6}$)alkylaminocarbonyl($C_{2-6}$)alkenyl, phenyl($C_{2-4}$)alkenyl, (wherein the phenyl group is optionally substituted by halo, nitro, cyano, $C_{1-6}$ alkyl, $C_{1-6}$ haloalkyl, $C_{1-6}$ alkoxy or $C_{1-6}$ haloalkoxy), $C_{2-6}$ alkynyl, aminocarbonyl($C_{2-6}$)-alkynyl, $C_{1-6}$ alkylaminocarbonyl($C_{2-6}$) alkynyl, di($C_{1-6}$)alkylaminocarbonyl($C_{2-6}$)alkynyl, $C_{3-7}$ cycloalkyl, $C_{3-7}$ halocycloalkyl, $C_{3-7}$ cyanocycloalkyl, $C_{1-3}$ alkyl($C_{3-7}$)cycloalkyl, $C_{1-3}$ alkyl-($C_{3-7}$)halocycloalkyl, $C_{5-6}$ cycloalkenyl, formyl, heterocyclyl (optionally substituted by halogen, nitro, cyano, $C_{1-6}$ alkyl, $C_{1-6}$ haloalkyl, $C_{1-6}$ alkoxy or $C_{1-6}$ haloalkoxy), $C_{1-8}$ alkylthio, or $R^{13}R^{14}N$ where $R^{13}$ and $R^{14}$ are independently hydrogen, $C_{1-6}$ alkyl, aryl (optionally substituted by halogen, $C_{1,3}$ alkyl, nitro, cyano, $C_{1-3}$ haloalkyl, $C_{1-6}$ alkoxy or $C_{1-6}$ haloalkoxy) or heteroaryl (optionally substituted by halogen or $C_{1-3}$ alkyl); $R^2$ and $R^3$ are independently hydrogen, $C_{1-6}$ alkyl, $C_{1-6}$ haloalkyl, $C_{1-6}$ alkoxy or cyano; each $R^4$ is independently halogen, nitro, cyano, $C_{1-8}$ alkyl, $C_{1-6}$ haloalkyl, $C_{1-6}$ cyanoalkyl, $C_{3-7}$ cycloalkyl($C_{1-6}$)alkyl, $C_{1-6}$ alkoxy($C_{1-6}$)alkyl, $C_{1-6}$ alkoxycarbonyl($C_{1-6}$)alkyl, $C_{1-6}$ alkylcarbonyl($C_{1-6}$)alkyl, $C_{1-6}$ alkylaminocarbonyl($C_{1-6}$)alkyl, di($C_{1-6}$)alkylaminocarbonyl-($C_{1-6}$)alkyl, phenyl($C_{1-6}$)alkyl (wherein the phenyl group is optionally substituted by halogen, nitro, cyano, $C_{1-6}$ alkyl, $C_{1-6}$ haloalkyl, $C_{1-6}$ alkoxy or $C_{1-6}$ haloalkoxy), heteroaryl($C_{1-6}$)alkyl (wherein the heteroaryl group is optionally substituted by halogen, nitro, cyano, $C_{1-6}$ alkyl, $C_{1-6}$ haloalkyl, $C_{1-6}$ alkoxy or $C_{1-6}$ haloalkoxy), $C_{2-6}$ alkenyl, $C_{2-6}$ haloalkenyl, $C_{2-6}$ alkynyl, $C_{1-6}$ alkoxycarbonyl, $C_{1-6}$ alkylcarbonyl, $C_{1-6}$ alkylaminocarbonyl, di($C_{1-6}$)alkylaminocarbonyl, $C_{3-7}$ cycloalkyl, phenyl (optionally substituted by halogen, nitro, cyano, $C_{1-6}$ alkyl, $C_{1-6}$ haloalkyl, $C_{1-6}$ alkoxy or $C_{1-6}$ haloalkoxy), heteroaryl (optionally substituted by halogen, nitro, cyano, $C_{1-6}$ alkyl, $C_{1-6}$ haloalkyl, $C_{1-6}$ alkoxy or $C_{1-6}$ haloalkoxy), $C_{1-8}$ alkoxy, $C_{1-8}$ haloalkoxy, aryloxy (where the aryl group is optionally substituted by halogen, nitro, cyano, $C_{1-6}$ alkyl, $C_{1-6}$ haloalkyl, $C_{1-6}$ alkoxy or $C_{1-6}$ haloalkoxy) or heteroaryloxy (where the heteroaryl group is optionally substituted by halogen, nitro, cyano, $C_{1-6}$ alkyl, $C_{1-6}$ haloalkyl, $C_{1-6}$ alkoxy or $C_{1-6}$ haloalkoxy); n is 0, 1, 2, 3 or 4; $R^8$ is $C_{1-10}$ alkyl optionally substituted by $C_{1-6}$ alkoxy, halogen or phenyl (itself optionally substituted by halogen, $C_{1-4}$ alkyl or $C_{1-4}$ alkoxy), $C_{2-6}$ alkenyl optionally substituted by $C_{1-6}$ alkoxy, halogen or phenyl (itself optionally substituted by halogen, $C_{1-4}$ alkyl or $C_{1-4}$ alkoxy) or $C_{2-6}$ alkynyl optionally substituted by $C_{1-6}$ alkoxy, halogen or phenyl (itself optionally substituted by halogen, $C_{1-4}$ alkyl or $C_{1-4}$ alkoxy); $R^9$ and $R^{10}$ are independently hydrogen, $C_{1-2}$ alkyl or halogen; and salts or N-oxides thereof.

Another group of preferred compounds are those of formula (ID) which are compounds of formula (I) wherein Y is a single bond or C=O; $R^1$ is hydrogen, $C_{1-8}$ alkyl, $C_{1-6}$ haloalkyl, $C_{1-6}$ cyanoalkyl, $C_{3-7}$ cycloalkyl($C_{1-6}$)alkyl, $C_{5-6}$ cycloalkenyl($C_{1-6}$)alkyl, $C_{1-6}$ alkoxy($C_{1-6}$)alkyl, $C_{3-6}$ alkenyloxy($C_{1-6}$)alkyl, $C_{3-6}$ alkynyloxy($C_{1-6}$)alkyl, aryloxy ($C_{1-6}$)alkyl, $C_{1-6}$ carboxyalkyl, $C_{1-6}$ alkylcarbonyl($C_{1-6}$) alkyl, $C_{2-6}$ alkenylcarbonyl-($C_{1-6}$)alkyl, $C_{2-6}$ alkynylcarbonyl($C_{1-6}$)alkyl, $C_{1-6}$ alkoxycarbonyl($C_{1-6}$)alkyl, $C_{3-6}$ alkenyloxycarbonyl($C_{1-6}$)alkyl, $C_{3-6}$ alkynyloxycarbonyl($C_{1-6}$) alkyl, aryloxycarbonyl($C_{1-6}$)-alkyl, $C_{1-6}$ alkylthio($C_{1-6}$) alkyl, $C_{1-6}$ alkylsulfinyl($C_{1-6}$)alkyl, $C_{1-6}$ alkylsulfonyl($C_{1-6}$) alkyl, aminocarbonyl($C_{1-6}$)alkyl, $C_{1-6}$ alkylaminocarbonyl ($C_{1-6}$)alkyl, di($C_{1-6}$)-alkylaminocarbonyl($C_{1-6}$)alkyl, phenyl ($C_{1-4}$)alkyl (wherein the phenyl group is optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), heteroaryl ($C_{1-4}$)alkyl (wherein the heteroaryl group may be substituted by halogen, nitro, cyano, $C_{1-6}$ alkyl, $C_{1-6}$ haloalkyl, $C_{1-6}$ alkoxy or $C_{1-6}$ haloalkoxy), heterocyclyl($C_{1-4}$)alkyl (wherein the heterocyclyl group may be substituted by halogen, cyano, $C_{1-6}$ alkyl, $C_{1-6}$ haloalkyl, $C_{1-6}$ alkoxy or $C_{1-6}$ haloalkoxy), $C_{1-6}$ alkoxycarbonyl, $C_{1-6}$ alkylcarbonyl, aminocarbonyl, $C_{1-6}$ alkylaminocarbonyl, di($C_{1-6}$)alkylaminocarbonyl, phenyl (optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), heteroaryl (optionally substituted by halogen, nitro, cyano, $C_{1-6}$ alkyl, $C_{1-6}$ haloalkyl, $C_{1-6}$ alkoxy or $C_{1-6}$ haloalkoxy), $C_{1-6}$ alkoxy, $C_{1-6}$ haloalkoxy, aryloxy (wherein the aryl group may be optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), heteroaryloxy (wherein the heteroaryl group may be optionally substituted with halogen, nitro, cyano, $C_{1-6}$ alkyl, $C_{1-6}$ haloalkyl, $C_{1-6}$ alkoxy or $C_{1-6}$ haloalkoxy), cyano, $C_{2-6}$ alkenyl, $C_{2-6}$ haloalkenyl, $C_{2-6}$ cyanoalkenyl, aminocarbonyl-($C_{2-6}$)alkenyl, $C_{1-6}$ alkylaminocarbonyl ($C_{2-6}$)alkenyl, di($C_{1-6}$)alkylaminocarbonyl($C_{2-6}$)alkenyl, phenyl($C_{2-4}$)alkenyl, (wherein the phenyl group is optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), $C_{2-6}$ alkynyl, aminocarbonyl($C_{2-6}$)-alkynyl, $C_{1-6}$ alkylaminocarbonyl($C_{2-6}$)alkynyl, di($C_{1-6}$)alkylaminocarbonyl($C_{2-6}$)alkynyl, $C_{3-7}$ cycloalkyl, $C_{3-7}$ halocycloalkyl, $C_{3-7}$ cyanocycloalkyl, $C_{1-3}$ alkyl($C_{3-7}$)cycloalkyl, $C_{1-3}$ alkyl-($C_{3-7}$)halocycloalkyl, $C_{5-6}$ cycloalkenyl, formyl, heterocyclyl (optionally substituted by halogen, nitro, cyano, $C_{1-6}$ alkyl, $C_{1-6}$ haloalkyl, $C_{1-6}$ alkoxy or $C_{1-6}$ haloalkoxy), $C_{1-8}$ alkylthio, or $R^{13}R^{14}N$ where $R^{13}$ and $R^{14}$ are independently hydrogen, $COR^{40}$, $C_{1-6}$ alkyl, aryl (optionally substituted by halogen, $C_{1,3}$ alkyl, nitro, cyano, $C_{1-3}$ haloalkyl, $C_{1-6}$ alkoxy or $C_{1-6}$ haloalkoxy), heteroaryl (optionally substituted by halogen or $C_{1-3}$ alkyl); $R^2$ and $R^3$ are independently hydrogen or methyl, preferably both hydrogen; each $R^4$ is independently halogen, nitro, cyano, $C_{1-8}$ alkyl, $C_{1-6}$ haloalkyl, $C_{1-6}$ cyanoalkyl, $C_{3-7}$ cycloalkyl($C_{1-6}$) alkyl, $C_{1-6}$ alkoxy($C_{1-6}$)alkyl, $C_{1-6}$ alkoxycarbonyl($C_{1-6}$) alkyl, $C_{1-6}$ alkylcarbonyl($C_{1-6}$)alkyl, $C_{1-6}$ alkylaminocarbonyl($C_{1-6}$)alkyl, di($C_{1-6}$)alkylaminocarbonyl($C_{1-6}$)alkyl, phenyl($C_{1-6}$)alkyl (wherein the phenyl group is optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), heteroaryl-($C_{1-6}$)alkyl (wherein the heteroaryl group is optionally substituted by halogen, nitro, cyano, $C_{1-6}$ alkyl, $C_{1-6}$ haloalkyl, $C_{1-6}$ alkoxy or $C_{1-6}$ haloalkoxy), $C_{2-6}$ alkenyl, $C_{2-6}$ haloalkenyl, $C_{2-6}$ alkynyl, $C_{1-6}$ alkoxycarbonyl, $C_{1-6}$ alkylcarbonyl, $C_{1-6}$ alkylaminocarbonyl, di($C_{1-6}$)alkylaminocarbonyl, $C_{3-7}$ cycloalkyl, phenyl (optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), heteroaryl (optionally substituted by halogen, nitro, cyano, $C_{1-6}$ alkyl, $C_{1-6}$ haloalkyl, $C_{1-6}$ alkoxy or $C_{1-6}$ haloalkoxy), $C_{1-8}$ alkoxy, $C_{1-8}$ haloalkoxy, aryloxy (where the aryl group is optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino) or heteroaryloxy (where the heteroaryl group is optionally substituted by halogen, nitro, cyano, $C_{1-6}$ alkyl, $C_{1-6}$ haloalkyl, $C_{1-6}$ alkoxy or $C_1$-6 haloalkoxy); n is 0, 1, 2, 3 or 4; $R^9$ is $C_{1-10}$ alkyl optionally substituted by $C_{1-6}$ alkoxy, halogen, phenyl (itself optionally substituted by halogen, $C_{1-4}$ alkyl or $C_{1-4}$ alkoxy), heteroaryl (itself optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino); or —$C(R^{51})(R^{52})$—$[CR^{53}=CR^{54}]_z$—$R^{55}$ where z is 1 or 2, $R^{51}$ and $R^{52}$ are each independently H, halo or $C_{1-2}$ alkyl, $R^{53}$ and $R^{54}$ are each independently H, halogen, $C_{1-4}$ alkyl or $C_{1-4}$ haloalkyl and $R^{55}$ is aryl (optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino) or heteroaryl (optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino); $R^9$ and $R^{13}$ are both hydrogen; $R^{40}$ is H, $C_{1-6}$ alkyl, $C_{1-6}$ haloalkyl, $C_{1-6}$ alkoxy, $C_{1-6}$ haloalkoxy, phenoxy (wherein the phenyl group may be optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), phenyl (optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), heteroaryl (optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino) or heteroaryloxy (optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino) and salts or N-oxides thereof.

Yet another group of preferred compounds are those of formula (IE), which are compounds of formula (I) wherein Y, $R^1$, $R^2$, $R^3$, $R^4$, $R^8$ and n are as defined for compounds of formula IC; $R^9$ and $R^{10}$ are independently hydrogen, $C_{1-2}$ alkyl or halogen, and preferably all are hydrogen; and salts or N-oxides thereof.

A further group of preferred compounds are those of formula (IF), which are compounds of formula (I) wherein Y, $R^1$, $R^4$, $R^8$, $R^9$, $R^{10}$ and n are as defined for compounds of formula (IE) and $R^2$ and $R^3$ are independently hydrogen, halogen, $C_{1-2}$ alkyl, $C_{1-2}$ haloalkyl, $C_{1-2}$ alkoxy, cyano, or $R^2$ and $R^3$ together are =O, or $R^2$ and $R^3$ together with the atoms to which they are attached form a 4, 5, 6, or 7 membered carbocyclic or heterocyclic ring; and salts or N-oxides thereof.

Yet another group of preferred compounds are those of formula (IG), which are compounds of formula (I) wherein Y, $R^1$, $R^2$, $R^3$, $R^8$, $R^9$, $R^{10}$ and n are as defined for compounds of formula (IF) and each $R^4$ is independently halogen, nitro, cyano, $C_{1-8}$ alkyl, $C_{1-8}$ haloalkyl, $C_{1-6}$ cyanoalkyl, $C_{3-7}$ cycloalkyl($C_{1-8}$)alkyl, $C_{1-8}$ alkoxy($C_{1-8}$)alkyl, $C_{1-6}$ alkoxycarbonyl($C_{1-8}$)alkyl, $C_{1-8}$ alkylcarbonyl($C_{1-8}$)alkyl, $C_{1-6}$ alkylaminocarbonyl($C_{1-8}$)alkyl, di($C_{1-8}$)alkylaminocarbonyl($C_{1-8}$)alkyl, phenyl($C_{1-8}$)alkyl (wherein the phenyl group is optionally substituted by halogen, $C_{1-8}$ alkyl, $C_{1-8}$ alkoxy, $C_{1-8}$ haloalkyl, $C_{1-4}$ haloalkoxy, CN, or $NO_2$), heteroaryl($C_{1-8}$)alkyl (wherein the heteroaryl group is optionally substituted by halogen, nitro, cyano, $C_{1-8}$ alkyl, $C_{1-8}$ haloalkyl, $C_{1-8}$ alkoxy or $C_{1-8}$ haloalkoxy), $C_{2-6}$ alkenyl, $C_{2-6}$ haloalkenyl, $C_{2-6}$ alkynyl, $C_{1-8}$ alkoxycarbonyl, $C_{1-8}$ alkylcarbonyl, $C_{1-6}$ alkylaminocarbonyl, di($C_{1-8}$)alkylaminocarbonyl, $C_{3-7}$ cycloalkyl, phenyl (optionally substituted by halogen, $C_{1-8}$ alkyl, $C_{1-8}$ alkoxy, $C_{1-8}$ haloalkyl, $C_{1-4}$ haloalkoxy, CN, or $NO_2$), heteroaryl (optionally substituted by halogen, nitro, cyano, $C_{1-8}$ alkyl, $C_{1-8}$ haloalkyl, $C_{1-6}$ alkoxy or $C_{1-8}$ haloalkoxy), $C_{1-8}$ alkoxy, $C_{1-8}$ haloalkoxy, aryloxy (where the aryl group is optionally substituted by halogen, $C_{1-8}$ alkyl, $C_{1-8}$ alkoxy, $C_{1-8}$ haloalkyl, $C_{1-4}$ haloalkoxy, CN, or $NO_2$) or heteroaryloxy (where the heteroaryl group is optionally substituted by halogen, nitro, cyano, $C_{1-8}$ alkyl, $C_{1-8}$ haloalkyl, $C_{1-8}$ alkoxy or $C_{1-8}$ haloalkoxy); and salts or N-oxides thereof.

A further group of preferred compounds are those of formula (IG'), which are compounds of formula (I) wherein Y, $R^1$, $R^2$, $R^3$, $R^8$, $R^9$, $R^{10}$ and n are as defined for compounds of formula (IB) and each $R^4$ is independently halogen, nitro, cyano, $C_{1-8}$ alkyl, $C_{1-6}$ haloalkyl, $C_{1-6}$ cyanoalkyl, $C_{3-7}$ cycloalkyl($C_{1-8}$)alkyl, $C_{1-8}$ alkoxy($C_{1-8}$)alkyl, $C_{1-6}$ alkoxycarbonyl($C_{1-8}$)alkyl, $C_{1-6}$ alkylcarbonyl($C_{1-8}$)alkyl, $C_{1-6}$ alkylaminocarbonyl($C_{1-8}$)alkyl, di($C_{1-6}$)alkylaminocarbonyl($C_{1-6}$)alkyl, phenyl($C_{1-6}$)alkyl (wherein the phenyl group is optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), heteroaryl($C_{1-6}$)alkyl (wherein the heteroaryl group is optionally substituted by halogen, nitro, cyano, $C_{1-6}$ alkyl, $C_{1-6}$ haloalkyl, $C_{1-6}$ alkoxy or $C_{1-6}$ haloalkoxy), $C_{2-6}$ alkenyl, $C_{2-6}$ haloalkenyl, $C_{2-6}$ alkynyl, $C_{1-6}$ alkoxycarbonyl, $C_{1-6}$ alkylcarbonyl, $C_{1-6}$ alkylaminocarbonyl, di($C_{1-6}$)alkyl-aminocarbonyl, $C_{3-7}$ cycloalkyl, phenyl (optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), heteroaryl (optionally substituted by halogen, nitro, cyano, $C_{1-6}$ alkyl, $C_{1-6}$ haloalkyl, $C_{1-6}$ alkoxy or $C_{1-6}$ haloalkoxy), $C_{1-8}$ alkoxy, $C_{1-8}$ haloalkoxy, phenoxy (where the phenyl group is optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino) or heteroaryloxy (where the heteroaryl group is optionally substituted by halogen, nitro, cyano, $C_{1-6}$ alkyl, $C_{1-6}$ haloalkyl, $C_{1-6}$ alkoxy or $C_{1-6}$ haloalkoxy); and salts or N-oxides thereof.

Another group of preferred compounds are those of formula (IH), which are compounds of formula (I) wherein $R^2$, $R^3$, $R^4$, $R^8$, $R^9$, $R^{10}$ and n are as defined for compounds of formula (IG) and Y is a single bond or C=O; $R^1$ is $C_{1-8}$ alkyl, $C_{1-6}$ haloalkyl, $C_{1-6}$ cyanoalkyl, $C_{3-7}$ cycloalkyl($C_{1-6}$) alkyl, $C_{5-6}$ cycloalkenyl($C_{1-6}$)alkyl, $C_{1-6}$ alkoxy($C_{1-6}$)-alkyl, $C_{3-6}$ alkenyloxy($C_{1-6}$)alkyl, $C_{3-6}$ alkynyloxy($C_{1-6}$)alkyl, aryloxy($C_{1-6}$)alkyl, $C_{1-6}$ carboxyalkyl, $C_{1-6}$ alkylcarbonyl($C_{1-6}$) alkyl, $C_{2-6}$ alkenylcarbonyl($C_{1-6}$)alkyl, $C_{2-6}$ alkynylcarbonyl ($C_{1-6}$)alkyl, $C_{1-6}$ alkoxycarbonyl($C_{1-6}$)alkyl, $C_{3-6}$ alkenyloxycarbonyl($C_{1-6}$)-alkyl, $C_{3-6}$ alkynyl-oxycarbonyl ($C_{1-6}$)alkyl, aryloxycarbonyl($C_{1-6}$)alkyl, $C_{1-6}$ alkylthio($C_{1-6}$) alkyl, $C_{1-6}$ alkylsulfinyl($C_{1-6}$)alkyl, $C_{1-6}$ alkylsulfonyl($C_{1-6}$) alkyl, aminocarbonyl($C_{1-6}$)alkyl, $C_{1-6}$ alkylaminocarbonyl ($C_{1-6}$)alkyl, di($C_{1-6}$)alkylaminocarbonyl($C_{1-6}$)alkyl, phenyl ($C_{1-4}$)alkyl (wherein the phenyl group is optionally substituted by halogen, $C_{1-6}$ alkyl, $C_{1-6}$ alkoxy, $C_{1-6}$ haloalkyl, $C_{1-4}$ haloalkoxy, CN, or $NO_2$), heteroaryl($C_{1-4}$) alkyl (wherein the heteroaryl group may be substituted by halogen, nitro, cyano, $C_{1-6}$ alkyl, $C_{1-6}$ haloalkyl, $C_{1-6}$ alkoxy or $C_{1-6}$ haloalkoxy), heterocyclyl($C_{1-4}$)alkyl (wherein the heterocyclyl group may be substituted by halogen, cyano, $C_{1-6}$ alkyl, $C_{1-6}$ haloalkyl, $C_{1-6}$ alkoxy or $C_{1-6}$ haloalkoxy), $C_{1-6}$ alkoxycarbonyl, $C_{1-6}$ alkylcarbonyl, aminocarbonyl, $C_{1-6}$ alkylaminocarbonyl, di($C_{1-6}$)-alkylaminocarbonyl, phenyl (optionally substituted by halogen, $C_{1-6}$ alkyl, $C_{1-6}$ alkoxy, $C_{1-6}$ haloalkyl, $C_{1-4}$ haloalkoxy, CN, or $NO_2$), heteroaryl (optionally substituted by halogen, nitro, cyano, $C_{1-6}$ alkyl, $C_{1-6}$ haloalkyl, $C_{1-6}$ alkoxy or $C_{1-6}$ haloalkoxy), $C_{1-6}$ alkoxy, $C_{1-6}$ haloalkoxy, aryloxy (where the arylyl group may be optionally substituted halogen, $C_{1-6}$ alkyl, $C_{1-6}$ alkoxy, $C_{1-6}$ haloalkyl, $C_{1-4}$ haloalkoxy, CN, or $NO_2$), cyano, $C_{2-6}$ alkenyl, $C_{2-6}$ haloalkenyl, $C_{2-6}$ cyanoalkenyl, aminocarbonyl($C_{2-6}$)alkenyl, $C_{1-6}$ alkylaminocarbonyl($C_{2-6}$)-alkenyl, di($C_{1-6}$)alkyl-aminocarbonyl($C_{2-6}$)alkenyl, phenyl($C_{2-4}$)alkenyl, (wherein the phenyl group is optionally substituted halogen, $C_{1-6}$ alkyl, $C_{1-6}$ alkoxy, $C_{1-6}$ haloalkyl, $C_{1-4}$ haloalkoxy, CN, or $NO_2$), $C_{2-6}$ alkynyl, aminocarbonyl($C_{2-6}$)alkynyl, alkylaminocarbonyl($C_{2-6}$)alkynyl, di($C_{1-6}$) alkylamino-carbonyl($C_{2-6}$)alkynyl, $C_{3-7}$ cycloalkyl, $C_{3-7}$ halocycloalkyl, $C_{3-7}$ cyanocycloalkyl, $C_{1-3}$ alkyl($C_{3-7}$)cycloalkyl, $C_{1-3}$ alkyl($C_{3-7}$)halocycloalkyl, $C_{3-6}$ cycloalkenyl, formyl, heterocyclyl (optionally substituted by halogen, nitro, cyano, $C_{1-6}$ alkyl, $C_{1-6}$ haloalkyl, $C_{1-6}$ alkoxy or $C_{1-6}$ haloalkoxy), $C_{1-8}$ alkylthio or $R^{13}R^{14}N$ where $R^{13}$ and $R^{14}$ are independently hydrogen, $C_{1-6}$ alkyl, aryl (optionally substituted by halogen, $C_{1-6}$ alkyl, $C_{1-6}$ alkoxy, $C_{1-6}$ haloalkyl, $C_{1-4}$ haloalkoxy, CN, or $NO_2$) or heteroaryl (optionally substituted by halogen or $C_{1-3}$ alkyl); and salts or N-oxides thereof.

Another group of preferred compounds are those of formula (IH'), which are compounds of formula (I) wherein $R^2$, $R^3$, $R^4$, $R^8$, $R^9$, $R^{10}$ and n are as defined for compounds of formula (IG') and $R^1$ is $C_{1-8}$ alkyl, $C_{1-6}$ haloalkyl, $C_{1-6}$ cyanoalkyl, $C_{3-7}$ cycloalkyl($C_{1-6}$)alkyl, $C_{5-6}$ cycloalkenyl ($C_{1-6}$)alkyl, $C_{1-6}$ alkoxy($C_{1-6}$)-alkyl, $C_{3-6}$ alkenyloxy($C_{1-6}$) alkyl, $C_{3-6}$ alkynyloxy($C_{1-6}$)alkyl, aryloxy($C_{1-6}$)alkyl, $C_{1-6}$ carboxyalkyl, $C_{1-6}$ alkylcarbonyl($C_{1-6}$)alkyl, $C_{2-6}$ alkenylcarbonyl($C_{1-6}$)alkyl, $C_{2-6}$ alkynylcarbonyl($C_{1-6}$)alkyl, $C_{1-6}$ alkoxycarbonyl($C_{1-6}$)alkyl, $C_{3-6}$ alkenyloxycarbonyl($C_{1-6}$)-alkyl, $C_{3-6}$ alkynyloxycarbonyl($C_{1-6}$)alkyl, aryloxycarbonyl ($C_{1-6}$)alkyl, $C_{1-6}$ alkylthio($C_{1-6}$)alkyl, $C_{1-6}$ alkylsulfinyl ($C_{1-6}$)alkyl, $C_{1-6}$ alkylsulfonyl($C_{1-6}$)alkyl, aminocarbonyl ($C_{1-6}$)alkyl, $C_{1-6}$ alkylaminocarbonyl($C_{1-6}$)alkyl, di($C_{1-6}$) alkylaminocarbonyl($C_{1-6}$)alkyl, phenyl($C_{1-4}$)alkyl (wherein the phenyl group is optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), heteroaryl-($C_{1-4}$)alkyl (wherein the heteroaryl group may be substituted by halogen, nitro, cyano, $C_{1-6}$ alkyl, $C_{1-6}$ haloalkyl, $C_{1-6}$ alkoxy or $C_{1-6}$ haloalkoxy), heterocyclyl($C_{1-4}$)alkyl (wherein the heterocyclyl group may be substituted by halogen, cyano, $C_{1-6}$ alkyl, $C_{1-6}$ haloalkyl, $C_{1-6}$ alkoxy or $C_{1-6}$ haloalkoxy), $C_{1-6}$ alkoxycarbonyl, $C_{1-6}$ alkylcarbonyl, aminocarbonyl, $C_{1-6}$ alkylaminocarbonyl, di($C_{1-6}$)-alkylaminocarbonyl, phenyl (optionally substituted halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), heteroaryl (optionally substituted by halogen, nitro, cyano, $C_{1-6}$ alkyl, $C_{1-6}$ haloalkyl, $C_{1-6}$ alkoxy or $C_{1-6}$ haloalkoxy), $C_{1-6}$ alkoxy, $C_{1-6}$ haloalkoxy, aryloxy (where the aryl group may be optionally substituted with halogen, nitro, cyano, $C_{1-6}$ alkyl, $C_{1-6}$ haloalkyl, $C_{1-6}$ alkoxy or $C_{1-6}$ haloalkoxy), cyano, $C_{2-6}$ alkenyl, $C_{2-6}$ haloalkenyl, $C_{2-6}$ cyanoalkenyl, aminocarbonyl($C_{2-6}$)alkenyl, $C_{1-6}$ alkylaminocarbonyl($C_{2-6}$)-alkenyl, di($C_{1-6}$)alkyl-aminocarbonyl($C_{2-6}$)alkenyl, phenyl($C_{2-4}$)alkenyl, (wherein the phenyl group is optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), $C_{2-6}$ alkynyl, aminocarbonyl($C_{2-6}$)alkynyl, alkylaminocarbonyl($C_{2-6}$)alkynyl, di($C_{1-6}$)alkylamino-carbonyl ($C_{2-6}$)alkynyl, $C_{3-7}$ cycloalkyl, $C_{3-7}$ halocycloalkyl, $C_{3-7}$ cyanocycloalkyl, $C_{1-3}$ alkyl($C_{3-7}$)cycloalkyl, $C_{1-3}$ alkyl ($C_{3-7}$)halocycloalkyl, $C_{5-6}$ cycloalkenyl, formyl, heterocyclyl (optionally substituted by halogen, nitro, cyano, $C_{1-6}$ alkyl, $C_{1-6}$ haloalkyl, $C_{1-6}$ alkoxy or $C_{1-6}$ haloalkoxy), $C_{1-8}$ alkylthio or $R^{13}R^{14}N$ where $R^{13}$ and $R^{14}$ are independently hydrogen, $C_{1-6}$ alkyl, $COR^{40}$, where $C_{1-6}$ alkylcarbonylamino, phenyloxycarbonylamino (wherein the phenyl group is optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), amino, $C_{1-6}$ alkylamino, phenylamino (wherein the phenyl group is optionally substituted halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino) and salts or N-oxides thereof.

A further group of preferred compounds are those of formula (IJ), which are compounds of formula (I) wherein Y, $R^1$, $R^2$, $R^3$, $R^4$, $R^9$, $R^{10}$ and n are as defined for compounds of formula (IH) and $R^8$ is $C_{1-10}$ alkyl optionally substituted by $C_{1-6}$ alkoxy, halogen or phenyl (itself optionally substituted by halogen, $C_{1-4}$ alkyl or $C_{1-4}$ alkoxy), $C_{2-6}$ alkenyl optionally substituted by $C_{1-6}$ alkoxy, halogen or phenyl (itself optionally substituted by halogen, $C_{1-4}$ alkyl or $C_{1-4}$ alkoxy) or $C_{2-6}$ alkynyl optionally substituted by $C_{1-6}$ alkoxy, halogen or phenyl (itself optionally substituted by halogen, $C_{1-4}$ alkyl or $C_{1-4}$ alkoxy); and salts or N-oxides thereof.

A further group of preferred compounds are those of formula (IJ'), which are compounds of formula (I) wherein Y, $R^1$, $R^2$, $R^3$, $R^4$, $R^9$, $R^{10}$ and n are as defined for compounds of formula (IH') and $R^8$ is $C_{1-6}$ alkyl optionally substituted by phenyl or heteroaryl (the phenyl and heteroaryl groups being optionally substituted halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino); or —C($R^{51}$) ($R^{52}$)—[$CR^{53}$=$CR^{54}$]$_z$—$R^{55}$ where z is 1 or 2, $R^{51}$ and $R^{52}$ are each independently H, halo or $C_{1-2}$ alkyl, $R^{53}$ and $R^{54}$ are each independently H, halogen, $C_{1-4}$ alkyl or $C_{1-4}$ haloalkyl and $R^{55}$ is aryl substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino, or heteroaryl substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino.

Yet another preferred group of compounds are those of formula (IK), which are compounds of formula (I) wherein Y is a single bond, C=O or S(O)$_q$ where q is 0, 1 or 2; $R^1$ is $C_{1-8}$ alkyl, $C_{1-6}$ haloalkyl, $C_{1-6}$ cyanoalkyl, $C_{3-7}$ cycloalkyl ($C_{1-6}$)alkyl, $C_{1-6}$ alkoxy($C_{1-6}$)alkyl, $C_{3-6}$ alkenyloxy-($C_{1-6}$) alkyl, $C_{3-6}$ alkynyloxy($C_{1-6}$)alkyl, aryloxy($C_{1-6}$)alkyl, $C_{1-6}$ carboxyalkyl, $C_{1-6}$ alkylcarbonyl($C_{1-6}$)alkyl, $C_{2-6}$ alkenylcarbonyl($C_{1-6}$)alkyl, $C_{2-6}$ alkynylcarbonyl($C_{1-6}$)alkyl, $C_{1-6}$ alkoxycarbonyl($C_{1-6}$)alkyl, $C_{3-6}$ alkenyloxycarbonyl($C_{1-6}$)-alkyl, $C_{3-6}$ alkynyloxycarbonyl($C_{1-6}$)alkyl, aryloxycarbonyl ($C_{1-6}$)alkyl, $C_{1-6}$ alkylthio($C_{1-6}$)-alkyl, $C_{1-6}$ alkylsulfinyl ($C_{1-6}$)alkyl, $C_{1-6}$ alkylsulfonyl($C_{1-6}$)alkyl, aminocarbonyl ($C_{1-6}$)alkyl, $C_{1-6}$ alkylaminocarbonyl($C_{1-6}$)alkyl, di($C_{1-6}$) alkylaminocarbonyl($C_{1-6}$)alkyl, phenyl($C_{1-4}$)alkyl (wherein the phenyl group is optionally substituted by halogen, nitro, cyano, $C_{1-6}$ alkyl, $C_{1-6}$ haloalkyl, $C_{1-6}$ alkoxy or $C_{1-6}$ haloalkoxy), heteroaryl($C_{1-4}$)alkyl (wherein the heteroaryl group may be substituted by halogen, nitro, cyano, $C_{1-6}$ alkyl, $C_{1-6}$ haloalkyl, $C_{1-6}$ alkoxy or $C_{1-6}$ haloalkoxy), heterocyclyl($C_{1-4}$)alkyl (wherein the heterocyclyl group may be substituted by halogen, cyano, $C_{1-6}$ alkyl, $C_{1-6}$ haloalkyl, $C_{1-6}$ alkoxy or $C_{1-6}$ haloalkoxy), phenyl (optionally substituted by halogen, nitro, cyano, $C_{1-6}$ alkyl, $C_{1-6}$ haloalkyl, $C_{1-6}$ alkoxy or $C_{1-6}$ haloalkoxy), heteroaryl (optionally substituted by halogen, nitro, cyano, $C_{1-6}$ alkyl, $C_{1-6}$ haloalkyl, $C_{1-6}$ alkoxy or $C_{1-6}$ haloalkoxy), $C_{1-6}$ alkoxy, $C_{1-6}$ haloalkoxy, $C_{2-6}$ alkenyl, $C_{2-6}$ haloalkenyl, $C_{2-6}$ cyanoalkenyl, $C_{2-6}$ alkynyl, $C_{3-7}$ cycloalkyl, formyl, heterocyclyl (optionally substituted by halogen, nitro, cyano, $C_{1-6}$ alkyl, $C_{1-6}$ haloalkyl, $C_{1-6}$ alkoxy or $C_{1-6}$ haloalkoxy) or $C_{1-6}$ alkylthio; $R^2$ and $R^3$ are independently hydrogen or $C_{1-4}$ alkyl; each $R^4$ is independently halogen, cyano, $C_{1-10}$ alkyl optionally substituted by $C_{1-6}$ alkoxy, halogen, phenyl (itself optionally substituted by halogen, $C_{1-4}$ alkyl or $C_{1-4}$ alkoxy), $C_{2-6}$ alkenyl optionally substituted by $C_{1-6}$ alkoxy, halogen, phenyl (itself optionally substituted by halogen, $C_{1-4}$ alkyl or $C_{1-4}$ alkoxy) or $C_{2-6}$ alkynyl optionally substituted by $C_{1-6}$ alkoxy, halogen, phenyl (itself optionally substituted by halogen, $C_{1-4}$ alkyl or $C_{1-4}$ alkoxy); n is 0, 1, 2, 3 or 4; $R^8$ is $C_{1-10}$ alkyl optionally substituted by $C_{1-6}$ alkoxy, halogen or phenyl (itself optionally substituted by halogen, $C_{1-4}$ alkyl or $C_{1-4}$ alkoxy), $C_{2-6}$ alkenyl optionally substituted by $C_{1-6}$ alkoxy, halogen or phenyl (itself optionally substituted by halogen, $C_{1-4}$ alkyl or $C_{1-4}$ alkoxy) or $C_{2-6}$ alkynyl optionally substituted by $C_{1-6}$ alkoxy, halogen or phenyl (itself optionally substituted by halogen, $C_{1-4}$ alkyl or $C_{1-4}$ alkoxy); $R^9$ and $R^{10}$ are both hydrogen; and salts or N-oxides thereof.

Yet another preferred group of compounds are those of formula (IL), which are compounds of formula (I) wherein Y is a single bond or C=O; $R^1$ is $C_{1-8}$ alkyl, $C_{1-6}$ haloalkyl, $C_{1-6}$ cyanoalkyl, $C_{3-7}$ cycloalkyl($C_{1-6}$)alkyl, $C_{1-6}$ alkoxy($C_{1-6}$)alkyl, $C_{3-6}$ alkenyloxy-($C_{1-6}$)alkyl, $C_{3-6}$ alkynyloxy($C_{1-6}$)alkyl, aryloxy($C_{1-6}$)alkyl, $C_{1-6}$ carboxyalkyl, $C_{1-6}$ alkylcarbonyl($C_{1-6}$)alkyl, $C_{2-6}$ alkenylcarbonyl($C_{1-6}$)alkyl, $C_{2-6}$ alkynylcarbonyl($C_{1-6}$)alkyl, $C_{1-6}$ alkoxycarbonyl($C_{1-6}$)alkyl, $C_{3-6}$ alkenyloxycarbonyl($C_{1-6}$)-alkyl, $C_{3-6}$ alkynyloxycarbonyl($C_{1-6}$)alkyl, aryloxycarbonyl($C_{1-6}$)alkyl, $C_{1-6}$ alkylthio($C_{1-6}$)-alkyl, $C_{1-6}$ alkylsulfinyl($C_{1-6}$)alkyl, $C_{1-6}$ alkylsulfonyl($C_{1-6}$)alkyl, aminocarbonyl($C_{1-6}$)alkyl, $C_{1-6}$ alkylaminocarbonyl($C_{1-6}$)alkyl, di($C_{1-6}$)alkylaminocarbonyl($C_{1-6}$)alkyl, phenyl($C_{1-4}$)alkyl (wherein the phenyl group is optionally substituted by halogen, $C_{1-4}$ alkyl, $C_{1-4}$ alkoxy, $C_{1-4}$ haloalkyl, $C_{1-4}$ haloalkoxy, CN, NO$_2$, aryl, heteroaryl, amino or dialkylamino), heteroaryl-($C_{1-4}$)alkyl (wherein the heteroaryl group may be substituted by halogen, nitro, cyano, $C_{1-6}$ alkyl, $C_{1-6}$ haloalkyl, $C_{1-6}$ alkoxy or $C_{1-6}$ haloalkoxy), heterocyclyl($C_{1-4}$)alkyl (wherein the heterocyclyl group may be substituted by halogen, cyano, $C_{1-6}$ alkyl, $C_{1-6}$ haloalkyl, $C_{1-6}$ alkoxy or $C_{1-6}$ haloalkoxy), phenyl (optionally substituted by halogen, $C_{1-4}$ alkyl, $C_{1-4}$ alkoxy, $C_{1-4}$ haloalkyl, $C_{1-4}$ haloalkoxy, CN, NO$_2$, aryl, heteroaryl, amino or dialkylamino), heteroaryl (optionally substituted by halogen, nitro, cyano, $C_{1-6}$ alkyl, $C_{1-6}$ haloalkyl, $C_{1-6}$ alkoxy or $C_{1-6}$ haloalkoxy), $C_{1-6}$ alkoxy, $C_{1-6}$ haloalkoxy, $C_{2-6}$ alkenyl, $C_{2-6}$ haloalkenyl, $C_{2-6}$ cyanoalkenyl, $C_{2-6}$ alkynyl, $C_{3-7}$ cycloalkyl, formyl, heterocyclyl (optionally substituted by halogen, nitro, cyano, $C_{1-6}$ alkyl, $C_{1-6}$ haloalkyl, $C_{1-6}$ alkoxy or $C_{1-6}$ haloalkoxy) or $C_{1-6}$ alkylthio, $C_{1-6}$ alkylcarbonylamino, phenyloxycarbonylamino (wherein the phenyl group is optionally substituted by halogen, $C_{1-4}$ alkyl, $C_{1-4}$ alkoxy, $C_{1-4}$ haloalkyl, $C_{1-4}$ haloalkoxy, CN, NO$_2$, aryl, heteroaryl, amino or dialkylamino), amino, $C_{1-6}$ alkylamino, phenylamino (wherein the phenyl group is optionally substituted halogen, $C_{1-4}$ alkyl, $C_{1-4}$ alkoxy, $C_{1-4}$ haloalkyl, $C_{1-4}$ haloalkoxy, CN, NO$_2$, aryl, heteroaryl, amino or dialkylamino); $R^2$ and $R^3$ are independently hydrogen or $C_{1-4}$ alkyl; each $R^4$ is independently halogen, cyano, $C_{1-10}$ alkyl optionally substituted by $C_{1-6}$ alkoxy, halogen, phenyl (itself optionally substituted by halogen, $C_{1-4}$ alkyl, $C_{1-4}$ alkoxy, $C_{1-4}$ haloalkyl, $C_{1-4}$ haloalkoxy, CN, NO$_2$, aryl, heteroaryl, amino or dialkylamino), $C_{2-6}$ alkenyl optionally substituted by $C_{1-6}$ alkoxy, halogen, phenyl (itself optionally substituted by halogen, $C_{1-4}$ alkyl, $C_{1-4}$ alkoxy, $C_{1-4}$ haloalkyl, $C_{1-4}$ haloalkoxy, CN, NO$_2$, aryl, heteroaryl, amino or dialkylamino) or $C_{2-6}$ alkynyl optionally substituted by $C_{1-6}$ alkoxy, halogen, phenyl (itself optionally substituted by halogen, $C_{1-4}$ alkyl, $C_{1-4}$ alkoxy, $C_{1-4}$ haloalkyl, $C_{1-4}$ haloalkoxy, CN, NO$_2$, aryl, heteroaryl, amino or dialkylamino); n is 0, 1, 2, 3 or 4; $R^8$ is $C_{1-10}$ alkyl optionally substituted by $C_{1-6}$ alkoxy, halogen or phenyl (itself optionally substituted by halogen, $C_{1-4}$ alkyl, $C_{1-4}$ alkoxy, $C_{1-4}$ haloalkyl, $C_{1-4}$ haloalkoxy, CN, NO$_2$, aryl, heteroaryl, amino or dialkylamino), $C_{2-6}$ alkenyl optionally substituted by $C_{1-6}$ alkoxy, halogen or phenyl (itself optionally substituted by halogen, $C_{1-4}$ alkyl, $C_{1-4}$ alkoxy, $C_{1-4}$ haloalkyl, $C_{1-4}$ haloalkoxy, CN, NO$_2$, aryl, heteroaryl, amino or dialkylamino) or $C_{2-6}$ alkynyl optionally substituted by $C_{1-6}$ alkoxy, halogen or phenyl (itself optionally substituted by halogen, $C_{1-4}$ alkyl, $C_{1-4}$ alkoxy, $C_{1-4}$ haloalkyl, $C_{1-4}$ haloalkoxy, CN, NO$_2$, aryl, heteroaryl, amino or dialkylamino), or $C(R^{51})(R^{52})$—$[CR^{53}=CR^{54}]z$-$R^{55}$ where z is 1 or 2, $R^{51}$ and $R^{52}$ are each independently H, halo or $C_{1-2}$ alkyl, $R^{53}$ and $R^{54}$ are each independently H, halogen, $C_{1-4}$ alkyl or $C_{1-4}$ haloalkyl and $R^{55}$ is phenyl substituted by halogen, $C_{1-4}$ alkyl, $C_{1-4}$ alkoxy, $C_{1-4}$ haloalkyl, $C_{1-4}$ haloalkoxy, CN, NO$_2$, aryl, heteroaryl, amino or dialkylamino or heteroaryl substituted by halogen, $C_{1-4}$ alkyl, $C_{1-4}$ alkoxy, $C_{1-4}$ haloalkyl, $C_{1-4}$ haloalkoxy, CN, NO$_2$, aryl, heteroaryl, amino or dialkylamino; $R^{40}$ is H, $C_{1-6}$ alkyl, $C_{1-6}$ haloalkyl, $C_{1-6}$ alkoxy, $C_{1-6}$ haloalkoxy, phenoxy (wherein the phenyl group may be optionally substituted with halogen, $C_{1-4}$ alkyl, $C_{1-4}$ alkoxy, $C_{1-4}$ haloalkyl, $C_{1-4}$ haloalkoxy, CN, NO$_2$, aryl, heteroaryl, amino or dialkylamino), phenyl (optionally substituted by halogen, $C_{1-4}$ alkyl, $C_{1-4}$ alkoxy, $C_{1-4}$ haloalkyl, $C_{1-4}$ haloalkoxy, CN, NO$_2$, aryl, heteroaryl, amino or dialkylamino), heteroaryl (optionally substituted by halogen, $C_{1-4}$ alkyl, $C_{1-4}$ alkoxy, $C_{1-4}$ haloalkyl, $C_{1-4}$ haloalkoxy, CN, NO$_2$, aryl, heteroaryl, amino or dialkylamino) or heteroaryloxy (optionally substituted by halogen, $C_{1-4}$ alkyl, $C_{1-4}$ alkoxy, $C_{1-4}$ haloalkyl, $C_{1-4}$ haloalkoxy, CN, NO$_2$, aryl, heteroaryl, amino or dialkylamino); $R^9$ and $R^{13}$ are both hydrogen or methyl; and salts or N-oxides thereof.

An even more preferred group of compounds are those of formula (IM), which are compounds of formula (I) wherein Y is a single bond or C=O; $R^1$ is $C_{1-8}$ alkyl, $C_{1-6}$ haloalkyl, $C_{1-6}$ cyanoalkyl, $C_{3-7}$ cycloalkyl($C_{1-6}$)alkyl, $C_{1-6}$ alkoxy($C_{1-6}$)alkyl, $C_{3-6}$ alkenyloxy-($C_{1-6}$)alkyl, $C_{3-6}$ alkynyloxy($C_{1-6}$)alkyl, aryloxy($C_{1-6}$)alkyl, $C_{1-6}$ carboxyalkyl, $C_{1-6}$ alkylcarbonyl-($C_{1-6}$)alkyl, $C_{2-6}$ alkenylcarbonyl($C_{1-6}$)alkyl, $C_{2-6}$ alkynylcarbonyl($C_{1-6}$)alkyl, $C_{1-6}$ alkoxycarbonyl($C_{1-6}$)alkyl, $C_{3-6}$ alkenyloxycarbonyl($C_{1-6}$)-alkyl, $C_{3-6}$ alkynyloxycarbonyl ($C_{1-6}$)alkyl, aryloxycarbonyl($C_{1-6}$)alkyl, $C_{1-6}$ alkylthio($C_{1-6}$)-alkyl, $C_{1-6}$ alkylsulfinyl($C_{1-6}$)-alkyl, $C_{1-6}$ alkylsulfonyl($C_{1-6}$)alkyl, aminocarbonyl($C_{1-6}$)alkyl, $C_{1-6}$ alkylaminocarbonyl($C_{1-6}$)-alkyl, di($C_{1-6}$)alkylaminocarbonyl($C_{1-6}$)alkyl, phenyl($C_{1-4}$)alkyl (wherein the phenyl group is optionally substituted by halogen, $C_{1-4}$ alkyl, $C_{1-4}$ alkoxy, $C_{1-4}$ haloalkyl, $C_{1-4}$ haloalkoxy, CN, NO$_2$, aryl, heteroaryl, amino or dialkylamino), heteroaryl($C_{1-4}$)alkyl (wherein the heteroaryl group may be substituted by halogen, nitro, cyano, $C_{1-6}$ alkyl, $C_{1-6}$ haloalkyl, $C_{1-6}$ alkoxy or $C_{1-6}$ haloalkoxy), heterocyclyl($C_{1-4}$)alkyl (wherein the heterocyclyl group may be substituted by halogen, cyano, $C_{1-6}$ alkyl, $C_{1-6}$ haloalkyl, $C_{1-6}$ alkoxy or $C_{1-6}$ haloalkoxy), phenyl (optionally substituted by halogen, $C_{1-4}$ alkyl, $C_{1-4}$ alkoxy, $C_{1-4}$ haloalkyl, $C_{1-4}$ haloalkoxy, CN, NO$_2$, aryl, heteroaryl, amino or dialkylamino), heteroaryl (optionally substituted by halogen, nitro, cyano, $C_{1-6}$ alkyl, $C_{1-6}$ haloalkyl, $C_{1-6}$ alkoxy or $C_{1-6}$ haloalkoxy), $C_{1-6}$ alkoxy, $C_{1-6}$ haloalkoxy, $C_{2-6}$ alkenyl, $C_{2-6}$ haloalkenyl, $C_{2-6}$ cyanoalkenyl, $C_{2-6}$ alkynyl, $C_{3-7}$ cycloalkyl, formyl, heterocyclyl (optionally substituted by halogen, nitro, cyano, $C_{1-6}$ alkyl, $C_{1-6}$ haloalkyl, $C_{1-6}$ alkoxy or $C_{1-6}$ haloalkoxy) or $C_{1-6}$ alkylthio, $C_{1-6}$ alkylcarbonylamino, phenyloxycarbonylamino (wherein the phenyl group is optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), amino, $C_{1-6}$ alkylamino, phenylamino (wherein the phenyl group is optionally substituted halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino); $R^2$ and $R^3$ are independently hydrogen or methyl, preferably both hydrogen; each $R^4$ is independently halogen, cyano, $C_{1-10}$ alkyl optionally substituted by $C_{1-6}$ alkoxy, halogen, phenyl (itself optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), $C_{2-6}$ alkenyl optionally substituted by $C_{1-6}$ alkoxy, halogen, phenyl (itself optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino) or $C_{2-6}$ alkynyl optionally substituted by $C_{1-6}$ alkoxy, halogen, phenyl (itself optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino); n is 0, 1, 2, 3 or 4; $R^8$ is phenyl($C_{1-4}$)alkyl (wherein the phenyl group is optionally substituted halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), heteroaryl($C_{1-4}$)alkyl (wherein the heteroaryl group is optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), $C(R^{51})(R^{52})$—$[CR^{53}=]z-R^{55}$ where z is 1 or 2 and more preferably z is 1, $R^{51}$ and $R^{52}$ are each independently H, halo or $C_{1-2}$ alkyl, $R^{53}$ and $R^{54}$ are each independently H, halogen, $C_{1-4}$ alkyl or $C_{1-4}$ haloalkyl and $R^{55}$ is phenyl substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino or heteroaryl substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino; $R^{40}$ is H, $C_{1-6}$ alkyl, $C_{1-6}$ haloalkyl, $C_{1-6}$ alkoxy, $C_{1-6}$ haloalkoxy, phenoxy (wherein the phenyl group may be optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), phenyl (optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), heteroaryl (optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino) or heteroaryloxy (optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino) and salts or N-oxides thereof.

It is preferred that Y is a single bond, C=O, C=S or $S(O)_q$ where q is 0, 1 or 2.

More preferably Y is a single bond, C=O or $SO_2$.

Most preferably Y is a single bond or C=O, especially C=O.

$R^1$ is preferably hydrogen, $C_{1-6}$ alkyl, $C_{1-6}$ cyanoalkyl, $C_{1-6}$ haloalkyl, $C_{3-7}$ cycloalkyl($C_{1-4}$)alkyl, $C_{1-6}$ alkoxy($C_{1-6}$)alkyl, heteroaryl($C_{1-6}$)alkyl (wherein the heteroaryl group may be optionally substituted by halo, nitro, cyano, $C_{1-6}$ alkyl, $C_{1-6}$ haloalkyl, $C_{1-6}$ alkoxy, $C_{1-6}$ haloalkoxy, $C_{1-6}$ alkylsulfonyl, $C_{1-6}$ alkylsulfinyl, $C_{1-6}$ alkylthio, $C_{1-6}$ alkoxycarbonyl, $C_{1-6}$ alkylcarbonylamino, arylcarbonyl, or two adjacent positions on the heteroaryl system may be cyclised to form a 5, 6 or 7 membered carbocyclic or heterocyclic ring, itself optionally substituted with halogen), aryl($C_{1-6}$)alkyl (wherein the aryl group may be optionally substituted by halo, nitro, cyano, $C_{1-6}$ alkyl, $C_{1-6}$ haloalkyl, $C_{1-6}$ alkoxy, $C_{1-6}$ haloalkoxy, $C_{1-6}$ alkylsulfonyl, $C_{1-6}$ alkylsulfinyl, $C_{1-6}$ alkylthio, $C_{1-6}$ alkoxycarbonyl, $C_{1-6}$ alkylcarbonylamino, arylcarbonyl, or two adjacent positions on the aryl system may be cyclised to form a 5, 6 or 7 membered carbocyclic or heterocyclic ring, itself optionally substituted with halogen), $C_{1-6}$ alkylcarbonylamino($C_{1-6}$)alkyl, aryl (which may be optionally substituted by halo, nitro, cyano, $C_{1-6}$ alkyl, $C_{1-6}$ haloalkyl, $C_{1-6}$ alkoxy, $C_{1-6}$ haloalkoxy, $C_{1-6}$ alkylsulfonyl, $C_{1-6}$ alkylsulfinyl, $C_{1-6}$ alkylthio, $C_{1-6}$ alkoxycarbonyl, $C_{1-6}$ alkylcarbonylamino, arylcarbonyl, or two adjacent positions on the aryl system may be cyclised to form a 5, 6 or 7 membered carbocyclic or heterocyclic ring, itself optionally substituted with halogen), heteroaryl (which may be optionally substituted by halo, nitro, cyano, $C_{1-6}$ alkyl, $C_{1-6}$ haloalkyl, $C_{1-6}$ alkoxy, $C_{1-6}$ haloalkoxy, $C_{1-6}$ alkylsulfonyl, $C_{1-6}$ alkylsulfinyl, $C_{1-6}$ alkylthio, $C_{1-6}$ alkoxycarbonyl, $C_{1-6}$ alkylcarbonylamino, arylcarbonyl, or two adjacent positions on the heteroaryl system may be cyclised to form a 5, 6 or 7 membered carbocyclic or heterocyclic ring, itself optionally substituted with halogen), $C_{1-6}$ alkoxy, $C_{1-6}$ haloalkoxy, phenoxy (wherein the phenyl group is optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), heteroaryloxy (optionally substituted by halo, nitro, cyano, $C_{1-6}$ alkyl, $C_{1-6}$ haloalkyl, $C_{1-6}$ alkoxy or $C_{1-6}$ haloalkoxy), heterocyclyloxy (optionally substituted by halo, $C_{1-6}$ alkyl, $C_{1-6}$ haloalkyl, $C_{1-6}$ alkoxy or $C_{1-6}$ haloalkoxy), cyano, $C_{2-6}$ alkenyl, $C_{2-6}$ alkynyl, $C_{3-6}$ cycloalkyl, $C_{5-7}$ cycloalkenyl, heterocyclyl (optionally substituted by halo, nitro, cyano, $C_{1-6}$ alkyl, $C_{1-6}$ haloalkyl, $C_{1-6}$ alkoxy or $C_{1-6}$ haloalkoxy), $C_{1-6}$ alkylthio, $C_{1-6}$ haloalkylthio or $NR^{13}R^{14}$ where $R^{13}$ and $R^{14}$ are independently hydrogen, $C_{2-6}$ alkyl, $C_{2-6}$ haloalkyl, phenyl (which may be optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino, dialkylamino or $C_{1-4}$ alkoxycarbonyl) or heteroaryl (which may be optionally substituted by halo, nitro, cyano, $C_{1-6}$ alkyl, $C_{1-6}$ haloalkyl, $C_{1-6}$ alkoxy or $C_{1-6}$ haloalkoxy, $C_{1-4}$ alkoxycarbonyl $C_{1-6}$ alkylcarbonylamino, phenyloxycarbonylamino (wherein the phenyl group is optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), amino, $C_{1-6}$ alkylamino or phenylamino (wherein the phenyl group is optionally substituted halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino).

More preferably $R^1$ is hydrogen, $C_{1-6}$ alkyl, $C_{1-6}$ haloalkyl, $C_{1-6}$ alkoxy($C_{1-6}$)alkyl, heteroaryl($C_{1-6}$)alkyl (wherein the heteroaryl group may be optionally substituted by halo, nitro, cyano, $C_{1-6}$ alkyl, $C_{1-6}$ haloalkyl, $C_{1-6}$ alkoxy, $C_{1-6}$ haloalkoxy, $C_{1-6}$ alkylsulfonyl, $C_{1-6}$ alkylsulfinyl, $C_{1-6}$ alkylthio, $C_{1-6}$ alkoxycarbonyl, $C_{1-6}$ alkylcarbonylamino, arylcarbonyl, or two adjacent positions on the heteroaryl system may be cyclised to form a 5, 6 or 7 membered carbocyclic or heterocyclic ring, itself optionally substituted with halogen), phenyl($C_{1-6}$)alkyl (wherein the phenyl group may be optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino, $C_{1-6}$ alkylsulfonyl, $C_{1-6}$ alkylsulfinyl, $C_{1-6}$ alkylthio, $C_{1-6}$ alkoxycarbonyl, $C_{1-6}$ alkylcarbonylamino, arylcarbonyl, or two adjacent positions on the phenyl ring may be cyclised to form a 5, 6 or 7 membered carbocyclic or heterocyclic ring, itself optionally substituted with halogen), $C_{1-6}$ alkylcarbonylamino($C_{1-6}$)

alkyl, phenyl (which may be optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino, $C_{1-6}$ alkylsulfonyl, $C_{1-6}$ alkylsulfinyl, $C_{1-6}$ alkylthio, $C_{1-6}$ alkoxycarbonyl, $C_{1-6}$ alkylcarbonylamino, arylcarbonyl, or two adjacent positions on the phenyl ring may be cyclised to form a 5, 6 or 7 membered carbocyclic or heterocyclic ring, itself optionally substituted with halogen), heteroaryl (which may be optionally substituted by halo, nitro, cyano, $C_{1-6}$ alkyl, $C_{1-6}$ haloalkyl, $C_{1-6}$ alkoxy, $C_{1-6}$ haloalkoxy, $C_{1-6}$ alkylsulfonyl, $C_{1-6}$ alkylsulfinyl, $C_{1-6}$ alkylthio, $C_{1-6}$ alkoxycarbonyl, $C_{1-6}$ alkylcarbonylamino, arylcarbonyl, or two adjacent positions on the heteroaryl system may be cyclised to form a 5, 6 or 7 membered carbocyclic or heterocyclic ring, itself optionally substituted with halogen), $C_{1-6}$ alkoxy, $C_{1-6}$ haloalkoxy, phenoxy (wherein the phenyl group is optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), heteroaryloxy (optionally substituted by halo, nitro, cyano, $C_{1-6}$ alkyl, $C_{1-6}$ haloalkyl, $C_{1-6}$ alkoxy or $C_{1-6}$ haloalkoxy), heterocyclyloxy (optionally substituted by halo, $C_{1-6}$ alkyl, $C_{1-6}$ haloalkyl, $C_{1-6}$ alkoxy or $C_{1-6}$ haloalkoxy), cyano, $C_{2-6}$ alkenyl, $C_{3-6}$ cycloalkyl, $C_{5-7}$ cycloalkenyl, heterocyclyl (optionally substituted by halo, cyano, $C_{1-6}$ alkyl, $C_{1-6}$ haloalkyl, $C_{1-6}$ alkoxy or $C_{1-6}$ haloalkoxy), $C_{1-6}$ alkylthio, $C_{1-6}$ haloalkylthio, $NR^{13}R^{14}$ where $R^{13}$ and $R^{14}$ are independently hydrogen, $COR^{40}$, $C_{2-6}$ alkyl, $C_{2-6}$ haloalkyl, phenyl (which may be optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino, dialkylamino, $C_{1-4}$ alkoxycarbonyl) or heteroaryl (which may be optionally substituted by halo, nitro, cyano, $C_{1-6}$ alkyl, $C_{1-6}$ haloalkyl, $C_{1-6}$ alkoxy, $C_{1-6}$ haloalkoxy, $C_{1-4}$ alkoxycarbonyl); $C_{1-6}$ alkylcarbonylamino, phenyloxycarbonylamino (wherein the phenyl group is optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), amino, $C_{1-6}$ alkylamino, phenylamino (wherein the phenyl group is optionally substituted halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino).

Even more preferably $R^1$ is $C_{1-6}$ alkyl, $C_{1-6}$ haloalkyl, $C_{1-6}$ alkoxy($C_{1-6}$)alkyl, heteroaryl($C_{1-3}$)alkyl (wherein the heteroaryl group may be optionally substituted by halo, nitro, cyano, $C_{1-6}$ alkyl, $C_{1-6}$ haloalkyl, $C_{1-6}$ alkoxy, $C_{1-6}$ haloalkoxy, $C_{1-6}$ alkylsulfonyl, $C_{1-6}$ alkoxycarbonyl, or two adjacent positions on the heteroaryl system may be cyclised to form a 5, 6 or 7 membered carbocyclic or heterocyclic ring, itself optionally substituted with halogen), phenyl ($C_{1-3}$)alkyl (wherein the phenyl group may be optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino, dialkylamino, $C_{1-6}$ alkylsulfonyl, $C_{1-6}$ alkoxycarbonyl, or two adjacent positions on the phenyl ring may be cyclised to form a 5, 6 or 7 membered carbocyclic or heterocyclic ring, itself optionally substituted with halogen), phenyl (which may be optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino, dialkylamino, $C_{1-6}$ alkylsulfonyl, $C_{1-6}$ alkoxycarbonyl, or two adjacent positions on the phenyl ring may be cyclised to form a 5, 6 or 7 membered carbocyclic or heterocyclic ring, itself optionally substituted with halogen), heteroaryl (which may be optionally substituted by halo, nitro, cyano, $C_{1-6}$ alkyl, $C_{1-6}$ haloalkyl, $C_{1-6}$ alkoxy, $C_{1-6}$ haloalkoxy, $C_{1-6}$ alkylsulfonyl, $C_{1-6}$ alkoxycarbonyl, or two adjacent positions on the heteroaryl system may be cyclised to form a 5, 6 or 7 membered carbocyclic or heterocyclic ring, itself optionally substituted with halogen), $C_{1-6}$ alkoxy, $C_{1-6}$ haloalkoxy, $C_{2-6}$ alkenyl, heterocyclyl (optionally substituted by halo, cyano, $C_{1-6}$ alkyl, $C_{1-6}$ haloalkyl, $C_{1-6}$ alkoxy or $C_{1-6}$ haloalkoxy), $C_{1-6}$ alkylthio, $C_{1-6}$ haloalkylthio or $NR^{13}R^{14}$ where $R^{13}$ and $R^{14}$ are independently hydrogen, $C_{2-6}$ alkyl or $C_{2-6}$ haloalkyl, $C_{2-6}$ alkylcarbonyl or phenylcarbonyl, (where the phenyl is optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino).

Yet more preferably $R^1$ is $C_{1-6}$ alkyl, $C_{1-6}$ haloalkyl, heteroaryl($C_{1-3}$)alkyl (wherein the heteroaryl group may be optionally substituted by halo, cyano, $C_{1-6}$ alkyl, $C_{1-6}$ haloalkyl) where the heteroaryl group is a pyridine, pyrimidine, pyrazine or pyridazine ring, heteroaryl (optionally substituted by halo, cyano, $C_{1-6}$ alkyl, $C_{1-6}$ haloalkyl) where the heteroaryl group is a pyridine, pyrimidine, pyrazine or pyridazine ring, $C_{1-6}$ alkoxy or heterocyclyl (optionally substituted by halo, cyano, $C_{1-3}$ alkyl, $C_{1-3}$ haloalkyl, or $C_{1-3}$ alkoxy).

Most preferably $R^1$ is pyridyl (optionally substituted by halo, $C_{1-3}$ alkyl or $C_{1-3}$ haloalkyl) or $C_{1-6}$ alkoxy, especially halo-substituted pyridyl.

It is preferred that $R^2$ and $R^3$ are independently hydrogen or $C_{1-4}$ alkyl.

More preferably $R^2$ and $R^3$ are independently hydrogen or methyl.

Even more preferably $R^2$ is hydrogen and $R^3$ is hydrogen or methyl;

Most preferably $R^2$ and $R^3$ are both hydrogen.

Preferably each $R^4$ is independently halogen, cyano, $C_{1-8}$ alkyl, $C_{1-8}$ haloalkyl, $C_{1-6}$ cyanoalkyl, $C_{1-6}$ alkoxy($C_{1-6}$) alkyl, $C_{3-7}$ cycloalkyl($C_{1-6}$)alkyl, $C_{5-6}$ cycloalkenyl($C_{1-6}$) alkyl, $C_{3-6}$ alkenyloxy($C_{1-6}$)alkyl, $C_{3-6}$ alkynyloxy($C_{1-6}$) alkyl, aryloxy($C_{1-6}$)alkyl, $C_{1-6}$ carboxyalkyl, $C_{1-6}$ alkylcarbonyl($C_{1-6}$)alkyl, $C_{2-6}$ alkenylcarbonyl($C_{1-6}$)alkyl, $C_{2-6}$ alkynylcarbonyl($C_{1-6}$)-alkyl, $C_{1-6}$ alkoxycarbonyl($C_{1-6}$) alkyl, $C_{3-6}$ alkenyloxycarbonyl($C_{1-6}$)alkyl, $C_{3-6}$ alkynyloxycarbonyl($C_{1-6}$)alkyl, aryloxycarbonyl($C_{1-6}$)alkyl, $C_{1-6}$ alkylthio($C_{1-6}$)alkyl, $C_{1-6}$ alkylsulfinyl($C_{1-6}$)alkyl, $C_{1-6}$ alkylsulfonyl($C_{1-6}$)alkyl, aminocarbonyl($C_{1-6}$)alkyl, $C_{1-6}$ alkylaminocarbonyl($C_{1-6}$)alkyl, di($C_{1-6}$)alkylaminocarbonyl ($C_{1-6}$)alkyl, phenyl($C_{1-4}$)alkyl (wherein the phenyl group is optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), heteroaryl($C_{1-4}$)alkyl (wherein the heteroaryl group is optionally substituted by halo, nitro, cyano, $C_{1-6}$ alkyl, $C_{1-6}$ haloalkyl, $C_{1-6}$ alkoxy or $C_{1-6}$ haloalkoxy), heterocyclyl($C_{1-4}$)alkyl (wherein the heterocyclyl group is optionally substituted by halo, nitro, cyano, $C_{1-6}$ alkyl, $C_{1-6}$ haloalkyl, $C_{1-6}$ alkoxy or $C_{1-6}$ haloalkoxy), $C_{2-6}$ alkenyl, aminocarbonyl($C_{2-6}$)alkenyl, $C_{1-6}$ alkylaminocarbonyl($C_{2-6}$)alkenyl, di($C_{1-6}$)alkylaminocarbonyl($C_{2-6}$) alkenyl, phenyl($C_{2-4}$)-alkenyl, (wherein the phenyl group is optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), $C_{2-6}$ alkynyl, trimethylsilyl($C_{2-6}$) alkynyl, aminocarbonyl($C_{2-6}$)alkynyl, $C_{1-6}$ alkylaminocarbonyl($C_{2-6}$)alkynyl, di($C_{1-6}$)alkylaminocarbonyl($C_{2-6}$)alkynyl, $C_{1-6}$ alkoxycarbonyl, $C_{3-7}$ cycloalkyl, $C_{3-7}$ halocycloalkyl, $C_{3-7}$ cyanocycloalkyl, $C_{1-3}$ alkyl($C_{3-7}$)-cycloalkyl, $C_{1-3}$ alkyl($C_{3-7}$)halocycloalkyl, phenyl (optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), heteroaryl (optionally substituted by halo, nitro, cyano, $C_{1-6}$ alkyl, $C_{1-6}$ haloalkyl, $C_{1-6}$ alkoxy or $C_{1-6}$ haloalkoxy), heterocyclyl (wherein the heterocyclyl group is optionally substituted by halo, nitro, cyano, $C_{1-6}$ alkyl, $C_{1-6}$ haloalkyl, $C_{1-6}$ alkoxy or $C_{1-6}$ haloalkoxy), or 2 adjacent groups $R^4$ together with the carbon atoms to which they are attached form a 4, 5, 6, or 7 membered carbocyclic or heterocyclic ring which may be optionally substituted by halogen, $C_{1-8}$ alkoxy, $C_{1-6}$ haloalkoxy, phenoxy (optionally substituted by halo, nitro, cyano, $C_{1-6}$ alkyl, $C_{1-6}$ haloalkyl, $C_{1-6}$ alkoxy or $C_{1-6}$ haloalkoxy), heteroaryloxy (optionally substituted by halo, nitro, cyano, $C_{1-6}$ alkyl, $C_{1-6}$ haloalkyl, $C_{1-6}$ alkoxy or $C_{1-6}$ haloalkoxy), $C_{1-8}$ alkylthio or $R^{19}R^{20}N$ where $R^{19}$ and $R^{20}$ are, independently, hydrogen, $C_{1-8}$ alkyl, $C_{3-7}$ cycloalkyl, $C_{3-6}$ alkenyl, $C_{3-6}$ alkynyl, $C_{2-6}$ haloalkyl, $C_{1-6}$ alkoxycarbonyl or $R^{19}$ and $R^{20}$ together with the N atom to which they are attached form a five, six or seven-membered heterocyclic ring which may contain one or two further heteroatoms selected from O, N or S and which may be optionally substituted by one or two $C_{1-6}$ alkyl groups; n is 0, 1, 2, 3 or 4.

More preferably each $R^4$ is independently halogen, cyano, $C_{1-8}$ alkyl, $C_{1-8}$ haloalkyl, $C_{1-8}$ cyanoalkyl, $C_{1-6}$ alkoxy($C_{1-6}$)alkyl, $C_{2-6}$ alkynyl, trimethylsilyl($C_{2-6}$)alkynyl, $C_{1-6}$ alkoxycarbonyl, $C_{3-7}$ cycloalkyl, $C_{1-3}$ alkyl ($C_{3-7}$) cycloalkyl, phenyl (optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), heterocyclyl (optionally substituted by halo, nitro, cyano, $C_{1-6}$ alkyl, $C_{1-6}$ haloalkyl, $C_{1-6}$ alkoxy or $C_{1-6}$ haloalkoxy), $C_{1-8}$ alkoxy, $C_{1-6}$ haloalkoxy, phenoxy (optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), heteroaryloxy (optionally substituted by halo, nitro, cyano, $C_{1-3}$ alkyl, $C_{1-3}$ haloalkyl, $C_{1-3}$ alkoxy or $C_{1-3}$ haloalkoxy), di($C_{1-8}$)alkylamino, or 2 adjacent groups $R^4$ together with the carbon atoms to which they are attached form a 4, 5, 6, or 7 membered carbocyclic or heterocyclic ring which may be optionally substituted by halogen; n is 0, 1, 2, 3 or 4.

Even more preferably each $R^4$ is independently halogen, cyano, $C_{1-8}$ alkyl, $C_{1-8}$ haloalkyl, $C_{1-8}$ cyanoalkyl, $C_{1-6}$ alkoxy($C_{1-6}$)alkyl, $C_{2-6}$ alkynyl, heterocyclyl (optionally substituted by $C_{1-6}$ alkyl), $C_{1-8}$ alkoxy, $C_{1-6}$ haloalkoxy, phenoxy (optionally substituted by halo, cyano, $C_{1-3}$ alkyl or $C_{1-3}$ haloalkyl), heteroaryloxy (optionally substituted by halo, cyano, $C_{1-3}$ alkyl or $C_{1-3}$ haloalkyl), di($C_{1-8}$)alkylamino or 2 adjacent groups $R^4$ together with the carbon atoms to which they are attached form a 4, 5, 6, or 7 membered carbocyclic or heterocyclic ring which may be optionally substituted by halogen; n is 0, 1, 2, 3 or 4;

Yet more preferably each $R^4$ is independently fluoro, chloro, bromo, cyano, $C_{1-4}$ alkyl, $C_{1-4}$ haloalkyl, $C_{1-4}$ cyanoalkyl or $C_{1-3}$ alkoxy($C_{1-3}$)alkyl; n is 0, 1 or 2;

Most preferably each $R^4$ is independently fluoro, chloro, bromo, $C_{1-4}$ alkyl or $C_{1-4}$ haloalkyl; n is 1 or 2.

Preferably $R^8$ is $C_{1-10}$ alkyl, $C_{1-10}$ haloalkyl, aryl($C_{1-6}$)alkyl (wherein the aryl group is optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), heteroaryl($C_{1-6}$)alkyl (wherein the heteroaryl group is optionally substituted halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), arylcarbonyl-($C_{1-6}$)alkyl (wherein the aryl group may be optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino and the alkyl group may be optionally substituted by aryl), $C_{2-8}$ alkenyl, $C_{2-8}$ haloalkenyl, aryl($C_{2-6}$)-alkenyl (wherein the aryl group is optionally substituted halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino, $C_{1-6}$ alkoxycarbonyl, or two adjacent substituents can cyclise to form a 5, 6 or 7 membered carbocyclic or heterocyclic ring), $C_{2-6}$ alkynyl, phenyl($C_{2-6}$)alkynyl (wherein the phenyl group is optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), $C_{3-7}$ cycloalkyl, $C_{1-6}$ alkoxycarbonyl, $C_{1-6}$ alkylcarbonyl, $C_{1-6}$ haloalkylcarbonyl or aryl($C_{2-6}$)alkenylcarbonyl (wherein the aryl group may be optionally substituted halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), or $C(R^{51})(R^{52})$—[$CR^{53}$=$CR^{54}$]z-$R^{55}$ where z is 1 or 2, $R^{51}$ and $R^{52}$ are each independently H, halo or $C_{1-2}$ alkyl, $R^{53}$ and $R^{54}$ are each independently H, halogen, $C_{1-4}$ alkyl or $C_{1-4}$ haloalkyl and $R^{55}$ is optionally substituted aryl or optionally substituted heteroaryl.

$R^8$ is more preferably $C_{1-6}$ alkyl, $C_{1-6}$ haloalkyl, aryl($C_{1-4}$)alkyl (wherein the aryl group is optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), heteroaryl($C_{1-6}$)alkyl (wherein the heteroaryl group is optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), $C_{2-6}$ alkenyl, aryl($C_{2-6}$)alkenyl (wherein the aryl group is optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), $C_{2-6}$ alkynyl, phenyl($C_{2-6}$)alkynyl (wherein the phenyl group is optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino); or $C(R^{51})(R^{52})$—[$CR^{53}$=$CR^{54}$]z-$R^{55}$ where z is 1 or 2, $R^{51}$ and $R^{52}$ are each independently H, halo or $C_{1-2}$ alkyl, $R^{53}$ and $R^{54}$ are each independently H, halogen, $C_{1-4}$ alkyl or $C_{1-4}$ haloalkyl and $R^{55}$ is optionally substituted aryl or optionally substituted heteroaryl Even more preferably $R^8$ is phenyl($C_{1-4}$)alkyl (wherein the phenyl group is optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), heteroaryl($C_{1-6}$)alkyl (wherein the heteroaryl group is optionally substituted halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), phenyl($C_{2-6}$)alkenyl (wherein the phenyl group is optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino) or phenyl($C_{2-6}$)alkynyl (wherein the phenyl group is optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino, or $C(R^{51})(R^{52})$—[$CR^{53}$=$CR^{54}$]z-$R^{55}$ where z is 1 or 2, $R^{51}$ and $R^{52}$ are each independently H, halo or $C_{1-2}$ alkyl, $R^{53}$ and $R^{54}$ are each independently H, halogen, $C_{1-4}$ alkyl or $C_{1-4}$ haloalkyl and $R^{55}$ is optionally substituted aryl or optionally substituted heteroaryl Even more preferably $R^8$ is phenyl$CH_2$— (wherein the phenyl group is optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), heteroaryl $CH_2$— (wherein the heteroaryl group is a bicyclic group optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), or $C(R^{51})(R^{52})$—[$CR^{53}$=]z-$R^{55}$ where z is 1 or 2, $R^{51}$ and $R^{52}$ are each independently H, halo or $C_{1-2}$ alkyl, $R^{53}$ and $R^{54}$ are each independently H, halogen, $C_{1-4}$ alkyl or $C_{1-4}$ haloalkyl and $R^{55}$ is optionally substituted aryl or optionally substituted heteroaryl Yet more preferably $R^8$ is phenyl($C_{2-4}$)alkenyl (wherein the phenyl group is optionally substituted by halo, nitro, cyano, $C_{1-3}$ alkyl, $C_{1-3}$ haloalkyl, $C_{1-3}$ alkoxy, $C_{1-3}$ alkoxycarbonyl or $C_{1-3}$ haloalkoxy) or phenyl($C_{2-4}$)alkynyl (wherein the phenyl group is optionally substituted by halo, nitro, cyano, $C_{1-3}$ alkyl, $C_{1-3}$ haloalkyl, $C_{1-3}$ alkoxy, $C_{1-3}$ alkoxycarbonyl or $C_{1-3}$ haloalkoxy); or $R^8$ is $C(R^{51})(R^{52})$—[$CR^{53}$=$CR^{54}$]z-$R^{55}$ where z is 1 or 2, $R^{51}$ and $R^{52}$ are each independently H, halo or $C_{1-2}$ alkyl, $R^{53}$ and $R^{54}$ are each independently H, halogen, $C_{1-4}$ alkyl or $C_{1-4}$ haloalkyl and $R^{55}$ is phenyl substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino or heteroaryl substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino.

Most preferably $R^8$ is $C(R^{51})(R^{52})$—[$CR^{53}$=$CR^{54}$]z-$R^{55}$ where z is 1 or 2, preferably 1, $R^{51}$ and $R^{52}$ are each independently H, halo or $C_{1-2}$ alkyl, $R^{53}$ and $R^{54}$ are each independently H, halogen, $C_{1-4}$ alkyl or $C_{1-4}$ haloalkyl and $R^{55}$ is phenyl substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino or heteroaryl substituted by halogen, $C_{1-4}$ alkyl, $C_{1-4}$ alkoxy, $C_{1-4}$ haloalkyl,
$C_{1-4}$ haloalkoxy, CN, $NO_2$, aryl, heteroaryl, amino or dialkylamino It is preferred that $R^9$ and $R^{10}$ are both hydrogen.

$R^{51}$ and $R^{52}$ are preferably hydrogen.

$R^{53}$ and $R^{54}$ are preferably hydrogen or halogen, especially hydrogen.

$R^{55}$ is preferably phenyl substituted with one to three substituents selected from halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino Certain compounds of formula (I) are novel and as such form a further aspect of the invention. For example there are provided novel compounds of formula (IK) as defined above and salts or N-oxides thereof provided that $R^8$ is not methyl and $YR^1$ is not $SO_2CH_3$, methyl, ethyl, phenyl or fluoro-substituted phenyl.

Further novel compounds are those of formula IN which are compounds of formula I wherein Y is a single bond or C=O; $R^1$ is $C_{1-6}$ alkyl, $C_{1-6}$ haloalkyl, heteroaryl($C_{1-3}$)alkyl (wherein the heteroaryl group may be optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino and the heteroaryl group is a pyridine, pyrimidine, pyrazine or pyridazine ring), heteroaryl (optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino and where the heteroaryl group is a pyridine, pyrimidine, pyrazine or pyridazine ring), $C_{1-6}$ alkoxy or heterocyclyl (optionally substituted by halo, cyano, $C_{1-3}$ alkyl, $C_{1-3}$ haloalkyl, or $C_{1-3}$ alkoxy); $R^4$ is independently fluoro, chloro, bromo, cyano, $C_{1-4}$ alkyl, $C_{1-4}$ haloalkyl, $C_{1-4}$ cyanoalkyl or $C_{1-3}$ alkoxy($C_{1-3}$)alkyl; n is 0, 1 or 2; $R^8$ is phenyl($C_{2-4}$)alkenyl (wherein the phenyl group is optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino, dialkylamino or $C_{1-3}$ alkoxycarbonyl) or phenyl ($C_{2-4}$)alkynyl (wherein the phenyl group is optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino, dialkylamino or $C_{1-3}$ alkoxycarbonyl) and $R^2R^3R^9$ and $R^{10}$ are all hydrogen.

Further novel compounds are those of formula IP which are compounds of formula I wherein Y is C(O); $R^1$ is pyridyl (optionally substituted by halo, $C_{1-3}$ alkyl or $C_{1-3}$ haloalkyl) or $C_{1-6}$ alkoxy; $R^2$, $R^3$, $R^9$ and $R^{10}$ are all hydrogen; $R^4$ is fluoro, chloro, bromo, $C_{1-4}$ alkyl or $C_{1-4}$ haloalkyl; n is 1 or 2 and $R^8$ is phenyl$CH_2$— (wherein the phenyl group is optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), heteroaryl $CH_2$— (wherein the heteroaryl group is a bicyclic group optionally substituted by halo, nitro, cyano, $C_{1-6}$ alkyl, $C_{1-6}$ haloalkyl, $C_{1-6}$ alkoxy or $C_{1-6}$ haloalkoxy), or $C(R^{51})(R^{52})$—[$CR^{53}$=$CR^{54}$]z-$R^{55}$ where z is 1 or 2, $R^{51}$ and $R^{52}$ are each independently H, halo or $C_{1-2}$ alkyl, $R^{53}$ and $R^{54}$ are each independently H, halogen, $C_{1-4}$ alkyl or $C_{1-4}$ haloalkyl and $R^{55}$ is optionally substituted aryl or optionally substituted heteroaryl provided that a) when $R^4$n is 5-fluoro and $R^1$ is 2,6-dichloropyrid-4-yl then $R^8$ is not 4-methylbenzyl, 3-methylbenzyl, 4-trifluormethoxybenzyl, 4-trifluormethybenzyl, 4-cyanobenzyl, 4-methylcarbonylbenzyl or cinnamyl and b) when $R^4$n is 5-fluoro and $R^1$ is 2-chloropyrid-4-yl then $R^8$ is not 3-chlorobenzyl, 3,5-difluorobenzyl, 4-trifluormethoxybenzyl, 4-trifluormethybenzyl, 4-cyanobenzyl or 4-methylcarbonylbenzyl.

The compounds in Tables I to XXXII below illustrate the compounds of the invention.

Table I provides 301 compounds of formula Ia

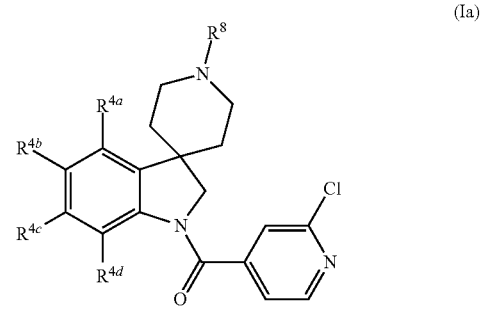

(Ia)

wherein the values of $R^8$, $R^{4a}$, $R^{4b}$, $R^{4c}$ and $R^{4d}$ are given in Table 1

TABLE 1

| Compound | $R^8$ | $R^{4a}$ | $R^{4b}$ | $R^{4c}$ | $R^{4d}$ |
|---|---|---|---|---|---|
| I-1 | Cinnamyl | H | H | H | H |
| I-2 | 4-chlorocinnamyl | H | H | H | H |
| I-3 | 4-fluorocinnamyl | H | H | H | H |
| I-4 | 4-nitrocinnamyl | H | H | H | H |
| I-5 | 4-methoxycinnamyl | H | H | H | H |
| I-6 | 4-methylcinnamyl | H | H | H | H |
| I-7 | 4-trifluoromethylcinnamyl | H | H | H | H |
| I-8 | 4-cyanocinnamyl | H | H | H | H |
| I-9 | 2,4-dichlorocinnamyl | H | H | H | H |
| I-10 | 2,4-difluorocinnamyl | H | H | H | H |
| I-11 | cinnamyl | Cl | H | H | H |
| I-12 | 4-chlorocinnamyl | Cl | H | H | H |
| I-13 | 4-fluorocinnamyl | Cl | H | H | H |
| I-14 | 4-nitrocinnamyl | Cl | H | H | H |
| I-15 | 4-methoxycinnamyl | Cl | H | H | H |
| I-16 | 4-methylcinnamyl | Cl | H | H | H |
| I-17 | 4-trifluoromethylcinnamyl | Cl | H | H | H |
| I-18 | 4-cyanocinnamyl | Cl | H | H | H |
| I-19 | 2,4-dichlorocinnamyl | Cl | H | H | H |
| I-20 | 2,4-difluorocinnamyl | Cl | H | H | H |
| I-21 | cinnamyl | H | Cl | H | H |
| I-22 | 4-chlorocinnamyl | H | Cl | H | H |
| I-23 | 4-fluorocinnamyl | H | Cl | H | H |
| I-24 | 4-nitrocinnamyl | H | Cl | H | H |

TABLE 1-continued

| Compound | R⁸ | R⁴ᵃ | R⁴ᵇ | R⁴ᶜ | R⁴ᵈ |
|---|---|---|---|---|---|
| I-25 | 4-methoxycinnamyl | H | Cl | H | H |
| I-26 | 4-methylcinnamyl | H | Cl | H | H |
| I-27 | 4-trifluoromethylcinnamyl | H | Cl | H | H |
| I-28 | 4-cyanocinnamyl | H | Cl | H | H |
| I-29 | 2,4-dichlorocinnamyl | H | Cl | H | H |
| I-30 | 2,4-difluorocinnamyl | H | Cl | H | H |
| I-31 | cinnamyl | H | H | Cl | H |
| I-32 | 4-chlorocinnamyl | H | H | Cl | H |
| I-33 | 4-fluorocinnamyl | H | H | Cl | H |
| I-34 | 4-nitrocinnamyl | H | H | Cl | H |
| I-35 | 4-methoxycinnamyl | H | H | Cl | H |
| I-36 | 4-methylcinnamyl | H | H | Cl | H |
| I-37 | 4-trifluoromethylcinnamyl | H | H | Cl | H |
| I-38 | 4-cyanocinnamyl | H | H | Cl | H |
| I-39 | 2,4-dichlorocinnamyl | H | H | Cl | H |
| I-40 | 2,4-difluorocinnamyl | H | H | Cl | H |
| I-41 | cinnamyl | H | H | H | Cl |
| I-42 | 4-chlorocinnamyl | H | H | H | Cl |
| I-43 | 4-fluorocinnamyl | H | H | H | Cl |
| I-44 | 4-nitrocinnamyl | H | H | H | Cl |
| I-45 | 4-methoxycinnamyl | H | H | H | Cl |
| I-46 | 4-methylcinnamyl | H | H | H | Cl |
| I-47 | 4-trifluoromethylcinnamyl | H | H | H | Cl |
| I-48 | 4-cyanocinnamyl | H | H | H | Cl |
| I-49 | 2,4-dichlorocinnamyl | H | H | H | Cl |
| I-50 | 2,4-difluorocinnamyl | H | H | H | Cl |
| I-51 | cinnamyl | F | H | H | H |
| I-52 | 4-chlorocinnamyl | F | H | H | H |
| I-53 | 4-fluorocinnamyl | F | H | H | H |
| I-54 | 4-nitrocinnamyl | F | H | H | H |
| I-55 | 4-methoxycinnamyl | F | H | H | H |
| I-56 | 4-methylcinnamyl | F | H | H | H |
| I-57 | 4-trifluoromethylcinnamyl | F | H | H | H |
| I-58 | 4-cyanocinnamyl | F | H | H | H |
| I-59 | 2,4-dichlorocinnamyl | F | H | H | H |
| I-60 | 2,4-difluorocinnamyl | F | H | H | H |
| I-61 | cinnamyl | H | F | H | H |
| I-62 | 4-chlorocinnamyl | H | F | H | H |
| I-63 | 4-fluorocinnamyl | H | F | H | H |
| I-64 | 4-nitrocinnamyl | H | F | H | H |
| I-65 | 4-methoxycinnamyl | H | F | H | H |
| I-66 | 4-methylcinnamyl | H | F | H | H |
| I-67 | 4-trifluoromethylcinnamyl | H | F | H | H |
| I-68 | 4-cyanocinnamyl | H | F | H | H |
| I-69 | 2,4-dichlorocinnamyl | H | F | H | H |
| I-70 | 2,4-difluorocinnamyl | H | F | H | H |
| I-71 | cinnamyl | H | H | F | H |
| I-72 | 4-chlorocinnamyl | H | H | F | H |
| I-73 | 4-fluorocinnamyl | H | H | F | H |
| I-74 | 4-nitrocinnamyl | H | H | F | H |
| I-75 | 4-methoxycinnamyl | H | H | F | H |
| I-76 | 4-methylcinnamyl | H | H | F | H |
| I-77 | 4-trifluoromethylcinnamyl | H | H | F | H |
| I-78 | 4-cyanocinnamyl | H | H | F | H |
| I-79 | 2,4-dichlorocinnamyl | H | H | F | H |
| I-80 | 2,4-difluorocinnamyl | H | H | F | H |
| I-81 | cinnamyl | H | H | H | F |
| I-82 | 4-chlorocinnamyl | H | H | H | F |
| I-83 | 4-fluorocinnamyl | H | H | H | F |
| I-84 | 4-nitrocinnamyl | H | H | H | F |
| I-85 | 4-methoxycinnamyl | H | H | H | F |
| I-86 | 4-methylcinnamyl | H | H | H | F |
| I-87 | 4-trifluoromethylcinnamyl | H | H | H | F |
| I-88 | 4-cyanocinnamyl | H | H | H | F |
| I-89 | 2,4-dichlorocinnamyl | H | H | H | F |
| I-90 | 2,4-difluorocinnamyl | H | H | H | F |
| I-91 | cinnamyl | Br | H | H | H |
| I-92 | 4-chlorocinnamyl | Br | H | H | H |
| I-93 | 4-fluorocinnamyl | Br | H | H | H |
| I-94 | 4-nitrocinnamyl | Br | H | H | H |
| I-95 | 4-methoxycinnamyl | Br | H | H | H |
| I-96 | 4-methylcinnamyl | Br | H | H | H |
| I-97 | 4-trifluoromethylcinnamyl | Br | H | H | H |
| I-98 | 4-cyanocinnamyl | Br | H | H | H |
| I-99 | 2,4-dichlorocinnamyl | Br | H | H | H |
| I-100 | 2,4-difluorocinnamyl | Br | H | H | H |
| I-101 | cinnamyl | H | Br | H | H |
| I-102 | 4-chlorocinnamyl | H | Br | H | H |
| I-103 | 4-fluorocinnamyl | H | Br | H | H |
| I-104 | 4-nitrocinnamyl | H | Br | H | H |
| I-105 | 4-methoxycinnamyl | H | Br | H | H |
| I-106 | 4-methylcinnamyl | H | Br | H | H |
| I-107 | 4-trifluoromethylcinnamyl | H | Br | H | H |
| I-108 | 4-cyanocinnamyl | H | Br | H | H |
| I-109 | 2,4-dichlorocinnamyl | H | Br | H | H |
| I-110 | 2,4-difluorocinnamyl | H | Br | H | H |
| I-111 | cinnamyl | H | H | Br | H |
| I-112 | 4-chlorocinnamyl | H | H | Br | H |
| I-113 | 4-fluorocinnamyl | H | H | Br | H |
| I-114 | 4-nitrocinnamyl | H | H | Br | H |
| I-115 | 4-methoxycinnamyl | H | H | Br | H |
| I-116 | 4-methylcinnamyl | H | H | Br | H |
| I-117 | 4-trifluoromethylcinnamyl | H | H | Br | H |
| I-118 | 4-cyanocinnamyl | H | H | Br | H |
| I-119 | 2,4-dichlorocinnamyl | H | H | Br | H |
| I-120 | 2,4-difluorocinnamyl | H | H | Br | H |
| I-121 | cinnamyl | H | H | H | Br |
| I-122 | 4-chlorocinnamyl | H | H | H | Br |
| I-123 | 4-fluorocinnamyl | H | H | H | Br |
| I-124 | 4-nitrocinnamyl | H | H | H | Br |
| I-125 | 4-methoxycinnamyl | H | H | H | Br |
| I-126 | 4-methylcinnamyl | H | H | H | Br |
| I-127 | 4-trifluoromethylcinnamyl | H | H | H | Br |
| I-128 | 4-cyanocinnamyl | H | H | H | Br |
| I-129 | 2,4-dichlorocinnamyl | H | H | H | Br |
| I-130 | 2,4-difluorocinnamyl | H | H | H | Br |
| I-131 | cinnamyl | H | Cl | H | Cl |
| I-132 | 4-chlorocinnamyl | H | Cl | H | Cl |
| I-133 | 4-fluorocinnamyl | H | Cl | H | Cl |
| I-134 | 4-nitrocinnamyl | H | Cl | H | Cl |
| I-135 | 4-methoxycinnamyl | H | Cl | H | Cl |
| I-136 | 4-methylcinnamyl | H | Cl | H | Cl |
| I-137 | 4-trifluoromethylcinnamyl | H | Cl | H | Cl |
| I-138 | 4-cyanocinnamyl | H | Cl | H | Cl |
| I-139 | 2,4-dichlorocinnamyl | H | Cl | H | Cl |
| I-140 | 2,4-difluorocinnamyl | H | Cl | H | Cl |
| I-141 | cinnamyl | H | F | H | F |
| I-142 | 4-chlorocinnamyl | H | F | H | F |
| I-143 | 4-fluorocinnamyl | H | F | H | F |
| I-144 | 4-nitrocinnamyl | H | F | H | F |
| I-145 | 4-methoxycinnamyl | H | F | H | F |
| I-146 | 4-methylcinnamyl | H | F | H | F |
| I-147 | 4-trifluoromethylcinnamyl | H | F | H | F |
| I-148 | 4-cyanocinnamyl | H | F | H | F |
| I-149 | 2,4-dichlorocinnamyl | H | F | H | F |
| I-150 | 2,4-difluorocinnamyl | H | F | H | F |
| I-151 | cinnamyl | Cl | F | H | H |
| I-152 | 4-chlorocinnamyl | Cl | F | H | H |
| I-153 | 4-fluorocinnamyl | Cl | F | H | H |
| I-154 | 4-nitrocinnamyl | Cl | F | H | H |
| I-155 | 4-methoxycinnamyl | Cl | F | H | H |
| I-156 | 4-methylcinnamyl | Cl | F | H | H |
| I-157 | 4-trifluoromethylcinnamyl | Cl | F | H | H |
| I-158 | 4-cyanocinnamyl | Cl | F | H | H |
| I-159 | 2,4-dichlorocinnamyl | Cl | F | H | H |
| I-160 | 2,4-difluorocinnamyl | Cl | F | H | H |
| I-161 | cinnamyl | H | F | Cl | H |
| I-162 | 4-chlorocinnamyl | H | F | Cl | H |
| I-163 | 4-fluorocinnamyl | H | F | Cl | H |
| I-164 | 4-nitrocinnamyl | H | F | Cl | H |
| I-165 | 4-methoxycinnamyl | H | F | Cl | H |
| I-166 | 4-methylcinnamyl | H | F | Cl | H |
| I-167 | 4-trifluoromethylcinnamyl | H | F | Cl | H |
| I-168 | 4-cyanocinnamyl | H | F | Cl | H |
| I-169 | 2,4-dichlorocinnamyl | H | F | Cl | H |
| I-170 | 2,4-difluorocinnamyl | H | F | Cl | H |
| I-171 | cinnamyl | H | Cl | Cl | H |
| I-172 | 4-chlorocinnamyl | H | Cl | Cl | H |
| I-173 | 4-fluorocinnamyl | H | Cl | Cl | H |
| I-174 | 4-nitrocinnamyl | H | Cl | Cl | H |
| I-175 | 4-methoxycinnamyl | H | Cl | Cl | H |
| I-176 | 4-methylcinnamyl | H | Cl | Cl | H |
| I-177 | 4-trifluoromethylcinnamyl | H | Cl | Cl | H |
| I-178 | 4-cyanocinnamyl | H | Cl | Cl | H |

TABLE 1-continued

| Compound | R⁸ | R⁴ᵃ | R⁴ᵇ | R⁴ᶜ | R⁴ᵈ |
|---|---|---|---|---|---|
| I-179 | 2,4-dichlorocinnamyl | H | Cl | Cl | H |
| I-180 | 2,4-difluorocinnamyl | H | Cl | Cl | H |
| I-181 | cinnamyl | H | I | H | H |
| I-182 | 4-chlorocinnamyl | H | I | H | H |
| I-183 | 4-fluorocinnamyl | H | I | H | H |
| I-184 | 4-nitrocinnamyl | H | I | H | H |
| I-185 | 4-methoxycinnamyl | H | I | H | H |
| I-186 | 4-methylcinnamyl | H | I | H | H |
| I-187 | 4-trifluoromethylcinnamyl | H | I | H | H |
| I-188 | 4-cyanocinnamyl | H | I | H | H |
| I-189 | 2,4-dichlorocinnamyl | H | I | H | H |
| I-190 | 2,4-difluorocinnamyl | H | I | H | H |
| I-191 | cinnamyl | H | OMe | H | H |
| I-192 | 4-chlorocinnamyl | H | OMe | H | H |
| I-193 | 4-fluorocinnamyl | H | OMe | H | H |
| I-194 | 4-nitrocinnamyl | H | OMe | H | H |
| I-195 | 4-methoxycinnamyl | H | OMe | H | H |
| I-196 | 4-methylcinnamyl | H | OMe | H | H |
| I-197 | 4-trifluoromethylcinnamyl | H | OMe | H | H |
| I-198 | 4-cyanocinnamyl | H | OMe | H | H |
| I-199 | 2,4-dichlorocinnamyl | H | OMe | H | H |
| I-200 | 2,4-difluorocinnamyl | H | OMe | H | H |
| I-201 | cinnamyl | H | Me | H | H |
| I-202 | 4-chlorocinnamyl | H | Me | H | H |
| I-203 | 4-fluorocinnamyl | H | Me | H | H |
| I-204 | 4-nitrocinnamyl | H | Me | H | H |
| I-205 | 4-methoxycinnamyl | H | Me | H | H |
| I-206 | 4-methylcinnamyl | H | Me | H | H |
| I-207 | 4-trifluoromethylcinnamyl | H | Me | H | H |
| I-208 | 4-cyanocinnamyl | H | Me | H | H |
| I-209 | 2,4-dichlorocinnamyl | H | Me | H | H |
| I-210 | 2,4-difluorocinnamyl | H | Me | H | H |
| I-211 | cinnamyl | H | CN | H | H |
| I-212 | 4-chlorocinnamyl | H | CN | H | H |
| I-213 | 4-fluorocinnamyl | H | CN | H | H |
| I-214 | 4-nitrocinnamyl | H | CN | H | H |
| I-215 | 4-methoxycinnamyl | H | CN | H | H |
| I-216 | 4-methylcinnamyl | H | CN | H | H |
| I-217 | 4-trifluoromethylcinnamyl | H | CN | H | H |
| I-218 | 4-cyanocinnamyl | H | CN | H | H |
| I-219 | 2,4-dichlorocinnamyl | H | CN | H | H |
| I-220 | 2,4-difluorocinnamyl | H | CN | H | H |
| I-221 | cinnamyl | H | CCH | H | H |
| I-222 | 4-chlorocinnamyl | H | CCH | H | H |
| I-223 | 4-fluorocinnamyl | H | CCH | H | H |
| I-224 | 4-nitrocinnamyl | H | CCH | H | H |
| I-225 | 4-methoxycinnamyl | H | CCH | H | H |
| I-226 | 4-methylcinnamyl | H | CCH | H | H |
| I-227 | 4-trifluoromethylcinnamyl | H | CCH | H | H |
| I-228 | 4-cyanocinnamyl | H | CCH | H | H |
| I-229 | 2,4-dichlorocinnamyl | H | CCH | H | H |
| I-230 | 2,4-difluorocinnamyl | H | CCH | H | H |
| I-231 | cinnamyl | H | COOMe | H | H |
| I-232 | 4-chlorocinnamyl | H | COOMe | H | H |
| I-233 | 4-fluorocinnamyl | H | COOMe | H | H |
| I-234 | 4-nitrocinnamyl | H | COOMe | H | H |
| I-235 | 4-methoxycinnamyl | H | COOMe | H | H |
| I-236 | 4-methylcinnamyl | H | COOMe | H | H |
| I-237 | 4-trifluoromethylcinnamyl | H | COOMe | H | H |
| I-238 | 4-cyanocinnamyl | H | COOMe | H | H |
| I-239 | 2,4-dichlorocinnamyl | H | COOMe | H | H |
| I-240 | 2,4-difluorocinnamyl | H | COOMe | H | H |
| I-241 | cinnamyl | H | Me | Cl | H |
| I-242 | 4-chlorocinnamyl | H | Me | Cl | H |
| I-243 | 4-fluorocinnamyl | H | Me | Cl | H |
| I-244 | 4-nitrocinnamyl | H | Me | Cl | H |
| I-245 | 4-methoxycinnamyl | H | Me | Cl | H |
| I-246 | 4-methylcinnamyl | H | Me | Cl | H |
| I-247 | 4-trifluoromethylcinnamyl | H | Me | Cl | H |
| I-248 | 4-cyanocinnamyl | H | Me | Cl | H |
| I-249 | 2,4-dichlorocinnamyl | H | Me | Cl | H |
| I250 | 2,4difluorocinnamyl | H | Me | Cl | H |
| I-251 | cinnamyl | Cl | Me | H | H |
| I-252 | 4-chlorocinnamyl | Cl | Me | H | H |
| I-253 | 4-fluorocinnamyl | Cl | Me | H | H |
| I-254 | 4-nitrocinnamyl | Cl | Me | H | H |
| I-255 | 4-methoxycinnamyl | Cl | Me | H | H |
| I-256 | 4-methylcinnamyl | Cl | Me | H | H |
| I-257 | 4-trifluoromethylcinnamyl | Cl | Me | H | H |
| I-258 | 4-cyanocinnamyl | Cl | Me | H | H |
| I-259 | 2,4-dichlorocinnamyl | Cl | Me | H | H |
| I-260 | 2,4-difluorocinnamyl | Cl | Me | H | H |
| I-261 | cinnamyl | H | Cl | H | Me |
| I-262 | 4-chlorocinnamyl | H | Cl | H | Me |
| I-263 | 4-fluorocinnamyl | H | Cl | H | Me |
| I-264 | 4-nitrocinnamyl | H | Cl | H | Me |
| I-265 | 4-methoxycinnamyl | H | Cl | H | Me |
| I-266 | 4-methylcinnamyl | H | Cl | H | Me |
| I-267 | 4-trifluoromethylcinnamyl | H | Cl | H | Me |
| I-268 | 4-cyanocinnamyl | H | Cl | H | Me |
| I-269 | 2,4-dichlorocinnamyl | H | Cl | H | Me |
| I-270 | 2,4-difluorocinnamyl | H | Cl | H | Me |
| I-271 | cinnamyl | H | H | 4-Cl—PhO | H |
| I-272 | 4-chlorocinnamyl | H | H | 4-Cl—PhO | H |
| I-273 | 4-fluorocinnamyl | H | H | 4-Cl—PhO | H |
| I-274 | 4-nitrocinnamyl | H | H | 4-Cl—PhO | H |
| I-275 | 4-methoxycinnamyl | H | H | 4-Cl—PhO | H |
| I-276 | 4-methylcinnamyl | H | H | 4-Cl—PhO | H |
| I-277 | 4-trifluoromethylcinnamyl | H | H | 4-Cl—PhO | H |
| I-278 | 4-cyanocinnamyl | H | H | 4-Cl—PhO | H |
| I-279 | 2,4-dichlorocinnamyl | H | H | 4-Cl—PhO | H |
| I-280 | 2,4-difluorocinnamyl | H | H | 4-Cl—PhO | H |
| I-281 | cinnamyl | H | 4-F—Ph | H | H |
| I-282 | 4-chlorocinnamyl | H | 4-F—Ph | H | H |
| I-283 | 4-fluorocinnamyl | H | 4-F—Ph | H | H |
| I-284 | 4-nitrocinnamyl | H | 4-F—Ph | H | H |
| I-285 | 4-methoxycinnamyl | H | 4-F—Ph | H | H |
| I-286 | 4-methylcinnamyl | H | 4-F—Ph | H | H |
| I-287 | 4-trifluoromethylcinnamyl | H | 4-F—Ph | H | H |
| I-288 | 4-cyanocinnamyl | H | 4-F—Ph | H | H |
| I-289 | 2,4-dichlorocinnamyl | H | 4-F—Ph | H | H |
| I-290 | 2,4-difluorocinnamyl | H | 4-F—Ph | H | H |
| I-291 | cinnamyl | H | CF₃O | H | H |
| I-292 | 4-chlorocinnamyl | H | CF₃O | H | H |
| I-293 | 4-fluorocinnamyl | H | CF₃O | H | H |
| I-294 | 4-nitrocinnamyl | H | CF₃O | H | H |
| I-295 | 4-methoxycinnamyl | H | CF₃O | H | H |
| I-296 | 4-methylcinnamyl | H | CF₃O | H | H |
| I-297 | 4-trifluoromethylcinnamyl | H | CF₃O | H | H |
| I-298 | 4-cyanocinnamyl | H | CF₃O | H | H |
| I-299 | 2,4-dichlorocinnamyl | H | CF₃O | H | H |
| I-300 | 2,4-difluorocinnamyl | H | CF₃O | H | H |
| I-301 | C(O)CH=CH-4-chlorophenyl | H | 4-CF₃—Ph | H | H |

Table II provides 301 compounds of formula Ib

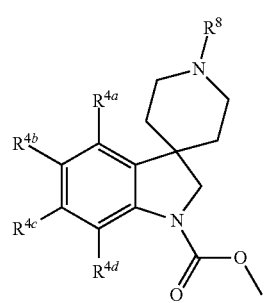

(Ib)

wherein the values of R⁸, R⁴ᵃ, R⁴ᵇ, R⁴ᶜ and R⁴ᵈ are given in Table 1

Table III provides 301 compounds of formula Ic

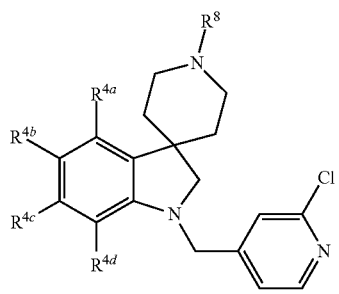
(Ic)

wherein the values of $R^8$, $R^{4a}$, $R^{4b}$, $R^{4c}$ and $R^{4d}$ are given in Table 1

Table IV provides 301 compounds of formula Id

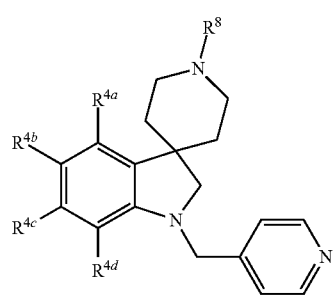
(Id)

wherein the values of $R^8$, $R^{4a}$, $R^{4b}$, $R^{4c}$ and $R^{4d}$ are given in Table 1

Table V provides 301 compounds of formula Ie

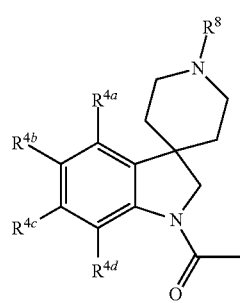
(Ie)

wherein the values of $R^8$, $R^{4a}$, $R^{4b}$, $R^{4c}$ and $R^{4d}$ are given in Table 1

Table VI provides 301 compounds of formula If

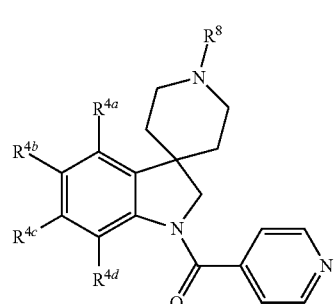
(If)

wherein the values of $R^8$, $R^{4a}$, $R^{4b}$, $R^{4c}$ and $R^{4d}$ are given in Table 1

Table VII provides 301 compounds of formula Ig

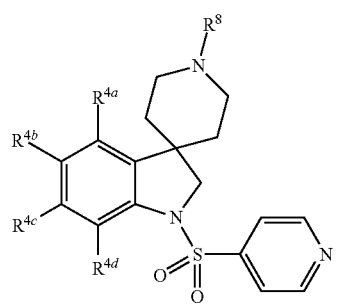
(Ig)

wherein the values of $R^8$, $R^{4a}$, $R^{4b}$, $R^{4c}$ and $R^{4d}$ are given in Table 1

Table VIII provides 301 compounds of formula Ih

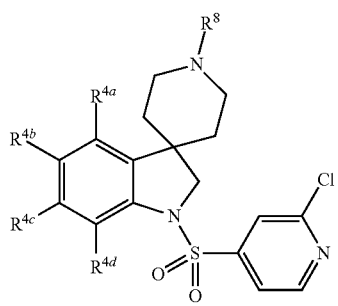
(Ih)

wherein the values of $R^8$, $R^{4a}$, $R^{4b}$, $R^{4c}$ and $R^{4d}$ are given in Table 1

Table IX provides 301 compounds of formula Ii

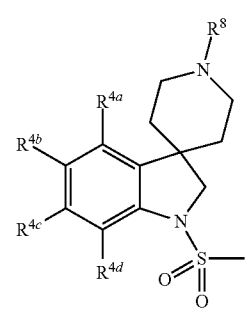
(Ii)

wherein the values of $R^8$, $R^{4a}$, $R^{4b}$, $R^{4c}$ and $R^{4d}$ are given in Table 1

Table X provides 301 compounds of formula Ij

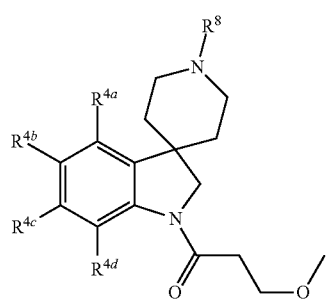

(Ij)

wherein the values of $R^8$, $R^{4a}$, $R^{4b}$, $R^{4c}$ and $R^{4d}$ are given in Table 1

Table XI provides 301 compounds of formula Ik

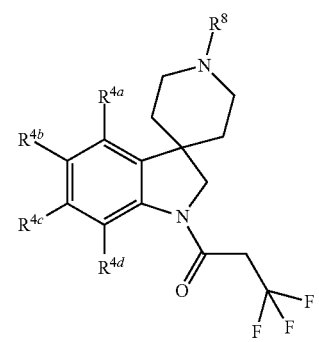

(Ik)

wherein the values of $R^8$, $R^{4a}$, $R^{4b}$, $R^{4c}$ and $R^{4d}$ are given in Table 1

Table XII provides 301 compounds of formula Il

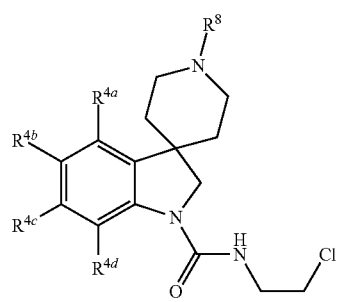

(Il)

wherein the values of $R^8$, $R^{4a}$, $R^{4b}$, $R^{4c}$ and $R^{4d}$ are given in Table 1

Table XIII provides 301 compounds of formula Im

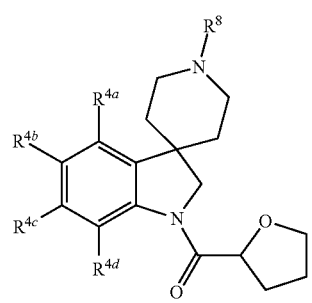

(Im)

wherein the values of $R^8$, $R^{4a}$, $R^{4b}$, $R^{4c}$ and $R^{4d}$ are given in Table 1

Table XIV provides 301 compounds of formula In

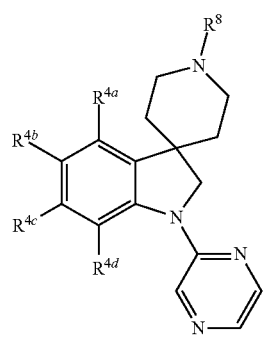

(In)

wherein the values of $R^8$, $R^{4a}$, $R^{4b}$, $R^{4c}$ and $R^{4d}$ are given in Table 1

Table XV provides 301 compounds of formula Io

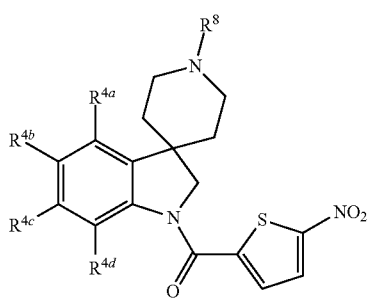

(Io)

wherein the values of $R^8$, $R^{4a}$, $R^{4b}$, $R^{4c}$ and $R^{4d}$ are given in Table 1

Table XVI provides 301 compounds of formula Ip

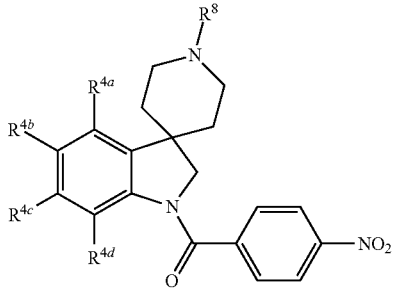
(Ip)

wherein the values of $R^8$, $R^{4a}$, $R^{4b}$, $R^{4c}$ and $R^{4d}$ are given in Table 1

Table XVII provides 301 compounds of formula Iq

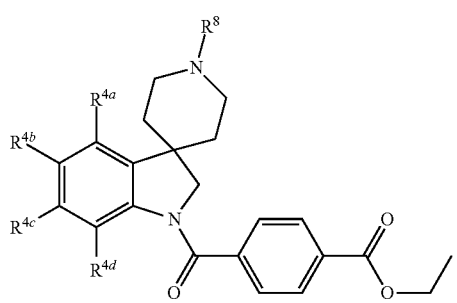
(Iq)

wherein the values of $R^8$, $R^{4a}$, $R^{4b}$, $R^{4c}$ and $R^{4d}$ are given in Table 1

Table XVIII provides 301 compounds of formula Ir

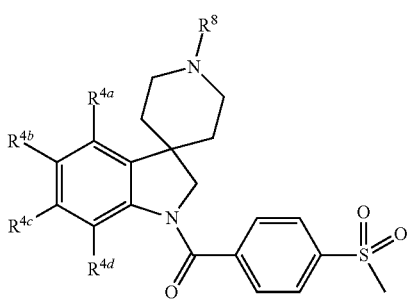
(Ir)

wherein the values of $R^8$, $R^{4a}$, $R^{4b}$, $R^{4c}$ and $R^{4d}$ are given in Table 1

Table XIX provides 301 compounds of formula Is

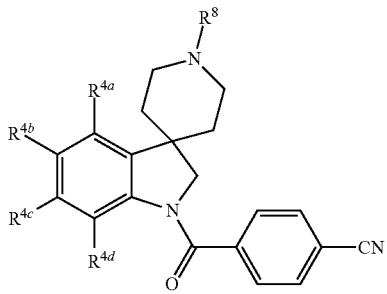
(Is)

wherein the values of $R^8$, $R^{4a}$, $R^{4b}$, $R^{4c}$ and $R^{4d}$ are given in Table 1

Table XX provides 301 compounds of formula It

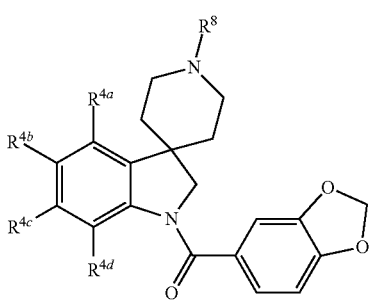
(It)

wherein the values of $R^8$, $R^{4a}$, $R^{4b}$, $R^{4c}$ and $R^{4d}$ are given in Table 1

Table XXI provides 301 compounds of formula Iu

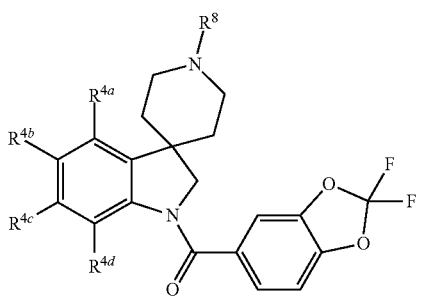
(Iu)

wherein the values of $R^8$, $R^{4a}$, $R^{4b}$, $R^{4c}$ and $R^{4d}$ are given in Table 1

Table XXII provides 301 compounds of formula Iv

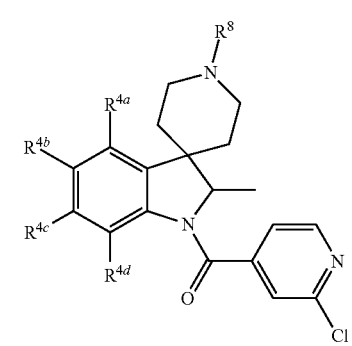
(Iv)

wherein the values of $R^8$, $R^{4a}$, $R^{4b}$, $R^{4c}$ and $R^{4d}$ are given in Table 1

Table XXIII provides 301 compounds of formula Iw

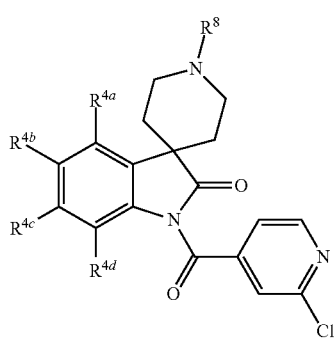

(Iw)

wherein the values of $R^8$, $R^{4a}$, $R^{4b}$, $R^{4c}$ and $R^{4d}$ are given in Table 1

Table XXIV provides 301 compounds of formula Ix

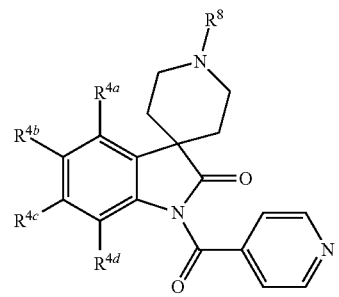

(Ix)

wherein the values of $R^8$, $R^{4a}$, $R^{4b}$, $R^{4c}$ and $R^{4d}$ are given in Table 1

Table XXV provides 301 compounds of formula Iy

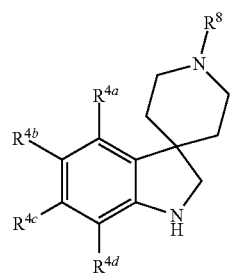

(Iy)

wherein the values of $R^8$, $R^{4a}$, $R^{4b}$, $R^{4c}$ and $R^{4d}$ are given in Table 1

Table XXVI provides 301 compounds of formula Iz

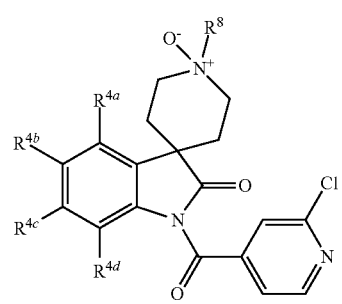

(Iz)

wherein the values of $R^8$, $R^{4a}$, $R^{4b}$, $R^{4c}$ and $R^{4d}$ are given in Table 1

Table XXVII provides 301 compounds of formula Iaa

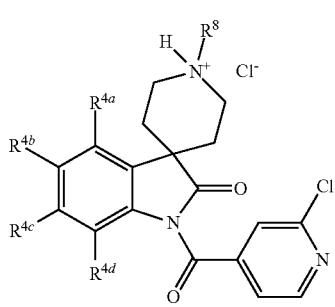

(Iaa)

wherein the values of $R^8$, $R^{4a}$, $R^{4b}$, $R^{4c}$ and $R^{4d}$ are given in Table 1

Table XXVIII provides 270 compounds of formula Iab

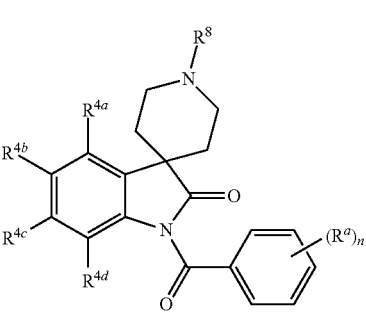

(Iab)

wherein the values of $R^8$, $R^{4a}$, $R^{4b}$, $R^{4c}$, $R^{4d}$ and $(R^a)_n$ are given in Table 2

TABLE 2

| Compound | $R^8$ | $R^{4a}$ | $R^{4b}$ | $R^{4c}$ | $R^{4d}$ | $(R^a)_n$ |
|---|---|---|---|---|---|---|
| XXVIII-1 | cinnamyl | H | H | H | H | 4-SMe |
| XXVIII-2 | 4-chlorocinnamyl | H | H | H | H | 4-SMe |
| XXVIII-3 | 4-fluorocinnamyl | H | H | H | H | 4-SMe |
| XXVIII-4 | 4-trifluoromethylcinnamyl | H | H | H | H | 4-SMe |
| XXVIII-5 | 4-cyanocinnamyl | H | H | H | H | 4-SMe |
| XXVIII-6 | cinnamyl | H | Cl | H | H | 4-SMe |
| XXVIII-7 | 4-chlorocinnamyl | H | Cl | H | H | 4-SMe |
| XXVIII-8 | 4-fluorocinnamyl | H | Cl | H | H | 4-SMe |

TABLE 2-continued

| Compound | R$^8$ | R$^{4a}$ | R$^{4b}$ | R$^{4c}$ | R$^{4d}$ | (R$^a$)$_n$ |
|---|---|---|---|---|---|---|
| XXVIII-9 | 4-trifluoromethylcinnamyl | H | Cl | H | H | 4-SMe |
| XXVIII-10 | 4-cyanocinnamyl | H | Cl | H | H | 4-SMe |
| XXVIII-11 | cinnamyl | H | F | H | H | 4-SMe |
| XXVIII-12 | 4-chlorocinnamyl | H | F | H | H | 4-SMe |
| XXVIII-13 | 4-fluorocinnamyl | H | F | H | H | 4-SMe |
| XXVIII-14 | 4-trifluoromethylcinnamyl | H | F | H | H | 4-SMe |
| XXVIII-15 | 4-cyanocinnamyl | H | F | H | H | 4-SMe |
| XXVIII-16 | cinnamyl | H | H | F | H | 4-SMe |
| XXVIII-17 | 4-chlorocinnamyl | H | H | F | H | 4-SMe |
| XXVIII-18 | 4-fluorocinnamyl | H | H | F | H | 4-SMe |
| XXVIII-19 | 4-trifluoromethylcinnamyl | H | H | F | H | 4-SMe |
| XXVIII-20 | 4-cyanocinnamyl | H | H | F | H | 4-SMe |
| XXVIII-21 | cinnamyl | H | F | H | F | 4-SMe |
| XXVIII-22 | 4-chlorocinnamyl | H | F | H | F | 4-SMe |
| XXVIII-23 | 4-fluorocinnamyl | H | F | H | F | 4-SMe |
| XXVIII-24 | 4-trifluoromethylcinnamyl | H | F | H | F | 4-SMe |
| XXVIII-25 | 4-cyanocinnamyl | H | F | H | F | 4-SMe |
| XXVIII-26 | cinnamyl | H | OMe | H | H | 4-SMe |
| XXVIII-27 | 4-chlorocinnamyl | H | OMe | H | H | 4-SMe |
| XXVIII-28 | 4-fluorocinnamyl | H | OMe | H | H | 4-SMe |
| XXVIII-29 | 4-trifluoromethylcinnamyl | H | OMe | H | H | 4-SMe |
| XXVIII-30 | 4-cyanocinnamyl | H | OMe | H | H | 4-SMe |
| XXVIII-31 | cinnamyl | H | H | H | H | 4-C(O)Ph |
| XXVIII-32 | 4-chlorocinnamyl | H | H | H | H | 4-C(O)Ph |
| XXVIII-33 | 4-fluorocinnamyl | H | H | H | H | 4-C(O)Ph |
| XXVIII-34 | 4-trifluoromethylcinnamyl | H | H | H | H | 4-C(O)Ph |
| XXVIII-35 | 4-cyanocinnamyl | H | H | H | H | 4-C(O)Ph |
| XXVIII-36 | cinnamyl | H | Cl | H | H | 4-C(O)Ph |
| XXVIII-37 | 4-chlorocinnamyl | H | Cl | H | H | 4-C(O)Ph |
| XXVIII-38 | 4-fluorocinnamyl | H | Cl | H | H | 4-C(O)Ph |
| XXVIII-39 | 4-trifluoromethylcinnamyl | H | Cl | H | H | 4-C(O)Ph |
| XXVIII-40 | 4-cyanocinnamyl | H | Cl | H | H | 4-C(O)Ph |
| XXVIII-41 | cinnamyl | H | F | H | H | 4-C(O)Ph |
| XXVIII-42 | 4-chlorocinnamyl | H | F | H | H | 4-C(O)Ph |
| XXVIII-43 | 4-fluorocinnamyl | H | F | H | H | 4-C(O)Ph |
| XXVIII-44 | 4-trifluoromethylcinnamyl | H | F | H | H | 4-C(O)Ph |
| XXVIII-45 | 4-cyanocinnamyl | H | F | H | H | 4-C(O)Ph |
| XXVIII-46 | cinnamyl | H | H | F | H | 4-C(O)Ph |
| XXVIII-47 | 4-chlorocinnamyl | H | H | F | H | 4-C(O)Ph |
| XXVIII-48 | 4-fluorocinnamyl | H | H | F | H | 4-C(O)Ph |
| XXVIII-49 | 4-trifluoromethylcinnamyl | H | H | F | H | 4-C(O)Ph |
| XXVIII-50 | 4-cyanocinnamyl | H | H | F | H | 4-C(O)Ph |
| XXVIII-51 | cinnamyl | H | F | H | F | 4-C(O)Ph |
| XXVIII-52 | 4-chlorocinnamyl | H | F | H | F | 4-C(O)Ph |
| XXVIII-53 | 4-fluorocinnamyl | H | F | H | F | 4-C(O)Ph |
| XXVIII-54 | 4-trifluoromethylcinnamyl | H | F | H | F | 4-C(O)Ph |
| XXVIII-55 | 4-cyanocinnamyl | H | F | H | F | 4-C(O)Ph |
| XXVIII-56 | cinnamyl | H | OMe | H | H | 4-C(O)Ph |
| XXVIII-57 | 4-chlorocinnamyl | H | OMe | H | H | 4-C(O)Ph |
| XXVIII-58 | 4-fluorocinnamyl | H | OMe | H | H | 4-C(O)Ph |
| XXVIII-59 | 4-trifluoromethylcinnamyl | H | OMe | H | H | 4-C(O)Ph |
| XXVIII-60 | 4-cyanocinnamyl | H | OMe | H | H | 4-C(O)Ph |
| XXVIII-61 | cinnamyl | H | H | H | H | 4-F |
| XXVIII-62 | 4-chlorocinnamyl | H | H | H | H | 4-F |
| XXVIII-63 | 4-fluorocinnamyl | H | H | H | H | 4-F |
| XXVIII-64 | 4-trifluoromethylcinnamyl | H | H | H | H | 4-F |
| XXVIII-65 | 4-cyanocinnamyl | H | H | H | H | 4-F |
| XXVIII-66 | cinnamyl | H | Cl | H | H | 4-F |
| XXVIII-67 | 4-chlorocinnamyl | H | Cl | H | H | 4-F |
| XXVIII-68 | 4-fluorocinnamyl | H | Cl | H | H | 4-F |
| XXVIII-69 | 4-trifluoromethylcinnamyl | H | Cl | H | H | 4-F |
| XXVIII-70 | 4-cyanocinnamyl | H | Cl | H | H | 4-F |
| XXVIII-71 | cinnamyl | H | F | H | H | 4-F |
| XXVIII-72 | 4-chlorocinnamyl | H | F | H | H | 4-F |
| XXVIII-73 | 4-fluorocinnamyl | H | F | H | H | 4-F |
| XXVIII-74 | 4-trifluoromethylcinnamyl | H | F | H | H | 4-F |
| XXVIII-75 | 4-cyanocinnamyl | H | F | H | H | 4-F |
| XXVIII-76 | cinnamyl | H | H | F | H | 4-F |
| XXVIII-77 | 4-chlorocinnamyl | H | H | F | H | 4-F |
| XXVIII-78 | 4-fluorocinnamyl | H | H | F | H | 4-F |
| XXVIII-79 | 4-trifluoromethylcinnamyl | H | H | F | H | 4-F |
| XXVIII-80 | 4-cyanocinnamyl | H | H | F | H | 4-F |
| XXVIII-81 | cinnamyl | H | F | H | F | 4-F |
| XXVIII-82 | 4-chlorocinnamyl | H | F | H | F | 4-F |
| XXVIII-83 | 4-fluorocinnamyl | H | F | H | F | 4-F |
| XXVIII-84 | 4-trifluoromethylcinnamyl | H | F | H | F | 4-F |
| XXVIII-85 | 4-cyanocinnamyl | H | F | H | F | 4-F |
| XXVIII-86 | cinnamyl | H | OMe | H | H | 4-F |

TABLE 2-continued

| Compound | R8 | R4a | R4b | R4c | R4d | (Ra)n |
|---|---|---|---|---|---|---|
| XXVIII-87 | 4-chlorocinnamyl | H | OMe | H | H | 4-F |
| XXVIII-88 | 4-fluorocinnamyl | H | OMe | H | H | 4-F |
| XXVIII-89 | 4-trifluoromethylcinnamyl | H | OMe | H | H | 4-F |
| XXVIII-90 | 4-cyanocinnamyl | H | OMe | H | H | 4-F |
| XXVIII-91 | cinnamyl | H | H | H | H | 3-CN |
| XXVIII-92 | 4-chlorocinnamyl | H | H | H | H | 3-CN |
| XXVIII-93 | 4-fluorocinnamyl | H | H | H | H | 3-CN |
| XXVIII-94 | 4-trifluoromethylcinnamyl | H | H | H | H | 3-CN |
| XXVIII-95 | 4-cyanocinnamyl | H | H | H | H | 3-CN |
| XXVIII-96 | cinnamyl | H | Cl | H | H | 3-CN |
| XXVIII-97 | 4-chlorocinnamyl | H | Cl | H | H | 3-CN |
| XXVIII-98 | 4-fluorocinnamyl | H | Cl | H | H | 3-CN |
| XXVIII-99 | 4-trifluoromethylcinnamyl | H | Cl | H | H | 3-CN |
| XXVIII-100 | 4-cyanocinnamyl | H | Cl | H | H | 3-CN |
| XXVIII-101 | cinnamyl | H | F | H | H | 3-CN |
| XXVIII-102 | 4-chlorocinnamyl | H | F | H | H | 3-CN |
| XXVIII-103 | 4-fluorocinnamyl | H | F | H | H | 3-CN |
| XXVIII-104 | 4-trifluoromethylcinnamyl | H | F | H | H | 3-CN |
| XXVIII-105 | 4-cyanocinnamyl | H | F | H | H | 3-CN |
| XXVIII-106 | cinnamyl | H | H | F | H | 3-CN |
| XXVIII-107 | 4-chlorocinnamyl | H | H | F | H | 3-CN |
| XXVIII-108 | 4-fluorocinnamyl | H | H | F | H | 3-CN |
| XXVIII-109 | 4-trifluoromethylcinnamyl | H | H | F | H | 3-CN |
| XXVIII-110 | 4-cyanocinnamyl | H | H | F | H | 3-CN |
| XXVIII-111 | cinnamyl | H | F | H | F | 3-CN |
| XXVIII-112 | 4-chlorocinnamyl | H | F | H | F | 3-CN |
| XXVIII-113 | 4-fluorocinnamyl | H | F | H | F | 3-CN |
| XXVIII-114 | 4-trifluoromethylcinnamyl | H | F | H | F | 3-CN |
| XXVIII-115 | 4-cyanocinnamyl | H | F | H | F | 3-CN |
| XXVIII-116 | cinnamyl | H | OMe | H | H | 3-CN |
| XXVIII-117 | 4-chlorocinnamyl | H | OMe | H | H | 3-CN |
| XXVIII-118 | 4-fluorocinnamyl | H | OMe | H | H | 3-CN |
| XXVIII-119 | 4-trifluoromethylcinnamyl | H | OMe | H | H | 3-CN |
| XXVIII-120 | 4-cyanocinnamyl | H | OMe | H | H | 3-CN |
| XXVIII-121 | cinnamyl | H | H | H | H | 4-n-Pr |
| XXVIII-122 | 4-chlorocinnamyl | H | H | H | H | 4-n-Pr |
| XXVIII-123 | 4-fluorocinnamyl | H | H | H | H | 4-n-Pr |
| XXVIII-124 | 4-trifluoromethylcinnamyl | H | H | H | H | 4-n-Pr |
| XXVIII-125 | 4-cyanocinnamyl | H | H | H | H | 4-n-Pr |
| XXVIII-126 | cinnamyl | H | Cl | H | H | 4-n-Pr |
| XXVIII-127 | 4-chlorocinnamyl | H | Cl | H | H | 4-n-Pr |
| XXVIII-128 | 4-fluorocinnamyl | H | Cl | H | H | 4-n-Pr |
| XXVIII-129 | 4-trifluoromethylcinnamyl | H | Cl | H | H | 4-n-Pr |
| XXVIII-130 | 4-cyanocinnamyl | H | Cl | H | H | 4-n-Pr |
| XXVIII-131 | cinnamyl | H | F | H | H | 4-n-Pr |
| XXVIII-132 | 4-chlorocinnamyl | H | F | H | H | 4-n-Pr |
| XXVIII-133 | 4-fluorocinnamyl | H | F | H | H | 4-n-Pr |
| XXVIII-134 | 4-trifluoromethylcinnamyl | H | F | H | H | 4-n-Pr |
| XXVIII-135 | 4-cyanocinnamyl | H | F | H | H | 4-n-Pr |
| XXVIII-136 | cinnamyl | H | H | F | H | 4-n-Pr |
| XXVIII-137 | 4-chlorocinnamyl | H | H | F | H | 4-n-Pr |
| XXVIII-138 | 4-fluorocinnamyl | H | H | F | H | 4-n-Pr |
| XXVIII-139 | 4-trifluoromethylcinnamyl | H | H | F | H | 4-n-Pr |
| XXVIII-140 | 4-cyanocinnamyl | H | H | F | H | 4-n-Pr |
| XXVIII-141 | cinnamyl | H | F | H | F | 4-n-Pr |
| XXVIII-142 | 4-chlorocinnamyl | H | F | H | F | 4-n-Pr |
| XXVIII-143 | 4-fluorocinnamyl | H | F | H | F | 4-n-Pr |
| XXVIII-144 | 4-trifluoromethylcinnamyl | H | F | H | F | 4-n-Pr |
| XXVIII-145 | 4-cyanocinnamyl | H | F | H | F | 4-n-Pr |
| XXVIII-146 | cinnamyl | H | OMe | H | H | 4-n-Pr |
| XXVIII-147 | 4-chlorocinnamyl | H | OMe | H | H | 4-n-Pr |
| XXVIII-148 | 4-fluorocinnamyl | H | OMe | H | H | 4-n-Pr |
| XXVIII-149 | 4-trifluoromethylcinnamyl | H | OMe | H | H | 4-n-Pr |
| XXVIII-150 | 4-cyanocinnamyl | H | OMe | H | H | 4-n-Pr |
| XXVIII-151 | cinnamyl | H | H | H | H | 2-OMe-4-SMe |
| XXVIII-152 | 4-chlorocinnamyl | H | H | H | H | 2-OMe-4-SMe |
| XXVIII-153 | 4-fluorocinnamyl | H | H | H | H | 2-OMe-4-SMe |
| XXVIII-154 | 4-trifluoromethylcinnamyl | H | H | H | H | 2-OMe-4-SMe |
| XXVIII-155 | 4-cyanocinnamyl | H | H | H | H | 2-OMe-4-SMe |
| XXVIII-156 | cinnamyl | H | Cl | H | H | 2-OMe-4-SMe |
| XXVIII-157 | 4-chlorocinnamyl | H | Cl | H | H | 2-OMe-4-SMe |
| XXVIII-158 | 4-fluorocinnamyl | H | Cl | H | H | 2-OMe-4-SMe |
| XXVIII-159 | 4-trifluoromethylcinnamyl | H | Cl | H | H | 2-OMe-4-SMe |
| XXVIII-160 | 4-cyanocinnamyl | H | Cl | H | H | 2-OMe-4-SMe |
| XXVIII-161 | cinnamyl | H | F | H | H | 2-OMe-4-SMe |
| XXVIII-162 | 4-chlorocinnamyl | H | F | H | H | 2-OMe-4-SMe |
| XXVIII-163 | 4-fluorocinnamyl | H | F | H | H | 2-OMe-4-SMe |
| XXVIII-164 | 4-trifluoromethylcinnamyl | H | F | H | H | 2-OMe-4-SMe |

TABLE 2-continued

| Compound | R⁸ | R⁴ᵃ | R⁴ᵇ | R⁴ᶜ | R⁴ᵈ | (Rᵃ)ₙ |
|---|---|---|---|---|---|---|
| XXVIII-165 | 4-cyanocinnamyl | H | F | H | H | 2-OMe-4-SMe |
| XXVIII-166 | cinnamyl | H | H | F | H | 2-OMe-4-SMe |
| XXVIII-167 | 4-chlorocinnamyl | H | H | F | H | 2-OMe-4-SMe |
| XXVIII-168 | 4-fluorocinnamyl | H | H | F | H | 2-OMe-4-SMe |
| XXVIII-169 | 4-trifluoromethylcinnamyl | H | H | F | H | 2-OMe-4-SMe |
| XXVIII-170 | 4-cyanocinnamyl | H | H | F | H | 2-OMe-4-SMe |
| XXVIII-171 | cinnamyl | H | F | H | F | 2-OMe-4-SMe |
| XXVIII-172 | 4-chlorocinnamyl | H | F | H | F | 2-OMe-4-SMe |
| XXVIII-173 | 4-fluorocinnamyl | H | F | H | F | 2-OMe-4-SMe |
| XXVIII-174 | 4-trifluoromethylcinnamyl | H | F | H | F | 2-OMe-4-SMe |
| XXVIII-175 | 4-cyanocinnamyl | H | F | H | F | 2-OMe-4-SMe |
| XXVIII-176 | cinnamyl | H | OMe | H | H | 2-OMe-4-SMe |
| XXVIII-177 | 4-chlorocinnamyl | H | OMe | H | H | 2-OMe-4-SMe |
| XXVIII-178 | 4-fluorocinnamyl | H | OMe | H | H | 2-OMe-4-SMe |
| XXVIII-179 | 4-trifluoromethylcinnamyl | H | OMe | H | H | 2-OMe-4-SMe |
| XXVIII-180 | 4-cyanocinnamyl | H | OMe | H | H | 2-OMe-4-SMe |
| XXVIII-181 | cinnamyl | H | H | H | H | 2-Cl-4-SO$_2$Me |
| XXVIII-182 | 4-chlorocinnamyl | H | H | H | H | 2-Cl-4-SO$_2$Me |
| XXVIII-183 | 4-fluorocinnamyl | H | H | H | H | 2-Cl-4-SO$_2$Me |
| XXVIII-184 | 4-trifluoromethylcinnamyl | H | H | H | H | 2-Cl-4-SO$_2$Me |
| XXVIII-185 | 4-cyanocinnamyl | H | H | H | H | 2-Cl-4-SO$_2$Me |
| XXVIII-186 | cinnamyl | H | Cl | H | H | 2-Cl-4-SO$_2$Me |
| XXVIII-187 | 4-chlorocinnamyl | H | Cl | H | H | 2-Cl-4-SO$_2$Me |
| XXVIII-188 | 4-fluorocinnamyl | H | Cl | H | H | 2-Cl-4-SO$_2$Me |
| XXVIII-189 | 4-trifluoromethylcinnamyl | H | Cl | H | H | 2-Cl-4-SO$_2$Me |
| XXVIII-190 | 4-cyanocinnamyl | H | Cl | H | H | 2-Cl-4-SO$_2$Me |
| XXVIII-191 | cinnamyl | H | F | H | H | 2-Cl-4-SO$_2$Me |
| XXVIII-192 | 4-chlorocinnamyl | H | F | H | H | 2-Cl-4-SO$_2$Me |
| XXVIII-193 | 4-fluorocinnamyl | H | F | H | H | 2-Cl-4-SO$_2$Me |
| XXVIII-194 | 4-trifluoromethylcinnamyl | H | F | H | H | 2-Cl-4-SO$_2$Me |
| XXVIII-195 | 4-cyanocinnamyl | H | F | H | H | 2-Cl-4-SO$_2$Me |
| XXVIII-196 | cinnamyl | H | H | F | H | 2-Cl-4-SO$_2$Me |
| XXVIII-197 | 4-chlorocinnamyl | H | H | F | H | 2-Cl-4-SO$_2$Me |
| XXVIII-198 | 4-fluorocinnamyl | H | H | F | H | 2-Cl-4-SO$_2$Me |
| XXVIII-199 | 4-trifluoromethylcinnamyl | H | H | F | H | 2-Cl-4-SO$_2$Me |
| XXVIII-200 | 4-cyanocinnamyl | H | H | F | H | 2-Cl-4-SO$_2$Me |
| XXVIII-201 | cinnamyl | H | F | H | F | 2-Cl-4-SO$_2$Me |
| XXVIII-202 | 4-chlorocinnamyl | H | F | H | F | 2-Cl-4-SO$_2$Me |
| XXVIII-203 | 4-fluorocinnamyl | H | F | H | F | 2-Cl-4-SO$_2$Me |
| XXVIII-204 | 4-trifluoromethylcinnamyl | H | F | H | F | 2-Cl-4-SO$_2$Me |
| XXVIII-205 | 4-cyanocinnamyl | H | F | H | F | 2-Cl-4-SO$_2$Me |
| XXVIII-206 | cinnamyl | H | OMe | H | H | 2-Cl-4-SO$_2$Me |
| XXVIII-207 | 4-chlorocinnamyl | H | OMe | H | H | 2-Cl-4-SO$_2$Me |
| XXVIII-208 | 4-fluorocinnamyl | H | OMe | H | H | 2-Cl-4-SO$_2$Me |
| XXVIII-209 | 4-trifluoromethylcinnamyl | H | OMe | H | H | 2-Cl-4-SO$_2$Me |
| XXVIII-210 | 4-cyanocinnamyl | H | OMe | H | H | 2-Cl-4-SO$_2$Me |
| XXVIII-211 | cinnamyl | H | H | H | H | 4-n-PrO |
| XXVIII-212 | 4-chlorocinnamyl | H | H | H | H | 4-n-PrO |
| XXVIII-213 | 4-fluorocinnamyl | H | H | H | H | 4-n-PrO |
| XXVIII-214 | 4-trifluoromethylcinnamyl | H | H | H | H | 4-n-PrO |
| XXVIII-215 | 4-cyanocinnamyl | H | H | H | H | 4-n-PrO |
| XXVIII-216 | cinnamyl | H | Cl | H | H | 4-n-PrO |
| XXVIII-217 | 4-chlorocinnamyl | H | Cl | H | H | 4-n-PrO |
| XXVIII-218 | 4-fluorocinnamyl | H | Cl | H | H | 4-n-PrO |
| XXVIII-219 | 4-trifluoromethylcinnamyl | H | Cl | H | H | 4-n-PrO |
| XXVIII-220 | 4-cyanocinnamyl | H | Cl | H | H | 4-n-PrO |
| XXVIII-221 | cinnamyl | H | F | H | H | 4-n-PrO |
| XXVIII-222 | 4-chlorocinnamyl | H | F | H | H | 4-n-PrO |
| XXVIII-223 | 4-fluorocinnamyl | H | F | H | H | 4-n-PrO |
| XXVIII-224 | 4-trifluoromethylcinnamyl | H | F | H | H | 4-n-PrO |
| XXVIII-225 | 4-cyanocinnamyl | H | F | H | H | 4-n-PrO |
| XXVIII-226 | cinnamyl | H | H | F | H | 4-n-PrO |
| XXVIII-227 | 4-chlorocinnamyl | H | H | F | H | 4-n-PrO |
| XXVIII-228 | 4-fluorocinnamyl | H | H | F | H | 4-n-PrO |
| XXVIII-229 | 4-trifluoromethylcinnamyl | H | H | F | H | 4-n-PrO |
| XXVIII-230 | 4-cyanocinnamyl | H | H | F | H | 4-n-PrO |
| XXVIII-231 | cinnamyl | H | F | H | F | 4-n-PrO |
| XXVIII-232 | 4-chlorocinnamyl | H | F | H | F | 4-n-PrO |
| XXVIII-233 | 4-fluorocinnamyl | H | F | H | F | 4-n-PrO |
| XXVIII-234 | 4-trifluoromethylcinnamyl | H | F | H | F | 4-n-PrO |
| XXVIII-235 | 4-cyanocinnamyl | H | F | H | F | 4-n-PrO |
| XXVIII-236 | cinnamyl | H | OMe | H | H | 4-n-PrO |
| XXVIII-237 | 4-chlorocinnamyl | H | OMe | H | H | 4-n-PrO |
| XXVIII-238 | 4-fluorocinnamyl | H | OMe | H | H | 4-n-PrO |
| XXVIII-239 | 4-trifluoromethylcinnamyl | H | OMe | H | H | 4-n-PrO |
| XXVIII-240 | 4-cyanocinnamyl | H | OMe | H | H | 4-n-PrO |
| XXVIII-241 | cinnamyl | H | H | H | H | 2-Me |
| XXVIII-242 | 4-chlorocinnamyl | H | H | H | H | 2-Me |

TABLE 2-continued

| Compound | R8 | R4a | R4b | R4c | R4d | (Ra)n |
|---|---|---|---|---|---|---|
| XXVIII-243 | 4-fluorocinnamyl | H | H | H | H | 2-Me |
| XXVIII-244 | 4-trifluoromethylcinnamyl | H | H | H | H | 2-Me |
| XXVIII-245 | 4-cyanocinnamyl | H | H | H | H | 2-Me |
| XXVIII-246 | cinnamyl | H | Cl | H | H | 2-Me |
| XXVIII-247 | 4-chlorocinnamyl | H | Cl | H | H | 2-Me |
| XXVIII-248 | 4-fluorocinnamyl | H | Cl | H | H | 2-Me |
| XXVIII-249 | 4-trifluoromethylcinnamyl | H | Cl | H | H | 2-Me |
| XXVIII-250 | 4-cyanocinnamyl | H | Cl | H | H | 2-Me |
| XXVIII-251 | cinnamyl | H | F | H | H | 2-Me |
| XXVIII-252 | 4-chlorocinnamyl | H | F | H | H | 2-Me |
| XXVIII-253 | 4-fluorocinnamyl | H | F | H | H | 2-Me |
| XXVIII-254 | 4-trifluoromethylcinnamyl | H | F | H | H | 2-Me |
| XXVIII-255 | 4-cyanocinnamyl | H | F | H | H | 2-Me |
| XXVIII-256 | cinnamyl | H | H | F | H | 2-Me |
| XXVIII-257 | 4-chlorocinnamyl | H | H | F | H | 2-Me |
| XXVIII-258 | 4-fluorocinnamyl | H | H | F | H | 2-Me |
| XXVIII-259 | 4-trifluoromethylcinnamyl | H | H | F | H | 2-Me |
| XXVIII-260 | 4-cyanocinnamyl | H | H | F | H | 2-Me |
| XXVIII-261 | cinnamyl | H | F | H | F | 2-Me |
| XXVIII-262 | 4-chlorocinnamyl | H | F | H | F | 2-Me |
| XXVIII-263 | 4-fluorocinnamyl | H | F | H | F | 2-Me |
| XXVIII-264 | 4-trifluoromethylcinnamyl | H | F | H | F | 2-Me |
| XXVIII-265 | 4-cyanocinnamyl | H | F | H | F | 2-Me |
| XXVIII-266 | cinnamyl | H | OMe | H | H | 2-Me |
| XXVIII-267 | 4-chlorocinnamyl | H | OMe | H | H | 2-Me |
| XXVIII-268 | 4-fluorocinnamyl | H | OMe | H | H | 2-Me |
| XXVIII-269 | 4-trifluoromethylcinnamyl | H | OMe | H | H | 2-Me |
| XXVIII-270 | 4-cyanocinnamyl | H | OMe | H | H | 2-Me |

Table XXIX provides 214 compounds of formula Iac

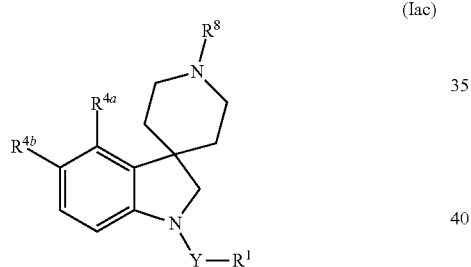

(Iac)

wherein the values of $R^8$, $R^{4a}$, $R^{4b}$, Y and $R^1$ are given in Table 3

TABLE 3

| Compound | R8 | R4a | R4b | Y | R1 |
|---|---|---|---|---|---|
| XXIX-1 | 2-(benzoxazolyl)methyl | H | Cl | C(O) | 2-chloropyrid-4-yl |
| XXIX-2 | 2-(benzoxazolyl)methyl | H | F | C(O) | 2-chloropyrid-4-yl |
| XXIX-3 | 2-(benzoxazolyl)methyl | H | Cl | bond | carbomethoxy |
| XXIX-4 | 2-(benzoxazolyl)methyl | H | F | bond | carbomethoxy |
| XXIX-5 | 2-(benzoxazolyl)methyl | H | Cl | bond | acetyl |
| XXIX-6 | 2-(benzoxazolyl)methyl | H | F | bond | acetyl |
| XXIX-7 | 2-methyl-3-(3',4'-methylenedioxyphenyl)prop-2-enyl | H | Cl | C(O) | 2-chloropyrid-4-yl |
| XXIX-8 | 2-methyl-3-(3',4'-methylenedioxyphenyl)prop-2-enyl | H | F | C(O) | 2-chloropyrid-4-yl |
| XXIX-9 | 2-methyl-3-(3',4'-methylenedioxyphenyl)prop-2-enyl | H | Cl | bond | Carbomethoxy |
| XXIX-10 | 2-methyl-3-(3',4'-methylenedioxyphenyl)prop-2-enyl | H | F | bond | carbomethoxy |
| XXIX-11 | 2-methyl-3-(3',4'-methylenedioxyphenyl)prop-2-enyl | H | Cl | bond | acetyl |
| XXIX-12 | 2-methyl-3-(3',4'-methylenedioxyphenyl)prop-2-enyl | H | F | bond | acetyl |
| XXIX-13 | 3-phenylprop-2-ynyl | H | Cl | C(O) | 2-chloropyrid-4-yl |

TABLE 3-continued

| | R8 | $R^{4a}$ | $R^{4b}$ | Y | R1 |
|---|---|---|---|---|---|
| XXIX-14 | 3-phenylprop-2-ynyl | H | F | C(O) | 2-chloropyrid-4-yl |
| XXIX-15 | 3-phenylprop-2-ynyl | H | Cl | bond | carbomethoxy |
| XXIX-16 | 3-phenylprop-2-ynyl | H | F | bond | carbomethoxy |
| XXIX-17 | 3-phenylprop-2-ynyl | H | Cl | bond | acetyl |
| XXIX-18 | 3-phenylprop-2-ynyl | H | F | bond | acetyl |
| XXIX-19 | trifluoroacetamido | H | Cl | C(O) | 2-chloropyrid-4-yl |
| XXIX-20 | trifluoroacetamido | H | F | C(O) | 2-chloropyrid-4-yl |
| XXIX-21 | trifluoroacetamido | H | Cl | bond | carbomethoxy |
| XXIX-22 | trifluoroacetamido | H | F | bond | carbomethoxy |
| XXIX-23 | trifluoroacetamido | H | Cl | bond | acetyl |
| XXIX-24 | trifluoroacetamido | H | F | bond | acetyl |
| XXIX-25 | 4-chlorocinnamate | H | Cl | C(O) | 2-chloropyrid-4-yl |
| XXIX-26 | 4-chlorocinnamate | H | F | C(O) | 2-chloropyrid-4-yl |
| XXIX-27 | 4-chlorocinnamate | H | Cl | bond | carbomethoxy |
| XXIX-28 | 4-chlorocinnamate | H | F | bond | carbomethoxy |
| XXIX-29 | 4-chlorocinnamate | H | Cl | bond | acetyl |
| XXIX-30 | 4-chlorocinnamate | H | F | bond | acetyl |
| XXIX-31 | 2-oxo-2-(2'-chloro-4'-methylphenyl)ethyl | H | Cl | C(O) | 2-chloropyrid-4-yl |
| XXIX-32 | 2-oxo-2-(2'-chloro-4'-methylphenyl)ethyl | H | F | C(O) | 2-chloropyrid-4-yl |
| XXIX-33 | 2-oxo-2-(2'-chloro-4'-methylphenyl)ethyl | H | Cl | bond | carbomethoxy |
| XXIX-34 | 2-oxo-2-(2'-chloro-4'-methylphenyl)ethyl | H | F | bond | carbomethoxy |
| XXIX-35 | 2-oxo-2-(2'-chloro-4'-methylphenyl)ethyl | H | Cl | bond | acetyl |
| XXIX-36 | 2-oxo-2-(2'-chloro-4'-methylphenyl)ethyl | H | F | bond | acetyl |
| XXIX-37 | 2-oxo-1,2-diphenylethyl | H | Cl | C(O) | 2-chloropyrid-4-yl |
| XXIX-38 | 2-oxo-1,2-diphenylethyl | H | F | C(O) | 2-chloropyrid-4-yl |
| XXIX-39 | 2-oxo-1,2-diphenylethyl | H | Cl | bond | carbomethoxy |
| XXIX-40 | 2-oxo-1,2-diphenylethyl | H | F | bond | carbomethoxy |
| XXIX-41 | 2-oxo-1,2-diphenylethyl | H | Cl | bond | acetyl |
| XXIX-42 | 2-oxo-1,2-diphenylethyl | H | F | bond | acetyl |
| XXIX-43 | 3,3-dichloroallyl | H | Cl | C(O) | 2-chloropyrid-4-yl |
| XXIX-44 | 3,3-dichloroallyl | H | F | C(O) | 2-chloropyrid-4-yl |
| XXIX-45 | 3,3-dichloroallyl | H | Cl | bond | carbomethoxy |
| XXIX-46 | 3,3-dichloroallyl | H | F | bond | carbomethoxy |
| XXIX-47 | 3,3-dichloroallyl | H | Cl | bond | acetyl |
| XXIX-48 | 3,3-dichloroallyl | H | F | bond | acetyl |
| XXIX-49 | t-butyloxycarbonyl | H | F | bond | H |
| XXIX-50 | t-butyloxycarbonyl | H | Cl | bond | H |
| XXIX-51 | t-butyloxycarbonyl | H | Cl | C(O) | 2-chloropyrid-4-yl |
| XXIX-52 | t-butyloxycarbonyl | H | F | C(O) | 2-chloropyrid-4-yl |

TABLE 3-continued

| | R8 | $R^{4a}$ | $R^{4b}$ | Y | R1 |
|---|---|---|---|---|---|
| XXIX-53 | t-butyloxycarbonyl | H | Cl | bond | carbomethoxy |
| XXIX-54 | t-butyloxycarbonyl | H | F | bond | carbomethoxy |
| XXIX-55 | t-butyloxycarbonyl | H | Cl | bond | acetyl |
| XXIX-56 | t-butyloxycarbonyl | H | F | bond | acetyl |
| XXIX-57 | 4-chlorocinnamyl | H | Cl | bond | 5-trifluoromethylpyrid-2-yl |
| XXIX-58 | 4-chlorocinnamyl | H | F | bond | 5-trifluoromethylpyrid-2-yl |
| XXIX-59 | 4-chlorocinnamyl | Br | H | bond | 5-trifluoromethylpyrid-2-yl |
| XXIX-60 | 4-fluorocinnamyl | H | Cl | bond | 5-trifluoromethylpyrid-2-yl |
| XXIX-61 | 4-fluorocinnamyl | H | F | bond | 5-trifluoromethylpyrid-2-yl |
| XXIX-62 | 4-fluorocinnamyl | Br | H | bond | 5-trifluoromethylpyrid-2-yl |
| XXIX-63 | 4-chlorocinnamyl | H | Cl | bond | pyrimidin-2-yl |
| XXIX-64 | 4-chlorocinnamyl | H | F | bond | pyrimidin-2-yl |
| XXIX-65 | 4-chlorocinnamyl | Br | H | bond | pyrimidin-2-yl |
| XXIX-66 | 4-fluorocinnamyl | H | Cl | bond | pyrimidin-2-yl |
| XXIX-67 | 4-fluorocinnamyl | H | F | bond | pyrimidin-2-yl |
| XXIX-68 | 4-fluorocinnamyl | Br | H | bond | pyrimidin-2-yl |
| XXIX-69 | 4-chlorocinnamyl | H | Cl | C(O) | pyrazinyl |
| XXIX-70 | 4-chlorocinnamyl | H | F | C(O) | pyrazinyl |
| XXIX-71 | 4-chlorocinnamyl | Br | H | C(O) | pyrazinyl |
| XXIX-72 | 4-fluorocinnamyl | H | Cl | C(O) | pyrazinyl |
| XXIX-73 | 4-fluorocinnamyl | H | F | C(O) | pyrazinyl |
| XXIX-74 | 4-fluorocinnamyl | Br | H | C(O) | pyrazinyl |
| XXIX-75 | 4-chlorocinnamyl | H | Cl | C(O) | 2-chloropyrid-5-yl |
| XXIX-76 | 4-chlorocinnamyl | H | F | C(O) | 2-chloropyrid-5-yl |
| XXIX-77 | 4-chlorocinnamyl | Br | H | C(O) | 2-chloropyrid-5-yl |
| XXIX-78 | 4-fluorocinnamyl | H | Cl | C(O) | 2-chloropyrid-5-yl |
| XXIX-79 | 4-fluorocinnamyl | H | F | C(O) | 2-chloropyrid-5-yl |
| XXIX-80 | 4-fluorocinnamyl | Br | H | C(O) | 2-chloropyrid-5-yl |
| XXIX-81 | 4-chlorocinnamyl | H | Cl | C(O) | 1,2,3-thiadiazol-4-yl |
| XXIX-82 | 4-chlorocinnamyl | H | F | C(O) | 1,2,3-thiadiazol-4-yl |
| XXIX-83 | 4-chlorocinnamyl | Br | H | C(O) | 1,2,3-thiadiazol-4-yl |
| XXIX-84 | 4-fluorocinnamyl | H | Cl | C(O) | 1,2,3-thiadiazol-4-yl |
| XXIX-85 | 4-fluorocinnamyl | H | F | C(O) | 1,2,3-thiadiazol-4-yl |
| XXIX-86 | 4-fluorocinnamyl | Br | H | C(O) | 1,2,3-thiadiazol-4-yl |
| XXIX-87 | 4-chlorocinnamyl | H | Cl | C(O) | 1-methyl-5-nitro-[1H]-pyrazol-4-yl |
| XXIX-88 | 4-chlorocinnamyl | H | F | C(O) | 1-methyl-5-nitro-[1H]-pyrazol-4-yl |
| XXIX-89 | 4-chlorocinnamyl | Br | H | C(O) | 1-methyl-5-nitro-[1H]-pyrazol-4-yl |
| XXIX-90 | 4-fluorocinnamyl | H | Cl | C(O) | 1-methyl-5-nitro-[1H]-pyrazol-4-yl |
| XXIX-91 | 4-fluorocinnamyl | H | F | C(O) | 1-methyl-5-nitro-[1H]-pyrazol-4-yl |

TABLE 3-continued

|  | R8 | $R^{4a}$ | $R^{4b}$ | Y | R1 |
|---|---|---|---|---|---|
| XXIX-92 | 4-fluorocinnamyl | Br | H | C(O) | 1-methyl-5-nitro-[1H]-pyrazol-4-yl |
| XXIX-93 | 4-chlorocinnamyl | H | Cl | C(O) | 5-carbomethoxy-pyrid-2-yl |
| XXIX-94 | 4-chlorocinnamyl | H | F | C(O) | 5-carbomethoxy-pyrid-2-yl |
| XXIX-95 | 4-chlorocinnamyl | Br | H | C(O) | 5-carbomethoxy-pyrid-2-yl |
| XXIX-96 | 4-fluorocinnamyl | H | Cl | C(O) | 5-carbomethoxy-pyrid-2-yl |
| XXIX-97 | 4-fluorocinnamyl | H | F | C(O) | 5-carbomethoxy-pyrid-2-yl |
| XXIX-98 | 4-fluorocinnamyl | Br | H | C(O) | 5-carbomethoxy-pyrid-2-yl |
| XXIX-99 | 4-chlorocinnamyl | H | Cl | C(O) | 4-chloropyrid-2-yl |
| XXIX-100 | 4-chlorocinnamyl | H | F | C(O) | 4-chloropyrid-2-yl |
| XXIX-101 | 4-chlorocinnamyl | Br | H | C(O) | 4-chloropyrid-2-yl |
| XXIX-102 | 4-fluorocinnamyl | H | Cl | C(O) | 4-chloropyrid-2-yl |
| XXIX-103 | 4-fluorocinnamyl | H | F | C(O) | 4-chloropyrid-2-yl |
| XXIX-104 | 4-fluorocinnamyl | Br | H | C(O) | 4-chloropyrid-2-yl |
| XXIX-105 | 4-chlorocinnamyl | H | Cl | C(O) | 2-methyl-6-trifluoromethylpyrid-3-yl |
| XXIX-106 | 4-chlorocinnamyl | H | F | C(O) | 2-methyl-6-trifluoromethylpyrid-3-yl |
| XXIX-107 | 4-chlorocinnamyl | Br | H | C(O) | 2-methyl-6-trifluoromethylpyrid-3-yl |
| XXIX-108 | 4-fluorocinnamyl | H | Cl | C(O) | 2-methyl-6-trifluoromethylpyrid-3-yl |
| XXIX-109 | 4-fluorocinnamyl | H | F | C(O) | 2-methyl-6-trifluoromethylpyrid-3-yl |
| XXIX-110 | 4-fluorocinnamyl | Br | H | C(O) | 2-methyl-6-trifluoromethylpyrid-3-yl |
| XXIX-111 | 4-chlorocinnamyl | H | Cl | C(O) | 5-methylisoxazol-3-yl |
| XXIX-112 | 4-chlorocinnamyl | H | F | C(O) | 5-methylisoxazol-3-yl |
| XXIX-113 | 4-chlorocinnamyl | Br | H | C(O) | 5-methylisoxazol-3-yl |
| XXIX-114 | 4-fluorocinnamyl | H | Cl | C(O) | 5-methylisoxazol-3-yl |
| XXIX-115 | 4-fluorocinnamyl | H | F | C(O) | 5-methylisoxazol-3-yl |
| XXIX-116 | 4-fluorocinnamyl | Br | H | C(O) | 5-methylisoxazol-3-yl |
| XXIX-117 | 4-chlorocinnamyl | H | Cl | C(O) | (pyrid-4-yl)methyl |
| XXIX-118 | 4-chlorocinnamyl | H | F | C(O) | (pyrid-4-yl)methyl |
| XXIX-119 | 4-chlorocinnamyl | Br | H | C(O) | (pyrid-4-yl)methyl |
| XXIX-120 | 4-fluorocinnamyl | H | Cl | C(O) | (pyrid-4-yl)methyl |
| XXIX-121 | 4-fluorocinnamyl | H | F | C(O) | (pyrid-4-yl)methyl |
| XXIX-122 | 4-fluorocinnamyl | Br | H | C(O) | (pyrid-4-yl)methyl |
| XXIX-123 | 4-chlorocinnamyl | H | Cl | C(O) | (thiophen-2-yl)methyl |
| XXIX-124 | 4-chlorocinnamyl | H | F | C(O) | (thiophen-2-yl)methyl |
| XXIX-125 | 4-chlorocinnamyl | Br | H | C(O) | (thiophen-2-yl)methyl |
| XXIX-126 | 4-fluorocinnamyl | H | Cl | C(O) | (thiophen-2-yl)methyl |
| XXIX-127 | 4-fluorocinnamyl | H | F | C(O) | (thiophen-2-yl)methyl |
| XXIX-128 | 4-fluorocinnamyl | Br | H | C(O) | (thiophen-2-yl)methyl |
| XXIX-129 | 4-chlorocinnamyl | H | Cl | C(O) | cyclopentyl |
| XXIX-130 | 4-chlorocinnamyl | H | F | C(O) | cyclopentyl |

TABLE 3-continued

|  | R8 | R^{4a} | R^{4b} | Y | R1 |
|---|---|---|---|---|---|
| XXIX-131 | 4-chlorocinnamyl | Br | H | C(O) | cyclopentyl |
| XXIX-132 | 4-fluorocinnamyl | H | Cl | C(O) | cyclopentyl |
| XXIX-133 | 4-fluorocinnamyl | H | F | C(O) | cyclopentyl |
| XXIX-134 | 4-fluorocinnamyl | Br | H | C(O) | cyclopentyl |
| XXIX-135 | 4-chlorocinnamyl | H | Cl | C(O) | acetylaminomethyl |
| XXIX-136 | 4-chlorocinnamyl | H | F | C(O) | acetylaminomethyl |
| XXIX-137 | 4-chlorocinnamyl | Br | H | C(O) | acetylaminomethyl |
| XXIX-138 | 4-fluorocinnamyl | H | Cl | C(O) | acetylaminomethyl |
| XXIX-139 | 4-fluorocinnamyl | H | F | C(O) | acetylaminomethyl |
| XXIX-140 | 4-fluorocinnamyl | Br | H | C(O) | acetylaminomethyl |
| XXIX-141 | 4-chlorocinnamyl | H | Cl | $SO_2$ | 4-acetylaminophenyl |
| XXIX-142 | 4-chlorocinnamyl | H | F | $SO_2$ | 4-acetylaminophenyl |
| XXIX-143 | 4-chlorocinnamyl | Br | H | $SO_2$ | 4-acetylaminophenyl |
| XXIX-144 | 4-fluorocinnamyl | H | Cl | $SO_2$ | 4-acetylaminophenyl |
| XXIX-145 | 4-fluorocinnamyl | H | F | $SO_2$ | 4-acetylaminophenyl |
| XXIX-146 | 4-fluorocinnamyl | Br | H | $SO_2$ | 4-acetylaminophenyl |
| XXIX-147 | 4-chlorocinnamyl | H | Cl | $SO_2$ | 3,5-dimethylisoxazol-4-yl |
| XXIX-148 | 4-chlorocinnamyl | H | F | $SO_2$ | 3,5-dimethylisoxazol-4-yl |
| XXIX-149 | 4-chlorocinnamyl | Br | H | $SO_2$ | 3,5-dimethylisoxazol-4-yl |
| XXIX-150 | 4-fluorocinnamyl | H | Cl | $SO_2$ | 3,5-dimethylisoxazol-4-yl |
| XXIX-151 | 4-fluorocinnamyl | H | F | $SO_2$ | 3,5-dimethylisoxazol-4-yl |
| XXIX-152 | 4-fluorocinnamyl | Br | H | $SO_2$ | 3,5-dimethylisoxazol-4-yl |
| XXIX-153 | 4-chlorocinnamyl | H | Cl | C(O) | (2-methoxyphenyl)amino |
| XXIX-154 | 4-chlorocinnamyl | H | F | C(O) | (2-methoxyphenyl)amino |
| XXIX-155 | 4-chlorocinnamyl | Br | H | C(O) | (2-methoxyphenyl)amino |
| XXIX-156 | 4-fluorocinnamyl | H | Cl | C(O) | (2-methoxyphenyl)amino |
| XXIX-157 | 4-fluorocinnamyl | H | F | C(O) | (2-methoxyphenyl)amino |
| XXIX-158 | 4-fluorocinnamyl | Br | H | C(O) | (2-methoxyphenyl)amino |
| XXIX-159 | 4-chlorocinnamyl | H | F | C(O) | cyclohexen-1-yl |
| XXIX-160 | 4-chlorocinnamyl | H | Cl | C(O) | cyclohexen-1-yl |
| XXIX-161 | 4-chlorocinnamyl | Br | H | C(O) | cyclohexen-1-yl |
| XXIX-162 | 4-fluorocinnamyl | H | Cl | C(O) | cyclohexen-1-yl |
| XXIX-163 | 4-fluorocinnamyl | H | F | C(O) | cyclohexen-1-yl |
| XXIX-164 | 4-fluorocinnamyl | Br | H | C(O) | cyclohexen-1-yl |
| XXIX-165 | 4-chlorocinnamyl | H | F | C(O) | quinolin-3-yl |
| XXIX-166 | 4-chlorocinnamyl | H | Cl | C(O) | quinolin-3-yl |
| XXIX-167 | 4-chlorocinnamyl | Br | H | C(O) | quinolin-3-yl |
| XXIX-168 | 4-fluorocinnamyl | H | Cl | C(O) | quinolin-3-yl |
| XXIX-169 | 4-fluorocinnamyl | H | F | C(O) | quinolin-3-yl |

TABLE 3-continued

|  | R8 | R$^{4a}$ | R$^{4b}$ | Y | R1 |
|---|---|---|---|---|---|
| XXIX-170 | 4-fluorocinnamyl | Br | H | C(O) | quinolin-3-yl |
| XXIX-171 | 4-chlorocinnamyl | H | F | C(O) | benzothiophen-2-yl |
| XXIX-172 | 4-chlorocinnamyl | H | Cl | C(O) | benzothiophen-2-yl |
| XXIX-173 | 4-chlorocinnamyl | Br | H | C(O) | benzothiophen-2-yl |
| XXIX-174 | 4-fluorocinnamyl | H | Cl | C(O) | benzothiophen-2-yl |
| XXIX-175 | 4-fluorocinnamyl | H | F | C(O) | benzothiophen-2-yl |
| XXIX-176 | 4-fluorocinnamyl | Br | H | C(O) | benzothiophen-2-yl |
| XXIX-177 | 4-chlorocinnamyl | H | F | C(O) | 5-nitro-[1H]-pyrazol-3-yl |
| XXIX-178 | 4-chlorocinnamyl | H | Cl | C(O) | 5-nitro-[1H]-pyrazol-3-yl |
| XXIX-179 | 4-chlorocinnamyl | Br | H | C(O) | 5-nitro-[1H]-pyrazol-3-yl |
| XXIX-180 | 4-fluorocinnamyl | H | Cl | C(O) | 5-nitro-[1H]-pyrazol-3-yl |
| XXIX-181 | 4-fluorocinnamyl | H | F | C(O) | 5-nitro-[1H]-pyrazol-3-yl |
| XXIX-182 | 4-fluorocinnamyl | Br | H | C(O) | 5-nitro-[1H]-pyrazol-3-yl |
| XXIX-183 | 4-chlorocinnamyl | H | F | C(O) | ([1H]-tetrazol-1-yl)methyl |
| XXIX-184 | 4-chlorocinnamyl | H | Cl | C(O) | ([1H]-tetrazol-1-yl)methyl |
| XXIX-185 | 4-chlorocinnamyl | Br | H | C(O) | ([1H]-tetrazol-1-yl)methyl |
| XXIX-186 | 4-fluorocinnamyl | H | Cl | C(O) | ([1H]-tetrazol-1-yl)methyl |
| XXIX-187 | 4-fluorocinnamyl | H | F | C(O) | ([1H]-tetrazol-1-yl)methyl |
| XXIX-188 | 4-fluorocinnamyl | Br | H | C(O) | ([1H]-tetrazol-1-yl)methyl |
| XXIX-189 | 4-chlorocinnamyl | H | Cl | bond | benzyl |
| XXIX-190 | 4-chlorocinnamyl | H | F | bond | benzyl |
| XXIX-191 | 4-chlorocinnamyl | Br | H | bond | benzyl |
| XXIX-192 | 4-fluorocinnamyl | H | Cl | bond | benzyl |
| XXIX-193 | 4-fluorocinnamyl | H | F | bond | benzyl |
| XXIX-194 | 4-fluorocinnamyl | Br | H | bond | benzyl |
| XXIX-195 | 4-chlorocinnamyl | H | F | C(O) | (4-cyanophenyl)amino |
| XXIX-196 | 4-chlorocinnamyl | H | Cl | C(O) | (4-cyanophenyl)amino |
| XXIX-197 | 4-chlorocinnamyl | Br | H | C(O) | (4-cyanophenyl)amino |
| XXIX-198 | 4-fluorocinnamyl | H | Cl | C(O) | (4-cyanophenyl)amino |
| XXIX-199 | 4-fluorocinnamyl | H | F | C(O) | (4-cyanophenyl)amino |
| XXIX-200 | 4-fluorocinnamyl | Br | H | C(O) | (4-cyanophenyl)amino |
| XXIX-201 | 4-chlorocinnamyl | H | Me$_3$SiCC | C(O) | 2-chloropyrid-4-yl |
| XXIX-202 | 4-fluorocinnamyl | H | Me$_3$SiCC | C(O) | 2-chloropyrid-4-yl |
| XXIX-203 | 4-chlorocinnamyl | H | Me$_3$SiCC | bond | carbomethoxy |
| XXIX-204 | 4-fluorocinnamyl | H | Me$_3$SiCC | bond | carbomethoxy |
| XXIX-205 | 4-chlorocinnamyl | H | Me$_3$SiCC | bond | acetyl |
| XXIX-206 | 4-fluorocinnamyl | H | Me$_3$SiCC | bond | acetyl |
| XXIX-207 | 4-chlorocinnamyl | H | OMe | SO$_2$ | n-butyl |
| XXIX-208 | 4-chlorocinnamyl | H | F | SO$_2$ | n-butyl |

TABLE 3-continued

| | R8 | $R^{4a}$ | $R^{4b}$ | Y | R1 |
|---|---|---|---|---|---|
| XXIX-209 | 4-chlorocinnamyl | H | Cl | $SO_2$ | n-butyl |
| XXIX-210 | 4-chlorocinnamyl | Br | H | $SO_2$ | n-butyl |
| XXIX-211 | 4-fluorocinnamyl | H | OMe | $SO_2$ | n-butyl |
| XXIX-212 | 4-fluorocinnamyl | H | Cl | $SO_2$ | n-butyl |
| XXIX-213 | 4-fluorocinnamyl | H | F | $SO_2$ | n-butyl |
| XXIX-214 | 4-fluorocinnamyl | Br | H | $SO_2$ | n-butyl |

Table XXX provides 121 compounds of formula Iad

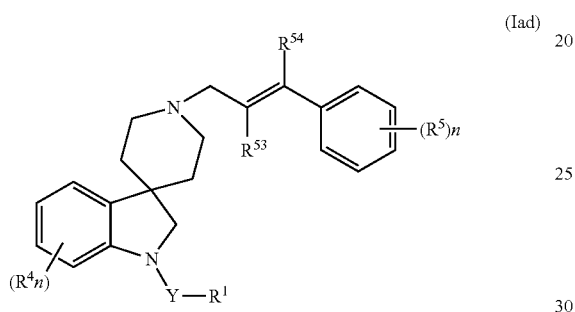

(Iad)

| | $R^4n$ | R53 | R54 | $R^s n$ | Y | R1 |
|---|---|---|---|---|---|---|
| XXX-1 | 6-$OCF_3$ | H | H | 4-Cl | C(O) | Me |
| XXX-2 | 6-$OCF_3$ | H | H | 4-Cl | C(O) | 2-chloropyrid-4-yl |
| XXX-3 | 4-$OCF_3$ | H | H | 4-Cl | C(O) | Me |
| XXX-4 | 6-$OCF_2CHF_2$ | H | H | 4-Cl | C(O) | Me |
| XXX-5 | 4-$OCF_2CHF_2$ | H | H | 4-Cl | C(O) | Me |
| XXX-6 | 4-$OCF_3$ | H | H | 4-Cl | C(O) | 2-chloropyrid-4-yl |
| XXX-7 | 6-$OCF_2CHF_2$ | H | H | 4-Cl | C(O) | 2-chloropyrid-4-yl |
| XXX-8 | 4-$OCF_2CHF_2$ | H | H | 4-Cl | C(O) | 2-chloropyrid-4-yl |
| XXX-9 | 7-O-Ph | H | H | 4-Cl | C(O) | Me |
| XXX-10 | 7-O-Ph | H | H | 4-Cl | C(O) | 2-chloropyrid-4-yl |
| XXX-11 | 5-$OCH_2CH_3$ | H | H | 4-Cl | C(O) | 2-chloropyrid-4-yl |
| XXX-12 | 6-$OCF_3$ | H | H | 4-Cl | C(O) | 2,6-dibromopyrid-4-yl |
| XXX-13 | 6-$OCF_3$ | H | H | 4-Cl | C(O) | 2,6-dichloropyrid-4-yl |
| XXX-14 | 6-$OCF_3$ | H | H | 4-Cl | C(O) | pyrid-3-yl |
| XXX-15 | 4-$OCF_2CHF_2$ | H | H | 4-Cl | C(O) | 2,6-dibromopyrid-4-yl |
| XXX-16 | 4-$OCF_2CHF_2$ | H | H | 4-Cl | C(O) | 2,6-dichloropyrid-4-yl |
| XXX-17 | 4-$OCF_2CHF_2$ | H | H | 4-Cl | C(O) | pyrid-3-yl |
| XXX-18 | 4-$OCF_3$ | H | H | 4-Cl | C(O) | 2,6-dibromopyrid-4-yl |
| XXX-19 | 4-$OCF_3$ | H | H | 4-Cl | C(O) | 2,6-dichloropyrid-4-yl |
| XXX-20 | 4-$OCF_3$ | H | H | 4-Cl | C(O) | pyrid-3-yl |
| XXX-21 | 6-$OCF_2CHF_2$ | H | H | 4-Cl | C(O) | 2,6-dibromopyrid-4-yl |
| XXX-22 | 6-$OCF_2CHF_2$ | H | H | 4-Cl | C(O) | 3,5-dichloropyrid-4-yl |
| XXX-23 | 4-$OCF_3$ | H | H | 4-Cl | C(O) | 4,6-dimethoxy-pyrimidin-2-yl |
| XXX-24 | 4-$OCF_2CHF_2$ | H | H | 4-Cl | C(O) | 4,6-dimethoxy-pyrimidin-2-yl |
| XXX-25 | 6-$OCF_3$ | H | H | 4-Cl | C(O) | 2-chloropyrid-3-yl |
| XXX-26 | 7-$OCF_3$ | H | H | 4-Cl | C(O) | 2-chloropyrid-3-yl |
| XXX-27 | 6-$OCF_2CHF_2$ | H | H | 4-Cl | C(O) | 2-chloropyrid-3-yl |

-continued

| | R⁴n | R53 | R54 | Rˢn | Y | R1 |
|---|---|---|---|---|---|---|
| XXX-28 | 4-OCF₂CHF₂ | H | H | 4-Cl | C(O) | 2-chloropyrid-3-yl |
| XXX-29 | 5-O-(4-trifluoromethyl-phenyl) | H | H | 4-Cl | C(O) | 2-chloropyrid-4-yl |
| XXX-30 | 5-OCF₃ | H | H | 4-Cl | C(O) | 2-chloropyrid-4-yl |
| XXX-31 | 5-F | H | H | 4-F | C(O) | 2-chloropyrid-4-yl |
| XXX-32 | 5-Cl | H | H | 2,4-Cl₂ | C(O) | 2-chloropyrid-4-yl |
| XXX-33 | 5,7-Cl₂ | H | H | 4-Cl | C(O) | Me |
| XXX-34 | 7-Cl | H | H | 4-Cl | C(O) | Me |
| XXX-35 | 7-Cl | H | H | 4-Cl | C(O) | 2-chloropyrid-4-yl |
| XXX-36 | 5,7-dimethyl | H | H | 4-Cl | C(O) | 2-chloropyrid-4-yl |
| XXX-37 | 4,7-dimethyl | H | H | 4-Cl | C(O) | 2-chloropyrid-4-yl |
| XXX-38 | 6-CF₃ | H | H | 4-Cl | C(O) | 2-chloropyrid-4-yl |
| XXX-39 | 4,6-Cl₂ | H | H | 4-Cl | C(O) | 2-chloropyrid-4-yl |
| XXX-40 | 4,6-Cl₂ | H | H | 4-Cl | C(O) | 2-chloropyrid-4-yl |
| XXX-41 | 5-isopropyl | H | H | 4-Cl | C(O) | 2-chloropyrid-4-yl |
| XXX-42 | 5-Br | H | H | 4-Cl | C(O) | 2-chloropyrid-4-yl |
| XXX-43 | 6,7-dimethyl | H | H | 4-Cl | C(O) | 2-chloropyrid-4-yl |
| XXX-44 | 5,6-Cl₂ | H | H | 4-Cl | C(O) | 2-chloropyrid-4-yl |
| XXX-45 | 4-CF₃ | H | H | 4-Cl | C(O) | 2-chloropyrid-4-yl |
| XXX-46 | 7-CH₂Cl | H | H | 4-Cl | C(O) | 2-chloropyrid-4-yl |
| XXX-47 | 7-Br | H | H | 4-Cl | C(O) | 2-chloropyrid-4-yl |
| XXX-48 | 5-tert-butyl | H | H | 4-Cl | C(O) | 2-chloropyrid-4-yl |
| XXX-49 | 4,6-dimethyl | H | H | 4-Cl | C(O) | 2-chloropyrid-4-yl |
| XXX-50 | 4-CF₃-7-Cl | H | H | 4-Cl | C(O) | 2-chloropyrid-4-yl |
| XXX-51 | 5-Cl | H | H | 4-CF₃ | C(O) | 2-chloropyrid-4-yl |
| XXX-52 | 5-Cl | H | H | 4-CH=CH₂ | C(O) | 2-chloropyrid-4-yl |
| XXX-53 | 5-Cl | H | H | 4-CF₃ | C(O) | 2-chloropyrid-4-yl |
| XXX-54 | 5-Cl | H | H | 4-Cl | C(O) | 2-chloropyrid-4-yl |
| XXX-55 | 5-Cl | H | H | 4-NO₂ | C(O) | 2-chloropyrid-4-yl |
| XXX-56 | 5-Cl | H | H | 3,5-(CF₃)₂ | C(O) | 2-chloropyrid-4-yl |
| XXX-57 | 5-Cl | H | H | 3-Br | C(O) | 2-chloropyrid-4-yl |
| XXX-58 | 5-Cl | H | H | 3-ethoxy | C(O) | 2-chloropyrid-4-yl |
| XXX-59 | 5-Cl | H | H | 2-Me | C(O) | 2-chloropyrid-4-yl |
| XXX-60 | 5-Cl | H | H | 4-Me | C(O) | 2-chloropyrid-4-yl |
| XXX-61 | 5-Cl | H | H | 3-Cl, 4-F | C(O) | 2-chloropyrid-4-yl |
| XXX-62 | 5-Cl | H | H | 3,5-Cl₂ | C(O) | 2-chloropyrid-4-yl |
| XXX-63 | 5-Cl | H | H | 4-N₃ | C(O) | 2-chloropyrid-4-yl |
| XXX-64 | 5-Cl | H | H | 2-Br | C(O) | 2-chloropyrid-4-yl |
| XXX-65 | 5-Cl | H | H | 2,6-dimethoxy | C(O) | 2-chloropyrid-4-yl |
| XXX-66 | 5-Cl | H | H | 4-ethoxy | C(O) | 2-chloropyrid-4-yl |
| XXX-67 | 5-Cl | H | H | 3-Cl | C(O) | 2-chloropyrid-4-yl |
| XXX-68 | 5-Cl | H | H | 3-Me, 4-OMe, 5-Cl | C(O) | 2-chloropyrid-4-yl |
| XXX-69 | 5-Cl | H | H | 4-OPh | C(O) | 2-chloropyrid-4-yl |
| XXX-70 | 5-Cl | H | H | 4-CN | C(O) | 2-chloropyrid-4-yl |
| XXX-71 | 5-Cl | H | H | 3-F, 4-Ph | C(O) | 2-chloropyrid-4-yl |
| XXX-72 | 5-Cl | H | H | 4-SMe | C(O) | 2-chloropyrid-4-yl |
| XXX-73 | 5-Cl | H | H | 3-Br | C(O) | 2-chloropyrid-4-yl |
| XXX-74 | 5-Cl | H | H | 4-F | C(O) | 2-chloropyrid-4-yl |
| XXX-75 | 5-Cl | H | H | 4-Br | C(O) | 2-chloropyrid-4-yl |
| XXX-76 | 5-Cl | H | H | 2,4-Cl₂ | C(O) | 2-chloropyrid-4-yl |
| XXX-77 | 5-Cl | H | H | 2,4-F₂ | C(O) | 2-chloropyrid-4-yl |
| XXX-78 | 5-Cl | H | H | 3-CF₃ | C(O) | 2-chloropyrid-4-yl |
| XXX-79 | 5-Cl | H | H | 3,4-diethoxy | C(O) | 2-chloropyrid-4-yl |
| XXX-80 | 5-Cl | H | H | 3-Me, 4-F | C(O) | 2-chloropyrid-4-yl |
| XXX-81 | 5-Cl | H | H | 4-Ph | C(O) | 2-chloropyrid-4-yl |
| XXX-82 | 5-Cl | H | Me | 4-Cl | C(O) | 2-chloropyrid-4-yl |
| XXX-83 | 5-Cl | H | Me | 4-Cl | C(O) | Me |
| XXX-84 | 5-Cl | H | Me | 4-F | C(O) | 2-chloropyrid-4-yl |
| XXX-85 | 5-Cl | H | Me | 4-F | C(O) | Me |
| XXX-86 | 5-Cl | H | H | 4-OCF₃ | C(O) | 2-chloropyrid-4-yl |
| XXX-87 | 5-Cl | H | H | 4-OCF₃ | C(O) | Me |
| XXX-88 | 5-Cl | H | F | H | C(O) | 2-chloropyrid-4-yl |
| XXX-89 | 5-Cl | H | F | 4-Cl | C(O) | 2-chloropyrid-4-yl |
| XXX-90 | 5-Cl | H | F | 4-Cl | C(O) | Me |
| XXX-91 | 5-Cl | H | CF₃ | 4-Cl | C(O) | 2-chloropyrid-4-yl |
| XXX-92 | 5-Cl | H | CF₃ | 4-Cl | C(O) | Me |
| XXX-93 | 5-F | H | H | 4-Cl | C(O) | imidazol-1-yl |
| XXX-94 | 5-F | H | H | 4-Cl | Bond | NH₂ |
| XXX-95 | 5-F | H | H | 4-Cl | Bond | —NHCO-2-chloropyrid-4-yl |
| XXX-96 | 5-Cl | H | H | 4-NO₂ | C(O) | Me |
| XXX-97 | 5-Cl | H | H | 4-Cl | Bond | NHCO-4- |

-continued

|  | R⁴n | R53 | R54 | Rˢn | Y | R1 |
|---|---|---|---|---|---|---|
|  |  |  |  |  |  | trifluoromethoxy-phenyl |
| XXX-98 | 5-Cl |  | H | 4-Cl | Bond | —NHCO-pyrid-4-yl |
| XXX-99 | 5-Cl |  | H | 4-Cl | Bond | —NHCO-3-chloropyrid-4-yl |
| XXX-100 | 5-F |  | H | 4-Cl | Bond | —NHCONH-4-trifluoromethoxy-phenyl |
| XXX-101 | 5-F |  | H | 4-Cl | Bond | —NHCONH-3-chlorophenyl |
| XXX-102 | 5-Cl |  | H | 4-Cl | Bond | —N=C(Me)NMe₂ |
| XXX-103 | 5-Cl |  | H | 4-Cl | Bond | —NHCONH-4-trifluoromethyl-phenyl |
| XXX-104 | 5-F |  | H | 4-Cl | C(O) | —NH-isopropyl |
| XXX-105 | 5-F |  | H | 4-Cl | C(O) | —NH(CH₂)₂OMe |
| XXX-106 | 5-F |  | H | 4-Cl | C(O) | —NHCH₂-pyrid-3-yl |
| XXX-107 | 5-F |  | H | 4-Cl | C(O) | —NH(CH₂)₂OH |
| XXX-108 | 5-F |  | H | 4-Cl | C(O) | —NH(CH₂)₂-morpholinyl |
| XXX-109 | 5-F |  | H | 4-Cl | C(O) | —NHCH₂-pyrid-4-yl |
| XXX-110 | 5-F |  | H | 4-Cl | C(O) | —NH-ethyl |
| XXX-111 | 5-F |  | H | 4-Cl | C(O) | —NH-methyl |
| XXX-112 | 5-F |  | H | 4-Cl | C(O) | —NH-benzyl |
| XXX-113 | 5-Cl | F | H | 4-Cl | C(O) | 2-chloropyrid-4-yl |
| XXX-114 | 5-Cl | F | H | 4-CF₃ | C(O) | 2-chloropyrid-4-yl |
| XXX-115 | 5-Cl | H | Cl | 4-Cl | C(O) | 2-chloropyrid-4-yl |
| XXX-116 | 5 + 6 —O—CF₂—O— | H | H | 4-Cl | C(O) | Me |
| XXX-117 | 5 + 6 —O—CF₂—O— | H | H | 4-Cl | C(O) | 2-chloropyrid-4-yl |
| XXX-118 | 5 + 6 —O—CH₂—O— | H | H | 4-Cl | C(O) | 2-chloropyrid-4-yl |
| XXX-119 | 5-F |  | H | 4-Cl | Bond | —NHCONH-4-chlorophenyl |
| XXX-120 | 5-F |  | H | 4-Cl | Bond | Ethyl |
| XXX-121 | 5-Cl |  | H | 4-Cl | Bond | NO |

Table XXXI provides 8 compounds of formula Iae

Table XXXII provides 10 compounds of formula Iaf

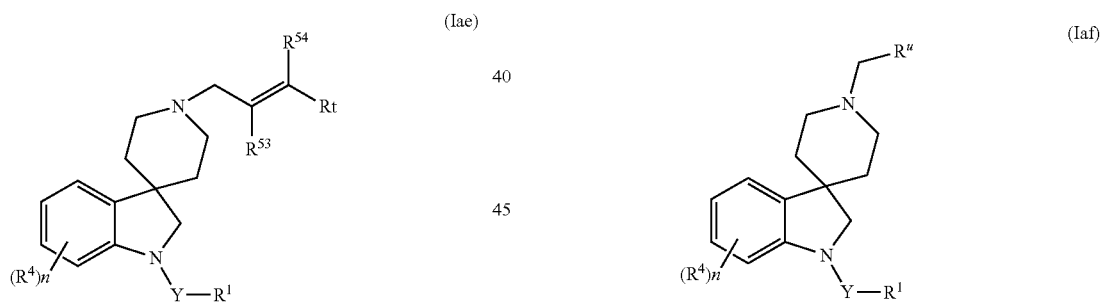

(Iae)

(Iaf)

|  | R⁴n | R53 | R54 | Rt | Y | R1 |
|---|---|---|---|---|---|---|
| XXXI-1 | 5-Cl | H | H | 5-trifluoromethyl-pyrid-2-yl | C(O) | 2-chloropyrid-4-yl |
| XXXI-2 | 5-F | H | H | 5-chloro-thiophen-2-yl | C(O) | 2-chloropyrid-4-yl |
| XXXI-3 | 5-Cl | H | H | thiophen-2-yl | C(O) | 2-chloropyrid-4-yl |
| XXXI-4 | 5-Cl | H | H | naphtha-2-yl | C(O) | 2-chloropyrid-4-yl |
| XXXI-5 | 5-Cl | H | H | —CH=CH-phenyl | C(O) | 2-chloropyrid-4-yl |
| XXXI-6 | 5-Cl | H | H | benzothiophen-2-yl | C(O) | 2-chloropyrid-4-yl |
| XXXI-7 | 5-Cl | H | H | —CH=CH-4-chlorophenyl | C(O) | 2-chloropyrid-4-yl |
| XXXI-8 | 5-Cl | H | H | Br | C(O) | 2-chloropyrid-4-yl |

| | R$^{4n}$ | Ru | Y | R1 |
|---|---|---|---|---|
| XXXII-1 | 5-Cl | 4-F—Ph | C(O) | 2-chloropyrid-4-yl |
| XXXII-2 | 5-Cl | 4-OCF$_3$—Ph | C(O) | 2-chloropyrid-4-yl |
| XXXII-3 | 5-Cl | 4-Cl—Ph | C(O) | 2-chloropyrid-4-yl |
| XXXII-4 | 5-F | 6-F-naphth-2-yl | C(O) | 2-chloropyrid-4-yl |
| XXXII-5 | 5-Cl | —CH(OH)CH$_2$O-4-Cl—Ph | C(O) | 2-chloropyrid-4-yl |
| XXXII-6 | 5-Cl | —C(Me)=NO—Ph | C(O) | 2-chloropyrid-4-yl |
| XXXII-7 | 5-Cl | 5-Cl-benzoxazol-2-yl | C(O) | 2-chloropyrid-4-yl |
| XXXII-8 | 5-Cl | 4-NHCOOCH(Me)$_2$—Ph | C(O) | 2-chloropyrid-4-yl |
| XXXII-9 | 5-Cl | 4-NHCOOCH(Me)$_2$—Ph | C(O) | 2-chloropyrid-4-yl |
| XXXII-10 | 5-Cl | (2-ethyl-terazol-5-yl)-4--Ph | C(O) | 2-chloropyrid-4-yl |

Mass spectra data were obtained for selected compounds of Tables I to XXIX on Micromass Platform 2 machines. The data are shown in Table 3.

TABLE 3

| Compound No | MS data |
|---|---|
| I-1 | 444 (95%), 446 (100%) |
| I-2 | 478 (100%), 480 (70%), 482 (15%) |
| I-3 | 462 (100%), 464 (95%) 500 (15%) |
| I-4 | 489 (100%), 491 (70%) |
| I-5 | 147 (100%), 474 (30%), 476 (80%) |
| I-12 | 512 (95%), 514 (100%), 516 (35%), 518 (5%) |
| I-21 | 478 (100%), 480 (70%), 482 (15%) |
| I-22 | 512 (100%), 514 (98%), 516 (35%), 518 (5%) |
| I-23 | 496 (100%), 498 (75%), |
| I-32 | 512 (90%), 514 (100%), 516 (35%), 518 (5%) |
| I-52 | 496 (100%), 498 (70%), 500 (15%) |
| I-61 | 462 (100%), 464 (30%) |
| I-62 | 496 (100%), 498 (80%), 500 (20%) |
| I-72 | 496 (100%), 498 (70%), 500 (15%) |
| I-82 | 496 (100%), 498 (75%), 500 (15%) |
| I-92 | 556 (55%), 558 (100%), 560 (40%), 562 (8%) |
| I-112 | 556 (55%), 558 (100%), 560 (40%), 562 (8%) |
| I-132 | 546 (75%), 548 (100%), 550 (40%), 552 (10%) |
| I-142 | 514 (100%), 516 (70%), 518 (15%) |
| I-152 | 530 (97%), 532 (100%), 534 (40%), 536 (5%) |
| I-162 | 530 (100%), 532 (97%), 534 (40%), 536 (5%) |

TABLE 3-continued

| Compound No | MS data |
|---|---|
| I-171 | 512 (98%), 514 (100%), 516 (35%), 518 (5%) |
| I-182 | 604 (100%), 606 (70%), 608 (15%) |
| I-192 | 508 (100%), 510 (80%), 512 (20%) |
| I-202 | 492 (100%), 494 (70%), 496 (15%) |
| I-212 | 503 (100%), 505 (70%), 507 (15%) |
| I-222 | 502 (100%), 504 (70%), 506 (15%) |
| I-232 | 536 (100%), 538 (70%), 540 (15%) |
| I-242 | 526 (100%), 528 (99%), 530 (35%), 532 (5%) |
| I-252 | 526 (100%), 528 (90%), 530 (35%), 532 (5%) |
| I-262 | 526 (95%), 528 (100%), 530 (35%), 532 (5%) |
| I-282 | 572 (100%), 574 (80%), 576 (20%) |
| I-292 | 562 (100%), 564 (70%), 566 (15%) |

TABLE 3-continued

| Compound No | MS data |
|---|---|
| II-22 | 431 (100%), 433 (60%), 435 (15%) |
| II-62 | 415 (100%), 417 (35%) |
| V-21 | 381 (100%), 383 (35%) |
| V-22 | 415 (100%), 417 (70%), 419 (15%) |
| V-62 | 399 (100%), 401 (40%) |
| V-192 | 411 (100%), 413 (60%) |
| V-202 | 395 (100%), 397 (80%) |
| VI-1 | 410 (100%) |
| VI-22 | 478 (100%), 480 (70%), 482 (15%) |
| VI-62 | 462 (100%), 464 (30%) |
| VI-101 | 488 (100%), 490 (100%) |
| VI-202 | 458 (100%), 460 (30%) |
| IX-62 | 435 (100%), 437 (40%) |
| X-22 | 459 (100%), 461 (75%), 463 (15%) |
| X-62 | 443 (100%), 445 (40%) |
| XI-62 | 467 (100%), 469 (40%) 561 (15%) |

TABLE 3-continued

| Compound No | MS data |
|---|---|
| XII-22 | 478 (100%), 480 (75%), 482 (35%), 484 (5%) |
| XIII-22 | 471 (100%), 473 (70%), 475 (15%) |
| XIII-62 | 455 (100%), 457 (35%) |
| XIV-22 | 451 (100%), 453 (70%), 455 (15%) |
| XV-22 | 528 (100%), 530 (70%), 532 (10%) |
| XVII-62 | 533 (100%), 535 (40%), |
| XVIII-22 | 555 (100%), 557 (80%) 559 (20%) |
| XVIII-202 | 535 (100%), 537 (40%) |
| XIX-22 | 502 (100%), 504 (70%), 506 (10%) |
| XIX-202 | 482 (100%), 484 (40%) |
| XX-22 | 521 (100%), 523 (75%), 525 (15%) |
| XX-62 | 505 (100%), 507 (40%) |
| XXI-22 | 557 (100%), 559 (70%), 561 (15%) |
| XXI-62 | 541 (100%), 543 (40%) |
| XXII-22 | 526 (100%), 528 (97%), 530 (30%), 532 (5%) |
| XXV-62 | 357 (100%), 359 (55%) |
| XXV-222 | 363 (100%), 365 (30%) |
| XXVI-1 | 460 (100%), 462 (100%) |
| XXVI-2 | 494 (100%), 496 (100%), 498 (20%) |
| XXVI-22 | 528 (100%), 530 (97%), 532 (30%), 534 (5%) |
| XXVIII-7 | 523 (100%), 525 (80%), 527 (20%) |
| XXVIII-27 | 519 (100%), 521 (40%) |
| XXVIII-42 | 565 (100%), 567 (40%) |
| XXVIII-67 | 495 (100%), 497 (70%), 499 (10%) |
| XXVIII-97 | 502 (100%), 504 (70%), 506 (10%) |
| XXVIII-132 | 503 (100%), 505 (40%) |
| XXVIII-162 | 537 (100%), 539 (40%) |
| XXVIII-187 | 589 (95%), 591 (100%), 593 (40%), 595 (5%) |

TABLE 3-continued

| Compound No | MS data |
|---|---|
| XXVIII-217 | 535 (100%), 537 (70%), 539 (10%) |
| XXVIII-252 | 475 (100%), 477 (40%) |
| XXIX-1 | 492 (100%), 494 (70%), 496 (15%) |
| XXIX-7 | 536 (100%), 538 (70%), 540 (15%) |
| XXIX-13 | 476 (100%), 478 (80%), 480 (20%) |
| XXIX-19 | 458 (100%), 460 (85%), 462 (15%) |
| XXIX-31 | 528 (100%), 530 (97%), 532 (30%), 534 (5%) |
| XXIX-37 | 556 (100%), 558 (70%), 560 (15%) |
| XXIX-43 | 470 (100%), 472 (100%), 474 (100%), 476 (30%) |
| XXIX-49 | 251 (100%), 307 (70%) |
| XXIX-69 | 479 (100%), 481 (70%), 483 (15%) |
| XXIX-75 | 512 (95%), 514 (100%), 516 (40%), 518 (5%) |
| XXIX-81 | 485 (100%), 487 (75%), 489 (20%) |
| XXIX-87 | 526 (100%), 528 (70%), 530 (10%) |
| XXIX-93 | 536 (100%), 538 (70%), 540 (15%) |
| XXIX-99 | 512 (95%), 514 (100%), 516 (30%), 518 (5%) |
| XXIX-105 | 560 (100%), 562 (70%), 564 (15%) |
| XXIX-111 | 482 (100%), 484 (70%), 486 (15%) |
| XXIX-117 | 373 (100%), 375 (70%), 377 (15%) 492 (20%), 494 (15%) |
| XXIX-123 | 497 (100%), 499 (75%), 501 (15%) |
| XXIX-129 | 469 (100%), 471 (75%), 473 (15%) |
| XXIX-135 | 472 (100%), 474 (70%), 476 (15%) |
| XXIX-141 | 570 (100%), 572 (75%), 574 (15%) |
| XXIX-147 | 532 (100%), 534 (80%), 536 (20%) |

TABLE 3-continued

| Compound No | MS data |
|---|---|
| XXIX-153 | 522 (100%), 524 (75%), 526 (15%) |
| XXIX-159 | 465 (100%), 467 (40%) |
| XXIX-165 | 512 (100%), 514 (40%) |
| XXIX-171 | 517 (100%), 519 (40%) |
| XXIX-177 | 427 (100%), 496 (80%), 498 (30%) |
| XXIX-183 | 467 (100%), 469 (35%) |
| XXIX-189 | 463 (100%), 465 (55%), 467 (15%) |
| XXIX-195 | 501 (100%), 503 (40%) |
| XXIX-196 | 517 (100%), 519 (70%), 521 (15%) |
| XXIX-201 | 574 (100%), 576 (80%), 578 (20%) |
| XXIX-207 | 489 (100%), 491 (40%) |

Mass spectra data were obtained for selected compounds of Tables XXX to XXXII using LCMS: LC5: 254 nm—gradient 10% A to 100% B A=H2O+0.01% HCOOH B=CH3CN/CH3OH+0.01% HCOOH positive electrospray 150-1000 m/z The data are shown in Table 4.

TABLE 4

| Compound | mp (° C.) | LCMS (Ret. Time, min) | LCMS (M + H) |
|---|---|---|---|
| XXX-1 | | 2'27 | 465 |
| XXX-2 | | 2'55 | 562 |
| XXX-3 | | 2'26 | 465 |
| XXX-4 | | 2'30 | 497 |
| XXX-5 | | 2'30 | 497 |
| XXX-6 | | 2'48 | 562 |
| XXX-7 | | 2'48 | 594 |
| XXX-8 | | 2'51 | 594 |
| XXX-9 | | 2'28 | 473 |
| XXX-10 | | 2'43 | 570 |
| XXX-11 | | 2'26 | 522 |
| XXX-12 | | 2'57 | 686 |
| XXX-13 | | 2'56 | 596 |
| XXX-14 | | 2'09 | 528 |
| XXX-15 | | 2'60 | 718 |
| XXX-16 | | 2'71 | 630 |
| XXX-17 | | 2'22 | 560 |
| XXX-18 | | 2'66 | 686 |
| XXX-19 | | 2'64 | 596 |
| XXX-20 | | 2'29 | 528 |
| XXX-21 | | 2'68 | 718 |
| XXX-22 | | 2'68 | 630 |
| XXX-23 | | 2'43 | 589 |
| XXX-24 | | 2'53 | 621 |
| XXX-25 | | 2'30 | 562 |
| XXX-26 | | 2'33 | 562 |
| XXX-27 | | 2'35 | 594 |
| XXX-28 | | 2'42 | 594 |
| XXX-29 | | 2'60 | 638 |
| XXX-30 | | | 562 |
| XXX-31 | | | 480 |
| XXX-32 | | | 546 |
| XXX-33 | 171-172 | 2' 27 | 449 |
| XXX-34 | 59-61 | 2' 01 | 415 |
| XXX-35 | 182-184 | 2' 33 | 512 |
| XXX-36 | 158-160 | 2' 43 | 506 |
| XXX-37 | 199-201 | 2' 42 | 506 |
| XXX-38 | | 2' 48 | 546 |
| XXX-39 | 157-159 | 2' 52 | 546 |
| XXX-40 | | 2' 46 | 546 |
| XXX-41 | | 2' 47 | 520 |
| XXX-42 | 140-142 | 2' 37 | 556 |
| XXX-43 | 106-110 | 2' 39 | 506 |
| XXX-44 | | 2' 53 | 546 |
| XXX-45 | 170-172 | 2' 39 | 546 |
| XXX-46 | 146-148 | 2' 36 | 506 |
| XXX-47 | 196-198 | 2' 31 | 556 |
| XXX-48 | 149-151 | 2' 49 | 534 |
| XXX-49 | 194-196 | 2' 33 | 506 |
| XXX-50 | 165-167 | 2' 48 | 580 |
| XXX-51 | | | 546 |
| XXX-52 | | | 504 |
| XXX-53 | | | 546 |
| XXX-54 | | | 513 |
| XXX-55 | | | 523 |
| XXX-56 | | | 614 |
| XXX-57 | | | 557 |
| XXX-58 | | | 522 |
| XXX-59 | | | 492 |
| XXX-60 | | | 492 |
| XXX-61 | | | 531 |
| XXX-62 | | | 547 |
| XXX-63 | | | 533 |
| XXX-64 | | | 557 |
| XXX-65 | | | 538 |
| XXX-66 | | | 522 |
| XXX-67 | | | 513 |
| XXX-68 | | | 557 |
| XXX-69 | | | 571 |
| XXX-70 | | | 503 |
| XXX-71 | | | 573 |
| XXX-72 | | | 525 |
| XXX-73 | | | 557 |
| XXX-74 | | | 496 |
| XXX-75 | | | 557 |
| XXX-76 | | | 547 |
| XXX-77 | | | 514 |
| XXX-78 | | | 546 |
| XXX-79 | | | 538 |

TABLE 4-continued

| Compound | mp (° C.) | LCMS (Ret. Time, min) | LCMS (M + H) |
|---|---|---|---|
| XXX-80 | | | 510 |
| XXX-81 | | | 555 |
| XXX-82 | | 2'45 | 528 |
| XXX-83 | | 2'22 | 429 |
| XXX-84 | | 2'30 | 510 |
| XXX-85 | | 2'05 | 413 |
| XXX-86 | 70 | 2'40 | 562 |
| XXX-87 | | 2'27 | 465 |
| XXX-88 | | 2'22 | 497 |
| XXX-89 | | 2'44 | 530 |
| XXX-90 | | 2'15 | 433 |
| XXX-91 | | | |
| XXX-92 | | 2'53 | 483 |
| XXX-93 | | 1'93 | 451 |
| XXX-94 | | 1'74 | 372 |
| XXX-95 | | 2'08 | 511 |
| XXX-96 | | 1'93 | 426 |
| XXX-97 | | 2'57 | 576 |
| XXX-98 | | 1'99 | 493 |
| XXX-99 | | 2'20 | 527 |
| XXX-100 | | 2'55 | 575 |
| XXX-101 | | 2'46 | 525 |
| XXX-102 | | 1'45 | 457 |
| XXX-103 | | 2'60 | 575 |
| XXX-104 | | 2'13 | 442 |
| XXX-105 | | 1'96 | 458 |
| XXX-106 | | 1'67 | 491 |
| XXX-107 | | 1'86 | 444 |
| XXX-108 | | 1'41 | 513 |
| XXX-109 | | 1'55 | 491 |
| XXX-110 | | 2'00 | 428 |
| XXX-111 | | 1'90 | 414 |
| XXX-112 | | 2'31 | 490 |
| XXX-113 | | 2'74 | 530 |
| XXX-114 | | 2'44 | 520 |
| XXX-115 | | 2'53 | 548 |
| XXX-116 | | 2'20 | 461 |
| XXX-117 | | 2'47 | 558 |
| XXX-118 | | 2'17 | 522 |
| XXX-120 | | | 399 |
| XXX-121 | | 2'05 | 427 |
| XXX1-1 | | | 547 |
| XXXI-2 | 147-148 | | |
| XXXI-3 | | | 484 |
| XXX1-4 | | | 528 |
| XXXI-5 | | | 504 |
| XXXI-6 | | | 535 |
| XXXI-7 | | | 539 |
| XXXI-8 | | 1'86 | 482 |
| XXXII-1 | | | 470 |
| XXXII-2 | | | 536 |
| XXXII-3 | | | 486 |
| XXXII-4 | | | 504 |
| XXXII-5 | | | 546 |
| XXXII-6 | | | 509 |
| XXXII-7 | | | 527 |
| XXXII-8 | | | 2'27 |
| XXXII-9 | | | 1'96 |
| XXXII-10 | | | 2'21 |

The compounds of the invention may be made in a variety of ways. For example they may be made by the reactions summarised in Scheme I.

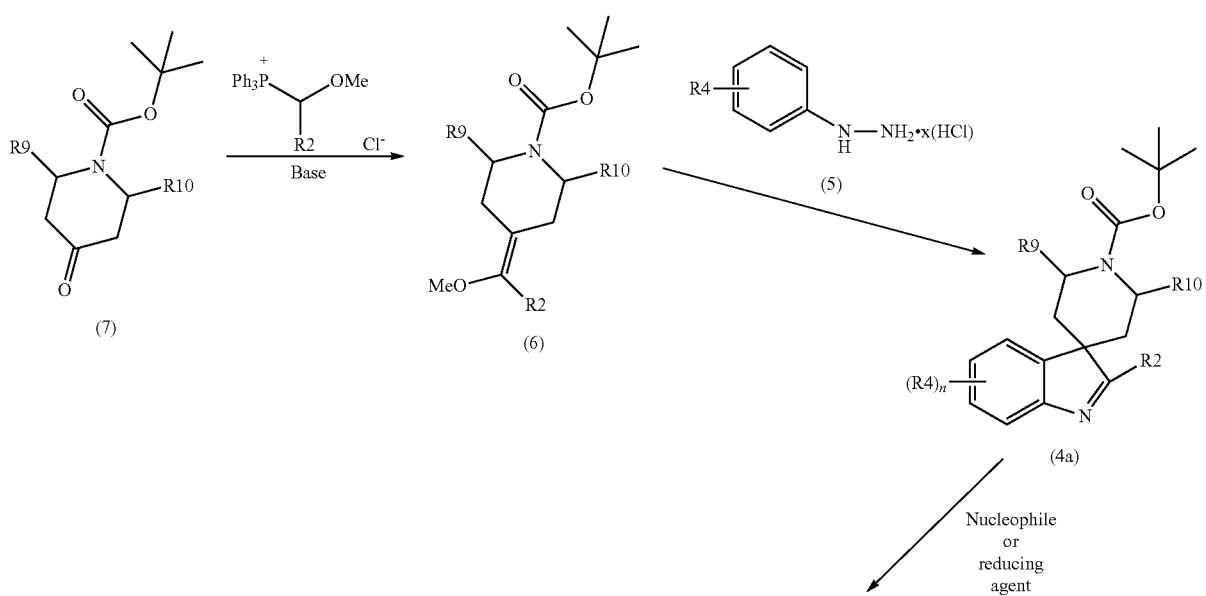

SCHEME I

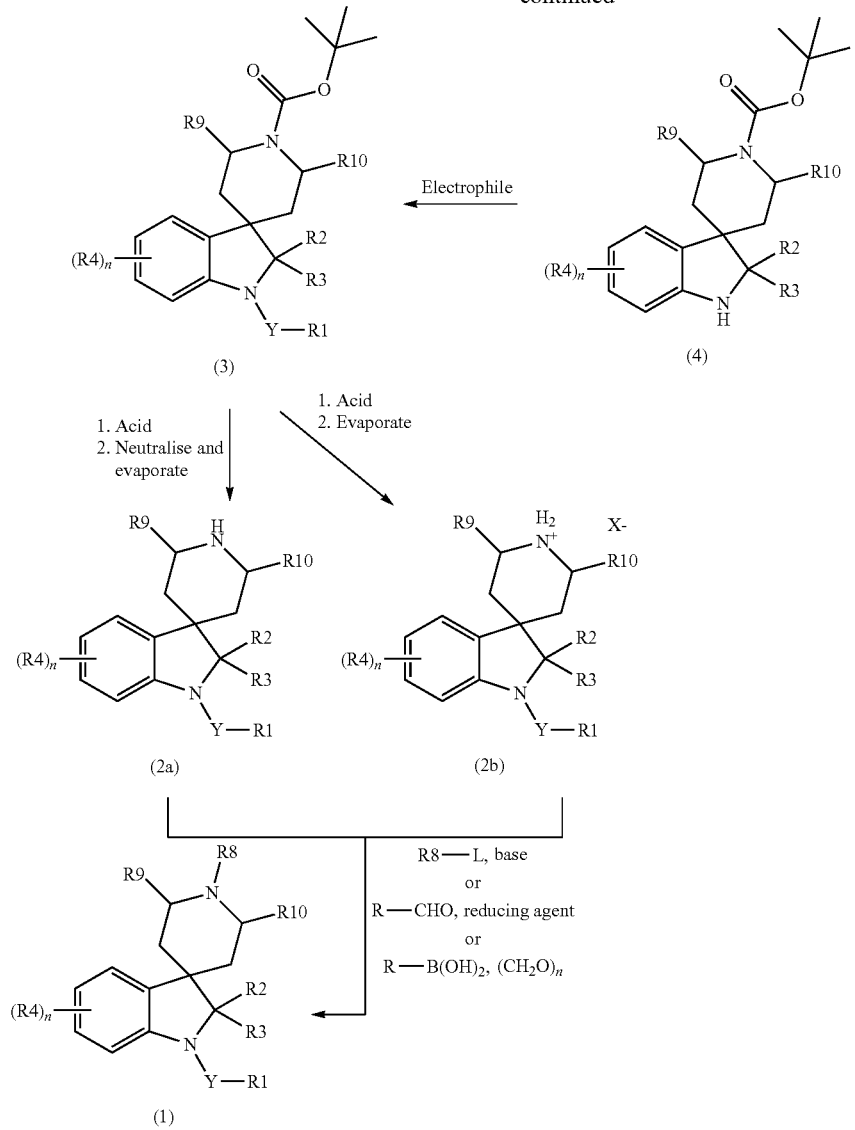

Thus a compound of formula 1 may be synthesised from compounds of formula 2a or 2b by reaction with an alkylating agent of the formula R8-L, where L is chloride, bromide, iodide or a sulfonate (e.g. mesylate or tosylate) or similar leaving group at a temperature of between ambient temperature and 100° C., typically 65° C., in an organic solvent such as dichloromethane, chloroform or 1,2-dichloroethane in the presence of a tertiary amine base such as triethylamine or diisopropylethylamine and optionally catalysed by halide salts such as sodium iodide, potassium iodide or tetrabutylammonium iodide.

Alternatively, a compound of formula 2a or 2b may be reacted with an aldehyde of the formula RCHO at a temperature between ambient temperature and 100° C. in an organic solvent such as tetrahydrofuran or ethanol or mixtures of solvents in the presence of a reducing agent such as borane-pyridine complex, sodium borohydride, sodium(triacetoxy)borohydride, sodium cyanoborohydride or such like, to produce a compound of formula 1 where R8 is $CH_2$—R.

Alternatively, a compound of formula 2a or 2b may be reacted with paraformaldehyde and a boronic acid of the formula R—$B(OH)_2$ at a temperature between ambient temperature and 100° C. in an organic solvent such as ethanol, 1,4-dioxane or water to produce a compound of formula 1 where R8 is $CH_2$—R.

A compound of formula 2a may be obtained from a compound of formula 3 by reaction with an acid such as trifluoroacetic acid at ambient temperature in an organic solvent such as dichloromethane, chloroform or 1,2-dichloroethane followed by neutralisation of the reaction mixture with an aqueous solution of an inorganic base such as sodium carbonate, sodium bicarbonate or similar compound.

Similarly a compound of formula 2b may be formed by reaction of a compound of formula 3 with an acid such as trifluoroacetic acid at ambient temperature in an organic solvent such as dichloromethane, chloroform or 1,2-dichloroethane followed by evaporation of the solvents and trituration with organic solvents such as ether or hexane.

Compounds of formula 3 may be obtained from compounds of formula 4 by reaction with a suitable electrophilic species. Compounds of formula 3 where Y is a carbonyl group may be formed by the reaction of compounds of formula 4 with a carboxylic acid derivative of formula —C(O)—Z where Z is chloride, hydroxy, alkoxy or acyloxy at a temperature between 0° C. and 150° C. optionally in an organic solvent such as dichloromethane, chloroform or 1,2-dichloroethane, optionally in the presence of a tertiary amine base such as triethylamine or diisopropylethylamine and optionally in the presence of a coupling agent such as dicyclohexylcarbodiimide. Compounds of formula 3 where Y is a carbonyl group and R1 is an amino substituent of formula R'—NH— may be formed by the reaction of compounds of formula 4 with an isocyanate of formula R'—N═C═O under similar conditions. Compounds of formula 3 where Y is a group of formula $S(O)_q$ may be formed from compounds of formula 4 by treatment with compounds of formula of —$S(O)_q$—Cl under similar conditions. Compounds of formula 3 where Y is a thiocarbonyl group and R1 is an amino substituent of formula R'—NH— may be formed by the reaction of compounds of formula 3 with an isothiocyanate of formula R'—N═C═S under similar conditions. Alternatively compounds of formula 3 where Y is a thiocarbonyl group and R1 is a carbon substituent may be formed by treatment of compounds of formula 3 where Y is a carbonyl group and R1 is a carbon substituent with a suitable thionating agent such as Lawesson's reagent.

In the above procedures, acid derivatives of the formula —C(O)—Z, isocyanates of formula R'—N═C═O, isothiocyanates of formula R'—N═C═S and sulfur electrophiles of formula R1-$S(O)_q$—Cl are either known compounds or may be formed from known compounds by known methods by a person skilled in the art.

Compounds of formula 4 may be obtained by reacting compounds of formula 5 with compounds of formula 6 at a temperature of between 0° C. and 100° C. in an organic solvent such as dichloromethane, chloroform or 1,2-dichloroethane in the presence of an acid such as hydrochloric acid or trifluoroacetic acid and a co-solvent such as water, methanol or ethanol, or in the presence of a Lewis acidic metal salt such as a zinc(II) dihalide. The intermediates formed (compounds of formula 4a) are subsequently treated with a nucleophile R3-M (where M is a metallic species. R3-M is for example a Grignard reagent) or, when R3 is hydrogen, a reducing agent such as sodium borohydride, sodium(triacetoxy)borohydride, sodium cyanoborohydride or similar at ambient temperature in organic solvent such as ethanol or chloroform. The basic procedure is described in Tetrahedron (1997), 53, 10983-10992.

Compounds of formula 6 may be obtained from compounds of formula 7 by reaction with a 1-alkoxy substituted phosphonium salt such as methoxymethyl(triphenyl)phosphonium chloride and a base such as potassium tert-butoxide at a temperature of 0° C. to room temperature in tetrahydrofuran.

Compounds of formula 5 and 7 are either known compounds or may be obtained from known compounds by known techniques.

Certain compounds of formula 2, 3, 4, 4a and 6 are novel and as such form a further aspect of the invention.

Further procedures for making compounds of formula 1' (compounds of formula I where $R^2$, $R^3$, $R^9$ and $R^{10}$ are all hydrogen) are illustrated in scheme II below

SCHEME II

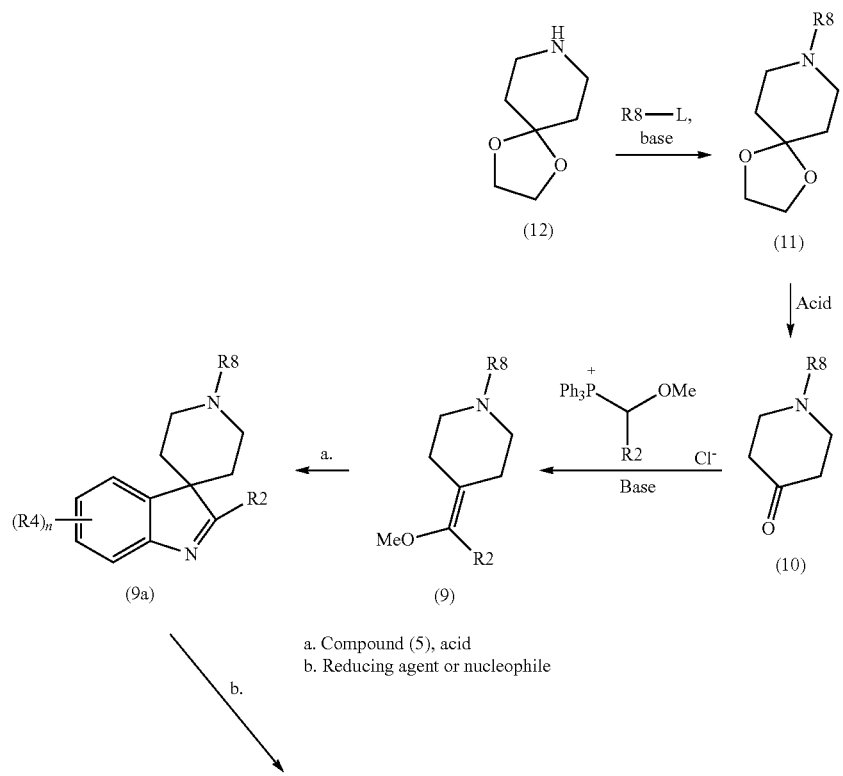

a. Compound (5), acid
b. Reducing agent or nucleophile

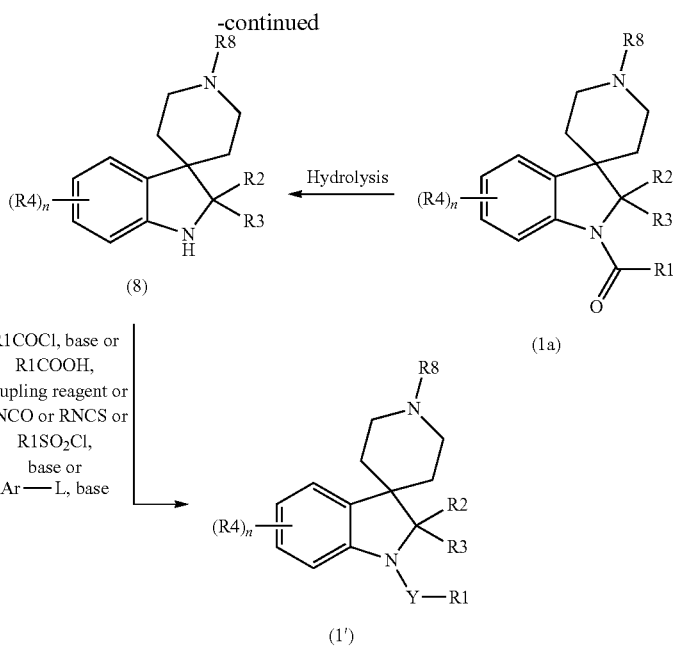

Thus a compound of formula 1' may be obtained from a compound of formula 8 by reaction with an acid chloride or chloroformate of the formula R1 COCl at a temperature between 0° C. and ambient in organic solvent such as dichloromethane, chloroform or 1,2-dichloroethane in the presence of a tertiary amine base such as triethylamine or diisopropylethylamine.

Alternatively, a compound of formula 1' may be obtained from a compound of formula 8 by reaction with a carboxylic acid of the formula R1COOH and a standard coupling agent such as 2-chloro-1,3-dimethyl-2-imidazolium hexafluorophosphate, or carbodiimide reagents such as dicyclohexylcarbodiimide or 1-(3-dimethylaminopropyl)-3-ethylcarbodiimide hydrochloride at a temperature between 0° C. and ambient in organic solvent such as dichloromethane or tetrahydrofuran in the presence of a tertiary amine base such as triethylamine or diisopropylethylamine.

A compound of formula 1' may alternatively be obtained from a compound of formula 8 by reaction with a isocyanate or isothiocyanate of the formula RNCO or RNCS respectively at a temperature between 0° C. and ambient in organic solvent such as dichloromethane or tetrahydrofuran, optionally in the presence of a tertiary amine base such as triethylamine or diisopropylethylamine.

A compound of formula 1' may also be obtained from a compound of formula 8 by reaction with a sulfonyl chloride of the formula $R1SO_2Cl$ at a temperature between 0° C. and ambient in organic solvent such as dichloromethane or tetrahydrofuran, in the presence of a tertiary amine base such as triethylamine or diisopropylethylamine.

Alternatively, a compound of formula 1' may be obtained from a compound of formula 8 by reaction with an aryl or heteroaryl compound of formula Ar-L where L is a leaving group such as halide (especially fluoride), such as a 2-halopyridine, a 2-halopyrimidine, a 4-halopyridine, a 2-halopyrazine or such like at a temperature between 50° C. and 150° C. in a solvent such as dimethylsulfoxide in the presence of a strong base such as sodium hydride.

Compounds of formula 8 may be obtained by reacting compounds of formula 9 with compounds of formula 5 (in scheme I) at a temperature of between ambient and 100° C. in organic solvent such as dichloromethane, chloroform or 1,2-dichloroethane in the presence of an acid such as trifluoroacetic acid for typically 4 to 12 hours, followed by addition of a reducing agent such as triethylsilane and reaction at a temperature of ambient to 100° C. until the reaction is complete.

Alternatively, Compounds of formula 8 may be obtained by reacting compounds of formula 9 with compounds of formula 5 at a temperature of between 0° C. and 100° C. in organic solvent such as dichloromethane, chloroform or 1,2-dichloroethane in the presence of an acid such as hydrochloric acid, or trifluoroacetic acid and a co-solvent of either water or methanol or ethanol, or in the presence of a Lewis acidic metal salt such as zinc(II) dihalide. The intermediates formed (compounds of formula (9a)) are subsequently treated with a reducing agent such as sodium borohydride, sodium(triacetoxy)borohydride, sodium cyanoborohydride or such like at ambient temperature in organic solvent such as ethanol or chloroform.

Compounds of formula 8 may also be obtained by the hydrolysis of compounds of formula 1a (which are also a sub-set of compounds of formula 1) preferably with an aqueous acid, typically 6 N hydrochloric acid at reflux temperature.

Compounds of formula 9 may be obtained from compounds of formula 10 by reaction with methoxymethyl (triphenyl)phosphonium chloride or the corresponding bromide salt and a base such as potassium tert-butoxide at a temperature of 0° C. to ambient in tetrahydrofuran.

Compounds of formula 10 may be obtained by reacting compounds of formula 11 with an aqueous solution of acid, typically 6 N hydrochloric acid at reflux temperature.

Compounds of formula 11 may be obtained from compounds of formula 12 by reaction with an electrophile of the formula R8-L, where L is chloride, bromide, iodide or a sulfonate (e.g. mesylate or tosylate) or similar leaving group at between ambient temperature and 100° C., typically around 60° C. in an organic solvent such as dichloromethane, chloroform or 1,2-dichloroethane in the presence of an excess of a tertiary amine base such as triethylamine or diisopropylethylamine and optionally catalysed by halide salts such as sodium iodide, potassium iodide or tetrabutylammonium iodide.

Compounds of formula 12 are known compounds or may be obtained from known compounds by known techniques.

Certain compounds of formula 8, 9, 9a, 10 and 11 are novel and as such form a further aspect of the invention.

The skilled person will readily recognise that it is possible to interconvert one compound of formula I to other compounds of formula I and examples of such procedures are given in schemes III, IV, V, Va and VI below.

SCHEME III

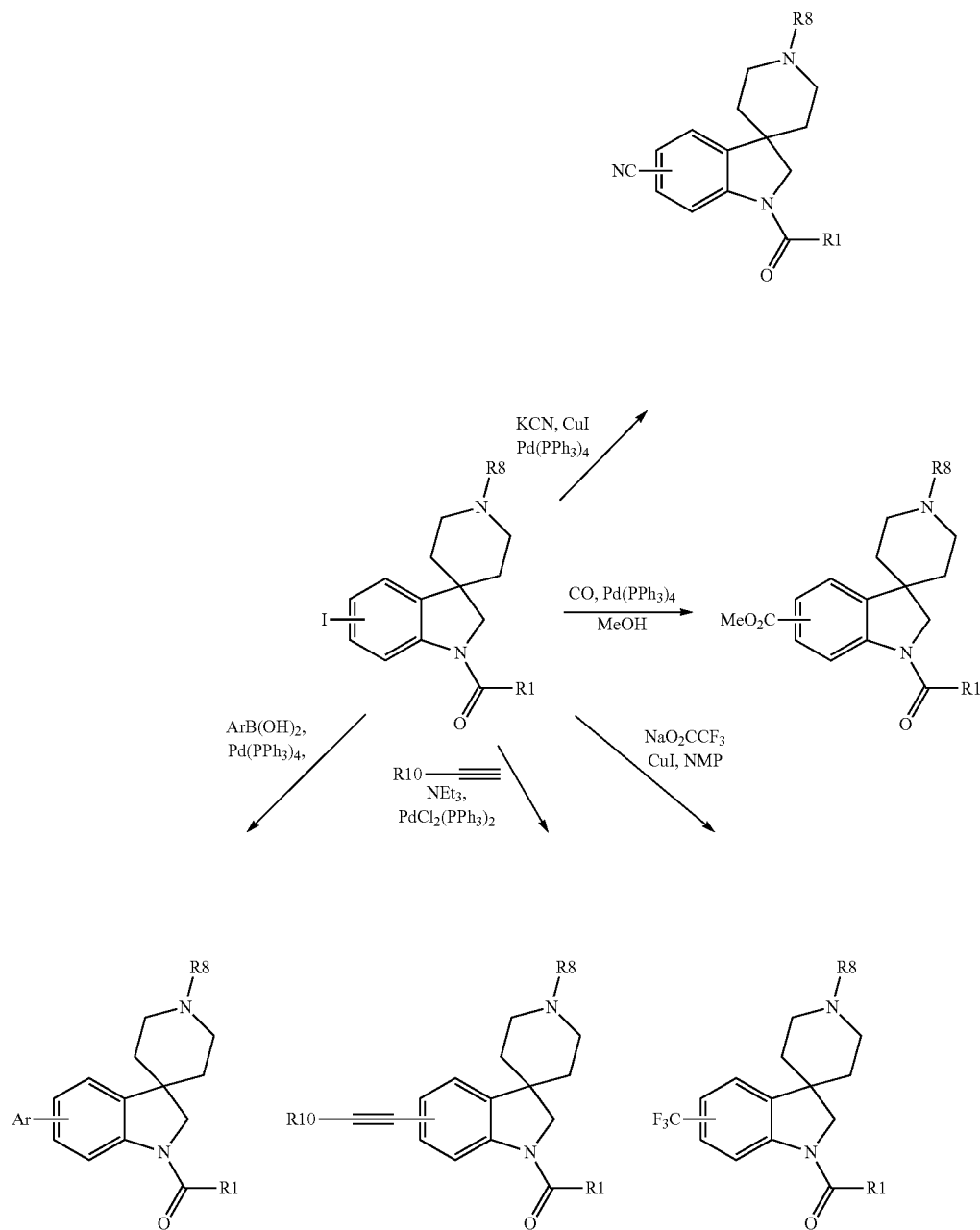

SCHEME IV
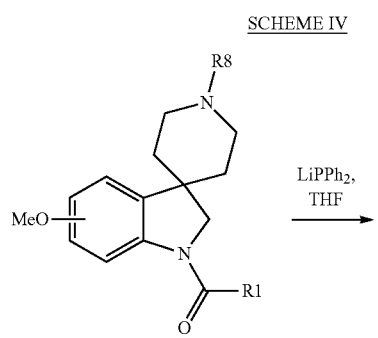
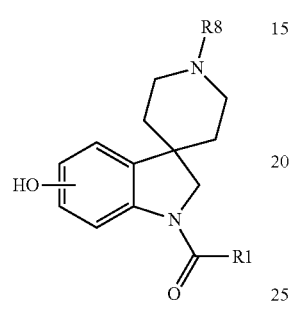
SCHEME V
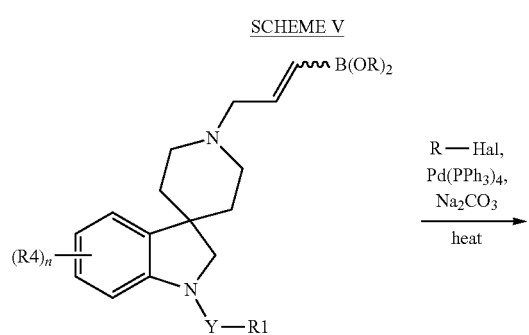
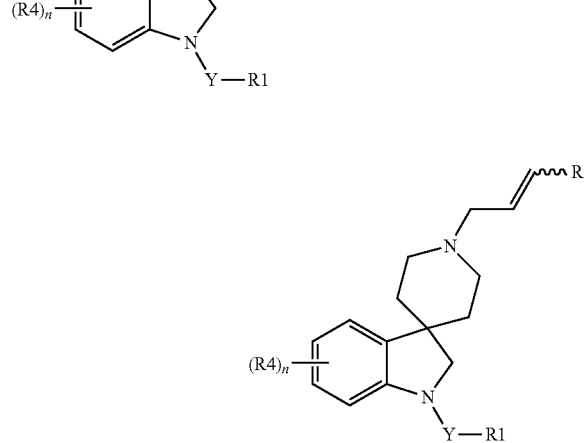
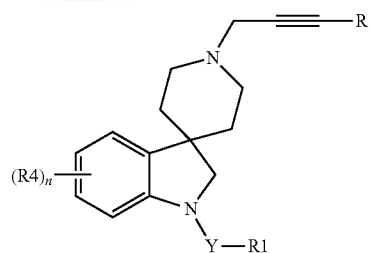
Scheme VA
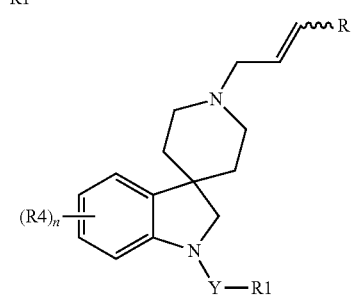
SCHEME VI
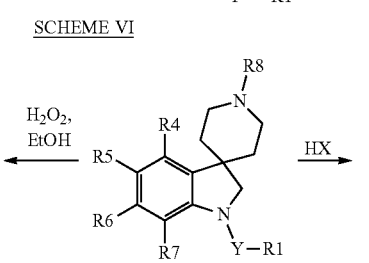
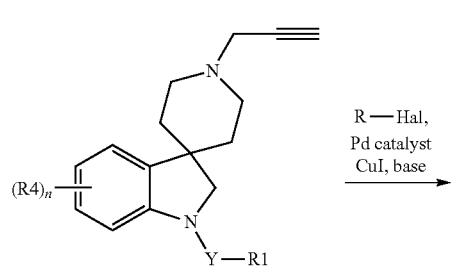
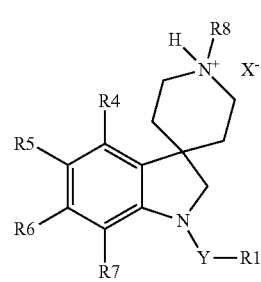
Compounds of formula I where $R^8$ is optionally substituted cinnamyl may be prepared by the reactions in scheme VII below where $R^4$, $R^{53}$, $R^{54}$ and $R^s$ are as defined above. The scheme is illustrated in Examples 8-12.

SCHEME VII
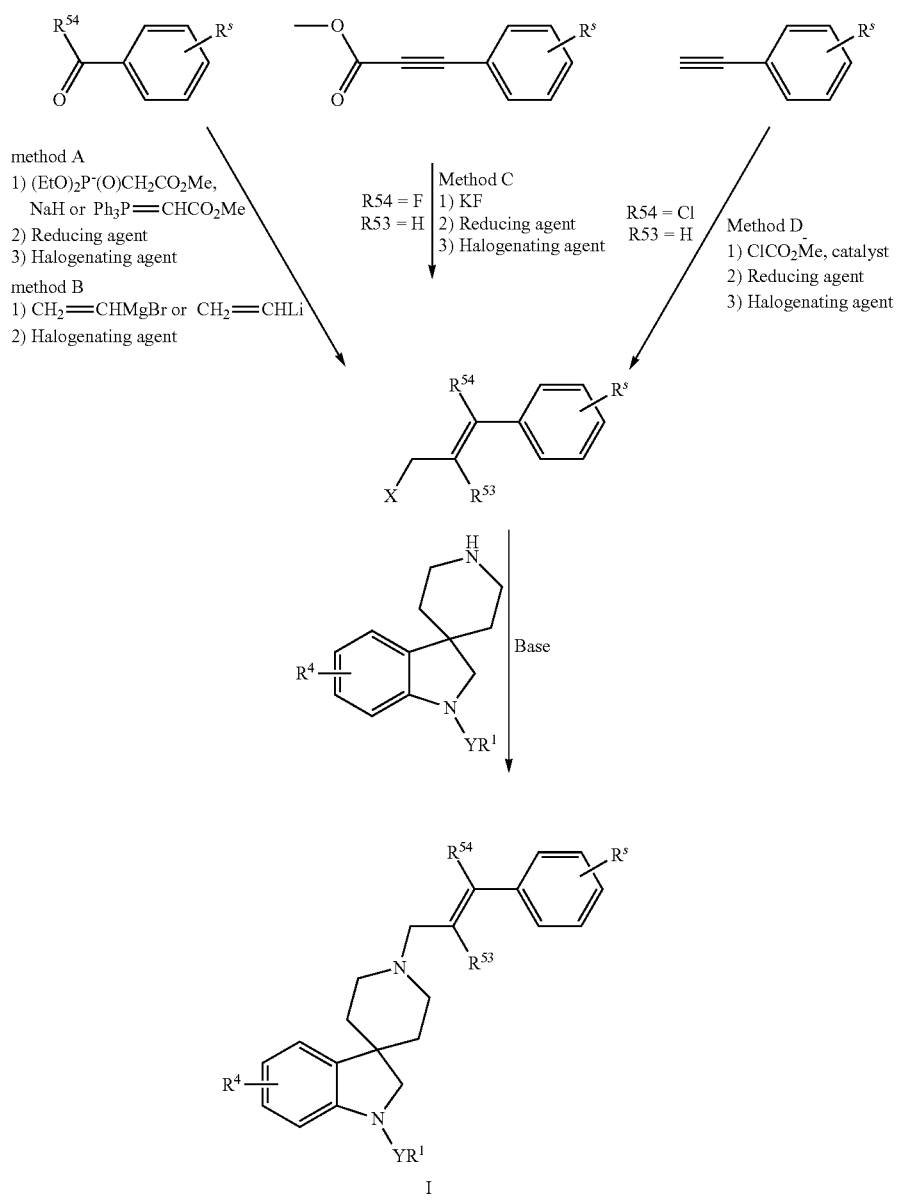
Compounds of formula (I) in which $R^2$ and $R^3$ together are an oxo group and $R^1$, $R^4$ and $R^8$ are as defined above may be made by the methods of WO 0145707 as set out in scheme VIII below.
SCHEME VIII
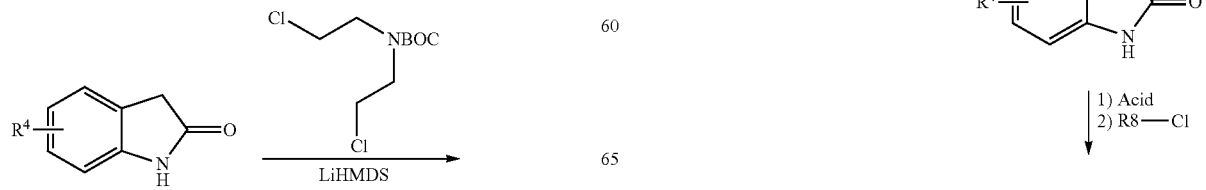

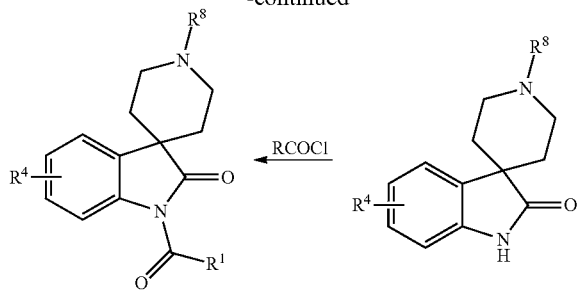

Compounds of formula (I) in which $R^2$ and $R^3$ together are an oxo group and and $R^8$ are as defined above may be made from compounds of formula 4a by the methods of scheme IX below.

SCHEME IX

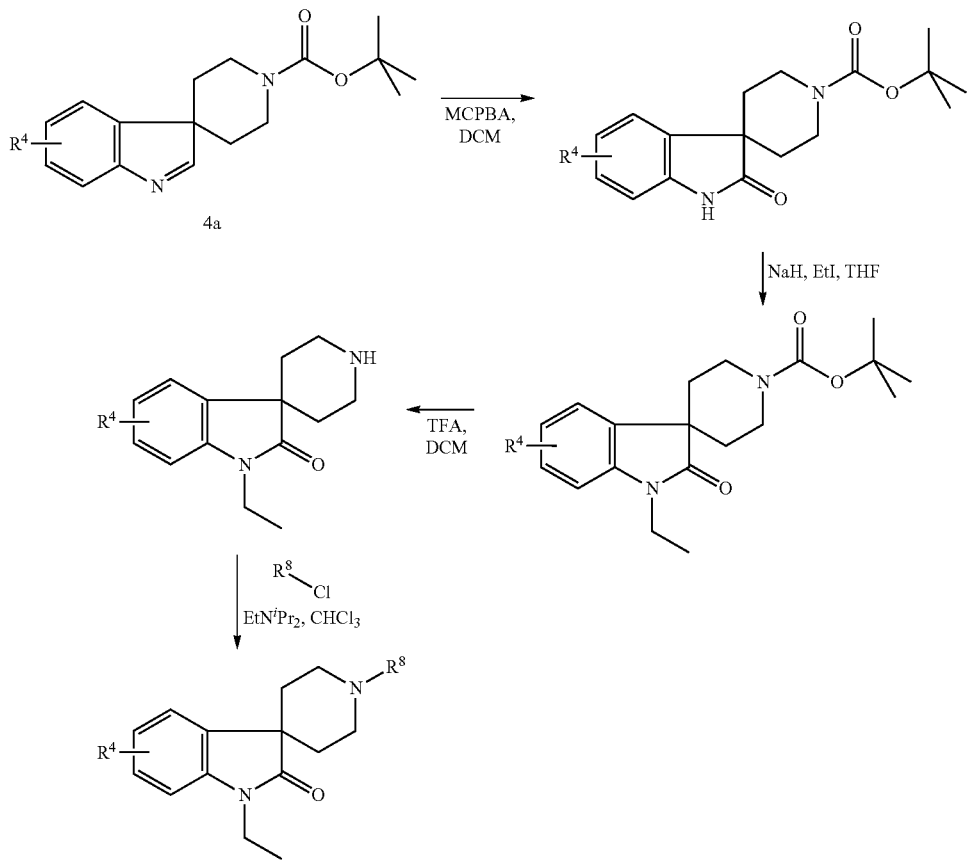

The compounds of formula (I) can be used to combat and control infestations of insect pests such as Lepidoptera, Diptera, Hemiptera, Thysanoptera, Orthoptera, Dictyoptera, Coleoptera, Siphonaptera, Hymenoptera and Isoptera and also other invertebrate pests, for example, acarine, nematode and mollusc pests. Insects, acarines, nematodes and molluscs are hereinafter collectively referred to as pests. The pests which may be combated and controlled by the use of the invention compounds include those pests associated with agriculture (which term includes the growing of crops for food and fibre products), horticulture and animal husbandry, companion animals, forestry and the storage of products of vegetable origin (such as fruit, grain and timber); those pests associated with the damage of man-made structures and the transmission of diseases of man and animals; and also nuisance pests (such as flies).

Examples of pest species which may be controlled by the compounds of formula (I) include: *Myzus persicae* (aphid), *Aphis gossypii* (aphid), *Aphis fabae* (aphid), *Lygus* spp. (capsids), *Dysdercus* spp. (capsids), *Nilaparvata lugens* (planthopper), *Nephotettixc incticeps* (leafhopper), *Nezara* spp. (stinkbugs), *Euschistus* spp. (stinkbugs), *Leptocorisa* spp. (stinkbugs), *Frankliniella occidentalis* (thrip), *Thrips* spp. (*thrips*), *Leptinotarsa decemlineata* (Colorado potato beetle), *Anthonomus grandis* (boll weevil), *Aonidiella* spp. (scale insects), *Trialeurodes* spp. (white flies), *Bemisia tabaci* (white fly), *Ostrinia nubilalis* (European corn borer), *Spodoptera littoralis* (cotton leafworm), *Heliothis virescens* (tobacco budworm), *Helicoverpa armigera* (cotton bollworm), *Helicoverpa zea* (cotton bollworm), *Sylepta derogata* (cotton leaf roller), *Pieris brassicae* (white butterfly), *Plutella xylostella* (diamond back moth), *Agrotis* spp. (cutworms), *Chilo suppressalis* (rice stem borer), *Locusta_migratoria* (locust), *Chortiocetes terminifera* (locust), *Diabrotica* spp. (rootworms), *Panonychus ulmi* (European red mite), *Panonychus citri* (citrus red mite), *Tetranychus urticae* (two-spotted spider mite), *Tetranychus cinnabarinus* (carmine spider mite), *Phyllocoptruta oleivora* (citrus rust mite), *Polyphagotarsonemus latus* (broad mite), *Brevipalpus* spp. (flat mites), *Boophilus microplus* (cattle tick), *Dermacentor variabilis* (American dog tick), *Cteno-*

*cephalides felis* (cat flea), *Liriomyza* spp. (leafminer), *Musca domestica* (housefly), *Aedes aegypti* (mosquito), *Anopheles* spp. (mosquitoes), *Culex* spp. (mosquitoes), *Lucillia* spp. (blowflies), *Blattella germanica* (cockroach), *Periplaneta americana* (cockroach), *Blatta orientalis* (cockroach), termites of the Mastotermitidae (for example *Mastotermes* spp.), the Kalotermitidae (for example *Neotermes* spp.), the Rhinotermitidae (for example *Coptotermes formosanus, Reticulitermes flavipes, R. speratu, R. virginicus, R. hesperus,* and *R. santonensis*) and the Termitidae (for example *Globitermes sulphureus*), *Solenopsis geminata* (fire ant), *Monomorium pharaonis* (pharaoh's ant), *Damalinia* spp. and *Linognathus* spp. (biting and sucking lice), *Meloidogyne* spp. (root knot nematodes), *Globodera* spp. and *Heterodera* spp. (cyst nematodes), *Pratylenchus* spp. (lesion nematodes), *Rhodopholus* spp. (banana burrowing nematodes), *Tylenchulus* spp. (citrus nematodes), *Haemonchus contortus* (barber pole worm), *Caenorhabditis elegans* (vinegar eelworm), *Trichostrongylus* spp. (gastro intestinal nematodes) and *Deroceras reticulatum* (slug).

The invention therefore provides a method of combating and controlling insects, acarines, nematodes or molluscs which comprises applying an insecticidally, acaricidally, nematicidally or molluscicidally effective amount of a compound of formula (I), or a composition containing a compound of formula (I), to a pest, a locus of pest, or to a plant susceptible to attack by a pest. The compounds of formula (I) are preferably used against insects, acarines or nematodes.

The term "plant" as used herein includes seedlings, bushes and trees.

In order to apply a compound of formula (I) as an insecticide, acaricide, nematicide or molluscicide to a pest, a locus of pest, or to a plant susceptible to attack by a pest, a compound of formula (I) is usually formulated into a composition which includes, in addition to the compound of formula (I), a suitable inert diluent or carrier and, optionally, a surface active agent (SFA). SFAs are chemicals which are able to modify the properties of an interface (for example, liquid/solid, liquid/air or liquid/liquid interfaces) by lowering the interfacial tension and thereby leading to changes in other properties (for example dispersion, emulsification and wetting). It is preferred that all compositions (both solid and liquid formulations) comprise, by weight, 0.0001 to 95%, more preferably 1 to 85%, for example 5 to 60%, of a compound of formula (I). The composition is generally used for the control of pests such that a compound of formula (I) is applied at a rate of from 0.1 g to 10 kg per hectare, preferably from 1 g to 6 kg per hectare, more preferably from 1 g to 1 kg per hectare.

When used in a seed dressing, a compound of formula (I) is used at a rate of 0.0001 g to 10 g (for example 0.001 g or 0.05 g), preferably 0.005 g to 10 g, more preferably 0.005 g to 4 g, per kilogram of seed.

In another aspect the present invention provides an insecticidal, acaricidal, nematicidal or molluscicidal composition comprising an insecticidally, acaricidally, nematicidally or molluscicidally effective amount of a compound of formula (I) and a suitable carrier or diluent therefor. The composition is preferably an insecticidal, acaricidal, nematicidal or molluscicidal composition.

In a still further aspect the invention provides a method of combating and controlling pests at a locus which comprises treating the pests or the locus of the pests with an insecticidally, acaricidally, nematicidally or molluscicidally effective amount of a composition comprising a compound of formula (I). The compounds of formula (I) are preferably used against insects, acarines or nematodes.

The compositions can be chosen from a number of formulation types, including dustable powders (DP), soluble powders (SP), water soluble granules (SG), water dispersible granules (WG), wettable powders (WP), granules (GR) (slow or fast release), soluble concentrates (SL), oil miscible liquids (OL), ultra low volume liquids (UL), emulsifiable concentrates (EC), dispersible concentrates (DC), emulsions (both oil in water (EW) and water in oil (EO)), microemulsions (ME), suspension concentrates (SC), aerosols, fogging/smoke formulations, capsule suspensions (CS) and seed treatment formulations. The formulation type chosen in any instance will depend upon the particular purpose envisaged and the physical, chemical and biological properties of the compound of formula (I).

Dustable powders (DP) may be prepared by mixing a compound of formula (I) with one or more solid diluents (for example natural clays, kaolin, pyrophyllite, bentonite, alumina, montmorillonite, kieselguhr, chalk, diatomaceous earths, calcium phosphates, calcium and magnesium carbonates, sulphur, lime, flours, talc and other organic and inorganic solid carriers) and mechanically grinding the mixture to a fine powder.

Soluble powders (SP) may be prepared by mixing a compound of formula (I) with one or more water-soluble inorganic salts (such as sodium bicarbonate, sodium carbonate or magnesium sulphate) or one or more water-soluble organic solids (such as a polysaccharide) and, optionally, one or more wetting agents, one or more dispersing agents or a mixture of said agents to improve water dispersibility/solubility. The mixture is then ground to a fine powder. Similar compositions may also be granulated to form water soluble granules (SG).

Wettable powders (WP) may be prepared by mixing a compound of formula (I) with one or more solid diluents or carriers, one or more wetting agents and, preferably, one or more dispersing agents and, optionally, one or more suspending agents to facilitate the dispersion in liquids. The mixture is then ground to a fine powder. Similar compositions may also be granulated to form water dispersible granules (WG).

Granules (GR) may be formed either by granulating a mixture of a compound of formula (I) and one or more powdered solid diluents or carriers, or from pre-formed blank granules by absorbing a compound of formula (I) (or a solution thereof, in a suitable agent) in a porous granular material (such as pumice, attapulgite clays, fuller's earth, kieselguhr, diatomaceous earths or ground corn cobs) or by adsorbing a compound of formula (I) (or a solution thereof, in a suitable agent) on to a hard core material (such as sands, silicates, mineral carbonates, sulphates or phosphates) and drying if necessary. Agents which are commonly used to aid absorption or adsorption include solvents (such as aliphatic and aromatic petroleum solvents, alcohols, ethers, ketones and esters) and sticking agents (such as polyvinyl acetates, polyvinyl alcohols, dextrins, sugars and vegetable oils). One or more other additives may also be included in granules (for example an emulsifying agent, wetting agent or dispersing agent).

Dispersible Concentrates (DC) may be prepared by dissolving a compound of formula (I) in water or an organic solvent, such as a ketone, alcohol or glycol ether. These solutions may contain a surface active agent (for example to improve water dilution or prevent crystallisation in a spray tank).

Emulsifiable concentrates (EC) or oil-in-water emulsions (EW) may be prepared by dissolving a compound of formula (I) in an organic solvent (optionally containing one or more wetting agents, one or more emulsifying agents or a mixture of said agents). Suitable organic solvents for use in ECs include aromatic hydrocarbons (such as alkylbenzenes or alkylnaphthalenes, exemplified by SOLVESSO 100, SOLVESSO 150 and SOLVESSO 200; SOLVESSO is a Registered Trade Mark), ketones (such as cyclohexanone or methylcyclohexanone) and alcohols (such as benzyl alcohol, furfuryl alcohol or butanol), N-alkylpyrrolidones (such as N-methylpyrrolidone or N-octylpyrrolidone), dimethyl amides of fatty acids (such as $C_8$-$C_{10}$ fatty acid dimethylamide) and chlorinated hydrocarbons. An EC product may spontaneously emulsify on addition to water, to produce an emulsion with sufficient stability to allow spray application through appropriate equipment. Preparation of an EW involves obtaining a compound of formula (I) either as a liquid (if it is not a liquid at room temperature, it may be melted at a reasonable temperature, typically below 70° C.) or in solution (by dissolving it in an appropriate solvent) and then emulsifying the resultant liquid or solution into water containing one or more SFAs, under high shear, to produce an emulsion. Suitable solvents for use in EWs include vegetable oils, chlorinated hydrocarbons (such as chlorobenzenes), aromatic solvents (such as alkylbenzenes or alkylnaphthalenes) and other appropriate organic solvents which have a low solubility in water.

Microemulsions (ME) may be prepared by mixing water with a blend of one or more solvents with one or more SFAs, to produce spontaneously a thermodynamically stable isotropic liquid formulation. A compound of formula (I) is present initially in either the water or the solvent/SFA blend. Suitable solvents for use in MEs include those hereinbefore described for use in in ECs or in EWs. An ME may be either an oil-in-water or a water-in-oil system (which system is present may be determined by conductivity measurements) and may be suitable for mixing water-soluble and oil-soluble pesticides in the same formulation. An ME is suitable for dilution into water, either remaining as a microemulsion or forming a conventional oil-in-water emulsion.

Suspension concentrates (SC) may comprise aqueous or non-aqueous suspensions of finely divided insoluble solid particles of a compound of formula (I). SCs may be prepared by ball or bead milling the solid compound of formula (I) in a suitable medium, optionally with one or more dispersing agents, to produce a fine particle suspension of the compound. One or more wetting agents may be included in the composition and a suspending agent may be included to reduce the rate at which the particles settle. Alternatively, a compound of formula (I) may be dry milled and added to water, containing agents hereinbefore described, to produce the desired end product.

Aerosol formulations comprise a compound of formula (I) and a suitable propellant (for example n-butane). A compound of formula (I) may also be dissolved or dispersed in a suitable medium (for example water or a water miscible liquid, such as n-propanol) to provide compositions for use in non-pressurised, hand-actuated spray pumps.

A compound of formula (I) may be mixed in the dry state with a pyrotechnic mixture to form a composition suitable for generating, in an enclosed space, a smoke containing the compound.

Capsule suspensions (CS) may be prepared in a manner similar to the preparation of EW formulations but with an additional polymerisation stage such that an aqueous dispersion of oil droplets is obtained, in which each oil droplet is encapsulated by a polymeric shell and contains a compound of formula (I) and, optionally, a carrier or diluent therefor. The polymeric shell may be produced by either an interfacial polycondensation reaction or by a coacervation procedure. The compositions may provide for controlled release of the compound of formula (I) and they may be used for seed treatment. A compound of formula (I) may also be formulated in a biodegradable polymeric matrix to provide a slow, controlled release of the compound.

A composition may include one or more additives to improve the biological performance of the composition (for example by improving wetting, retention or distribution on surfaces; resistance to rain on treated surfaces; or uptake or mobility of a compound of formula (I)). Such additives include surface active agents, spray additives based on oils, for example certain mineral oils or natural plant oils (such as soy bean and rape seed oil), and blends of these with other bio-enhancing adjuvants (ingredients which may aid or modify the action of a compound of formula (I)).

A compound of formula (I) may also be formulated for use as a seed treatment, for example as a powder composition, including a powder for dry seed treatment (DS), a water soluble powder (SS) or a water dispersible powder for slurry treatment (WS), or as a liquid composition, including a flowable concentrate (FS), a solution (LS) or a capsule suspension (CS). The preparations of DS, SS, WS, FS and LS compositions are very similar to those of, respectively, DP, SP, WP, SC and DC compositions described above. Compositions for treating seed may include an agent for assisting the adhesion of the composition to the seed (for example a mineral oil or a film-forming barrier).

Wetting agents, dispersing agents and emulsifying agents may be surface SFAs of the cationic, anionic, amphoteric or non-ionic type.

Suitable SFAs of the cationic type include quaternary ammonium compounds (for example cetyltrimethyl ammonium bromide), imidazolines and amine salts.

Suitable anionic SFAs include alkali metals salts of fatty acids, salts of aliphatic monoesters of sulphuric acid (for example sodium lauryl sulphate), salts of sulphonated aromatic compounds (for example sodium dodecylbenzenesulphonate, calcium dodecylbenzenesulphonate, butylnaphthalene sulphonate and mixtures of sodium di-isopropyl- and tri-isopropyl-naphthalene sulphonates), ether sulphates, alcohol ether sulphates (for example sodium laureth-3-sulphate), ether carboxylates (for example sodium laureth-3-carboxylate), phosphate esters (products from the reaction between one or more fatty alcohols and phosphoric acid (predominately mono-esters) or phosphorus pentoxide (predominately di-esters), for example the reaction between lauryl alcohol and tetraphosphoric acid; additionally these products may be ethoxylated), sulphosuccinamates, paraffin or olefine sulphonates, taurates and lignosulphonates.

Suitable SFAs of the amphoteric type include betaines, propionates and glycinates.

Suitable SFAs of the non-ionic type include condensation products of alkylene oxides, such as ethylene oxide, propylene oxide, butylene oxide or mixtures thereof, with fatty alcohols (such as oleyl alcohol or cetyl alcohol) or with alkylphenols (such as octylphenol, nonylphenol or octylcresol); partial esters derived from long chain fatty acids or hexitol anhydrides; condensation products of said partial esters with ethylene oxide; block polymers (comprising ethylene oxide and propylene oxide); alkanolamides; simple esters (for example fatty acid polyethylene glycol esters); amine oxides (for example lauryl dimethyl amine oxide); and lecithins.

Suitable suspending agents include hydrophilic colloids (such as polysaccharides, polyvinylpyrrolidone or sodium carboxymethylcellulose) and swelling clays (such as bentonite or attapulgite).

A compound of formula (I) may be applied by any of the known means of applying pesticidal compounds. For example, it may be applied, formulated or unformulated, to the pests or to a locus of the pests (such as a habitat of the pests, or a growing plant liable to infestation by the pests) or to any part of the plant, including the foliage, stems, branches or roots, to the seed before it is planted or to other media in which plants are growing or are to be planted (such as soil surrounding the roots, the soil generally, paddy water or hydroponic culture systems), directly or it may be sprayed on, dusted on, applied by dipping, applied as a cream or paste formulation, applied as a vapour or applied through distribution or incorporation of a composition (such as a granular composition or a composition packed in a water-soluble bag) in soil or an aqueous environment.

A compound of formula (I) may also be injected into plants or sprayed onto vegetation using electrodynamic spraying techniques or other low volume methods, or applied by land or aerial irrigation systems.

Compositions for use as aqueous preparations (aqueous solutions or dispersions) are generally supplied in the form of a concentrate containing a high proportion of the active ingredient, the concentrate being added to water before use. These concentrates, which may include DCs, SCs, ECs, EWs, MEs SGs, SPs, WPs, WGs and CSs, are often required to withstand storage for prolonged periods and, after such storage, to be capable of addition to water to form aqueous preparations which remain homogeneous for a sufficient time to enable them to be applied by conventional spray equipment. Such aqueous preparations may contain varying amounts of a compound of formula (I) (for example 0.0001 to 10%, by weight) depending upon the purpose for which they are to be used.

A compound of formula (I) may be used in mixtures with fertilisers (for example nitrogen-, potassium- or phosphorus-containing fertilisers). Suitable formulation types include granules of fertiliser. The mixtures suitably contain up to 25% by weight of the compound of formula (I).

The invention therefore also provides a fertiliser composition comprising a fertiliser and a compound of formula (I).

The compositions of this invention may contain other compounds having biological activity, for example micronutrients or compounds having fungicidal activity or which possess plant growth regulating, herbicidal, insecticidal, nematicidal or acaricidal activity.

The compound of formula (I) may be the sole active ingredient of the composition or it may be admixed with one or more additional active ingredients such as a pesticide, fungicide, synergist, herbicide or plant growth regulator where appropriate. An additional active ingredient may: provide a composition having a broader spectrum of activity or increased persistence at a locus; synergise the activity or complement the activity (for example by increasing the speed of effect or overcoming repellency) of the compound of formula (I); or help to overcome or prevent the development of resistance to individual components. The particular additional active ingredient will depend upon the intended utility of the composition. Examples of suitable pesticides include the following:

a) Pyrethroids, such as permethrin, cypermethrin, fenvalerate, esfenvalerate, deltamethrin, cyhalothrin (in particular lambda-cyhalothrin), bifenthrin, fenpropathrin, cyfluthrin, tefluthrin, fish safe pyrethroids (for example ethofenprox), natural pyrethrin, tetramethrin, s-bioallethrin, fenfluthrin, prallethrin or 5-benzyl-3-furylmethyl-(E)-(1R,3S)-2,2-dimethyl-3-(2-oxothiolan-3-ylidenemethyl)cyclopropane carboxylate;

b) Organophosphates, such as, profenofos, sulprofos, acephate, methyl parathion, azinphos-methyl, demeton-s-methyl, heptenophos, thiometon, fenamiphos, monocrotophos, profenofos, triazophos, methamidophos, dimethoate, phosphamidon, malathion, chlorpyrifos, phosalone, terbufos, fensulfothion, fonofos, phorate, phoxim, pirimiphos-methyl, pirimiphos-ethyl, fenitrothion, fosthiazate or diazinon;

c) Carbamates (including aryl carbamates), such as pirimicarb, triazamate, cloethocarb, carbofuran, furathiocarb, ethiofencarb, aldicarb, thiofurox, carbosulfan, bendiocarb, fenobucarb, propoxur, methomyl or oxamyl;

d) Benzoyl ureas, such as diflubenzuron, triflumuron, hexaflumuron, flufenoxuron or chlorfluazuron;

e) Organic tin compounds, such as cyhexatin, fenbutatin oxide or azocyclotin;

f) Pyrazoles, such as tebufenpyrad and fenpyroximate;

g) Macrolides, such as avermectins or milbemycins, for example abamectin, emamectin benzoate, ivermectin, milbemycin, spinosad or azadirachtin;

h) Hormones or pheromones;

i) Organochlorine compounds such as endosulfan, benzene hexachloride, DDT, chlordane or dieldrin;

j) Amidines, such as chlordimeform or amitraz;

k) Fumigant agents, such as chloropicrin, dichloropropane, methyl bromide or metam;

l) Chloronicotinyl compounds such as imidacloprid, thiacloprid, acetamiprid, nitenpyram or thiamethoxam;

m) Diacylhydrazines, such as tebufenozide, chromafenozide or methoxyfenozide;

n) Diphenyl ethers, such as diofenolan or pyriproxifen;

o) lndoxacarb;

p) Chlorfenapyr; or q) Pymetrozine.

In addition to the major chemical classes of pesticide listed above, other pesticides having particular targets may be employed in the composition, if appropriate for the intended utility of the composition. For instance, selective insecticides for particular crops, for example stemborer specific insecticides (such as cartap) or hopper specific insecticides (such as buprofezin) for use in rice may be employed. Alternatively insecticides or acaricides specific for particular insect species/stages may also be included in the compositions (for example acaricidal ovo-larvicides, such as clofentezine, flubenzimine, hexythiazox or tetradifon; acaricidal motilicides, such as dicofol or propargite; acaricides, such as bromopropylate or chlorobenzilate; or growth regulators, such as hydramethylnon, cyromazine, methoprene, chlorfluazuron or diflubenzuron).

Examples of fungicidal compounds which may be included in the composition of the invention are (E)-N-methyl-2-[2-(2,5-dimethylphenoxymethyl)phenyl]-2-methoxy-iminoacetamide (SSF-129), 4-bromo-2-cyano-N,N-dimethyl-6-trifluoromethylbenzimidazole-1-sulphonamide, α-[N-(3-chloro-2,6-xylyl)-2-methoxyacetamido]-γ-butyrolactone, 4-chloro-2-cyano-N,N-dimethyl-5-p-tolylimidazole-1-sulfonamide (IKF-916, cyamidazosulfamid), 3-5-dichloro-N-(3-chloro-1-ethyl-1-methyl-2-oxopropyl)-4-methylbenzamide (RH-7281, zoxamide), N-allyl-4,5-dimethyl-2-trimethylsilylthiophene-3-carboxamide (MON65500), N-(1-cyano-1,2-dimethylpropyl)-2-(2,4-dichlorophenoxy)propionamide (AC382042), N-(2-methoxy-5-pyridyl)-cyclopropane carboxamide, acibenzolar (CGA245704), alanycarb, aldimorph, anilazine, azaconazole, azoxystrobin, benalaxyl, benomyl, biloxazol, bitertanol, blasticidin S, bromuconazole, bupirimate, captafol, captan, carbendazim, carbendazim chlorhydrate, carboxin, carpropamid, carvone, CGA41396, CGA41397, chinomethionate, chlorothalonil, chlorozolinate, clozylacon, copper containing compounds such as copper oxychloride, copper oxyquinolate, copper sulphate, copper tallate and Bordeaux mixture, cymoxanil, cyproconazole, cyprodinil, debacarb, di-2-pyridyl disulphide 1,1'-dioxide, dichlofluanid, diclomezine, dicloran, diethofencarb, difenoconazole, difenzoquat, diflumetorim, O,O-di-iso-propyl-S-benzyl thiophosphate, dimefluazole, dimetconazole, dimethomorph, dimethirimol, diniconazole, dinocap, dithianon, dodecyl dimethyl ammonium chloride, dodemorph, dodine, doguadine, edifenphos, epoxiconazole, ethirimol, ethyl(Z)—N-benzyl-N-([methyl(methyl-thioethylideneaminooxycarbonyl)amino]thio)-β-alaninate, etridiazole, famoxadone, fenamidone (RPA407213), fenarimol, fenbuconazole, fenfuram, fenhexamid (KBR2738), fenpiclonil, fenpropidin, fenpropimorph, fentin acetate, fentin hydroxide, ferbam, ferimzone, fluazinam, fludioxonil, flumetover, fluoroimide, fluquinconazole, flusilazole, flutolanil, flutriafol, folpet, fuberidazole, furalaxyl, furametpyr, guazatine, hexaconazole, hydroxyisoxazole, hymexazole, imazalil, imibenconazole, iminoctadine, iminoctadine triacetate, ipconazole, iprobenfos, iprodione, iprovalicarb (SZX0722), isopropanyl butyl carbamate, isoprothiolane, kasugamycin, kresoxim-methyl, LY186054, LY211795, LY248908, mancozeb, maneb, mefenoxam, mepanipyrim, mepronil, metalaxyl, metconazole, metiram, metiram-zinc, metominostrobin, myclobutanil, neoasozin, nickel dimethyldithiocarbamate, nitrothal-isopropyl, nuarimol, ofurace, organomercury compounds, oxadixyl, oxasulfuron, oxolinic acid, oxpoconazole, oxycarboxin, pefurazoate, penconazole, pencycuron, phenazin oxide, phosetyl-AI, phosphorus acids, phthalide, picoxystrobin (ZA1963), polyoxin D, polyram, probenazole, prochloraz, procymidone, propamocarb, propiconazole, propineb, propionic acid, pyrazophos, pyrifenox, pyrimethanil, pyroquilon, pyroxyfur, pyrrolnitrin, quaternary ammonium compounds, quinomethionate, quinoxyfen, quintozene, sipconazole (F-155), sodium pentachlorophenate, spiroxamine, streptomycin, sulphur, tebuconazole, tecloftalam, tecnazene, tetraconazole, thiabendazole, thifluzamid, 2-(thiocyanomethylthio)benzothiazole, thiophanate-methyl, thiram, timibenconazole, tolclofos-methyl, tolylfluanid, triadimefon, triadimenol, triazbutil, triazoxide, tricyclazole, tridemorph, trifloxystrobin (CGA279202), triforine, triflumizole, triticonazole, validamycin A, vapam, vinclozolin, zineb and ziram.

The compounds of formula (I) may be mixed with soil, peat or other rooting media for the protection of plants against seed-borne, soil-borne or foliar fungal diseases.

Examples of suitable synergists for use in the compositions include piperonyl butoxide, sesamex, safroxan and dodecyl imidazole.

Suitable herbicides and plant-growth regulators for inclusion in the compositions will depend upon the intended target and the effect required.

An example of a rice selective herbicide which may be included is propanil. An example of a plant growth regulator for use in cotton is PIX™.

Some mixtures may comprise active ingredients which have significantly different physical, chemical or biological properties such that they do not easily lend themselves to the same conventional formulation type. In these circumstances other formulation types may be prepared. For example, where one active ingredient is a water insoluble solid and the other a water insoluble liquid, it may nevertheless be possible to disperse each active ingredient in the same continuous aqueous phase by dispersing the solid active ingredient as a suspension (using a preparation analogous to that of an SC) but dispersing the liquid active ingredient as an emulsion (using a preparation analogous to that of an EW). The resultant composition is a suspoemulsion (SE) formulation.

The invention is illustrated by the following Examples:

EXAMPLE 1

This Example illustrates the preparation of compound V-22, 1-Acetyl-5-chloro-1'-[trans-3-(4-chlorophenyl)allyl]spiro[indoline-3,4'-piperidine]

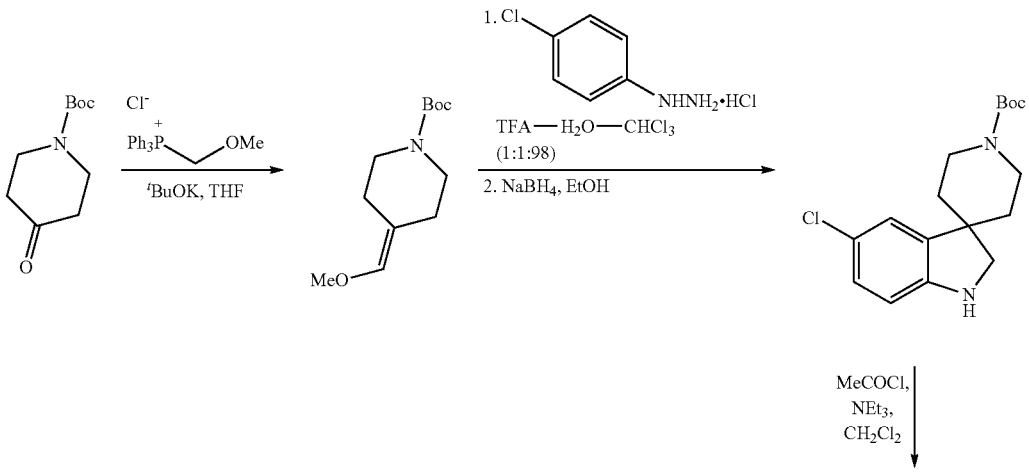

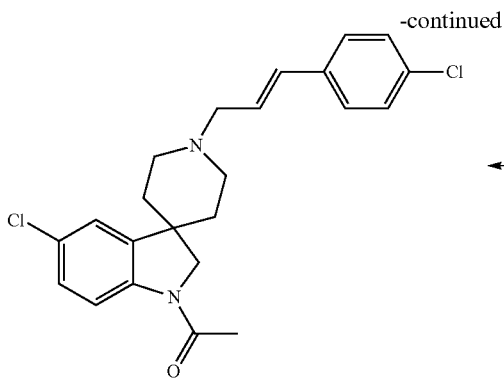 -continued 1. 30% TFA—CH$_2$Cl$_2$
2. NaHCO$_3$
3. 4-chlorocinnamyl chloride, iPr$_2$NEt, CHCl$_3$

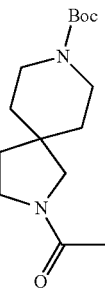

Step 1: Preparation of 4-methoxymethylenepiperidine-1-carboxylic acid tert-butyl ester Potassium tert-butoxide (21.3 g) was added in portions to a stirred solution of methoxymethyltriphenylphosphonium chloride (65.3 g) in anhydrous THF (500 ml) under an atmosphere of nitrogen at 4° C. A vivid orange colour was noted and the reaction was left as such for 1 h. 4-Oxopiperidine-1-carboxylic acid tert-butyl ester 1 (25 g) was added slowly not letting the temperature rise above 10° C. and the mixture was then allowed to warm to room temperature overnight.

The reaction mixture was poured onto water (150 ml), extracted three times with ethyl acetate (100 ml) and the combined organics were washed with brine (300 ml), dried over anhydrous sodium sulphate and concentrated in vacuo to yield a brown oil (50 g). Flash chromatography [SiO$_2$; hexane, then ethyl acetate-hexane (10:90)] yielded 26.4 g (77%) of the desired enol ether.

$^1$H NMR (400 MHz, CDCl$_3$) 1.5 (9H, m), 2.0-2.2 (m, 4H), 3.4 (m, 4H), 3.5 (s, 3H), 5.9 (s, 1H). MS (ES+) 228 (M+H$^+$), 172 (M-$^t$butene+H$^+$)

Step 2: Preparation of 5-chlorospiro[indoline-3,4'-piperidine]-1'-carboxylic acid tert-butyl ester Trifluoroacetic acid (12 ml) was added to a stirred solution of 4-methoxymethylene-piperidine-1-carboxylic acid tert-butyl ester (12.5 g), 4-chlorophenylhydrazine hydrochloride (9.75 g) and ethanol (1 ml) in chloroform (1200 ml) at 4 PC under an atmosphere of nitrogen. The mixture was then stirred at 50° C. overnight, turning a dark green colour. The reaction was quenched with concentrated ammonia solution (200 ml) in ice water (500 ml), the organic layer turning orange. The organic layer was separated and the aqueous was further extracted twice with dichloromethane. The combined organics were washed with brine (300 ml), dried over anhydrous sodium sulphate and concentrated in vacuo to yield 13 g of the crude imine 5-chlorospiro[3H-indole-3,4'-piperidine]-1'-carboxylic acid tert-butyl ester (purity approximately 80% by NMR). $^1$H NMR (400 MHz, CDCl$_3$) 1.5 (9H, m), 1.70 (m, 2H), 1.85 (m, 2H), 3.50 (m, 2H), 4.05 (m, 2H), 7.35 (m, 2H), 7.60 (s, 1H), 8.35 (s, 1H). MS (ES+) 321/323 (M+H$^+$), 265/267 (M-$^t$butene+H$^+$), 221/223 (M-Boc+H$^+$).

Sodium borohydride (6.0 g) was added to a stirred solution of crude imine (12 g) in absolute ethanol (500 ml) under an atmosphere of nitrogen. The reaction was stirred for 15 min and left to stand overnight. The mixture was concentrated in vacuo and the residue re-dissolved in dichloromethane (100 ml). The organics were washed with water (100 ml) and brine (100 ml), dried over anhydrous sodium sulphate and concentrated in vacuo to yield a brown solid. Flash chromatography [SiO$_2$: ethyl acetate-hexane-triethylamine (25:75:1)] yielded 9.8 g (56%, over both steps) of the desired indoline. M.p. 165-166° C. $^1$H NMR (400 MHz, CDCl$_3$) 1.5 (9H, s), 1.70 (m, 4H), 2.9 (m, 2H), 3.50 (s, 2H), 3.75 (br s, 1H), 4.05 (m, 2H), 6.55 (d, J=6 Hz, 1H), 7.00 (m, 2H). MS (ES+) 323/325 (M+H$^+$), 267/269 (M-$^t$butene+H$^+$), 223/225 (M-Boc+H$^+$).

Step 3: Preparation of 1-acetyl-5-chlorospiro[indoline-3,4'-piperidine]-1'-carboxylic acid tert-butyl ester Acetyl chloride (2.8 ml) was added dropwise to a stirred solution of 5-chlorospiro[indoline-3,4'-piperidine]-1'-carboxylic acid tert-butyl ester (9.8 g) and triethylamine (15 ml) in anhydrous dichloromethane (400 ml) under an atmosphere of nitrogen. The reaction was stirred for 1 h and was then quenched with saturated sodium bicarbonate solution (200 ml). The organic layer was dried over anhydrous sodium sulphate and concentrated in vacuo to yield 9.8 g (87%) of the desired amide as an off-white solid. M.p. 64-66° C. $^1$H NMR (400 MHz, CDCl$_3$) δ 6:1 mixture of rotamers. Major rotamer 1.5 (9H, s), 1.70 (m, 2H), 1.85 (m, 2H), 2.25 (s, 3H), 2.85 (m, 2H), 3.90 (s, 2H), 4.2 (m, 2H), 6.97 (d, J=1 Hz, 1H), 7.20 (dd, J=7 & 1 Hz, 1H), 8.15 (d, J=7 Hz, 1H). Minor rotamer 1.5 (9H, s), 1.70 (m, 2H), 1.85 (m, 2H), 2.45 (s, 3H), 2.85 (m, 2H), 4.05 (s, 2H), 4.2 (m, 2H), 7.2 (d, J=1 Hz, 1H), 7.25 (dd, J=7 & 1 Hz, 1H), 7.48 (d, J=7 Hz, 1H).

Step 4: Preparation of 1-acetyl-5-chlorospiro[indoline-3,4'-piperidine]

Trifluoroacetic acid (25 ml) was added to a stirred solution of 1-acetyl-5-chlorospiro[indoline-3,4'-piperidine]-1'-carboxylic acid tert-butyl ester (8 g) in anhydrous dichloromethane (250 ml) under an atmosphere of nitrogen. The reaction was left as such for 3 h. The reaction was washed with saturated bicarbonate solution (200 ml) and dried over sodium sulphate and concentrated in vacuo to yield an off white solid. Flash chromatography [SiO$_2$: methanol-dichloromethane-triethylamine (90:5:5)] yielded 5.6 g (61%) of the desired 1-Acetyl-5-chlorospiro[indoline-3,4'-piperidine]. $^1$H NMR (400 MHz, CDCl$_3$) δ 6:1 mixture of rotamers. Major rotamer 1.70 (m, 2H), 1.80 (m, 2H), 2.27 (s, 3H), 2.75 (t, J=12 Hz, 2H), 3.15 (m, 2H), 3.90 (s, 2H), 7.12 (d, J=1 Hz, 1H), 7.18 (dd, J=7 & 1 Hz, 1H), 8.15 (d, J=7 Hz, 1H). Minor rotamer (partial data) 2.44 (s, 3H), 2.86 (m, 2H), 3.10 (m, 2H), 4.05 (s, 2H). MS (ES+) 265/267 (M+H$^+$).

Step 5: Preparation of 1-acetyl-5-chloro-1'-[trans-3-(4-chlorophenyl)allyl]spiro[indoline-3,4'-piperidine]

A solution of 4-chlorocinnamyl chloride (4.0 g) in chloroform (120 ml) was added slowly to a stirred mixture of 1-acetyl-5-chlorospiro[indoline-3,4'-piperidine] (5.3 g) and diisopropylethylamine (6.7 ml) in chloroform (120 ml) under an atmosphere of nitrogen at room. The reaction was heated to 50° C. for 30 h. The reaction mixture was concentrated in vacuo to yield a red oil. Flash chromatography [SiO$_2$; ethyl acetate-hexane-triethylamine (50:50:1)] yielded 5.1 g (68%) of the desired compound. $^1$H NMR (400 MHz, CDCl$_3$) δ 5:1 mixture of rotamers. Major rotamer 1.70 (d, J=12 Hz, 2H), 2.0 (td, J=12 & 2 Hz), 2.08 (t, J=12 Hz, 2H), 2.25 (s, 3H), 3.03 (d, J=12 Hz, 2H), 3.20 (d, J=7 Hz, 2H), 3.96 (s, 2H), 6.28 (dt, J=12 & 5 Hz, 1H), 6.50 (d, J=12 Hz, 1H), 7.13 (d, J=1 Hz, 1H), 7.18 (dd, J=7 & 1 Hz, 1H), 7.3 (m, 4H), 8.15 (d, J=7 Hz, 1H). Minor rotamer (partial data) 2.42 (s, 3H), 4.00 (s, 2H). MS (ES+) 415/417/419 (M+H$^+$).

Compounds II-301, V-21, XXIX-49, V-192, V-62, V-202 XXX-1, XXX-11, XXXI-1, XXX-118, XXX-12, XXX-13, XXX-14, XXX-15, XXX-16, XXX-17, XXX-18, XXX-19, XXX-2, XXX-20, XXX-21, XXX-22, XXX-23, XXX-24, XXX-25, XXX-26, XXX-27, XXX-28, XXX-29, XXX-3, XXX-4, XXX-5, XXX-6, XXX-7, XXXII-7, XXX-8, XXXI-2, XXXI-8, XXXII-1, XXXII-10, XXXII-2, XXXII-3, XXXII-4, XXXII-5, XXXII-6, XXXII-8 and XXXII-9 were prepared according to procedures analogous to those described in Example 1.

EXAMPLE 2

This Example illustrates the preparation of compound I-1, 1-(2-Chloropyridin-4-yl)carbonyl-1'-[trans-3-phenylallyl] spiro[indoline-3,4'-piperidine]

Spiro[indoline-3,4'-piperidine]-1'-carboxylic acid tert-butyl ester was prepared according to a procedure analogous to that described in steps 1 and 2 of Example 1.

Step 1: 1-(2-chloropyridin-4-yl)carbonylspiro[indoline-3,4'-piperidine]-1'-carboxylic acid tert-butyl ester Thionyl chloride (20 ml) was added to 2-chloroisonicotinic acid (1.2 g) at room temperature. DMF (2 drops) was added and the mixture was heated to reflux for 1 hour. The excess thionyl chloride was evaporated and the residue was dissolved in dichloromethane (50 ml). Triethylamine (2 ml) was added followed by dropwise addition of a solution of spiro[indoline-3,4'-piperidine]-1'-carboxylic acid tert-butyl ester (1.7 g) dissolved in dichloromethane (20 ml). The mixture was stirred for 48 hours. The reaction mixture was washed with pH 9.4 buffer (100 ml) and the aqueous layer was extracted with dichloromethane. The combined organic layers were dried (magnesium sulfate), filtered and evaporated. The crude product was purified by chromatography [SiO$_2$; ethyl acetate-hexane-triethylamine (50:50:1), increasing polarity to (100:0:1)] to give 2.4 g (94%) of the desired amide. M.p. 212° C.; $^1$H NMR (400 MHz, d$_6$-DMSO) 1.50 (s, 9H), 1.6-1.8 (m, 4H), 2.8 (br s, 2H), 3.9 (br s, 2H), 4.08 (d, 2H), 7.0-7.2 (m, 3H), 7.30 (d, J=6 Hz, 1H), 8.43 (d, J=6 Hz, 1H), 7.40 (s, 1H), 8.0-8.2 (br m, 1H); MS (ES+) 428/430 (M+H$^+$), 372/374 (M+H$^+$-isobutene).

Step 2: Preparation of 1-(2-chloropyridin-4-yl)carbonylspiro[indoline-3,4'-piperidine]trifluoroacetic Acid Salt Trifluoroacetic acid (30 ml) was added to a solution of solution of 1-(2-chloropyridin-4-yl)carbonylspiro[indoline-

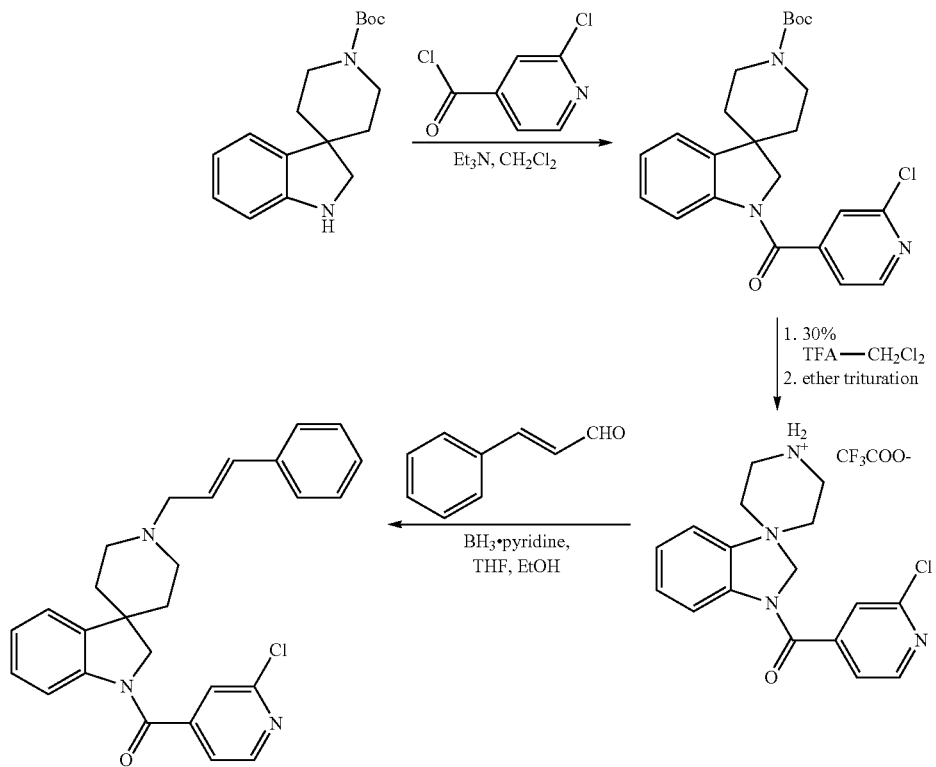

3,4'-piperidine]-1'-carboxylic acid tert-butyl ester (2.3 g) in anhydrous dichloromethane (50 ml), the solution darkening upon addition. The reaction was left as such for 15 min. The reaction mixture was evaporated in vacuo and the dark residue re-suspended in dry ether (100 ml). The residue was triturated until it became a free-flowing beige precipitate. The precipitate was collected by filtration and dried in a stream of nitrogen to give 2.28 g (96%) of the desired amine salt. M.p. 245° C. (decomposition). $^1$H NMR (400 MHz, d$_6$-DMSO) 1.8 (m, 2H), 1.9 (m, 2H), 2.9 (m, 2H), 3.25 (m, 2H), 3.98 (s, 2H), 7.15-7.3 (m, 2H), 7.24 (d, J=8 Hz, 1H), 7.56 (d, J=7 Hz, 1H), 7.62 (s, 1H), 8.1 (br s, 1H), 8.56 (d, J=7 Hz, 1H), 8.8 (br s, 2H). MS (ES+) 328/330 (M+H$^+$).

Step 3: Preparation of 1-(2-chloropyridin-4-yl)carbonyl-1'-[trans-3-phenylallyl]spiro[indoline-3,4'-piperidine]

1-(2-Chloropyridin-4-yl)carbonylspiro[indoline-3,4'-piperidine]trifluoroacetic acid salt (0.44 g) and trans-cinnamaldehyde (0.29 g) were suspended in tetrahydrofuran (8 ml) and ethanol (6 ml). Borane-pyridine complex (0.26 ml) was added and the reaction stirred vigorously overnight at room temperature. The mixture was evaporated and partitioned between dichloromethane and water. The organics were dried over anhydrous magnesium sulfate and evaporated in vacuo. Flash chromatography [SiO$_2$; ethyl acetate-hexane-triethylamine (25:75:1), increasing polarity to (50:50:1)] yielded 0.42 g (94%) of the desired product.

$^1$H NMR (400 MHz, CDCl$_3$) δ 3:1 mixture of rotamers. Major rotamer 1.70 (m, 2H), 1.8-2.1 (m, 4H), 3.0 (m, 2H), 3.20 (m, 2H), 3.75 (m, 2H), 6.3 (m, 1H), 6.52 (d, J=12 Hz, 1H), 7.1-7.4 (m, 9H), 7.46 (d, J=2 Hz, 1H), 8.2 (br m, 1H), 8.6 (m, 1H). MS (ES+) 444/446 (M+H$^+$).

Compounds I-5, I-4, XXIX-7, XXIX-13, I-182, I-142, I-132, XXII-22, VI-1, VI-101, I-22, XXX-96, XXIX-31 (with an alkylation as the final step), XXIX-37 (with an alkylation as the final step), XXIX-43 (with an alkylation as the final step), XXVII-1 (followed by treatment with HCl in ether), XXVII-2 (followed by treatment with HCl in ether), XXVII-22 (followed by treatment with HCl in ether), XXVI-1 (followed by treatment with hydrogen peroxide in methanol) and XXIX-25 (with an acylation as the final step) were prepared according to procedures analogous to those described in Example 2.

EXAMPLE 3

This Example illustrates the preparation of compound VI-22, 1-(Pyridin-4-yl)-carbonyl-5-chloro-1'-[trans-3-(4-chlorophenyl)allyl]spiro[indoline-3,4'-piperidine]

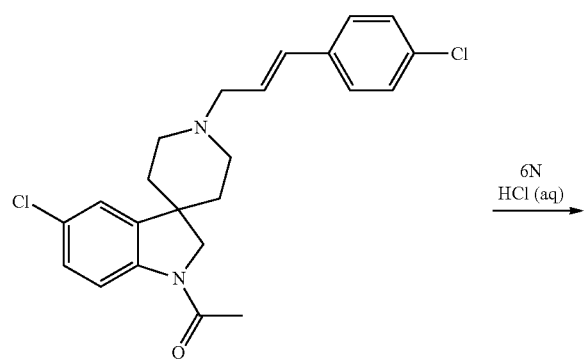

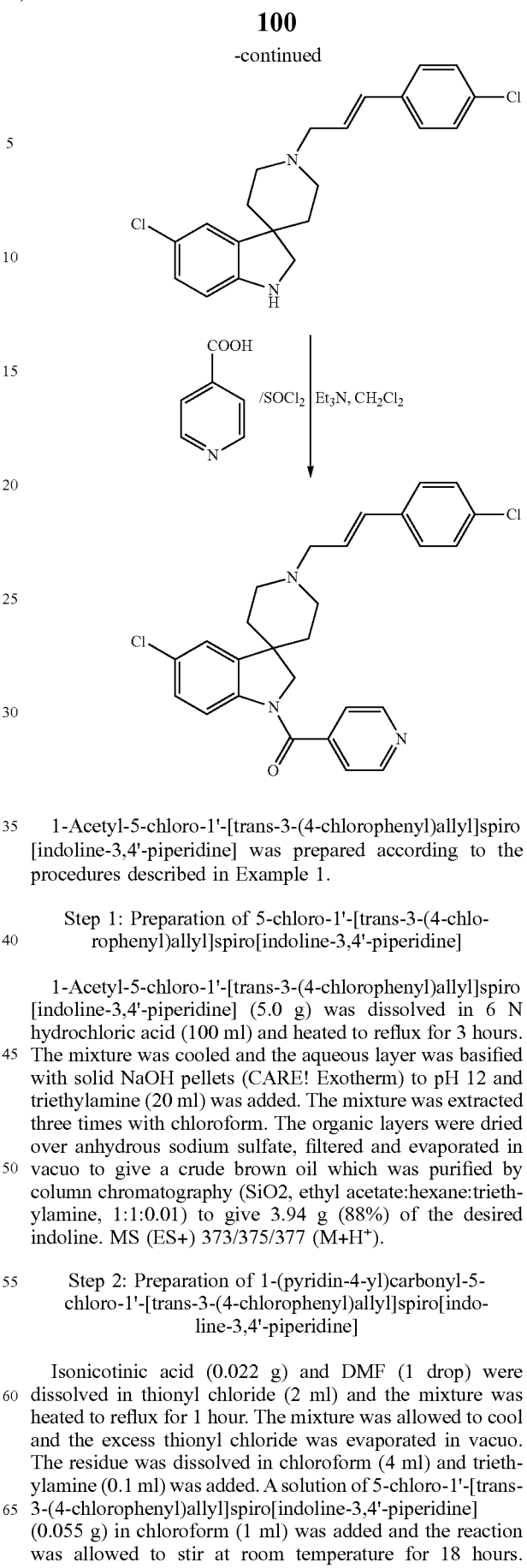

1-Acetyl-5-chloro-1'-[trans-3-(4-chlorophenyl)allyl]spiro[indoline-3,4'-piperidine] was prepared according to the procedures described in Example 1.

Step 1: Preparation of 5-chloro-1'-[trans-3-(4-chlorophenyl)allyl]spiro[indoline-3,4'-piperidine]

1-Acetyl-5-chloro-1'-[trans-3-(4-chlorophenyl)allyl]spiro[indoline-3,4'-piperidine] (5.0 g) was dissolved in 6 N hydrochloric acid (100 ml) and heated to reflux for 3 hours. The mixture was cooled and the aqueous layer was basified with solid NaOH pellets (CARE! Exotherm) to pH 12 and triethylamine (20 ml) was added. The mixture was extracted three times with chloroform. The organic layers were dried over anhydrous sodium sulfate, filtered and evaporated in vacuo to give a crude brown oil which was purified by column chromatography (SiO2, ethyl acetate:hexane:triethylamine, 1:1:0.01) to give 3.94 g (88%) of the desired indoline. MS (ES+) 373/375/377 (M+H$^+$).

Step 2: Preparation of 1-(pyridin-4-yl)carbonyl-5-chloro-1'-[trans-3-(4-chlorophenyl)allyl]spiro[indoline-3,4'-piperidine]

Isonicotinic acid (0.022 g) and DMF (1 drop) were dissolved in thionyl chloride (2 ml) and the mixture was heated to reflux for 1 hour. The mixture was allowed to cool and the excess thionyl chloride was evaporated in vacuo. The residue was dissolved in chloroform (4 ml) and triethylamine (0.1 ml) was added. A solution of 5-chloro-1'-[trans-3-(4-chlorophenyl)allyl]spiro[indoline-3,4'-piperidine] (0.055 g) in chloroform (1 ml) was added and the reaction was allowed to stir at room temperature for 18 hours.

Aqueous sodium carbonate solution (1M, 20 ml) was added and the mixture was extracted into chloroform (3×20 ml). The combined organic layers were dried (magnesium sulfate), filtered and evaporated in vacuo to give a crude brown oil which was purified by chromatography (SiO2, ethyl acetate:hexane:triethylamine 0:1:0.01 to 1:0:0.01) to give 0.034 g (49%) of the desired amide. MS (ES+) 478/480/482 (M+H$^+$).

Compounds XXV-62, I-192, I-202, XXIX-189, VI-202 and VI-62 were prepared according to procedures analogous to those described in Example 3.

EXAMPLE 4

This Example illustrates the preparation of compound XIX-202, 1-(4-cyanobenzoyl)-5-methyl-1'-[trans-3-(4-chlorophenyl)allyl]spiro[indoline-3,4'-piperidine]

was added. A solution of 4-chlorocinnamyl chloride (1.2 g) dissolved in chloroform (2 ml) was added and mixture was heated to 70° C. overnight. The solvents were evaporated in vacuo and flash chromatography [SiO$_2$; ethyl acetate-hexane-triethylamine (50:50:2)] yielded 1.38 g (76%) of the desired ketal as a yellow oil. $^1$H NMR (400 MHz, CDCl$_3$) 1.78 (t, J=4 Hz, 4H), 2.60 (br s, 4H), 3.18 (d, J=5 Hz, 2H), 3.96 (s, 4H), 6.27 (dt, J=12 & 5 Hz, 1H) 6.47 (d, J=12 Hz, 2H), 7.28 (m, 4H). MS (ES+) 294/296 M+H$^+$.

Step 2: Preparation of 1-[trans-3-(4-chlorophenyl)allyl]-4-oxopiperidine

8-[trans-3-(4-Chlorophenyl)allyl]-1,4-dioxa-8-azaspiro [4.5]decane (1.38 g) was dissolved in methanol (40 ml) and 6 N hydrochloric acid (120 ml) was added. The mixture was heated to reflux for 4 h. The mixture cooled and was basified

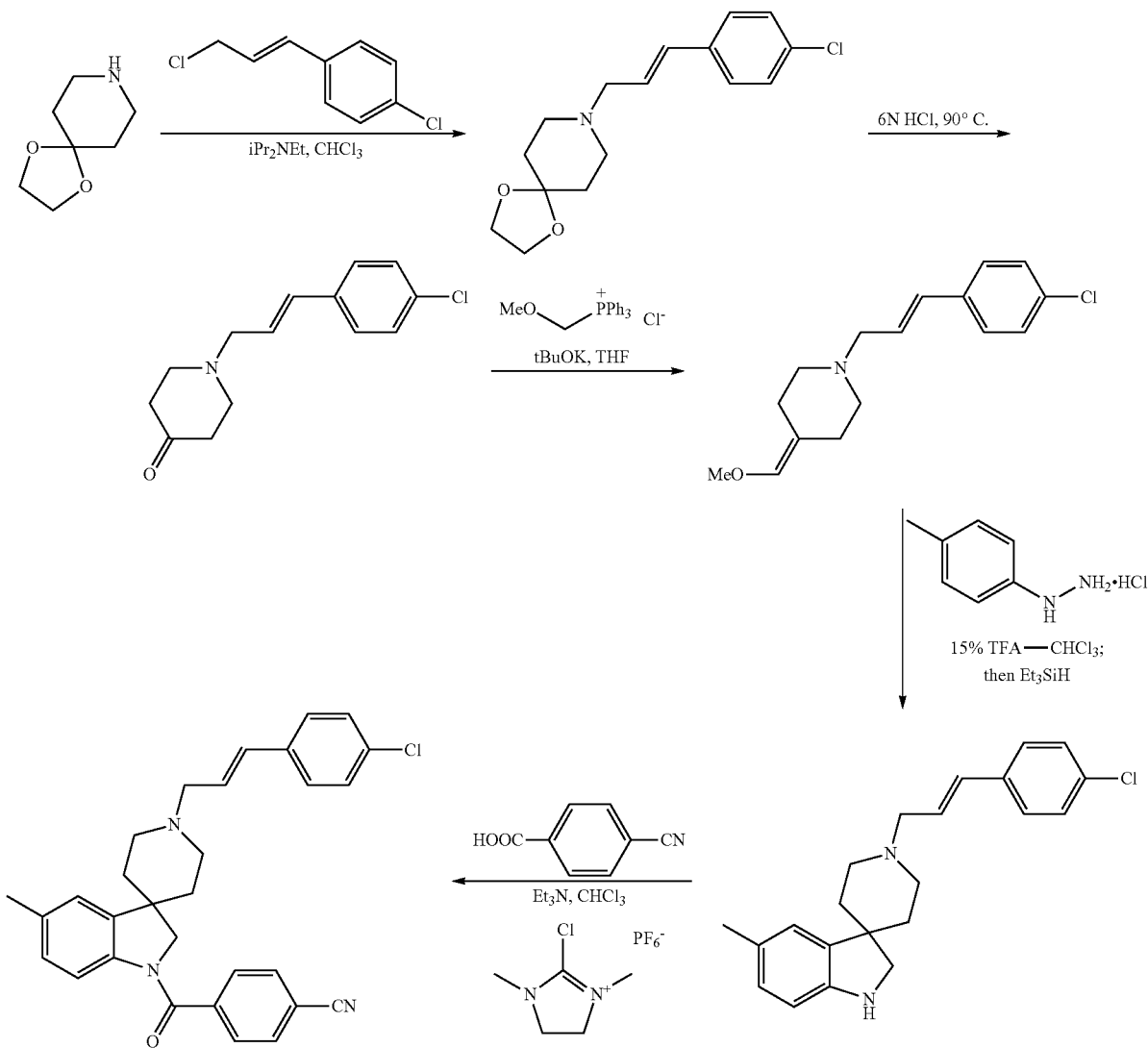

Step 1: Preparation of 8-[trans-3-(4-chlorophenyl) allyl]-1,4-dioxa-8-azaspiro[4.5]decane 1,4-Dioxa-8-azaspiro[4.5]decane (0.88 g) was dissolved in chloroform (5 ml) and diisopropylethylamine (2.1 ml)

to pH 14 with solid sodium hydroxide pellets (CARE! Exotherm), the solution becoming opaque. The aqueous was extracted three times with ether. The organics were washed with brine, dried over anhydrous MgSO$_4$ and evaporated to give 1.17 g (100%) of the desired ketone $^1$H NMR (400

MHz, CDCl₃) 2.38 (m, 4H), 2.70 (m, 4H), 3.15 (d, J=5 Hz, 2H), 3.96 (s, 4H), 6.17 (dt, J=12 & 5 Hz, 1H), 6.40 (d, J=12 Hz, 1H), 7.20 (m, 4H). MS (ES+) 250/252 M+H⁺.

Step 3: Preparation of 1-[trans-3-(4-chlorophenyl) allyl]-4-methoxymethylenepiperidine Methoxymethyltriphenylphosphonium chloride (2.4 g) was dissolved in tetrahydrofuran (20 ml) and was cooled to 4° C. Potassium tert-butoxide (0.78 g) was added, turning the solution a bright orange colour. The reaction was left as such for 30 min. A solution of 1-[trans-3-(4-chlorophenyl) allyl]-4-oxopiperidine (0.85 g) dissolved in tetrahydrofuran (10 ml) was added and the mixture was stirred for 10 min. The solvents were evaporated in vacuo and the residue re-suspended in ether. The organics were washed with water and dried over anhydrous magnesium sulfate. Flash chromatography [SiO₂; ethyl acetate-hexane-triethylamine (50:50:2)] gave 0.85 g (89%) of the desired enol ether. ¹H NMR (400 MHz, CDCl₃) 2.10 (t, J=6 Hz, 2H), 2.35 (t, J=6 Hz, 2H), 2.4 (m, 4H), 3.13 (d, J=5 Hz, 2H), 3.55 (s, 3H), 5.80 (s, 1H), 6.30 (dt, J=11 & 5 Hz, 1H), 6.45 (d, J=11 Hz, 1H), 7.28 (m, 4H). MS (ES+) 278/280 (M+H⁺).

Step 4: Preparation of 5-methyl-1'-[trans-3-(4-chlorophenyl)allyl]spiro[indoline-3,4'-piperidine]

Trifluoroacetic acid (0.75 ml) was added to a stirred solution of 1-[trans-3-(4-chlorophenyl)allyl]-4-methoxymethylenepiperidine- and 4-tolylhydrazine hydrochloride (28 mg) in chloroform (5 ml) and the reaction was heated to 50°C for 5 h. Triethylsilane (2 ml) was added and the reaction was heated at 50° C. for a further 5 h. The mixture was allowed to cool and was quenched in concentrated ammonia solution/ice chips (20 ml). The aqueous phase was extracted twice with chloroform and the combined organics were dried over anhydrous magnesium sulphate and concentrated in vacuo to yield 0.04 g (63%) of the desired indoline. ¹H NMR (400 MHz, CDCl₃) 1.75 (d, J=9 Hz, 2H), 1.96 (td, J=8 & 2, 2H), 2.13 (t, J=9 Hz, 2H), 2.25 (s, 3H), 2.95 (d, J=10 Hz, 2H), 3.19 (d, J=5 Hz, 2H), 3.42 (s, 2H), 6.30 (dt, J=11 &5 Hz, 1H), 6.48 (d, J=11 Hz, 1H), 6.58 (d, J=7 Hz, 1H), 6.85 (d, J=7 Hz, 1H), 6.9 (s, 1H), 7.30 (m, 4H). MS (ES+) 353/355 (M+H⁺), 203 (M-4-chlorocinnamyl+H⁺).

Step 5: Preparation of 1-(4-cyanobenzoyl)-5-methyl-1'-[trans-3-(4-chlorophenyl)allyl]spiro[indoline-3,4'-piperdine]

This step was achieved using a Zymark XP2 synthetic chemistry robot. A solution of 5-methyl-1'-[trans-3-(4-chlorophenyl)allyl]spiro[indoline-3,4'-piperidine] (2 ml of a solution derived from dissolving 1.43 g in 100 ml of THF) was added to a robot tube and the solvent was removed in vacuo. 4-Cyanobenzoic acid (28 mg) was weighed into a different robot tube. A solution of 2-chloro-1,3-dimethyl-2-imidazolinium hexafluorophosphate (2 ml of a solution derived from dissolving 4.80 g in 180 ml of chloroform) and a solution of triethylamine (2 ml of a solution derived from dissolving 8.68 ml in 250 ml of chloroform) were added to the acid and the tube was agitated and allowed to stand for 30 minutes. A 2 ml aliquot of the acid solution was added to the tube containing the dry amine. This tube was agitated and allowed to stand overnight. The reaction mixture was washed with 1M aqueous sodium carbonate solution and the solvents were evaporated. The crude mixture was purified by MS directed liquid chromatography to give the desired amide, 2.9 mg. MS (ES+) 482/484 (M+H⁺).

Compounds I-61, I-171, XXVIII-97, XIX-22, XXVIII-67, XXVIII-7, XX-22, XXIX-69, XXIX-75, XVIII-22, XXVIII-217, XXIX-81, XXIX-87, XV-22, XXIX-93, XXIX-99, XXVIII-187, XXI-22, XXIX-105, XXIX-111, XXIX-117, XXIX-123, XIII-22, XXIX-129, X-22, XXIX-135, XXIX-141, XXIX-147, XXIX-153, XII-22, XXIX-196, II-22, XXIX-159, XXVIII-252, XXVIII-27, XXVIII-42, XVIII-202, XX-62, XXIX-165, XXVIII-162, XXVIII-132, XXIX-171, XXIX-177, XXI-62, XVII-62, XIII-62, X-62, XXIX-183, XI-62, IX-62, XXIX-207, XXIX-195, II-62, I-92, I-112, I-12, I-32, I-52, I-72, I-152, I-162, I-82, I-252, I-242, I-262, I-292, I-62 XXX-10, XXX-116, XXX-117, XXX-30, XXX-33, XXX-34, XXX-35, XXX-36, XXX-37, XXX-38, XXX-39, XXX-40, XXX-41, XXX-42, XXX-43, XXX-44, XXX-45, XXX-46, XXX-47, XXX-48, XXX-49, XXX-50, XXX-9 and XXX-93 were prepared according to procedures analogous to those described in Example 4.

EXAMPLE 5

This example illustrates the preparation of compound XIV-22, 1-(2-Pyrazinyl)-5-chloro-1'-[trans-3-(4-chlorophenyl)allyl]spiro[indoline-3,4'-piperidine]

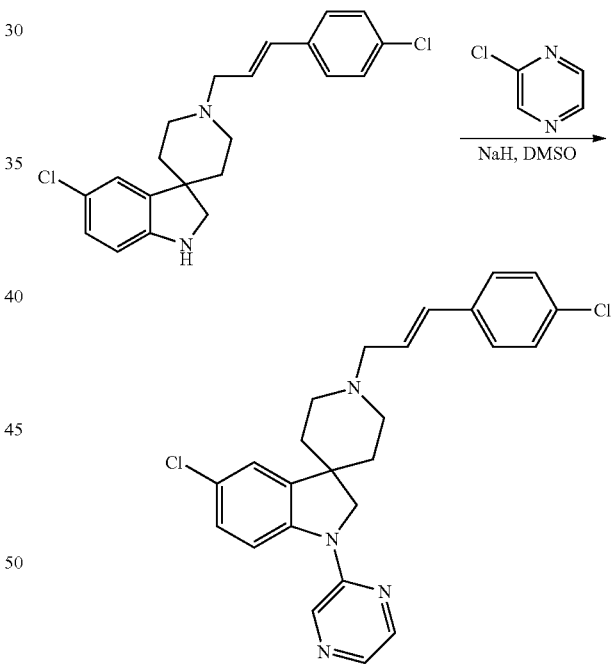

5-Chloro-1'-[trans-3-(4-chlorophenyl)allyl]spiro[indoline-3,4'-piperidine] was prepared according to the procedures described in Example 3.

Sodium hydride (50 mg) was added to a stirred solution of 5-chloro-1'-[trans-3-(4-chlorophenyl)allyl]spiro[indoline-3,4'-piperidine] (35 mg) and 2-chloropyrazine (43 mg) in anhydrous DMSO (5 ml) under an atmosphere of nitrogen. The reaction was heated to 60° C. overnight. The reaction mixture was diluted with brine (20 ml) and extracted four times with dichloromethane (20 ml). The combined organics were dried over magnesium sulphate and concentrated in vacuo (1 mmHg) to yield a brown oil. Flash chromatography [SiO$_2$, ethyl acetate-hexane-triethylamine gradient (0:98:2) to (98:0:2)] yielded 25 mg (55%) of the desired product. $^1$H NMR (400 MHz, CDCl$_3$) 1.75 (m, 2H), 2.05 (td, J=8 & 2, 2H), 2.18 (t, J=9 Hz, 2H), 3.05 (d, J=9 Hz, 2H), 3.22 (d, J=5 Hz, 2H), 3.94 (s, 2H), 6.30 (dt, J=11 & 5 Hz, 1H), 6.51 (d, J=11 Hz, 1H), 7.18 (m, 2H), 7.30 (m, 4H), 8.05 (d, J=1 Hz, 1H), 8.17 (d, J=6 Hz, 1H), 8.25 (m, 2H). MS (ES+) 451/453/455 M+H$^+$.

Compounds XXIX-57 and XXIX-63 were prepared according to procedures analogous to those described in Example 5.

EXAMPLE 6

This Example illustrates the preparation of compound XXII-3, 1-(2-Chloropyridin-4-yl)carbonyl-1'-[trans-3-(4-fluorophenyl)allyl]spiro[indoline-3,4'-piperidine]

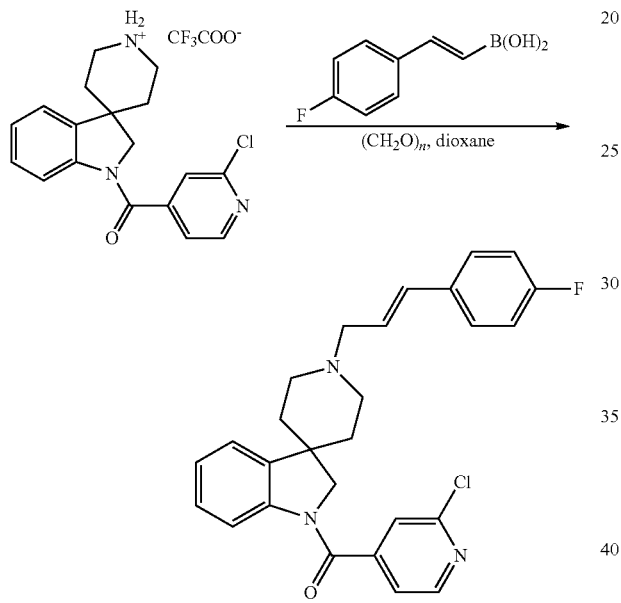

1-(2-Chloropyridin-4-yl)carbonylspiro[indoline-3,4'-piperidine]trifluoroacetic acid salt was prepared according to the procedures described in Example 2.

1-(2-Chloropyridin-4-yl)carbonylspiro[indoline-3,4'-piperidine]trifluoroacetic acid salt (0.25 g) was suspended in dioxane (2 ml) and paraformaldehyde (0.08 g) was added. The mixture was stirred and heated to 90° C. for 20 minutes. 2-(4-fluorophenyl)vinylboronic acid (0.10 g) was dissolved in dioxane (2 ml) and the resulting solution was added to the salt/paraformaldehyde mixture and the resulting mixture was heated to 90° C. for 24 hours. The mixture was allowed to cool and evaporated to dryness in vacuo. The residue was partitioned between dichloromethane and water, and the organic layer was washed with aqueous sodium carbonate solution (1M) and evaporated. The crude product was purified by column chromatography (SiO$_2$, first column in dichloromethane:triethylamine 95:5, then a second column starting with neat dichloromethane, then a gradient from ethyl acetate:hexane:triethylamine 25:75:1 to 95:0:5) to give 0.20 g (76%) of the desired product. MS (ES+) 462/464 M+H$^+$.

Compounds I-23, XXIX-1, I-21, I-2, XXVI-2 (followed by treatment with hydrogen peroxide in methanol) and XXVI-22 (followed by treatment with hydrogen peroxide in methanol), were prepared according to procedures analogous to those described in Example 6.

EXAMPLE 7

This Example illustrates the preparation of compound I-212, 5-Cyano-1-(2-chloropyridin-4-yl)carbonyl-1'-[trans-3-(4-chlorophenyl)allyl]spiro[indoline-3,4'-piperidine]

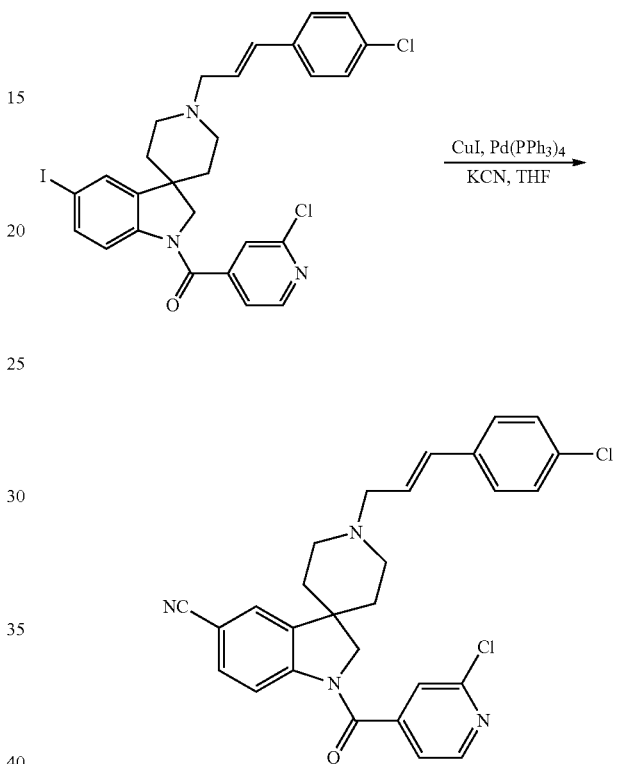

5-Iodo-1-(2-chloropyridin-4-yl)carbonyl-1'-[trans-3-(4-chlorophenyl)allyl]spiro[indoline-3,4'-piperidine] was prepared by procedures analogous to those described in Example 2. 5-Iodo-1-(2-chloropyridin-4-yl)carbonyl-1'-[trans-3-(4-chlorophenyl)allyl]spiro[indoline-3,4'-piperidine] (0.05 g) was dissolved in anhydrous THF (5 ml) under an atmosphere of dry nitrogen. Potassium cyanide (0.011 g) and copper (I) iodide (0.016 g) were added and the mixture was degassed for 15 minutes. Tetrakis(triphenylphosphine) palladium (0.005 g) was added and the mixture was heated to reflux for 28 hours. The reaction mixture was diluted with dichloromethane (50 ml) and washed with water (30 ml). The aqueous layer was extracted with dichloromethane (2×40 ml) and the combined organic layers were dried (magnesium sulfate), filtered and evaporated in vacuo to give a colourless oil that was purified by prep. TLC (SiO$_2$, EtOAc:Hexane:Et$_3$N 1:1:0.01) to give 0.041 g (95%) of the desired product. MS (ES+) 503/505/507 M+H$^+$.

Compounds XXIX-201, I-282, I-232 were prepared according to standard procedures analogous to those described in Example 7. Compound XXV-222 was prepared by treating compound XXIX-201 with potassium carbonate in methanol. Compound I-222 was prepared by re-acylation of compound XXV-222 under standard conditions.

EXAMPLE 8

This example illustrates the preparation of compound XXX-51

1-(2-chloropyridin-4-yl)carbonyl-5-chloro-1'-[(E)-3-(4-trifluoromethyl-phenyl) allyl]spiro[indolin-3,4'-piperidine]

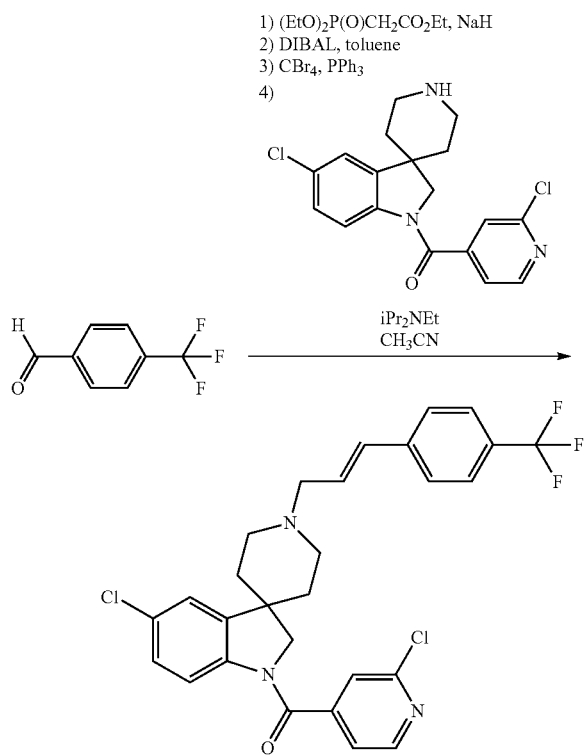

Step 1: Preparation of (E)-3-(4-trifluoromethyl-phenyl)-acrylic acid ethyl ester Ethyl diethylphosphonoacetate (84 g) in 1,2-dimethoxyethane (100 ml) was added dropwise to a suspension of sodium hydride (55% in oil, 15 g) in 1,2-dimethoxyethane (500 ml) at room temperature. 4-Trifluorobenzaldehyde (43.5 g) dissolved in 1,2-dimethoxyethane (100 ml) was then added and the resulting mixture was stirred at room temperature for 4 h. The reaction was quenched by addition of water (400 ml), diluted with diethyl ether (700 ml), the organic phase was separated, washed with brine, dried over sodium sulfate and concentrated in vacuo. The crude product was recrystallised from hexane to give 37 g of the desired product (61%) which was characterized by its mass and NMR spectra.

Step 2: Preparation of (E)-3-(4-trifluoromethyl-phenyl)-prop-2-en-1-ol

To a solution of the ester obtained in step 1 (37.1 g) in toluene (310 ml) at 0° C. was added dropwise diisobutyl-aluminium hydride (1.2M in toluene, 317 ml) and the solution was stirred at 0° C. for 1 h. Water (47.6 ml) was carefully added at 0° C. followed by sodium hydroxide 2M (47.6 ml) and finally water (95.1 ml). The mixture was allowed to stir at room temperature for 1 h. After filtration, the solution was washed with hydrochloric acid 2N, water and brine, dried over sodium sulfate and concentrated in vacuo to give 29.5 g of the desired alcohol as a solid (96%) which was characterized by its mass and NMR spectra.

Step 3: Preparation of 1-((E)-3-bromo-propenyl)-4-trifluoromethyl-benzene

To a solution of the alcohol obtained in step 2 (10 g) in dimethylacetamide (100 ml) at room temperature were added triphenylphosphine (23 g) and carbon tetrabromide (29 g). The resulting solution was stirred at room temperature for 1 h, poured into water and extracted with ethyl acetate. The organic phase was washed with water and brine, dried over sodium sulfate and filtered over silica gel to give 13 g of the desired product as a white solid (95%) which was characterized by its mass and NMR spectra.

Step 4: Preparation of 1-(2-chloropyridin-4-yl)carbonyl-5-chloro-1'-[(E)-3-(4-trifluoromethyl-phenyl) allyl]spiro[indolin-3,4'-piperidine]

To a stirred suspension of (2-chloropyridin-4-yl)carbonyl-5-chloro-spiro[indolin-3,4'-piperidine] (20 g) and diisopropylethylamine (18.2 ml) in acetonitrile (200 ml) was added the allylic bromide obtained in step 3 (11.6 g) and the reaction mixture was stirred overnight at room temperature. The solution was diluted with ethyl acetate (200 ml), washed with brine (3×100 ml), dried over sodium sulfate and concentrated in vacuo. The residue was purified by column chromatography (SiO$_2$, ethyl acetate:hexane:triethylamine 95:5:0.1 to ethyl acetate:methanol:triethylamine 95:5:0.1) to give 18.9 g of the desired product (82%). Mp=130° C.

Compounds XXX-82, XXX-83, XXX-84, XXX-85, XXX-86, XXX-87, XXX-91 and XXX-92 were prepared according to standard procedures analogous to those described in Example 8.

EXAMPLE 9

This example illustrates the preparation of compound XXX-113

1-(2-chloropyridin-4-yl)carbonyl-5-chloro-1'-[(Z)-3-(4-chlorophenyl)-2-fluoro-allyl]spiro[indolin-3,4'-piperidine]

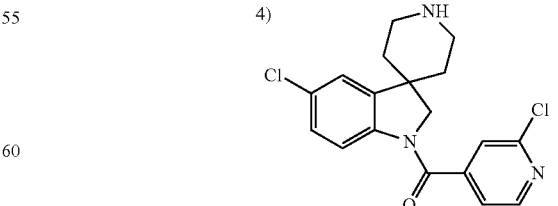

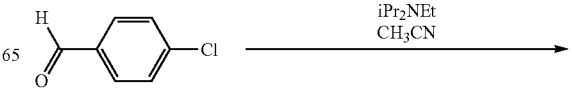

-continued

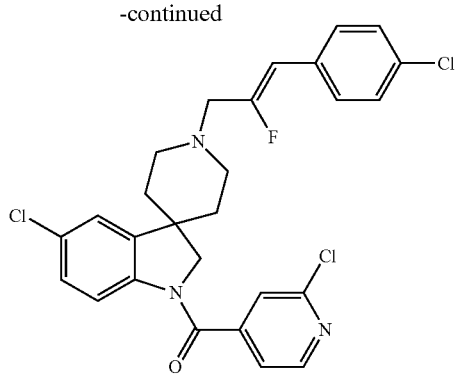

Step 1: Preparation of (Z)-3-(4-chloro-phenyl)-2-fluoro-acrylic acid methyl ester By analogy with: Cousseau, J. et al. Tetrahedron Lett. 1993, 43, 6903 4-Chlorobenzaldehyde (0.66 g) was added to a suspension of diethylfluorooxalacetate, sodium salt (1 g, prepared from diethyl oxalate, ethylfluoroacetate and sodium hydride according to Alberg et al. J. Am. Chem. Soc. 1992, 3542) in tetrahydrofuran (20 ml) at 0° C., and the resulting mixture was stirred 1 h at 0° C. then 3 h at 80° C. The reaction mixture was concentrated in vacuo, diluted with diethyl ether, washed with aqueous sodium bicarbonate, water and brine, dried over sodium sulfate and concentrated in vacuo to afford a crude residue (1.2 g) which was used diretly in the next step.

Step 2: Preparation of (Z)-3-(4-chloro-phenyl)-2-fluoro-prop-2-en-1-ol

Step 3: Preparation of 1-((Z)-3-bromo-2-fluoro-propenyl)-4-chloro-benzene

Step 4: Preparation of 1-(2-chloropyridin-4-yl)carbonyl-5-chloro-1'-[(Z)-3-(4-chlorophenyl)-2-fluoro-allyl]spiro[indolin-3,4'-piperidine]

Step 2 to 4 were carried out following the procedure described in Example 8, step 2-4 to give 0.17 g of the desired product (41%) which was characterized by its mass and NMR spectra. MS (ES+) 530.

Compound XXX-114 was prepared according to standard procedures analogous to those described in Example 9.

EXAMPLE 10

This example illustrates the preparation of I-25

1-(2-chloropyridin-4-yl)carbonyl-5-chloro-1'-[trans-3-(4-methoxyphenyl)allyl]spiro[indolin-3,4'-piperidine]

1) $H_2C=CHMgBr$
2) $SOCl_2$
3)

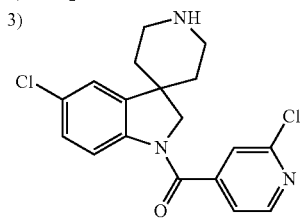

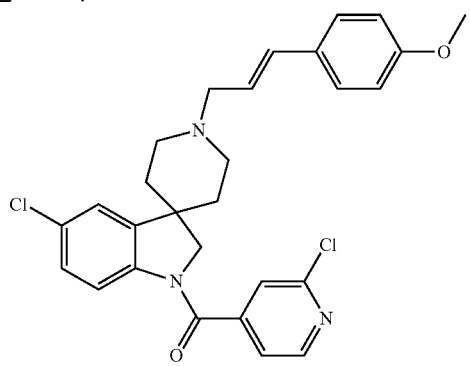

Step 1: Preparation of 1-(4-Methoxy-phenyl)-prop-2-en-1-ol

To a solution of p-anisaldehyde (1.54 ml) in tetrahydrofuran (20 ml) at 10° C. under argon was added dropwise vinyl magnesium bromide (1M in THF, 12.5 ml). The solution was stirred overnight at room temperature and quenched by addition of saturated aqueous ammonium chloride (20 ml). The organic phase was separated, dried over sodium sulfate and concentrated in vacuo. The residue was purified by column chromatography ($SiO_2$, ethyl acetate: cyclohexan 7:3) to give 1.05 g of the desired product as a colorless oil (51%) which was characterized by its mass and NMR spectra.

Step 2: Preparation of 1-((E)-3-Chloro-propenyl)-4-methoxy-benzene

To a solution of the allylic alcohol obtained in step 1 (200 mg) in diethyl ether (3 ml) was added thionyl chloride (0.087 ml) and the solution was stirred at room temperature for 1 h. The solution was concentrated in vacuo to give 221 mg of the desired product (100%) as a colorless solid. Mp=70° C.

Step 3: Preparation of 1-(2-chloropyridin-4-yl)carbonyl-5-chloro-1'-[trans-3-(4-methoxy-phenyl)allyl] spiro[indolin-3,4'-piperidine]

Alkylation of 1-(2-chloropyridin-4-yl)carbonyl-5-chloro-spiro[indolin-3,4'-piperidine] (0.43 g) with 1-((E)-3-chloropropenyl)-4-methoxy-benzene obtained in step 2 (0.22 g) was carried out following the procedure described in example 101, step 4 to afford 0.36 g of the title compound (59%) which was characterized by its mass and NMR spectra. MS (ES+) 509. Mp=83-85° C.

EXAMPLE 11

This example illustrates the preparation of XXX-115

1-(2-chloropyridin-4-yl)carbonyl-5-chloro-1'-[(Z)-3-(4-chlorophenyl)-3-chloro-allyl]spiro[indolin-3,4'-piperidine]

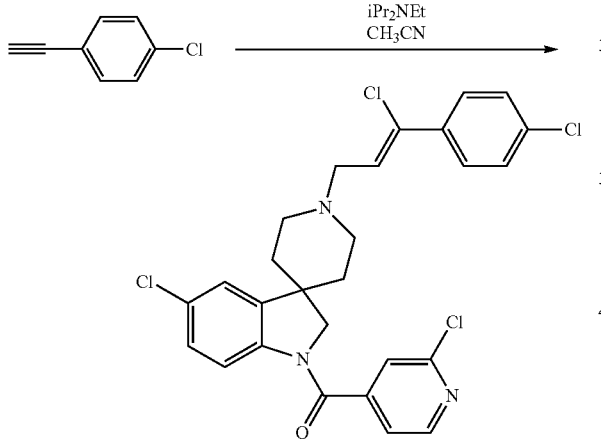

Step 1: Preparation of (Z)-3-chloro-3-(4-chlorophenyl)-acrylic acid methyl ester By analogy with: Tanaka, M. et al. J. Am. Chem. Soc. 1998, 120, 12365

To a solution of 4-chlorophenylacetylene (100 mg) and Rh(CO)(PPh$_3$)$_2$Cl (5 mg) in toluene (3 ml) was added methyl chloroformate (0.17 ml) and the mixture was stirred in a sealed tube at 110° C. for 10 h. The reaction mixture was concentrated in vacuo and subjected to column chromatography (SiO$_2$, ethyl acetate:cyclohexan 1:9) to give 104 mg of the desired product as a brown solid (61%) which was characterized by its mass and NMR spectra. Mp=40° C.

Step 2: Preparation of (Z)-3-chloro-3-(4-chlorophenyl)-prop-2-en-1-ol

Following the procedure described in Example 8, step 2, (Z)-3-chloro-3-(4-chloro-phenyl)-acrylic acid methyl ester (462 mg) was converted into the desired product (391 mg, 96%) which was characterized by its mass and NMR spectra.

Step 3: Preparation of 1-chloro-4-((Z)-1,3-dichloro-propenyl)-benzene

To a solution of (Z)-3-chloro-3-(4-chloro-phenyl)-prop-2-en-1-ol (101 mg) in toluene (3 ml) was added thionyl chloride (0.11 ml) and one drop of dimethylformamide. After 1 h, the solution was concentrated in vacuo to afford 120 mg of the desired allylic chloride (100%) as a colorless oil.

Step 4: Preparation of 1-(2-chloropyridin-4-yl)carbonyl-5-chloro-1'-[(Z)-3-(4-chlorophenyl)-3-chloro-allyl]spiro[indolin-3,4'-piperidine]

Alkylation of 1-(2-chloropyridin-4-yl)carbonyl-5-chloro-spiro[indolin-3,4'-piperidine] (0.18 g) with 1-chloro-4-((Z)-1,3-dichloro-propenyl)-benzene obtained in step 3 (0.11 g) was carried out following the procedure described in example 101, step 4 to afford 0.17 g of the title compound (64%) as a foam which was characterized by its mass and NMR spectra. MS (ES+) 548.

EXAMPLE 12

This example illustrates the preparation of XXX-90

1-(2-chloropyridin-4-yl)carbonyl-5-chloro-1'-[(Z)-3-(4-chlorophenyl)-3-fluoro-allyl]spiro[indolin-3,4'-piperidine]

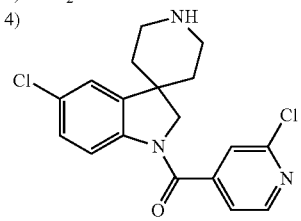

113

Step 1: Preparation of (Z)-3-(4-Chloro-phenyl)-3-fluoro-acrylic acid methyl ester By analogy with: Cousseau, J. J. Chem. Soc. Chem. Commun. 1989, 1493 To a solution of (4-chloro-phenyl)-propynoic acid methyl ester (5.36 g) in dimethylformamide (60 ml) was added cesium fluoride (11.4 g) and potassium hydrogen fluoride (2.73 g) in water (5.4 ml) and the mixture was stirred at 80° C. for 8 h. The reaction mixture was cooled to room temperature, diluted with ethyl acetate (50 ml), the organic phase washed with water (3×50 ml) and brine (3×20 ml), dried over sodium sulfate and concentrated in vacuo. The residue was purified by column chromatography (SiO$_2$, ethyl acetate:cyclohexan 1:9) to give 1.06 g of the desired product (20%) which was characterized by its mass and NMR spectra.

Step 2: Preparation of (Z)-3-(4-chloro-phenyl)-3-fluoro-prop-2-en-1-ol

Step 3: Preparation of 1-Chloro-4-((Z)-3-chloro-1-fluoro-propenyl)-benzene

Step 4: Preparation of 1-(2-chloropyridin-4-yl)carbonyl-5-chloro-1'-[(Z)-3-(4-chlorophenyl)-3-fluoro-allyl]spiro[indolin-3,4'-piperidine]

Step 2 to 4 were carried out following the procedure described in Example 11, step 2-4 to give 163 mg of the desired product (42%) which was characterized by its mass and NMR spectra. MS (ES+) 531.

Compounds XXX-88 and XXX-90 were prepared according to standard procedures analogous to those described in Example 12.

EXAMPLE 13

This example illustrates the preparation of compound XXX-121 and XXX-94, 1-carboxylic acid (4-chloro-phenyl)-amide-5-fluoro-1'-[trans-3-(4-chlorophenyl)allyl]spiro[indoline-3,4'-piperidine].

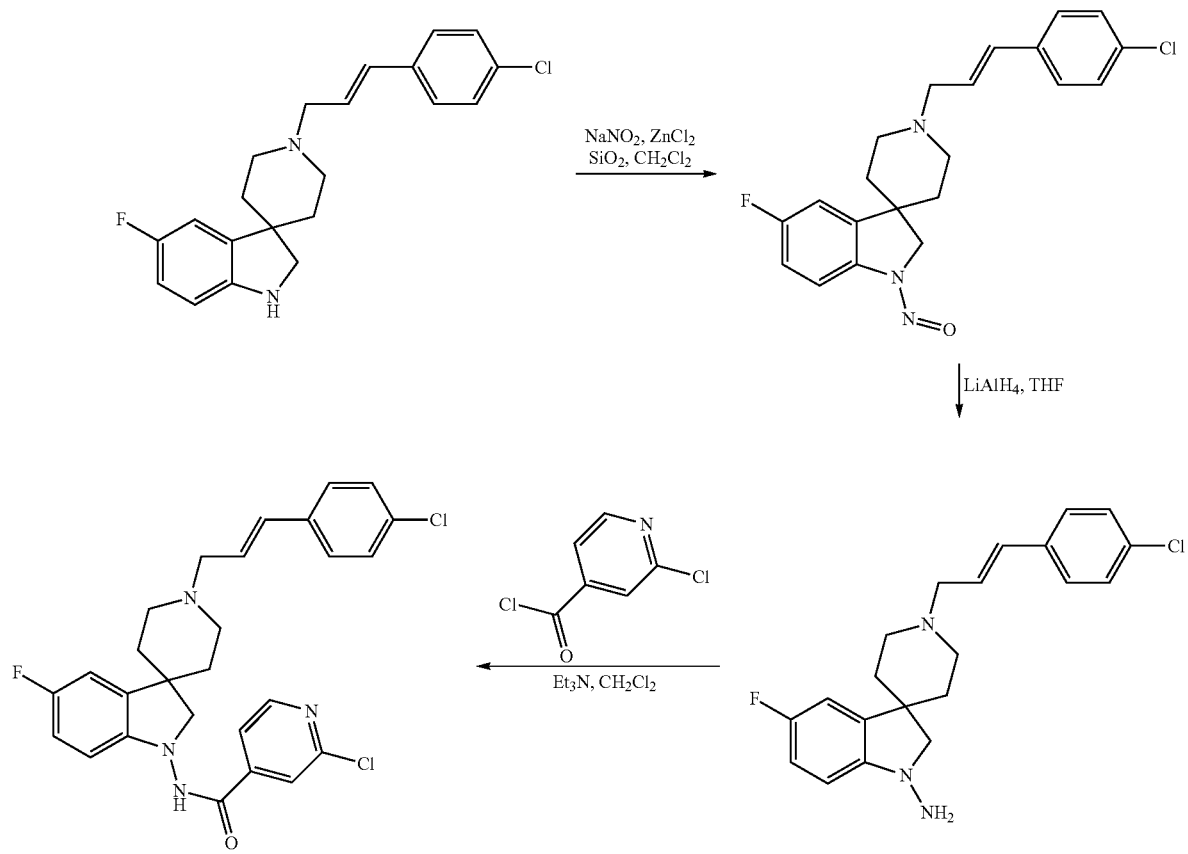 [SMILES: Fc1ccc2c(c1)C1(CCN(C/C=C/c3ccc(Cl)cc3)CC1)CN2 ; O=NN1CC2(CCN(C/C=C/c3ccc(Cl)cc3)CC2)c2cc(F)ccc21 ; O=C(NN1CC2(CCN(C/C=C/c3ccc(Cl)cc3)CC2)c2cc(F)ccc21)c1ccnc(Cl)c1 ; O=C(Cl)c1ccnc(Cl)c1 ; NN1CC2(CCN(C/C=C/c3ccc(Cl)cc3)CC2)c2cc(F)ccc21]

5-Fluoro-1'-[trans-3-(4-chlorophenyl)allyl]spiro[indoline-3,4'-piperidine] was prepared according to a procedure analogous to that described in steps 1 to 4 of Example 4.

Step 1: Preparation of Compound XXX-121, 1-nitroso-5-fluoro-1'-[trans-3-(4-chlorophenyl)allyl]spiro[indoline-3,4'-piperdine]

A solution of 5-fluoro-1'-[trans-3-(4-chlorophenyl)allyl]spiro[indoline-3,4'-piperidine] (5 g) in dichloromethane (15 ml) was added to a suspension of wet silica gel (50% w/w in water, 2.9 g) and zinc chloride (5.73 g) in dichloromethane (15 ml) and the resulting mixture was stirred for 3.5 hours at room temperature. The reaction mixture was diluted with ethyl acetate and the insoluble residues were removed by filtration. The filtrate was washed with saturated aqueous sodium bicarbonate solution, water and brine, dried over sodium sulfate and the solvents were evaporated in vacuo to afford 5.13 g (95%) of the desired nitroso-amine as a solid. MS (ES+) 386.

Step 2: Preparation of 1-amino-5-fluoro-1'-[trans-3-(4-chlorophenyl)allyl]spiro[indoline-3,4'-piperidine]

A solution of 1-nitroso-5-fluoro-1'-[trans-3-(4-chlorophenyl)allyl]spiro[indoline-3,4'-piperidine] (5 g) in tetrahydrofuran (60 ml) was added dropwise to a suspension of lithium aluminium hydride (1.47 g) in tetrahydrofuran (60 ml) at 0° C. and the resulting mixture was stirred at room temperature for 2.5 hours. Water (4.8 ml) was carefully added, followed by 15% aqueous sodium hydroxide (4.8 ml), and finally water (14.4 ml). The mixture was stirred for 0.5 hours, diluted with ethyl acetate, dried over sodium sulfate, and filtered. The solvents were evaporated in vacuo to afford 5.1 g (100%) of the desired amino-indoline as a solid. MS (ES+) 372.

Step 3: Preparation of 1-carboxylic acid (4-chlorophenyl)-amide-5-fluoro-1'-[trans-3-(4-chlorophenyl)allyl]spiro[indoline-3,4'-piperidine]

2-Chloroisonicotinoyl chloride (1.2 g) was added to a stirred solution of 1-amino-5-fluoro-1'-[trans-3-(4-chlorophenyl)allyl]spiro[indoline-3,4'-piperidine] (0.2 g) and triethylamine (0.3 ml) in dichloromethane (4 ml) at room temperature. The mixture was stirred for 2 hours. The reaction mixture was washed with water and the aqueous layer was extracted with dichloromethane. The combined organic layers were dried (sodium sulfate), filtered and evaporated. The crude product was purified by chromatography [SiO₂, ethyl acetate-methanol (96:4) to give 0.13 g (48%) of the desired product. MS (ES+) 511.

Compounds XXX-95, XXX-97, XXX-98 and XXX-99 were prepared according to standard procedures analogous to those described in Example 13

EXAMPLE 14

This example illustrates the preparation of compound XXX-119, 1-(4-chloro-phenyl)-urea-5-fluoro-1'-[trans-3-(4-chlorophenyl)allyl]spiro[indoline-3,4'-piperidine].

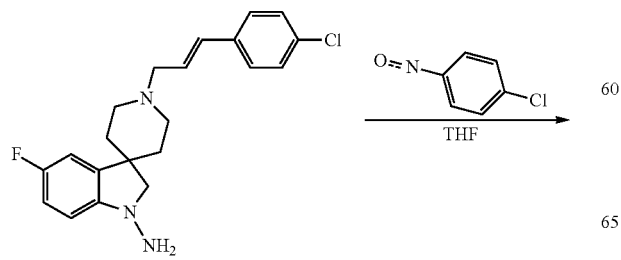

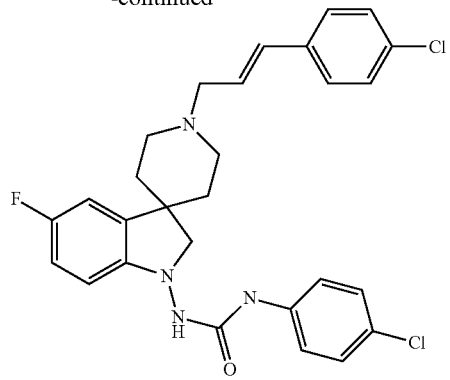

To a solution of 1-amino-5-fluoro-1'-[trans-3-(4-chlorophenyl)allyl]spiro[indoline-3,4'-piperidine] (0.2 g) in tetrahydrofuran (2 ml) was added 4-chlorophenyl isocyanate (70 mg) and the mixture was stirred at room temperature for 10 min. The solvent was evaporated in vacuo and the residue purified by preparative HPLC to afford the title compound (49%) as a solid. MS (ES+) 525.

Compounds XXX-100, XXX-101, XXX-102 and XXX-103 were prepared according to standard procedures analogous to those described in Example 14.

EXAMPLE 15

This example illustrates the preparation of compound XXX-102 N'-[5-chloro-1'-[trans-3-(4-chlorophenyl)allyl]spiro[indoline-3,4'-piperidine]-1-yl]-N,N-dimethylacetamidine To a solution of 1-amino-5-chloro-1'-[trans-3-(4-chlorophenyl)allyl]spiro[indoline-3,4'-piperidine] (0.15 g) in tetrahydrofuran (2 ml) was added N,N-dimethylacetamide dimethyl acetal (0.2 g) and the mixture was stirred at 70° C. for 24 hours. The solvent was evaporated in vacuo and the residue purified by chromatography [SiO$_2$; ethyl acetate-methanol (9:1) to give 35 mg (20%) of the desired product. MS (ES+) 457.

EXAMPLE 16

This example illustrates the preparation of compound XXX-105 1-[carboxylic acid (2-methoxy-ethyl)-amide]-5-chloro-1'-[trans-3-(4-chlorophenyl)allyl]spiro[indoline-3,4'-piperidine].

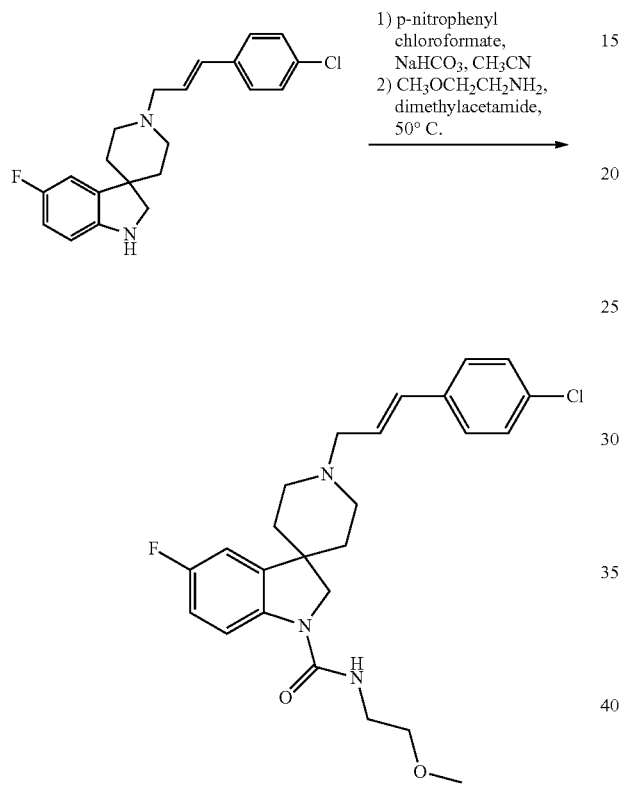

5-Chloro-1'-[trans-3-(4-chlorophenyl)allyl]spiro[indoline-3,4'-piperidine] (2.5 g) was added to a suspension of sodium bicarbonate (1.7 g) in acetonitrile (45 ml) and the resulting mixture cooled to 0° C. 4-Nitrophenyl chloroformate (2.54 g) was then added dropwise and the resulting solution stirred at 0° C. for 2 hours. 3 ml of the solution was added to a solution of 2-methoxy-ethylamine (315 mg) and triethylamine (0.3 ml) in dimethylformamide (10 ml) and the resulting mixture was stirred at 50° C. for 3 hours. The solution was cooled to room temperature, poured into water, extracted three times with ethyl acetate. The organic phase was dried over sodium sulfate, filtered, and the solvents were removed in vacuo. The residue was purified by reverse-phase HPLC to afford the desired product (57% yield). MS (ES+) 458.

Compounds XXX-104, XXX-106, XXX-107, XXX-108, XXX-109, XXX-110, XXX-111 and XXX-112 were prepared according to standard procedures analogous to those described in Example 16.

EXAMPLE 17

Preparation of compound XXVI-1—1,2-Dihydro-1-(4-nitrobenzoyl)-1'-(3-phenyl-2-propenyl)-spiro[3H-indole-3-4'-piperidine]

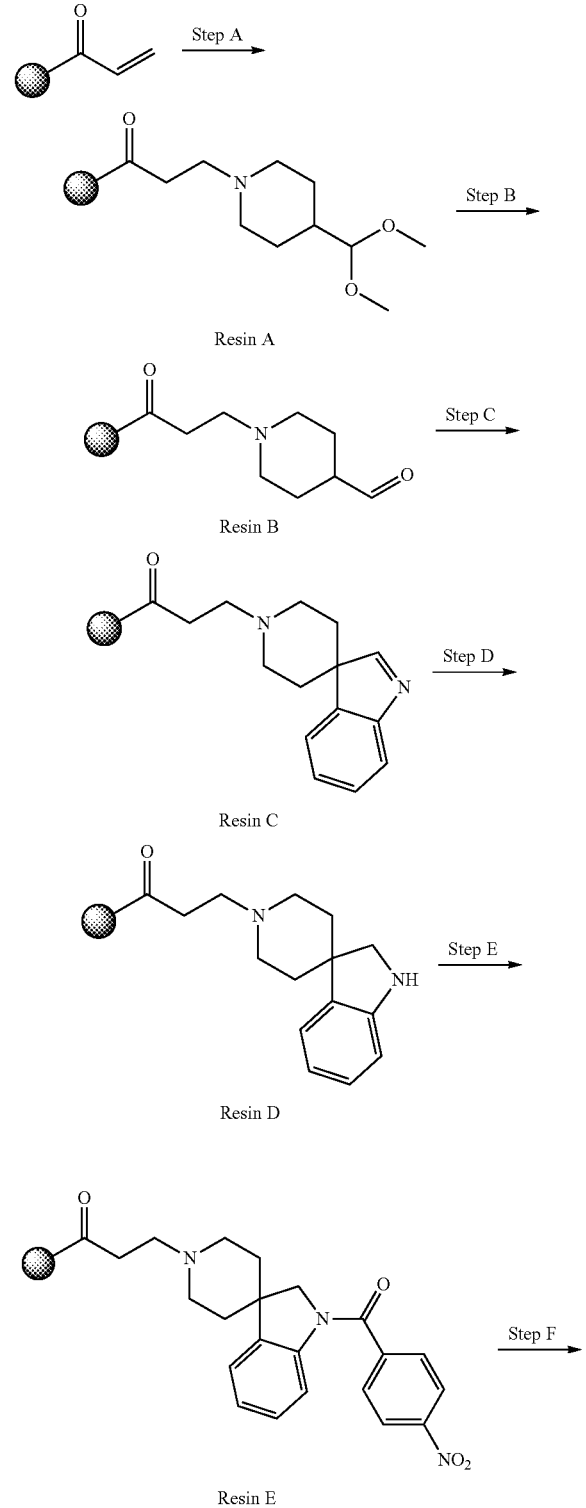

-continued

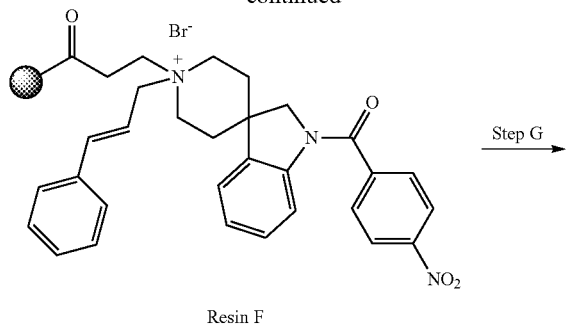

Resin F

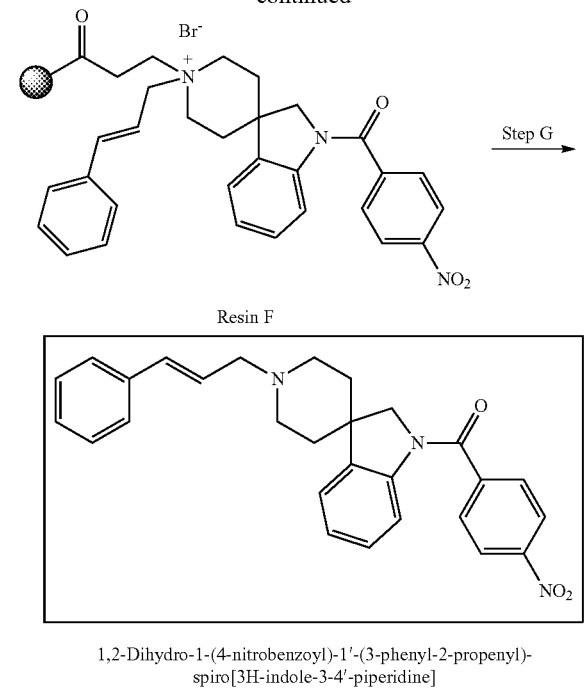

1,2-Dihydro-1-(4-nitrobenzoyl)-1'-(3-phenyl-2-propenyl)-
spiro[3H-indole-3-4'-piperidine]

In the experimental details to follow, standard wash will refer to the following washing sequence: dimethylformamide, dichloromethane, dimethylformamide, dichloromethane, methanol, dichloromethane, methanol (×2), tert-butyl methyl ether (×2) and resin swelling protocol will be based on a standard of 10 ml of solvent per gram of resin. Compound identities and purities were determined using High Performance Liquid Chromatography coupled Mass Spectrometry (HPLC-MS) and Proton Nuclear Magnetic Resonance (1H NMR) on selected compounds. REM resin was prepared from commercially available (hydroxymethyl) polystyrene resin and acryloyl chloride. The loading of the resins were assumed to be constant at 1.2 mmolg$^{-1}$ throughout the synthesis.

Step A: Loading of 4-Formylpiperidine Dimethyl Acetal onto REM Resin (Resin A)

REM resin (10 g, 12 mmol) was swollen in dimethylformamide (100 ml). A solution of 4-formylpiperidine dimethyl acetal (2.86 g, 18 mmol) in dimethylformamide (10 ml) was then added. The reaction was left to shake at room temperature for 18 hours. The resulting resin was then filtered, washed according to the standard procedure and dried in vacuo to afford 11.83 g (96% yield) of the desired resin A.

Step B: Preparation of Solid Supported 4-Formylpiperidine (Resin B)

A 100 ml solution of trifluoroacetic acid/dichloromethane/water (49:49:2) was added to resin A (10 g, 12 mmol) and the mixture was then shaken at room temperature for 2 hours. The resulting resin was then filtered, washed using dichloromethane (×3), methanol, dichloromethane, methanol, tert-butyl methyl ether (×2) and dried in vacuo to afford 9.48 g of the desired resin B, which was stored at 50° C. under nitrogen.

Step C: Preparation of Solid Supported Spiro[3H-indole-3,4'-piperidine] (Resin C)

To resin B (1 g, 1.2 mmol) was added a solution of 5% trifluoroacetic acid in dichloromethane (10 ml) followed by addition of anisole (0.0026 g, 0.024 mmol). The mixture was degassed with nitrogen for 10 minutes, and phenylhydrazine (0.39 g, 3.6 mmol) was added. The reaction mixture was stirred under nitrogen and heated to reflux for 36 hours. The mixture was then filtered, washed according to the standard wash cycle and dried in vacuo to afford 1.09 g of the desired resin C, which was used immediately in Step D.

Step D: Preparation of Solid Supported 1,2-Dihydro-spiro[3H-indole-3,4'-piperidine] (Resin D)

To resin C (1 g, 1.2 mmol), swollen in anhydrous dichloromethane (10 ml) was added sodium triacetoxyborohydride (0.51 g, 2.4 mmol) as a solid. The reaction mixture was stirred at room temperature under nitrogen for 2 hours. The resin was then filtered, washed according to the standard wash cycle and dried in vacuo to afford 0.95 g of the desired resin D, which was stored at 50° C. under nitrogen.

Step E: Preparation of Solid Supported 1,2-Dihydro-1-(4-nitrobenzoyl)-spiro[3H-indole-3,4'-piperidine] (Resin E)

Resin D (0.5 g, 0.6 mmol) was swollen in anhydrous dichloromethane (5 ml). To the mixture was added 4-nitrobenzoyl chloride (0.33 g, 1.8 mmol) and N,N-diisopropylethylamine (0.42 ml, 2.4 mmol). After shaking at room temperature for 18 hours, the resin was filtered, washed according to the standard wash cycle and dried in vacuo to afford 0.53 g of the desired resin E.

Step F: Quaternization of Solid Supported 1,2-Dihydro-1-(4-nitrobenzoyl)-spiro[3H-indole-3,4'-piperidine] (Resin F)

To resin E (0.1 g, 0.12 mmol) in anhydrous dimethylformamide (1 ml) was added cinnamyl bromide (0.12 g, 0.6 mmol). The reaction mixture was shaken at room temperature for 48 hours. The resulting resin was then washed according to the standard wash cycle to afford 0.11 g of the desired resin F, which was used immediately in Step G.

Step G: Preparation of 1,2-Dihydro-1-(4-nitrobenzoyl)-1'-(3-phenyl-2-propenyl)-spiro[3H-indole-3,4'-piperidine]

To resin F (0.11 g, 0.132 mmol) in anhydrous dimethylformamide (1.1 ml) was added Amberlite IRA-93 (previously washed with 10% N,N-diisopropylethylamine/dimethylformamide) (0.11 g). The mixture was shaken at room temperature for 36 hours. The dimethylformamide filtrate was then collected and concentrated under reduced pressure. The resin was further washed with dichloromethane and methanol. All filtrates were then combined and concentrated in vacuo to afford 0.052 g (88% yield) of the desired compound as a pale yellow oil.

By an analogous procedure other compounds were prepared including compound XVI-21, 5-Chloro-1,2-dihydro-1-(4-nitrobenzoyl)-1'-(3-phenyl-2-propenyl)-spiro[3H-indole-3-4'-piperidine]

EXAMPLE 18

This example illustrates the preparation of compound XXX-72, 1-(2-chloropyridin-4-yl)carbonyl-5-chloro-1'-[(Z)-3-(4-methylthiophenyl)allyl]spiro[indolin-3,4'-piperidine]

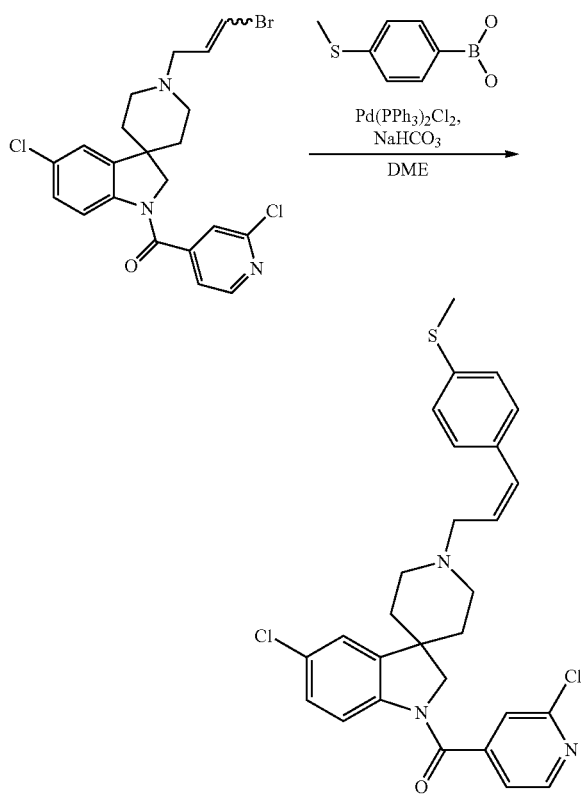

To 13.1 mg 4-thiomethylboronic acid in a "Zisser-block" were added 14.5 mg 1-(2-chloropyridin-4-yl)carbonyl-5-chloro-1'-[(E/Z)-3-bromo-allyl]spiro[indolin-3,4'-piperidine] in 0.05 ml dimethoxyethane, 8 mg sodium bicarbonate in 0.3 ml H2O and 2 mg bis-(triphenylphosphin)palladium (II) dichloride. The mixture was stirred at 75° C. for 13 hours. The organic layer was separated and evaporated in vacuo and the residue purified by chromatography (H2O-acetonitrile gradient) to yield the desired product MS (ES+) 525. By an analogous procedure other compounds were prepared including compounds XXXI-4, XXX-51, XXX-52, XXX-53, XXX-54, XXX-55, XXX-56, XXX-57, XXX-58, XXX-59, XXX-60, XXX-61, XXX-62, XXX-63, XXX-64, XXX-65, XXX-66, XXX-67, XXX-68, XXX-69, XXX-70, XXX-71, XXX-73, XXX-74, XXX-75, XXX-76, XXX-77, XXX-78, XXX-79, XXX-80, XXX-81, XXXI-3, XXXI-5, XXXI-6 and XXXI-7.

EXAMPLE 19

This Example illustrates the pesticidal/insecticidal properties of compounds of formula (I). Test against were performed as follows:

*Spodoptera littoralis* (Egyptian Cotton Leafworm)
Cotton leaf discs were placed on agar in a 24-well microtiter plate and sprayed with test solutions at an application rate of 200 ppm. After drying, the leaf discs were infested with 5 $L_1$ larvae. The samples were checked for mortality, repellent effect, feeding behaviour, and growth regulation 3 days after treatment (DAT). The following compounds gave at least 80% control of *Spodoptera littoralis*:

I-2, I-12, I-21, I-22, I-23, I-32, I-52, I-61, I-62, I-72, I-82, I-92, I-112, I-132, I-142,
I-152, I-162, I-182, I-192, I-202, I-212, I-222, I-232, I-242, I-252, I-262, I-282, II-62, V-22, VI-22, VI-62, VI-202, X-22, X-62, XI-62, XII-22, XIII-62, XIV-22, XV-22, XVII-62, XVIII-22, XIX-22, XIX-202, XX-22, XX-62, XXI-22, XXI-62, XXII-22, XXVI-2, XXVI-22, XXVII-2, XXVII-22, XXIX-43, XXIX-93, XXIX-195, XXIX-196, XXIX-201, XXX-10, XXX-106, XXX-107, XXX-118, XXX-15, XXX-16, XXX-18, XXX-24, XXX-26,
XXX-28, XXX-3, XXX-36, XXX-43, XXX-48, XXX-49, XXX-52, XXX-55, XXX-57,
XXX-60, XXX-67, XXX-83, XXX-84, XXX-87, XXX-88, XXX-99, XXXI-8, XXXII-4, XXX-104, XXX-105, XXX-109, XXX-112, XXX-113, XXX-114, XXX-117, XXX-12, XXX-13, XXXI-4, XXX-19, XXX-2, XXX-20, XXX-30, XXX-38, XXX-39, XXX-40,
XXX-41, XXX-42, XXX-44, XXX-45, XXX-50, XXX-53, XXX-59, XXX-6, XXX-61,
XXX-62, XXX-65, XXX-7, XXX-70, XX-8, XXX-82, XXX-89, XXX-95, XXXI-2,
XXXI-7, XXX-11, XXXI-1, XXX-110, XXX-111, XXX-31, XXX-51, XXX-66, XXX-86, XXX-93 and XXXI-5.

*Heliothis virescens* (Tobacco Budworm):
Eggs (0-24 h old) were placed in 24-well microtiter plate on artificial diet and treated with test solutions at an application rate of 200 ppm by pipetting. After an incubation period of 4 days, samples were checked for egg mortality, larval mortality, and growth regulation. The following compounds gave at least 80% control of *Heliothis virescen*:

I-1, I-2, I-3, I-4, I-5, I-12, I-21, I-22, I-23, I-32, I-52, I-61, I-62, I-72, I-82, I-92, I-112, I-132, I-142, I-152, I-162, I-171, I-182, I-192, I-202, I-212, I-222, I-232, I-242, I-252, I-262, I-282, I-292, II-301, II-22, II-62, V-21, V-22, V-62, V-192, V-202, VI-1, VI-22, VI-62, VI-101, VI-202, IX-62, X-22, X-62, XI-62, XII-22, XIII-22, XIII-62, XIV-22, XV-22, XVII-62, XVIII-22, XVIII-202, XIX-22, XIX-202, XX-22, XX-62, XXI-22, XXI-62, XXII-22, XXV-222, XXVI-2, XXVI-22, XXVII-2, XXVII-22, XXVIII-7, XXVIII-27, XXVIII-42, XXVIII-67, XXVIII-97, XXVIII-132, XXVIII-187, XXVIII-217, XXVIII-252, XXIX-1, XXIX-7, XXIX-13, XXIX-57, XXIX-63, XXIX-75, XXIX-81, XXIX-87, XXIX-93, XXIX-111, XXIX-117, XXIX-123, XXIX-129, XXIX-141, XXIX-147, XXIX-153, XXIX-159, XXIX-165, XXIX-171, XXIX-183, XXIX-195, XXIX-196, XXIX-201, XXX-100, XXX-107, XXX-108, XXX-109, XXX-116, XXX-14, XXX-15, XXX-17, XXX-23, XXX-32, XXX-35, XXX-4, XXX-43, XXX-46, XXX-55, XXX-56, XXX-63, XXX-64, XXX-7, XXX-71, XXX-72, XXX-73, XXX-76, XXX-77, XXX-78, XXX-79, XXX-80, XXX-81, XXX-85, XXX-88, XXX-92, XXX-94, XXX-98, XXXII-1, XXXII-2, XXXII-3, XXXII-5, XXXII-8, XXXII-9, XXX-1, XXX-10, XXX-105, XXX-106, XXX-112, XXX-115, XXX-118, XXX-12, XXX-16, XXX-18, XXX-19, XXX-21, XXX-22, XXX-24, XXX-26, XXX-28, XXX-29, XXX-33, XXX-34, XXX-37, XXX-50, XXX-54, XXX-58, XXX-60, XXX-65, XXX-67, XXX-68, XXX-74, XXX-75, XXX-83, XXX-87, XXX-9, XXX-91, XXX-93, XXX-96,
XXX-99, XXXI-3, XXXI-6, XXXII-10, XXXII-4, XXXII-6, XXXI-1, XXX-110, XXX-111, XXX-113, XXX-114, XXX-117, XXX-13, XXXI-4, XXX-2, XXX-20, XXX-3, XXX-30, XXX-31, XXX-36, XXX-38, XXX-40, XXX-41,

XXX-44, XXX-45, XXX-48, XXX-49, XXX-5, XXX-53, XXX-57, XXX-59, XXX-6, XXX-61, XXX-62, XXX-7, XXX-8,
XXX-82, XXX-89, XXX90, XXXI-2, XXX-120 and XXXI-7.

*Plutella xylostella* (Diamond Back Moth):

24-well microtiter plate (MTP) with artificial diet was treated with test solutions at an application rate of 18.2 ppm by pipetting. After drying, the MTP's were infested with larvae (L2) (10-15 per well). After an incubation period of 5 days, samples were checked for larval mortality, antifeedant and growth regulation. The following compounds gave at least 80% control of *Plutella xylostella*:
I-1, I-2, I-3, I-4, I-5, I-12, I-21, I-22, I-23, I-32, I-52, I-61, I-62, I-72, I-82, I-92, I-112, I-132, I-142, I-152, I-162, I-171, I-192, I-202, I-212, I-222, I-242, I-252, I-262, I-282, I-292, II-22, II-62, V-22, V-62, V-202, VI-22, VI-62, IX-62, X-22, X-62, XI-62, XII-22, XIII-62, XIV-22, XV-22, XVII-62, XX-22, XXI-62, XXII-22, XXV-62, XXVI-2, XXVI-22, XXVII-1, XXVII-2, XXVII-22, XXVIII-97, XXVIII-187, XXIX-129, XXIX-135, XXIX-159, XXIX-177, XXIX-189, XXIX-195, XXIX-196, XXX-10, XXX-100, XXX-109, XXX-112, XXX-117, XXX-16, XXX-18, XXX-19, XXX-21, XXX-28, XXX-34, XXX-36, XXX-43, XXX-48, XXX-5, XXX-50, XXX-54, XXX-59, XXX-60, XXX-66, XXX-68, XXX-69, XXX-75, XXX-83, XXX-90, XXX-91, XXX-98, XXXI-2, XXXI-7, XXXII-4, XXXII-8, XXXII-9, XXX-101, XXX-104, XXX-107, XXX-110, XXX-111, XXX-118, XXX-12, XXX-13, XXXI-4, XXX-22, XXX-3, XXX-30, XXX-37, XXX-39, XXX-40, XXX-41, XXX-42, XXX-44, XXX-49, XXX-57, XXX-61, XXX-7, XXX-89, XXX-105, XXX-106, XXXI-1, XXX-113, XXX-114, XXX-31, XXX-35, XXX-38, XXX-45, XXX-46, XXX-47, XXX-53, XXX-62, XXX-67, XXX-70, XXX-8, XXX-86, XXXI-5, XXX-2, XXX-120 and XXX-51

*Myzus persicae* (Green Peach Aphid):

Sunflower leaf discs were placed on agar in a 24-well microtiter plate and sprayed with test solutions at an application rate of 200 ppm. After drying, the leaf discs were infested with an aphid population of mixed ages. After an incubation period of 6 DAT, samples were checked for mortality. The following compounds gave at least 80% control of *Myzus persicae*:
I-2, I-21, II-62, XI-62, XXVII-2, XXVIII-162, XXIX-49 XXX-111, XXX-13, XXX-29, XXX-34 and XXX-47.

*Tetranychus urticae* (Two-Spotted Spider Mite):

Bean leaf discs on agar in 24-well microtiter plates wer sprayed with test solutions at an application rate of 200 ppm. After drying, the leaf discs are infested with mite populations of mixed ages. 8 days later, discs are checked for egg mortality, larval mortality, and adult mortality. The following compounds gave at least 80% control of *Tetranychus urticae*:
I-202, XIII-22, XIX-202, XXVI-1, XXVIII-162, XXIX-207, XXX-57 and XXXI-2.

*Aedes aegypti* (Yellow Fever Mosquito):

10-15 *Aedes* larvae (L2) together with a nutrition mixture are placed in 96-well microtiter plates. Test solutions at an application rate of 2 ppm are pipetted into the wells. 2 days later, insects were checked for mortality and growth inhibition. The following compounds gave at least 80% control of *Aedes aegypti*
I-4, I-5, I-12, I-21, I-22, I-23, I-32, I-52, I-61, I-62, I-72, I-82, I-92, I-112, I-132, I-142, I-152, I-162, I-202, I-212, I-222, I-232, I-242, I-252, I-262, I-292, II-22, II-62, V-22, VI-22, VI-62, VI-202, XIV-22, XV-22, XVII-62, XVIII-22, XIX-22, XX-22, XXI-22, XXI-62, XXII-22, XXVI-2, XXVI-22, XXVII-22, XXVIII-7, XXVIII-27, XXVIII-67, XXVIII-97, XXVIII-187, XXIX-13, XXIX-19, XXIX-25, XXIX-31, XXIX-37, XXIX-69, XXIX-75, XXIX-93, XXIX-99, XXIX-105, XXIX-117, XXIX-123, XXIX-129, XXIX-135, XXIX-159, XXIX-183, XXX-102, XXX-105, XXX-11, XXX-110, XXX-117, XXX-24, XXX-28, XXX-31, XXX-34, XXX-4, XXX-48, XXX-49, XXX-52, XXX-57, XXX-59, XXX-60, XXX-61, XXX-67, XXX-68, XXX-7, XXX-70, XXX-75, XXX-78, XXX-79, XXX-82, XXX-83, XXX-84, XXX-87, XXX-88, XXX90, XXX-93, XXX-94, XXX-97, XXXI-2, XXXI-7, XXXI-8, XXXII-10, XXXII-4, XXX-104, XXX-106, XXXI-1, XXX-111, XXX-113, XXX-114, XXX-118, XXX-12, XXX-13, XXXI-4, XXX-16, XXX-17, XXX-18, XXX-19, XXX-2, XXX-20, XXX-22, XXX-26, XXX-3, XXX-30, XXX-35, XXX-38, XXX-39, XXX-44, XXX-46, XXX-47, XXX-5, XXX-50, XXX-53, XXX-62, XXX-86, XXX-98, XXXI-5, XXX-109, XXX-45, XXX-51, XXX-6, XXX-66 XXX-121 and XXX-8.

The invention claimed is:
1. A compound of formula IN

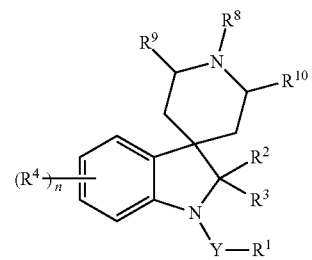

wherein
Y is C=O;
R$^1$ is C$_{1-6}$alkyl, C$_{1-6}$haloalkyl, heteroaryl(C$_{1-3}$)alkyl (wherein the heteroaryl group may be optionally substituted by halogen, C$_{1-4}$alkyl, C$_{1-4}$alkoxy, C$_{1-4}$haloalkyl, C$_{1-4}$haloalkoxy, CN, NO$_2$, aryl, heteroaryl, amino or dialkylamino and the heteroaryl group is a pyridine, pyrimidine, pyrazine or pyridazine ring), heteroaryl (optionally substituted by halogen, C$_{1-4}$alkyl, C$_{1-4}$alkoxy, C$_{1-4}$haloalkyl, C$_{1-4}$haloalkoxy, CN, NO$_2$, aryl, heteroaryl, amino or dialkylamino and where the heteroaryl group is a pyridine, pyrimidine, pyrazine or pyridazine ring), C$_{1-6}$alkoxy or heterocyclyl (optionally substituted by halo, cyano, C$_{1-3}$alkyl, C$_{1-3}$haloalkyl, or C$_{1-3}$alkoxy);
each R$^4$ is independently fluoro, chloro, bromo, cyano, C$_{1-4}$alkyl, C$_{1-4}$haloalkyl, C$_{1-4}$cyanoalkyl or C$_{1-3}$alkoxy (C$_{1-3}$)alkyl; n is 0, 1 or 2;
R$^8$ is phenyl(C$_{2-4}$)alkenyl (wherein the phenyl group is optionally substituted by halogen, C$_{1-4}$alkyl, C$_{1-4}$alkoxy, C$_{1-4}$haloalkyl, C$_{1-4}$haloalkoxy, CN, NO$_2$, aryl, heteroaryl, amino, dialkylamino or C$_{1-3}$alkoxycarbonyl) or phenyl(C$_{2-4}$)alkynyl (wherein the phenyl group is optionally substituted by halogen, C$_{1-4}$alkyl, C$_{1-4}$alkoxy, C$_{1-4}$haloalkyl, C$_{1-4}$haloalkoxy, CN, NO$_2$, aryl, heteroaryl, amino, dialkylamino or C$_{1-3}$alkoxycarbonyl); or
R$^8$ is —C(R$^{51}$)(R$^{52}$)—[CR$^{53}$=CR$^{54}$]z-R$^{55}$ where z is 1, R$^{51}$ and R$^{52}$ are each independently H, halo or C$_{1-2}$ alkyl, R$^{53}$ and R$^{54}$ are each independently H, halogen, C$_{1-4}$alkyl or C$_{1-4}$haloalkyl and R$^{55}$ is phenyl substituted by halogen, C$_{1-4}$alkyl, C$_{1-4}$alkoxy, C$_{1-4}$haloalkyl, $C_{1-4}$haloalkoxy, CN, $NO_2$, aryl, heteroaryl, amino or dialkylamino or heteroaryl substituted by halogen, $C_{1-4}$alkyl, $C_{1-4}$alkoxy, $C_{1-4}$haloalkyl, $C_{1-4}$haloalkoxy, CN, $NO_2$, aryl, heteroaryl, amino or dialkylamino; and $R^2 R^3 R^9$ and $R^{10}$ are all hydrogen; and salts or N-oxides thereof.

2. An insecticidal, acaricidal or nematicidal composition comprising an insecticidally, acaricidally or nematicidally effective amount of a compound of formula IN as defined in claim 1.

3. A compound according to claim 1 wherein $R^1$ is pyridyl (optionally substituted by halo, $C_{1-3}$alkyl or $C_{1-3}$haloalkyl) or $C_{1-6}$alkoxy.

4. A compound according to claim 1 wherein each $R^4$ is independently fluoro, chloro, bromo, $C_{1-4}$alkyl or $C_{1-4}$haloalkyl; n is 1 or 2.

5. A compound according to claim 1 wherein $R^8$ is —$C(R^{51})(R^{52})$—$[CR^{53}=CR^{54}]z$-$R^{55}$ where z is 1, $R^{51}$ and $R^{52}$ are each independently H, halo or $C_{1-2}$ alkyl, $R^{53}$ and $R^{54}$ are each independently H, halogen, $C_{1-4}$alkyl or $C_{1-4}$haloalkyl and $R^{55}$ is phenyl substituted by halogen, $C_{1-4}$alkyl, $C_{1-4}$alkoxy, $C_{1-4}$haloalkyl, $C_{1-4}$haloalkoxy, CN, $NO_2$, aryl, heteroaryl, amino or dialkylamino or heteroaryl substituted by halogen, $C_{1-4}$alkyl, $C_{1-4}$alkoxy, $C_{1-4}$haloalkyl, $C_{1-4}$haloalkoxy, CN, $NO_2$, aryl, heteroaryl, amino or dialkylamino.

6. A compound according to claim 1 wherein $R^1$ is pyridyl (optionally substituted by halo, $C_{1-3}$alkyl or $C_{1-3}$haloalkyl) or $C_{1-6}$alkoxy; each $R^4$ is independently fluoro, chloro, bromo, $C_{1-4}$alkyl or $C_{1-4}$haloalkyl; n is 1 or 2; and $R^8$ is —$C(R^{51})(R^{52})$—$[CR^{53}=CR^{54}]z$-$R^{55}$ where z is 1, $R^{51}$ and $R^{52}$ are each independently H, halo or $C_{1-2}$ alkyl, $R^{53}$ and $R^{54}$ are each independently H, halogen, $C_{1-4}$alkyl or $C_{1-4}$haloalkyl and $R^{55}$ is phenyl substituted by halogen, $C_{1-4}$alkyl, $C_{1-4}$alkoxy, $C_{1-4}$haloalkyl, $C_{1-4}$haloalkoxy, CN, $NO_2$, aryl, heteroaryl, amino or dialkylamino or heteroaryl substituted by halogen, $C_{1-4}$alkyl, $C_{1-4}$alkoxy, $C_{1-4}$haloalkyl, $C_{1-4}$haloalkoxy, CN, $NO_2$, aryl, heteroaryl, amino or dialkylamino; and salts or N-oxides thereof.

\* \* \* \* \*